United States Patent
Yoshikuni et al.

(10) Patent No.: US 11,674,145 B2
(45) Date of Patent: Jun. 13, 2023

(54) PATHWAY INTEGRATION AND EXPRESSION IN HOST CELLS

(71) Applicant: THE REGENTS OF THE UNIVERSITY OF CALIFORNIA, Oakland, CA (US)

(72) Inventors: Yasuo Yoshikuni, Orinda, CA (US); Gaoyan Wang, Pleasanton, CA (US); Zhiying Zhao, Danville, CA (US); Robert Cameron Coates, Lafayette, CA (US); Jan-Fang Cheng, Orinda, CA (US); David Robinson, Martinez, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1089 days.

(21) Appl. No.: 16/072,174

(22) PCT Filed: Jan. 24, 2017

(86) PCT No.: PCT/US2017/014788
§ 371 (c)(1),
(2) Date: Jul. 23, 2018

(87) PCT Pub. No.: WO2017/176347
PCT Pub. Date: Oct. 12, 2017

(65) Prior Publication Data
US 2019/0048354 A1    Feb. 14, 2019

Related U.S. Application Data

(60) Provisional application No. 62/286,947, filed on Jan. 25, 2016.

(51) Int. Cl.
| | |
|---|---|
| *C12N 15/74* | (2006.01) |
| *C12N 15/78* | (2006.01) |
| *C12N 15/70* | (2006.01) |
| *C12N 15/90* | (2006.01) |

(52) U.S. Cl.
CPC ............ *C12N 15/78* (2013.01); *C12N 15/70* (2013.01); *C12N 15/74* (2013.01); *C12N 15/902* (2013.01)

(58) Field of Classification Search
None
See application file for complete search history.

(56) References Cited

U.S. PATENT DOCUMENTS

| | | | |
|---|---|---|---|
| 2010/0281551 A1* | 11/2010 | Kaminaka | C12N 15/102 435/325 |
| 2012/0329115 A1 | 12/2012 | Santos et al. | |
| 2015/0079680 A1 | 3/2015 | Bradley et al. | |

OTHER PUBLICATIONS

Muroi et al., TG1 integrase-based system for site-specific gene integration into bacterial genomes. Applied Microbiology and Biotechnology (2013), 97: 4039-4048 (Year: 2013).*
Hirano et al., Site-specific recombinases as tools for heterologous gene integration. Applied Microbiology and Biotechnology (2011), 92: 227-239 (Year: 2011).*
Chiang et al., "Construction of a Mariner-Based Transposon for Epitope-Tagging and Genomic Targeting", Gene, vol. 296, 2002, pp. 179-185.
International Preliminary Report on Patentability received for PCT Patent Application No. PCT/US2017/014788, dated Aug. 9, 2018, 13 pages.
International Search Report and Written Opinion received for PCT Patent Application No. PCT/US2017/014788, dated Dec. 13, 2017, 19 pages.
Invitation to Pay Additional Fees received for PCT Patent Application No. PCT/US2017/014788, mailed on Oct. 19, 2017, 13 pages.
Kolb, Andreas F., "Genome Engineering Using Site-Specific Recombinases", Cloning and Stem Cells, vol. 4, No. 1, 2002, pp. 65-80.
Liu et al., "The Univector Plasmid-Fusion System, A Method for Rapid Construction of Recombinant DNA without Restriction Enzymes", Current Biology, vol. 8, No. 24, 1998, pp. 1300-1309.
Santos et al., "Engineering Complex Biological Systems in Bacteria through Recombinase-Assisted Genome Engineering", Nature Protocols, vol. 9, No. 6, May 15, 2014, pp. 1320-1336.
Santos et al., "Implementation of Stable and Complex Biological Systems through Recombinase-Assisted Genome Engineering", Nature Communications, vol. 4, No. 2503, 2013, pp. 1-10.
Yu et al., "Minimization of the *Escherichia coli* Genome using a Tn5-Targeted Cre/loxP Excision System", Nature Biotechnology, vol. 20, Oct. 2002, pp. 1018-1023.

* cited by examiner

*Primary Examiner* — Samuel C Woolwine
*Assistant Examiner* — Catherine Konopka
(74) *Attorney, Agent, or Firm* — Morrison & Foerster LLP

(57) ABSTRACT

Provided herein are methods for integrating a gene of interest into a chromosome of a host cell. In some embodiments, the methods include introducing into a host cell a first plasmid comprising a transposase coding sequence and a donor sequence, which includes a selectable marker coding sequence flanked by a first and a second lox site and is itself flanked by inverted repeats recognized by the transposase. Following transposase-mediated chromosomal integration of the donor sequence into the host cell, a second plasmid is introduced, which comprises the gene of interest and a second selectable marker coding sequence, both flanked by a first and a second lox site. The gene of interest is chromosomally integrated into the host cell by recombinase-mediated cassette exchange (RMCE) between the donor sequence and the second plasmid via Cre-/cuc recombination. Further provided herein are host cells, vectors, and methods of producing a product related thereto.

24 Claims, 49 Drawing Sheets

Specification includes a Sequence Listing.

(1). Transpose the landing pad randomly into the chromosome (2). Integrate T7 driven pathway into the chromosome by Cre-Lox recombination

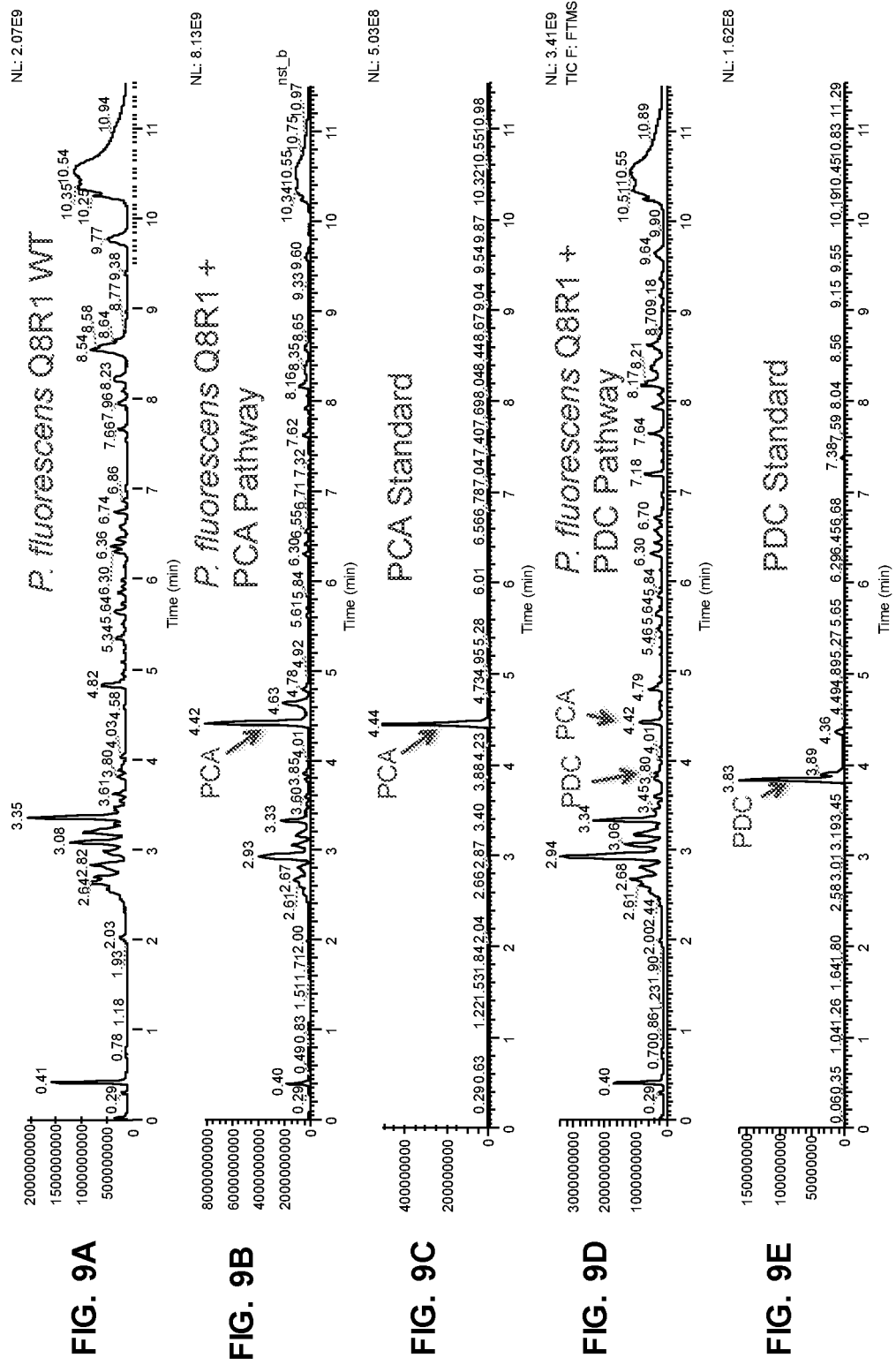

(1). Transpose the landing pad carrying T7 RNA polymerase and Cre-lox sites randomly into the chromosome (2). Integrate T7 driven pathway into the chromosome by Cre-Lox recombination for expression

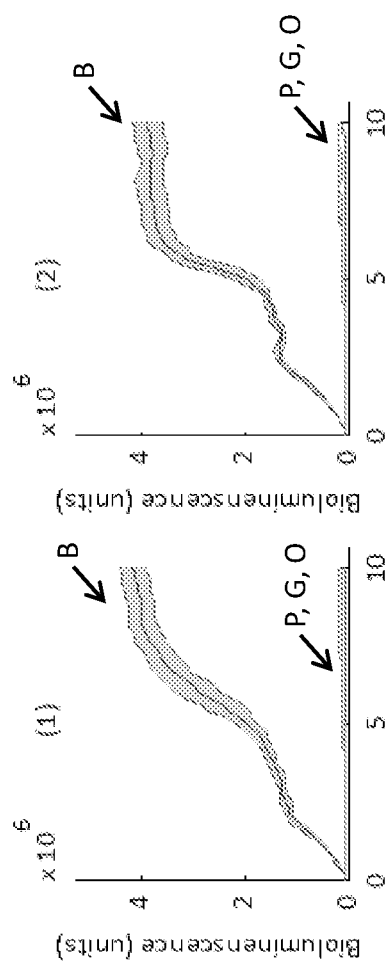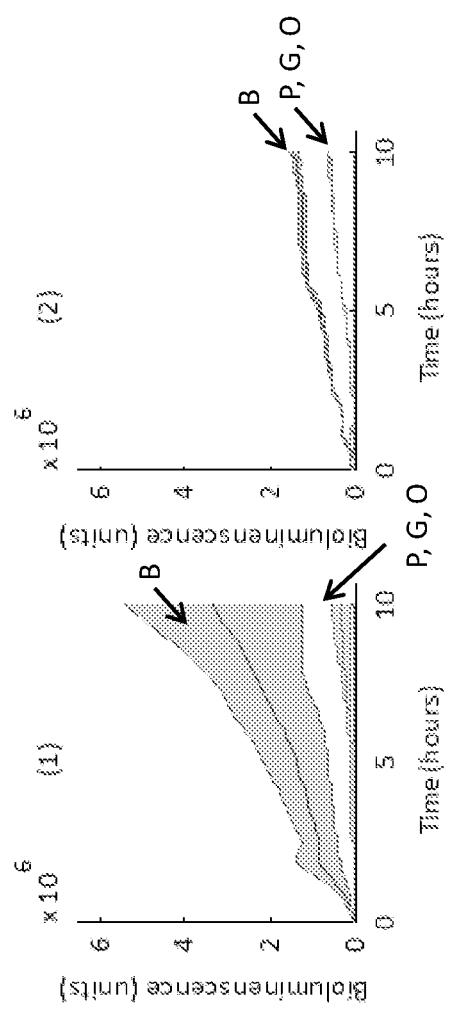

Integrate T7 driven pathway into the chromosome by Cre-Lox recombination for expression

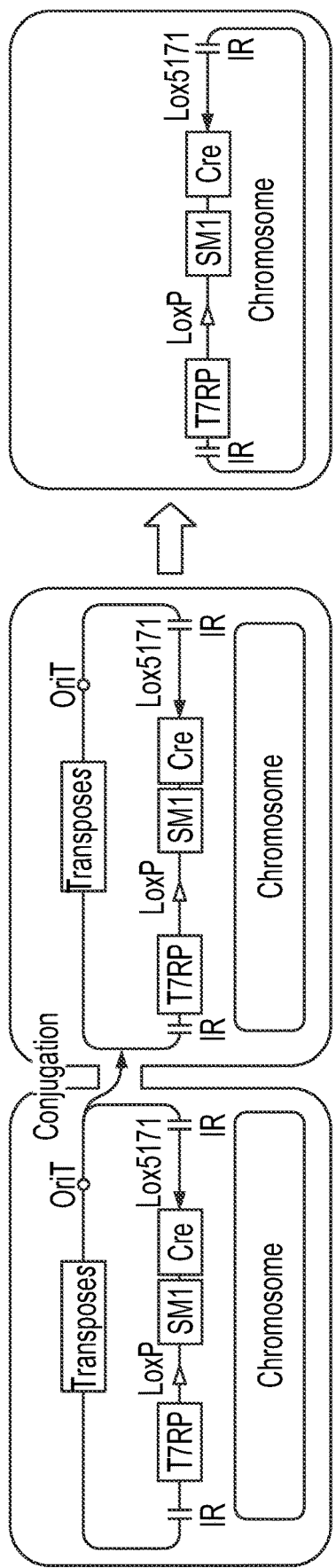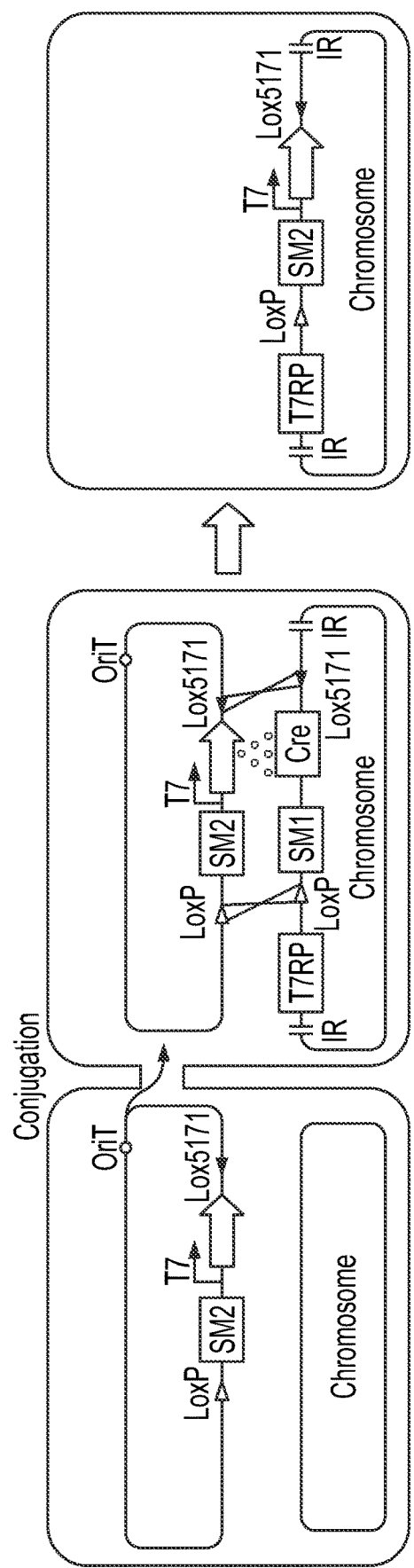
FIG. 17

| | Engineered strain (IPTG) | | | | Control (IPTG) | | | |
|---|---|---|---|---|---|---|---|---|
| | 0mM | 0.01mM | 0.1mM | 1.0mM | 0mM | 0.01mM | 0.1mM | 1.0mM |
| 1_SB094_Pseudomonas flourescens Q8r1 | | | | | | | | |
| 2_SB119_Pseudomonas simiae WCS417 | | | | | | | | |
| 3_SB203_Photorhabdus luminescens subsp. laumondii TTO1 | | | | | | | | |
| 4_SB212_Photorhabdus luminescens subsp. luminescens | | | | | | | | |
| 5_SB213_Photorhabdus temperata subsp. khanii | | | | | | | | |
| 6_SB214_Xenorhabdus doucetiae | | | | | | | | |
| 7_SB217_Serratia odorifera | | | | | | | | |
| 8_SB218_Erwinia oleae | | | | | | | | |
| 9_SB220_Erwinia pyrifoliae | | | | | | | | |
| 10_SB222_Yersinia bercovieri | | | | | | | | |
| 11_SB223_Yersinia mollaretii | | | | | | | | |
| 12_SB226_Dickeya dadantii subsp. dadantii | | | | | | | | |
| 13_SB227_Dickeya dadantii subsp. dieffenbachiae | | | | | | | | |
| 14_SB228_Dickeya solani | | | | | | | | |
| 15_SB229_Dickeya zeae | | | | | | | | |
| 16_SB235_Aeromonas encheleia | | | | | | | | |
| 17_SB237_Aeromonas piscicola | | | | | | | | |
| 18_SB238_Aeromonas salmonicida subsp. pectinolytica | | | | | | | | |
| 19_SB239_Aeromonas salmonicida subsp. salmonicida | | | | | | | | |
| 20_SB396_Pantoea agglomerans | | | | | | | | |
| 21_SB098_Pseudomonas putida KT2440 | | | | | | | | |
| 22_SB233_Pectobacterium carotovorum subsp. odoriferum | | | | | | | | |
| 23_SB236_Aeromonas molluscorum | | | | | | | | |

FIG. 18A

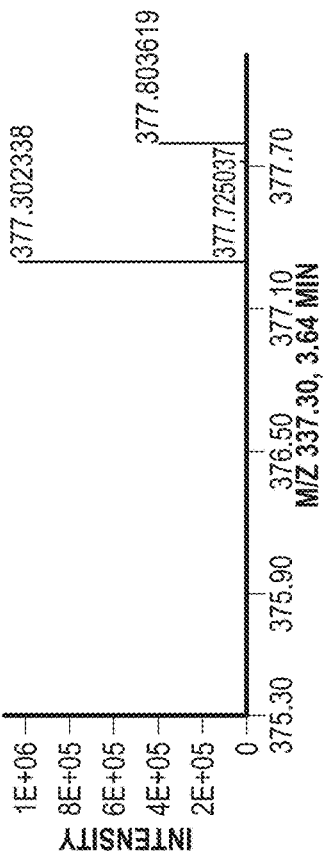
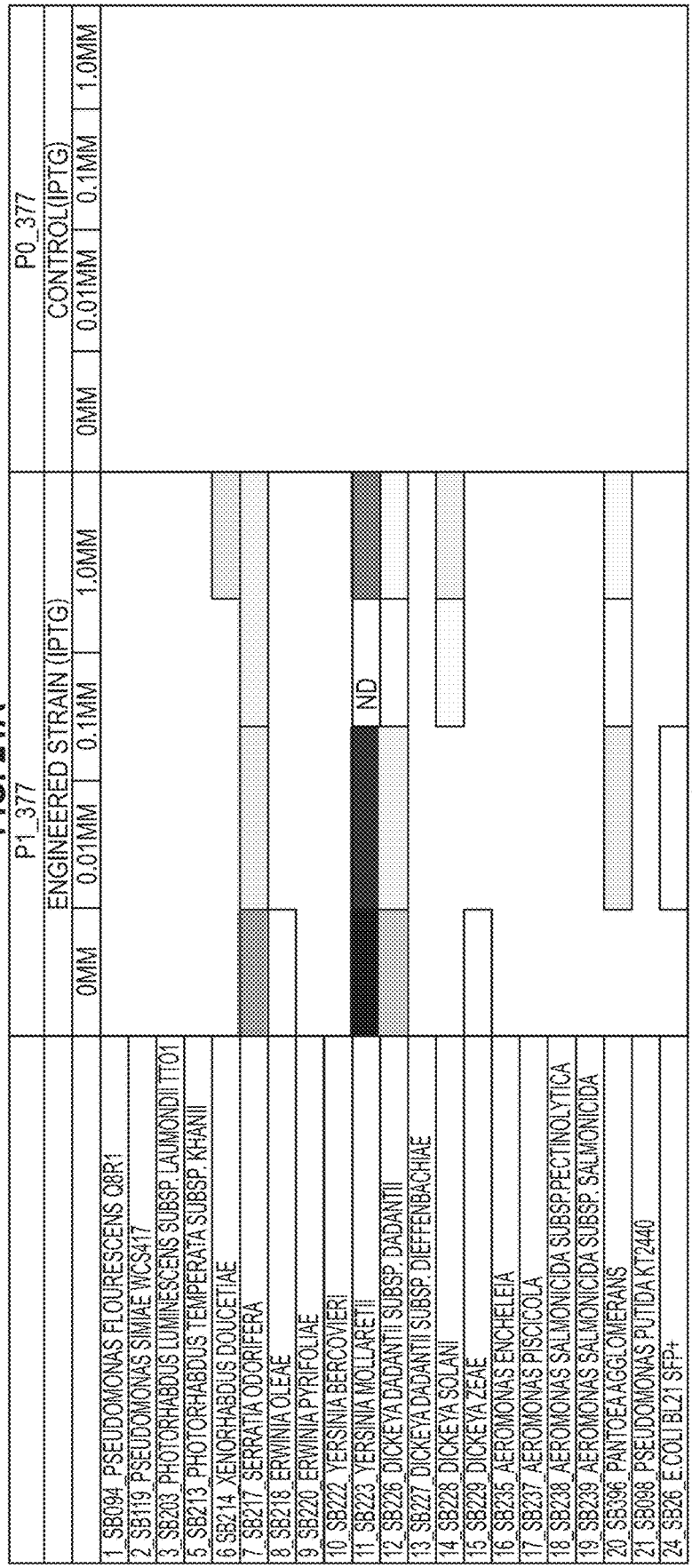
FIG. 21A
FIG. 21B

PATHWAY INTEGRATION AND EXPRESSION IN HOST CELLS

CROSS-REFERENCE TO RELATED APPLICATIONS

This application is a U.S. National Phase patent application of PCT/US2017/014788, filed Jan. 24, 2017, which claims the priority benefit of U.S. Provisional Application No. 62/286,947, filed Jan. 25, 2016, the disclosures of which are hereby incorporated by reference in their entirety.

STATEMENT OF GOVERNMENT SUPPORT

This invention was made with Government support under Grant No. DE-AC02-05CH11231 awarded by the Department of Energy. The Government has certain rights in this invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 220032001500SEQLIST.txt, date recorded: Jun. 27, 2018, size: 84 KB).

FIELD

The present disclosure relates, inter alia, to methods for integrating a gene of interest into a host chromosome by integrating a donor sequence comprising two lox sites and a selectable marker flanked by inverted repeats into a host cell through transposase-mediated integration, followed by introducing a second plasmid comprising a gene or pathway of interest and a selectable marker flanked by two lox sites into the host cell, wherein the gene or pathway of interest is integrated into the chromosome of the host cell through recombinase mediated-cassette exchange. Further provided herein are vectors, cells, and methods related thereto.

BACKGROUND

Several decades have passed since microbes were first used as miniscule factories for antibiotics, vitamins and enzymes (Murphy, C. D., *Organic & Biomol. Chem*, 10(10): 1949-1957(2012)). Since then, genes, pathways, reporter constructions, and regulatory elements have been recombinantly engineered into bacteria, plant cells, yeasts, and mammalian cells for screening, bio-manufacturing, and even therapeutic applications (see, e.g., Nielsen, J. and Jewett, M. C. (2008) *FEMS Yeast Res.* 8:122-31; Kis, Z. et al. (2015) J. R. Soc. Interface 12:20141000). Genetic engineering technologies have enabled scientists to manipulate host cells for desired products with optimized features, but only a small number of model eukaryotes and bacteria have been domesticated as hosts.

Three common techniques have been used to introduce and express genes in host cells (Ongley, S. E., et al., *Nat. Prod. Reports*, 30(8): 1121-1138 (2013). One such technique is plasmid based expression, but only a very few model host cells, particularly bacterial cells, have expression plasmids developed. A second technique is homologous recombination-based integration, but the efficiency is low in many host cells, and this method is limited to hosts that have relatively high recombination efficiency. A third technique is transposition-based chromosomal integration, but the efficiency decreases as the length of insert (e.g., a pathway of interest) increases, and it is nearly impossible to insert different pathways into the same chromosomal location. In addition, with respect to bacterial host cells, those approaches mainly focus on manipulating a small range of domesticated model bacteria, and the expression of introduced genes or pathways is limited by the physiology of these strains (transcription, translation, post-translational modification, tolerance to products and availability of substrates and co-factors; see, e.g., Kang, Y., et al., *Protein Expression and Purification*, 55(2):325-333 (2007).

Therefore, a highly efficient and universal technology to potentially integrate and express genes or pathways in any host cell would be very desirable, thereby providing a common tool box for genome engineering and other important applications (such as microbiome engineering for agriculture and renewable energy, pharmaceutical synthesis, commodity chemical and biofuel production, and the like).

SUMMARY

To meet these and other demands, provided herein are methods and compositions for pathway integration and expression in bacteria.

Accordingly, certain aspects of the present disclosure relate to a method for integrating a gene of interest into a chromosome of a host cell, the method including providing a bacterial host cell comprising a donor sequence comprising a first selectable marker coding sequence flanked by a first and a second lox site, wherein the first and the second lox sites are different, and wherein the donor sequence is integrated in a chromosome of the bacterial host cell; providing a plasmid comprising the gene of interest and a second selectable marker coding sequence, wherein the gene of interest and the second selectable marker are both flanked by a first and a second lox site, wherein the first and the second lox sites are different; and introducing the plasmid into the bacterial host cell, wherein at least one of the plasmid and the donor sequence comprises a Cre recombinase coding sequence, and wherein upon introduction of the plasmid into the bacterial host cell, Cre recombinase is expressed from the Cre recombinase coding sequence, and the gene of interest is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence. Further provided herein is a method for integrating a gene of interest into a chromosome of a host cell, the method including providing a host cell comprising a donor sequence comprising a first selectable marker coding sequence flanked by a first and a second lox site, wherein the first and the second lox sites are different, and wherein the donor sequence is integrated in a chromosome of the host cell; providing a plasmid comprising the gene of interest and a second selectable marker coding sequence, wherein the gene of interest and the second selectable marker are both flanked by a first and a second lox site, wherein the first and the second lox sites are different; and introducing the plasmid into the host cell, wherein at least one of the plasmid and the donor sequence comprises a Cre recombinase coding sequence, and wherein upon introduction of the plasmid into the bacterial host cell, Cre recombinase is expressed from the Cre recombinase coding sequence, and the gene of interest is integrated into the chromosome of the host cell by the Cre recombinase through recombinase-mediated cassette exchange (RMCE) between the first lox site of the second plasmid and the first lox site of the donor sequence, and between the second lox site of the second plasmid and the second lox site of the donor sequence, wherein the host cell is a fungal, animal, or plant host cell. Further provided herein is a method for modulating expression of a gene of interest in a bacterial host cell, the method including: providing a bacterial host cell comprising a donor sequence comprising: (i) a Cre recombinase coding sequence, wherein the Cre recombinase coding sequence is flanked by a first and a second lox site, and wherein the first and the second lox sites are different; and (ii) a first selectable marker coding sequence flanked by the second lox site and a third lox site, wherein the third lox site is different from the first and second lox sites, and wherein the donor sequence is integrated in a chromosome of the bacterial host cell; providing a plasmid comprising a catalytically dead Cas9 protein coding sequence and a second selectable marker coding sequence, wherein the catalytically dead Cas9 protein coding sequence and the second selectable marker are both flanked by the second lox site and the third lox site; introducing the plasmid into the bacterial host cell, wherein upon introduction of the plasmid into the bacterial host cell, Cre recombinase is expressed from the Cre recombinase coding sequence, and the catalytically dead Cas9 protein coding sequence is integrated into the chromosome of the bacterial host cell by the Cre recombinase through recombinase-mediated cassette exchange (RMCE) between the second lox site of the plasmid and the second lox site of the donor sequence, and between the third lox site of the second plasmid and the third lox site of the donor sequence; providing a second plasmid comprising a guide RNA sequence that targets a guide RNA target sequence of the gene of interest and a third selectable marker coding sequence, wherein the guide RNA sequence and the third selectable marker are both flanked by the first lox site and the second lox site; and introducing the second plasmid into the bacterial host cell, wherein upon introduction of the second plasmid into the bacterial host cell, Cre recombinase is expressed from the Cre recombinase coding sequence, and the guide RNA sequence is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest. Further provided herein is a method for modulating expression of a gene of interest in a bacterial host cell, the method including: providing a bacterial host cell comprising a donor sequence comprising: (i) a Cre recombinase coding sequence, wherein the Cre recombinase coding sequence is flanked by a first and a second lox site, and wherein the first and the second lox sites are different; and (ii) a first selectable marker coding sequence flanked by the second lox site and a third lox site, wherein the third lox site is different from the first and second lox sites, and wherein the donor sequence is integrated in a chromosome of the bacterial host cell; providing a first plasmid comprising a catalytically dead Cas9 protein coding sequence, a guide RNA sequence that targets a guide RNA target sequence of the gene of interest, and a second selectable marker coding sequence, wherein the catalytically dead Cas9 protein coding sequence, the guide RNA sequence, and the second selectable marker are flanked by the second lox site and the third lox site; introducing the first plasmid into the bacterial host cell, wherein upon introduction of the first plasmid into the bacterial host cell, Cre recombinase is expressed from the Cre recombinase coding sequence, and the catalytically dead Cas9 protein coding sequence and guide RNA sequence are integrated into the chromosome of the bacterial host cell by the Cre recombinase through recombinase-mediated cassette exchange (RMCE) between the second lox site of the first plasmid and the second lox site of the donor sequence, and between the third lox site of the first plasmid and the third lox site of the donor sequence; providing a second plasmid comprising the gene of interest and a third selectable marker coding sequence, wherein the gene of interest and the third selectable marker are both flanked by the first lox site and the second lox site; and introducing the second plasmid into the bacterial host cell, wherein upon introduction of the second plasmid into the bacterial host cell, Cre recombinase is expressed from the Cre recombinase coding sequence, and the gene of interest is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest. Further provided herein is a method for modulating expression of a gene of interest in a bacterial host cell, the method including: providing a bacterial host cell comprising a donor sequence comprising: (i) a Cre recombinase coding sequence, wherein the Cre recombinase coding sequence is flanked by a first and a second lox site, and wherein the first and the second lox sites are different; and (ii) a first selectable marker coding sequence flanked by the second lox site and a third lox site, wherein the third lox site is different from the first and second lox sites, and wherein the donor sequence is integrated in a chromosome of the bacterial host cell; providing a plasmid comprising a guide RNA sequence that targets a guide RNA target sequence of the gene of interest and a second selectable marker coding sequence, wherein the guide RNA sequence and the second selectable marker are both flanked by the first lox site and the second lox site; and introducing the plasmid into the bacterial host cell, wherein upon introduction of the plasmid into the bacterial host cell, Cre recombinase is expressed from the Cre recombinase coding sequence, and the guide RNA sequence is integrated into the chromosome of the bacterial host cell by the Cre recombinase through recombinase-mediated cassette exchange (RMCE) between the first lox site of the second and the first lox site of the donor sequence, and between the second lox site of the second plasmid and the second lox site of the donor sequence; providing a second plasmid comprising a catalytically dead Cas9 protein coding sequence and a third selectable marker coding sequence, wherein the catalytically dead Cas9 protein coding sequence and the third selectable marker are both flanked by the second lox site and the third lox site; introducing the second plasmid into the bacterial host cell, wherein upon introduction of the second plasmid into the bacterial host cell, Cre recombinase is expressed from the Cre recombinase coding sequence, and the catalytically dead Cas9 protein coding sequence is integrated into the chromosome of the bacterial host cell by the Cre recombinase through recombinase-mediated cassette exchange (RMCE) between the second lox site of the second plasmid and the second lox site of the donor sequence, and between the third lox site of the second plasmid and the third lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest. Further provided herein is a method for modulating expression of a gene of interest in a bacterial host cell, the method including: providing a bacterial host cell comprising a donor sequence comprising: (i) a Cre recombinase coding sequence, wherein the Cre recombinase coding sequence is flanked by a first and a second lox site, and wherein the first and the second lox sites are different; and (ii) a first selectable marker coding sequence flanked by the second lox site and a third lox site, wherein the third lox site is different from the first and second lox sites, and wherein the donor sequence is integrated in a chromosome of the bacterial host cell; providing a plasmid comprising the gene of interest and a second selectable marker coding sequence, wherein the gene of interest and the second selectable marker are both flanked by the first lox site and the second lox site; and introducing the plasmid into the bacterial host cell, wherein upon introduction of the plasmid into the bacterial host cell, Cre recombinase is expressed from the Cre recombinase coding sequence, and the gene of interest is integrated into the chromosome of the bacterial host cell by the Cre recombinase through recombinase-mediated cassette exchange (RMCE) between the first lox site of the plasmid and the first lox site of the donor sequence, and between the second lox site of the plasmid and the second lox site of the donor sequence; providing a second plasmid comprising a catalytically dead Cas9 protein coding sequence, a guide RNA sequence that targets a guide RNA target sequence of the gene of interest, and a third selectable marker coding sequence, wherein the catalytically dead Cas9 protein coding sequence, the guide RNA sequence, and the third selectable marker are flanked by the second lox site and the third lox site; introducing the second plasmid into the bacterial host cell, wherein upon introduction of the second plasmid into the bacterial host cell, Cre recombinase is expressed from the Cre recombinase coding sequence, and the catalytically dead Cas9 protein coding sequence and guide RNA sequence are integrated into the chromosome of the bacterial host cell by the Cre recombinase through recombinase-mediated cassette exchange (RMCE) between the second lox site of the second plasmid and the second lox site of the donor sequence, and between the third lox site of the second plasmid and the third lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest. Further provided herein is a method for modulating expression of a gene of interest in a bacterial host cell, the method including: providing a bacterial host cell comprising a donor sequence comprising: (i) a first landing pad comprising a Cre recombinase coding sequence, wherein the landing pad is flanked by a first and a second lox site, and wherein the first and the second lox sites are different; and (ii) a second landing pad, wherein the second landing pad comprises a first selectable marker coding sequence and is flanked by the second lox site and a third lox site, wherein the third lox site is different from the first and second lox sites, and wherein the donor sequence is integrated in a chromosome of the bacterial host cell; providing a plasmid comprising a catalytically dead Cas9 protein coding sequence and a second selectable marker coding sequence, wherein the catalytically dead Cas9 protein coding sequence and the second selectable marker are both flanked by the second lox site and the third lox site; introducing the plasmid into the bacterial host cell, wherein upon introduction of the plasmid into the bacterial host cell, Cre recombinase is expressed from the Cre recombinase coding sequence, and the catalytically dead Cas9 protein coding sequence is integrated into the second landing pad by the Cre recombinase through recombinase-mediated cassette exchange (RMCE) between the second lox site of the plasmid and the second lox site of the donor sequence, and between the third lox site of the plasmid and the third lox site of the donor sequence; providing a second plasmid comprising a guide RNA sequence that targets a guide RNA target sequence of the gene of interest and a third selectable marker coding sequence, wherein the guide RNA sequence and the third selectable marker are both flanked by the first lox site and the second lox site; and introducing the second plasmid into the bacterial host cell, wherein upon introduction of the second plasmid into the bacterial host cell, Cre recombinase is expressed from the Cre recombinase coding sequence, and the guide RNA sequence is integrated into the first landing pad by the Cre recombinase through recombinase-mediated cassette exchange (RMCE) between the first lox site of the second plasmid and the first lox site of the donor sequence, and between the second lox site of the second plasmid and the second lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest. Further provided herein is a method for modulating expression of a gene of interest in a bacterial host cell, the method including: providing a bacterial host cell comprising a donor sequence comprising: (i) a first landing pad comprising a Cre recombinase coding sequence, wherein the landing pad is flanked by a first and a second lox site, and wherein the first and the second lox sites are different; and (ii) a second landing pad, wherein the second landing pad comprises a first selectable marker coding sequence and is flanked by the second lox site and a third lox site, wherein the third lox site is different from the first and second lox sites, and wherein the donor sequence is integrated in a chromosome of the bacterial host cell; providing a first plasmid comprising a catalytically dead Cas9 protein coding sequence, a guide RNA sequence that targets a guide RNA target sequence of the gene of interest, and a second selectable marker coding sequence, wherein the catalytically dead Cas9 protein coding sequence, the guide RNA sequence, and the second selectable marker are flanked by the second lox site and the third lox site; introducing the first plasmid into the bacterial host cell, wherein upon introduction of the first plasmid into the bacterial host cell, Cre recombinase is expressed from the Cre recombinase coding sequence, and the catalytically dead Cas9 protein coding sequence and guide RNA sequence are integrated into the second landing pad by the Cre recombinase through recombinase-mediated cassette exchange (RMCE) between the second lox site of the first plasmid and the second lox site of the donor sequence, and between the third lox site of the first plasmid and the third lox site of the donor sequence; providing a second plasmid comprising the gene of interest and a third selectable marker coding sequence, wherein the gene of interest and the third selectable marker are both flanked by the first lox site and the second lox site; and introducing the second plasmid into the bacterial host cell, wherein upon introduction of the second plasmid into the bacterial host cell, Cre recombinase is expressed from the Cre recombinase coding sequence, and the gene of interest is integrated into the first landing pad by the Cre recombinase through recombinase-mediated cassette exchange (RMCE) between the first lox site of the second plasmid and the first lox site of the donor sequence, and between the second lox site of the second plasmid and the second lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest. Further provided herein is a method for modulating expression of a gene of interest in a bacterial host cell, the method including: providing a bacterial host cell comprising a donor sequence comprising: (i) a first landing pad comprising a Cre recombinase coding sequence, wherein the landing pad is flanked by a first and a second lox site, and wherein the first and the second lox sites are different; and (ii) a second landing pad, wherein the second landing pad comprises a first selectable marker coding sequence and is flanked by the second lox site and a third lox site, wherein the third lox site is different from the first and second lox sites, and wherein the donor sequence is integrated in a chromosome of the bacterial host cell; providing a plasmid comprising a guide RNA sequence that targets a guide RNA target sequence of the gene of interest and a second selectable marker coding sequence, wherein the guide RNA sequence and the second selectable marker are both flanked by the first lox site and the second lox site; and introducing the plasmid into the bacterial host cell, wherein upon introduction of the plasmid into the bacterial host cell, Cre recombinase is expressed from the Cre recombinase coding sequence, and the guide RNA sequence is integrated into the first landing pad by the Cre recombinase through recombinase-mediated cassette exchange (RMCE) between the first lox site of the plasmid and the first lox site of the donor sequence, and between the second lox site of the plasmid and the second lox site of the donor sequence; providing a second plasmid comprising a catalytically dead Cas9 protein coding sequence and a third selectable marker coding sequence, wherein the catalytically dead Cas9 protein coding sequence and the third selectable marker are both flanked by the second lox site and the third lox site; introducing the second plasmid into the bacterial host cell, wherein upon introduction of the second plasmid into the bacterial host cell, Cre recombinase is expressed from the Cre recombinase coding sequence, and the catalytically dead Cas9 protein coding sequence is integrated into the second landing pad by the Cre recombinase through recombinase-mediated cassette exchange (RMCE) between the second lox site of the second plasmid and the second lox site of the donor sequence, and between the third lox site of the second plasmid and the third lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest. Further provided herein is a method for modulating expression of a gene of interest in a bacterial host cell, the method including: providing a bacterial host cell comprising a donor sequence comprising: (i) a first landing pad comprising a Cre recombinase coding sequence, wherein the landing pad is flanked by a first and a second lox site, and wherein the first and the second lox sites are different; and (ii) a second landing pad, wherein the second landing pad comprises a first selectable marker coding sequence and is flanked by the second lox site and a third lox site, wherein the third lox site is different from the first and second lox sites, and wherein the donor sequence is integrated in a chromosome of the bacterial host cell; providing a plasmid comprising the gene of interest and a second selectable marker coding sequence, wherein the gene of interest and the second selectable marker are both flanked by the first lox site and the second lox site; and introducing the plasmid into the bacterial host cell, wherein upon introduction of the plasmid into the bacterial host cell, Cre recombinase is expressed from the Cre recombinase coding sequence, and the gene of interest is integrated into the first landing pad by the Cre recombinase through recombinase-mediated cassette exchange (RMCE) between the first lox site of the plasmid and the first lox site of the donor sequence, and between the second lox site of the plasmid and the second lox site of the donor sequence; providing a second plasmid comprising a catalytically dead Cas9 protein coding sequence, a guide RNA sequence that targets a guide RNA target sequence of the gene of interest, and a third selectable marker coding sequence, wherein the catalytically dead Cas9 protein coding sequence, the guide RNA sequence, and the third selectable marker are flanked by the second lox site and the third lox site; introducing the second plasmid into the bacterial host cell, wherein upon introduction of the second plasmid into the bacterial host cell, Cre recombinase is expressed from the Cre recombinase coding sequence, and the catalytically dead Cas9 protein coding sequence and guide RNA sequence are integrated into the second landing pad by the Cre recombinase through recombinase-mediated cassette exchange (RMCE) between the second lox site of the second plasmid and the second lox site of the donor sequence, and between the third lox site of the second plasmid and the third lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest. Further provided herein is a kit comprising a first vector comprising: (i) a transposase coding sequence; and (ii) a donor sequence, wherein the donor sequence is flanked by inverted repeats recognized by the transposase, wherein the donor sequence comprises a first selectable marker coding sequence flanked by a first and a second lox site, and wherein the first and the second lox sites are different; and a second vector comprising: (i) one or more restriction or targeted cloning sites suitable for recombining a gene of interest into the second vector; and (ii) a second selectable marker, wherein the second selectable marker and the one or more restriction or targeted cloning sites are flanked by the first and the second lox sites.

Accordingly, certain aspects of the present disclosure relate to a method for integrating a gene of interest into a chromosome of a host cell, the method including (a) providing a first plasmid including: (i) a transposase coding sequence; and (ii) a donor sequence, wherein the donor sequence is flanked by inverted repeats recognized by the transposase, wherein the donor sequence includes a first selectable marker coding sequence flanked by a first and a second lox site, and wherein the first and the second lox sites are different; (b) introducing the first plasmid into the host cell, wherein upon introduction of the first plasmid into the host cell, transposase is expressed from the transposase coding sequence, and the donor sequence is integrated into a chromosome of the host cell between the inverted repeats by the transposase; (c) providing a second plasmid comprising the gene of interest and a second selectable marker coding sequence, wherein the gene of interest and the second selectable marker are both flanked by a first and a second lox site, wherein the first and the second lox sites are different; and (d) introducing the second plasmid into the host cell, wherein at least one of the second plasmid and the donor sequence includes a Cre recombinase coding sequence, and wherein upon introduction of the second plasmid into the bacterial host cell, Cre recombinase is expressed from the Cre recombinase coding sequence, and the gene of interest is integrated into the chromosome of the host cell by the Cre recombinase through recombinase-mediated cassette exchange (RMCE) between the first lox site of the second plasmid and the first lox site of the donor sequence, and between the second lox site of the second plasmid and the second lox site of the donor sequence. Further provided herein is a method for integrating a gene of interest into a chromosome of a bacterial host cell, the method including: providing a first bacterial donor cell comprising a first plasmid, the first plasmid comprising: (i) a transposase coding sequence; and (ii) a donor sequence, wherein the donor sequence is flanked by inverted repeats recognized by the transposase, wherein the donor sequence includes a first selectable marker coding sequence flanked by a first and a second lox site, and wherein the first and the second lox sites are different; (b) introducing the first plasmid into the bacterial host cell by conjugation with the first bacterial donor cell, wherein upon introduction of the first plasmid into the bacterial host cell, transposase is expressed from the transposase coding sequence, and the donor sequence is integrated into the chromosome of the bacterial host cell between the inverted repeats by the transposase; (c) providing a second bacterial donor cell comprising a second plasmid, the second plasmid comprising the gene of interest and a second selectable marker coding sequence, wherein the gene of interest and the second selectable marker are both flanked by a first and a second lox site, wherein the first and the second lox sites are different; and (d) introducing the second plasmid into the bacterial host cell, wherein at least one of the second plasmid and the donor sequence includes a Cre recombinase coding sequence, and wherein upon introduction of the second plasmid into the bacterial host cell, Cre recombinase is expressed from the Cre recombinase coding sequence, and the gene of interest is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence. Also provided herein is a bacterial host cell including a chromosomally integrated donor sequence, wherein the donor sequence includes a selectable marker coding sequence flanked by a first and a second lox site, wherein the donor sequence is flanked in the chromosome of the bacterial host cell by inverted repeats recognized by a transposase, and wherein the first and the second lox sites are different. Also provided herein is a vector comprising: (a) a transposase coding sequence; and (b) a donor sequence, wherein the donor sequence is flanked by inverted repeats recognized by the transposase, wherein the donor sequence includes a selectable marker coding sequence flanked by a first and a second lox site, and wherein the first and the second lox sites are different. In some embodiments, the vector comprises the polynucleotide sequence of SEQ ID NO:4. Further provided herein is a vector comprising the polynucleotide sequence of SEQ ID NO:10. Further provided herein is a vector comprising the polynucleotide sequence of SEQ ID NO:11. Further provided herein is a method for producing a phenazine, including: (a) providing a bacterial host cell comprising a chromosomally integrated donor sequence, wherein the donor sequence includes a first selectable marker sequence flanked by a first and a second lox site, wherein the first and the second lox sites are different, and wherein the donor sequence is flanked by inverted repeats recognized by a transposase; (b) introducing a plasmid into the bacterial host cell, the plasmid including a phenazine biosynthesis pathway coding sequence and a second selectable marker coding sequence, wherein the phenazine biosynthesis pathway coding sequence and the second selectable marker coding sequence are both flanked by a first and a second lox site, wherein at least one of the chromosomally integrated donor sequence and the plasmid includes a Cre recombinase coding sequence, and wherein upon introduction of the plasmid into the bacterial host cell, Cre recombinase is expressed from the Cre recombinase coding sequence, and the phenazine biosynthesis pathway coding sequence is integrated into the chromosome of the bacterial host cell by the Cre recombinase through recombinase-mediated cassette exchange (RMCE) between the first lox site of the plasmid and the first lox site of the donor sequence, and between the second lox site of the plasmid and the second lox site of the donor sequence; and (c) culturing the bacterial host cell comprising the chromosomally integrated phenazine biosynthesis pathway coding sequence in a culture medium under conditions whereby the phenazine biosynthesis pathway coding sequence is expressed in the cell, and whereby the phenazine biosynthesis pathway produces the phenazine. Further provided herein is a method for producing a class IIa bacteriocin, including: (a) providing a bacterial host cell including a chromosomally integrated donor sequence, wherein the donor sequence includes a first selectable marker sequence flanked by a first and a second lox site, wherein the first and the second lox sites are different, and wherein the donor sequence is flanked by inverted repeats recognized by a transposase; (b) introducing a plasmid into the bacterial host cell, the plasmid including a class IIa bacteriocin biosynthesis pathway coding sequence and a second selectable marker coding sequence, wherein the class IIa bacteriocin biosynthesis pathway coding sequence and the second selectable marker coding sequence are both flanked by a first and a second lox site, wherein at least one of the chromosomally integrated donor sequence and the plasmid includes a Cre recombinase coding sequence, and wherein upon introduction of the plasmid into the bacterial host cell, Cre recombinase is expressed from the Cre recombinase coding sequence, and the class IIa bacteriocin biosynthesis pathway coding sequence is integrated into the chromosome of the bacterial host cell by the Cre recombinase through recombinase-mediated cassette exchange (RMCE) between the first lox site of the plasmid and the first lox site of the donor sequence, and between the second lox site of the plasmid and the second lox site of the donor sequence; and (c) culturing the bacterial host cell including the chromosomally integrated class IIa bacteriocin biosynthesis pathway coding sequence in a culture medium under conditions whereby the class IIa bacteriocin biosynthesis pathway coding sequence is expressed in the cell, and whereby the class IIa bacteriocin biosynthesis pathway produces the class IIa bacteriocin.

In some embodiments, prior to providing the bacterial host cell, the donor sequence is integrated into the chromosome of the bacterial host cell by: providing a bacterial donor cell comprising a donor plasmid, the donor plasmid comprising: (i) a transposase coding sequence; and (ii) the donor sequence, wherein the donor sequence is flanked by inverted repeats recognized by the transposase; and introducing the donor plasmid into the bacterial host cell by conjugation with the bacterial donor cell, wherein upon introduction of the donor plasmid into the bacterial host cell, transposase is expressed from the transposase coding sequence, and the donor sequence is integrated into the chromosome of the bacterial host cell between the inverted repeats by the transposase. In some embodiments, prior to providing the bacterial host cell, the donor sequence is integrated into the chromosome of the bacterial host cell by: providing a bacterial donor cell comprising a donor plasmid, the donor plasmid comprising: (i) an integrase coding sequence; and (ii) the donor sequence, wherein the donor sequence contains an attP site; and introducing the donor plasmid into the bacterial host cell by conjugation with the bacterial donor cell, wherein upon introduction of the donor plasmid into the bacterial host cell, integrase is expressed from the integrase coding sequence, and the donor sequence is integrated into the chromosome of the bacterial host cell mediated through the recombination between the attP site and an attB site on the chromosome of the bacterial host cell. In some embodiments, prior to providing the bacterial host cell, the donor sequence is integrated into the chromosome of the bacterial host cell by homologous recombination. In some embodiments, prior to providing the bacterial host cell, the donor sequence is integrated into the chromosome of the bacterial host cell by: providing the donor sequence, wherein the donor sequence is flanked by inverted repeats recognized by a transposase; and introducing the donor sequence into the bacterial host cell in the presence of the transposase, wherein upon introduction of the donor sequence into the bacterial host cell, the donor sequence is integrated into the chromosome of the bacterial host cell between the inverted repeats by the transposase.

In some embodiments, the bacterial host cell is not an *E. coli* cell. In certain embodiments the host cell is a yeast, animal, or plant host cell. In certain embodiments the host cell is a fungal, animal, or plant host cell. In certain embodiments that may be combined with any of the preceding embodiments the host cell is a mammalian host cell. In certain embodiments that may be combined with any of the preceding embodiments, the host cell is a bacterial host cell. In certain embodiments that may be combined with any of the preceding embodiments, the host cell is a Proteobacteria cell. In certain embodiments that may be combined with any of the preceding embodiments, the bacterial host cell is a cell selected from the group consisting of Alphaproteotacteria, Betaproteotacteria, Gammaproteobacteria, Deltaproteotacteria, Epsilonproteotacteria, and Zetaproteotacteria. In certain embodiments that may be combined with any of the preceding embodiments, the bacterial host cell is a cell of a genus selected from the group consisting of *Escherichia*, *Pseudomonas*, *Photorhabdus*, *Xenorhabdus*, *Serratia*, *Erwinia*, *Yersinia*, *Dickeya*, *Pectobacterium*, *Rhizobium*, *Brevundimonas*, *Ralstonia*, and *Aeromonas*. In certain embodiments that may be combined with any of the preceding embodiments, the bacterial host cell is a cell of a genus selected from the group consisting of *Pseudomonas*, *Photorhabdus*, *Xenorhabdus*, *Serratia*, *Erwinia*, *Yersinia*, *Dickeya*, *Pectobacterium*, *Rhizobium*, *Brevundimonas*, *Ralstonia*, and *Aeromonas*. In certain embodiments that may be combined with any of the preceding embodiments, the bacterial host cell is a cell selected from the group consisting of Bacteroidetes, Cyanobacteria, Firmicutes, and Actinobacteria. In certain embodiments, the bacterial host cell is a cell of the genus *Arthrobacter*. In certain embodiments that may be combined with any of the preceding embodiments, the first and the second bacterial donor cells are both Gammaproteobacteria or Firmicutes cells. In certain embodiments that may be combined with any of the preceding embodiments, the first and the second bacterial donor cells are both *E. coli* cells. In certain embodiments that may be combined with any of the preceding embodiments, the bacterial donor cell is an *E. coli* cell, and the bacterial host cell is not an *E. coli* cell. In certain embodiments that may be combined with any of the preceding embodiments, the first lox site of the second plasmid and the first lox site of the donor sequence are the same lox site selected from loxP, lox5171, lox2272, lox511, loxm2, loxm3, loxm7, loxm11, lox71, and lox66. In certain embodiments that may be combined with any of the preceding embodiments, the second lox site of the second plasmid and the second lox site of the donor sequence are heterospecific to the first lox site of the second plasmid and the first lox site of the donor sequence, and wherein the second lox site of the second plasmid and the second lox site of the donor sequence are the same lox site selected from loxP, lox5171, lox2272, lox511, loxm2, loxm3, loxm7, loxm11, lox71, and lox66. In certain embodiments that may be combined with any of the preceding embodiments, the transposase is a transposase selected from Mariner, Tn1, Tn2, Tn3, Tn4, Tn5, Tn6, Tn7, Tn8, Tn9, Tn10, and Tn917. In certain embodiments that may be combined with any of the preceding embodiments, the first selectable marker coding sequence encodes a first antibiotic resistance marker. In certain embodiments that may be combined with any of the preceding embodiments, the method further comprises after step (b), growing the host cell under conditions in which the first antibiotic resistance marker is expressed, wherein the host cell is grown in the presence of a first antibiotic to which the first antibiotic resistance marker confers resistance, such that the host cell comprising the donor sequence is selected. In certain embodiments that may be combined with any of the preceding embodiments, the first selectable marker coding sequence encodes a first auxotrophic marker, and wherein the host cell lacks an endogenous ability to produce a compound generated by the first auxotrophic marker. In certain embodiments that may be combined with any of the preceding embodiments, after step (b), growing the host cell under conditions in which the first auxotrophic marker is expressed, wherein the host cell is grown in the absence of the compound generated by the first auxotrophic marker, such that the host cell that has the donor sequence is selected. In certain embodiments that may be combined with any of the preceding embodiments, the second selectable marker is different from the first selectable marker. In certain embodiments that may be combined with any of the preceding embodiments, the second selectable marker coding sequence encodes a second antibiotic resistance marker.

In certain embodiments that may be combined with any of the preceding embodiments, after step (d), growing the host cell under conditions in which the second antibiotic resistance marker is expressed, wherein the host cell is grown in the presence of a second antibiotic to which the second antibiotic resistance marker confers resistance, such that the host cell that has the gene of interest and the second selectable marker coding sequence is selected. In certain embodiments that may be combined with any of the preceding embodiments, the second selectable marker coding sequence encodes a second auxotrophic marker, and wherein the host cell lacks an endogenous ability to produce a second compound generated by the second auxotrophic marker. In certain embodiments that may be combined with any of the preceding embodiments, after step (d), growing the host cell under conditions in which the second auxotrophic marker is expressed, wherein the host cell is grown in the absence of the second compound generated by the second auxotrophic marker, such that the host cell that has the gene of interest and the second selectable marker coding sequence is selected. In certain embodiments that may be combined with any of the preceding embodiments, the donor sequence further comprises a coding sequence for a protein that promotes sequence-specific gene transcription, and wherein the coding sequence for the protein that promotes sequence-specific gene transcription is flanked by the inverted repeats but not by the first and the second lox sites. In certain embodiments that may be combined with any of the preceding embodiments, the protein that promotes sequence-specific gene transcription promotes transcription downstream of a first promoter sequence, wherein the gene of interest is operably linked to the first promoter sequence, and wherein the first promoter sequence is flanked by the first and the second lox sites. In certain embodiments that may be combined with any of the preceding embodiments, the protein that promotes sequence-specific gene transcription is a sequence-specific RNA polymerase. In certain embodiments that may be combined with any of the preceding embodiments, wherein the protein that promotes sequence-specific gene transcription is a T7 RNA polymerase.

In certain embodiments that may be combined with any of the preceding embodiments, the second plasmid includes the Cre recombinase coding sequence. In certain embodiments that may be combined with any of the preceding embodiments, the donor sequence includes the Cre recombinase coding sequence, and wherein the Cre recombinase coding sequence is flanked by the first and the second lox sites. In certain embodiments that may be combined with any of the preceding embodiments, the Cre recombinase coding sequence is operably linked to a promoter active in the host cell. In certain embodiments that may be combined with any of the preceding embodiments, the promoter is a constitutive promoter. In certain embodiments that may be combined with any of the preceding embodiments, the promoter is a Cas9 promoter. In certain embodiments that may be combined with any of the preceding embodiments, the gene of interest includes a coding sequence of one or more enzymes. In certain embodiments that may be combined with any of the preceding embodiments, the one or more enzymes catalyze one or more steps in synthesis of a polysaccharide, lipopolysaccharide, nonribosomal peptide (NRP), polyketide, siderophore, terpene, lantipeptide, bacteriocin, homoserine lactone, butyrolactone, ectoine, thiopeptide, phenazine, terpenoid, alkaloid, flavonoid, amino acid, biofuel, commodity chemical, vitamin, or fatty acid. In certain embodiments that may be combined with any of the preceding embodiments, the second plasmid includes two or more genes of interest, and wherein the two or more genes of interest are flanked by the first and the second lox sites. In certain embodiments that may be combined with any of the preceding embodiments, the two or more genes of interest are operably linked to the same promoter, the same promoter being flanked by the first and the second lox sites. In certain embodiments that may be combined with any of the preceding embodiments, the two or more genes of interest are operably linked to two or more promoters, each promoter of the two or more promoters being flanked by the first and the second lox sites. In certain embodiments that may be combined with any of the preceding embodiments, the first and the second lox sites flank a sequence of greater than about 7 kb. In certain embodiments that may be combined with any of the preceding embodiments, the first and the second lox sites flank a sequence of less than about 200 kb. In certain embodiments that may be combined with any of the preceding embodiments, the vector comprises the polynucleotide sequence of SEQ ID NO:4. In certain embodiments that may be combined with any of the preceding embodiments, the second plasmid is introduced into the host cell by electroporation. In certain embodiments that may be combined with any of the preceding embodiments, the second plasmid is introduced into the bacterial host cell by conjugation with the second bacterial donor cell. In certain embodiments the donor sequence is introduced into the chromosome of the bacterial host cell by electroporation with a plasmid including a transposase coding sequence of the transposase and the donor sequence, wherein upon introduction of the plasmid into the bacterial host cell, the transposase is expressed from the transposase coding sequence, and the donor sequence is integrated into the chromosome of the bacterial host cell between the inverted repeats by the transposase. In certain embodiments that may be combined with any of the preceding embodiments the donor sequence is introduced into the chromosome of the bacterial host cell by conjugation with a bacterial donor cell that includes a plasmid comprising a transposase coding sequence of the transposase and the donor sequence, wherein upon introduction of the plasmid into the bacterial host cell, the transposase is expressed from the transposase coding sequence, and the donor sequence is integrated into the chromosome of the bacterial host cell between the inverted repeats by the transposase. In certain embodiments that may be combined with any of the preceding embodiments the donor sequence includes a Cre recombinase coding sequence, and wherein the Cre recombinase coding sequence is flanked by the first and the second lox sites. In certain embodiments that may be combined with any of the preceding embodiments the donor sequence includes a coding sequence for a protein that promotes sequence-specific gene transcription, and wherein the coding sequence for the protein that promotes sequence-specific gene transcription is flanked by the inverted repeats but not by the first and the second lox sites. In certain embodiments that may be combined with any of the preceding embodiments the protein that promotes sequence-specific gene transcription promotes transcription downstream of a first promoter sequence, wherein the gene of interest is operably linked to the first promoter sequence, and wherein the first promoter sequence is flanked by the first and the second lox sites. In certain embodiments that may be combined with any of the preceding embodiments the protein that promotes sequence-specific gene transcription is a sequence-specific RNA polymerase. In certain embodiments that may be combined with any of the preceding embodiments the protein that promotes sequence-specific gene transcription is a T7 RNA polymerase. In certain embodiments that may be combined with any of the preceding embodiments the gene of interest and the selectable marker coding sequence are both flanked by a first and a second lox site, wherein the first and the second lox sites are flanked by inverted repeats recognized by a transposase, and wherein the first and the second lox sites are different. In certain embodiments that may be combined with any of the preceding embodiments the gene of interest is integrated into the chromosome of the bacterial host cell by: (a) electroporation with a plasmid including the gene of interest flanked by a first and a second lox site; and (b) recombinase-mediated cassette exchange (RMCE) between the first lox site of the plasmid and a first lox site of a donor sequence integrated into the chromosome of the bacterial host cell, and between the second lox site of the plasmid and a second lox site of the donor sequence, wherein the donor sequence is integrated into the chromosome of the bacterial host cell between the inverted repeats by the transposase, wherein a Cre recombinase is expressed from a coding sequence present on at least one of the plasmid including the gene of interest and the donor sequence. In certain embodiments that may be combined with any of the preceding embodiments the gene of interest is integrated into the chromosome of the bacterial host cell by: (a) conjugation with a bacterial donor cell to introduce into the bacterial host cell a plasmid including the gene of interest flanked by a first and a second lox site; and (b) recombinase-mediated cassette exchange (RMCE) between the first lox site of the plasmid and a first lox site of a donor sequence integrated into the chromosome of the bacterial host cell, and between the second lox site of the plasmid and a second lox site of the donor sequence, wherein the donor sequence is integrated into the chromosome of the bacterial host cell between the inverted repeats by the transposase, wherein a Cre recombinase is expressed from a coding sequence present on at least one of the plasmid comprising the gene of interest and the donor sequence.

In certain embodiments that may be combined with any of the preceding embodiments, the method includes (d) purifying the phenazine produced by the bacterial host cell from the culture medium. In certain embodiments that may be combined with any of the preceding embodiments, the phenazine is phenazine 1-carboxylic acid, and wherein the phenazine biosynthesis pathway is a phzABCDEFG pathway. In certain embodiments that may be combined with any of the preceeding embodiments, the phenazine is phenazine 1,6-dicarboxylic acid, and wherein the phenazine biosynthesis pathway is a phzABGCDEF pathway.

In certain embodiments that may be combined with any of the preceding embodiments, the method includes purifying the class IIa bacteriocin produced by the bacterial host cell from the culture medium. In certain embodiments that may be combined with any of the preceding embodiments, the class IIa bacteriocin is Sakacin A, and the class IIa bacteriocin biosynthesis pathway is a sapAKRTE pathway. In certain embodiments that may be combined with any of the preceding embodiments, the class IIa bacteriocin is Sakacin P, and the class IIa bacteriocin biosynthesis pathway is a sppKRTE pathway. In certain embodiments that may be combined with any of the preceding embodiments, the class IIa bacteriocin is Leucocin A, and the class IIa bacteriocin biosynthesis pathway is a IcaBAECD pathway. In certain embodiments that may be combined with any of the preceding embodiments, the class IIa bacteriocin is Mesentericin Y105, and the class IIa bacteriocin biosynthesis pathway is a mesIYCDE pathway. In certain embodiments that may be combined with any of the preceding embodiments, the class IIa bacteriocin is Pediocin AcH, and the class IIa bacteriocin biosynthesis pathway is apapABCD pathway. In certain embodiments that may be combined with any of the preceding embodiments, the class IIa bacteriocin is Divercin V41, and the class IIa bacteriocin biosynthesis pathway is a dvnAT1T2IRK pathway. In certain embodiments that may be combined with any of the preceding embodiments, the class IIa bacteriocin is Enterocin A, and the class IIa bacteriocin biosynthesis pathway is a entFAI pathway. In certain embodiments that may be combined with any of the preceding embodiments, the class IIa bacteriocin is Enterocin P, and the class IIa bacteriocin biosynthesis pathway is a entP pathway. In certain embodiments that may be combined with any of the preceding embodiments, the class IIa bacteriocin is Curvacin A, and the class IIa bacteriocin biosynthesis pathway is a curA pathway.

In certain embodiments that may be combined with any of the preceding embodiments, the pathway of interest an orphan pathway. In certain embodiments that may be combined with any of the preceding embodiments, the gene or pathway of interest is nonribosomal peptide (NRP) or polyketide synthesis.

In certain embodiments that may be combined with any of the preceding embodiments, the gene or pathway of interest is involved in in terpene or terpenoid synthesis. In certain embodiments that may be combined with any of the preceding embodiments, the gene or pathway of interest is involved in vanillin, benzaldehyde (bitter almond, cherry) and 4-(R)-decanolide (fruity±fatty) synthesis. In certain embodiments that may be combined with any of the preceding embodiments, the gene or pathway of interest is involved in benzaldehyde, butyric acid, 2,3-butanedione, citronellal, (+)-curcumene, γ-decalactone, δ-decalactone, (+)-dehydro-curcumene, (−)isopulegol, (−)-methol, nor-patchoulenol, (+)-nuciferal, phenolethanol, β-binene, raspberry ketone, thaumatin, monellin, or (+)-turmerone.

In certain embodiments that may be combined with any of the preceding embodiments, the method includes (d) purifying the vanillin, benzaldehyde (bitter almond, cherry), 4-(R)-decanolide (fruity±fatty), benzaldehyde, butyric acid, 2,3-butanedione, citronellal, (+)-curcumene, γ-decalactone, δ-decalactone, (+)-dehydro-curcumene, (−)isopulegol, (−)-methol, nor-patchoulenol, (+)-nuciferal, phenolethanol, β-binene, raspberry ketone, thaumatin, monellin, or (+)-turmerone produced by the host cell.

In some embodiments, the gene or pathway of interest is involved in synthesis of a bacteriocin. In some embodiments the bacteriocin is Leucin A, Mesentericin Y105, Mundticin, Piscicolin 126, Bavaricin A, Sakacin P, Pediocin PA-1, Bavaricin MN, Divercin V41, Enterocin A, Enterocin P, Carnobacteriocin BM1, Sakacin A, Carnobacterocin B2, Bacteriocin 31, or Acidocin A.

In certain embodiments that may be combined with any of the preceding embodiments, the method includes (d) purifying the Leucin A, Mesentericin Y105, Mundticin, Piscicolin 126, Bavaricin A, Sakacin P, Pediocin PA-1, Bavaricin MN, Divercin V41, Enterocin A, Enterocin P, Carnobacteriocin BM1, Sakacin A, Carnobacterocin B2, Bacteriocin 31, or Acidocin A. produced by the host cell.

In certain embodiments that may be combined with any of the preceding embodiments, the gene or pathway of interest is involved in production of a polysaccharide, siderophore, lantipeptide, homoserine lactone, butyrolactone, ectoine, thiopeptide alkaloids, flavonoid, commodity chemical or a vitamin.

In certain embodiments that may be combined with any of the preceding embodiments, the method includes (d) purifying the polysaccharide, siderophore, lantipeptide, homoserine lactone, butyrolactone, ectoine, thiopeptide alkaloids, flavonoid, commodity chemical or a vitamin produced by the host cell.

In certain embodiments that may be combined with any of the preceding embodiments, the gene or pathway of interest is involved in omega-3 or omaga-6 fatty acid synthesis. In certain embodiments that may be combined with any of the preceding embodiments, the gene of interest is any of Δ6-desaturase (D6D), fatty acid desaturase 2 (FADS2), Δ5-desaturase (D5D).

In certain embodiments that may be combined with any of the preceding embodiments, the method includes (d) purifying the omega-3 or omega-6 fatty acid.

In some embodiments, at least one of the first and the second plasmid is introduced into the host cell via conjugation. In some embodiments, at least one of the first and the second plasmid is introduced into the host cell via electroporation. In some embodiments, the catalytically dead Cas9 protein/guide RNA complex bind the guide RNA target sequence of the gene of interest and repress expression of the gene of interest. In some embodiments, the catalytically dead Cas9 protein is fused with a transcriptional activator protein, and wherein the catalytically dead Cas9:transcriptional activator fusion protein/guide RNA complex binds the guide RNA target sequence of the gene of interest and promotes expression of the gene of interest. In some embodiments, after introducing the second plasmid into the bacterial host cell, the combined amount of sequence between the first and second lox sites and the second and third lox sites is up to about 400 kb.

In some embodiments of any of the above embodiments, the kit comprises a third vector comprising (i) one or more restriction or targeted cloning sites suitable for recombining a gene of interest into the second vector; and (ii) a second selectable marker, wherein the second selectable marker and the one or more restriction or targeted cloning sites are flanked by the first and the second lox sites. In some embodiments, the second vector is a multiple-copy plasmid, and wherein the third vector is a single-copy plasmid. In some embodiments, the donor sequence further comprises a Cre recombinase coding sequence flanked by the first and the second lox sites. In some embodiments, the first and the second lox sites are both selected from the group consisting of loxP, lox5171, lox2272, lox511, loxm2, loxm3, loxm7, loxm11, lox71, and lox66. In some embodiments, the transposase coding sequence is a coding sequence of a transposase selected from the group consisting of Mariner, Tn1, Tn2, Tn3, Tn4, Tn5, Tn6, Tn7, Tn8, Tn9, Tn10, and Tn917. In some embodiments, the first and the second lox sites flank a sequence of greater than about 7 kb. In some embodiments, the first and the second lox sites flank a sequence of less than about 200 kb. In some embodiments, the first vector comprises the polynucleotide sequence of SEQ ID NO:4. In some embodiments, the second vector comprises the polynucleotide sequence of SEQ ID NO:10. In some embodiments, the third vector comprises the polynucleotide sequence of SEQ ID NO:11. In some embodiments, the kit further comprises instructions for using the kit to integrate the gene of interest into a chromosome of a host cell.

It is to be understood that one, some, or all of the properties of the various embodiments described above and herein may be combined to form other embodiments of the present invention. These and other aspects of the present disclosure will become apparent to one of skill in the art. These and other embodiments of the present disclosure are further described by the detailed description that follows.

BRIEF DESCRIPTION OF THE DRAWINGS

FIGS. 9A-9E show LCMS chromatograms of P. fluorescens with and without the PCA and PDC pathways. New peaks (PCA at 4.4 min and PDC at 3.8 min, as labeled) are observable for the recombinant strains and correspond to standards for PCA and PDC.

FIG. 17 shows an example of the transposition, Cre-LoxP, and T7 RNA polymerase combined strategy. The E. coli donor strain is conjugated to a recipient strain, resulting in random integration of the landing pad into the chromosome (1). The resulting strain is then conjugated to an E. coli donor strain, which harbors the T7 RNA polymerase promoter. After conjugation and recombination by Cre, the gene pathway of interest is integrated into the recipient strain under control of the T7 RNA polymerase promoter (2).

FIGS. 18A-18C show heat maps of luminescence intensity from engineered gamma proteobacteria strains containing the landing pad with luxCDABE integration (FIG. 18A) or orphan secondary metabolite T7-PLU3263 pathway integration (FIG. 18B-18C) upon induction with 0, 0.01, 0.1, and 1.0 mM IPTG. FIG. 18B indicates luminmide A production; FIG. 18C indicates luminmide B production. In each figure, black indicates high luminescence intensity and white demonstrates low luminescence intensity.

FIGS. 21A-21B show the production of a secondary metabolite (m/z 377.30) with a retention time of 3.64 minutes (FIG. 21A) and luminescence intensity (FIG. 21B) from engineered gamma proteobacteria strains containing the landing pad with orphan secondary metabolite T7-Plu0897-Plu0899 pathway integration upon induction with 0, 0.01, 0.1, and 1.0 mM IPTG. In each figure, black indicates high luminescence intensity and white demonstrates low luminescence intensity.

FIGS. 25A & 25C illustrate the sgRNA target sites for dCas9 and aCas9, respectively. Bioluminesence was measured for strains containing dCas9 integrated into the first loxP site and a set of sgRNA fragments integrated into the second site of the landing pad (FIG. 25B). Bioluminescence was measured for engineered strains containing aCas9 integrated into the first loxP site and a set of sgRNA fragments integrated into the second site of the landing pad (FIG. 25D).

DETAILED DESCRIPTION

Figure 1:
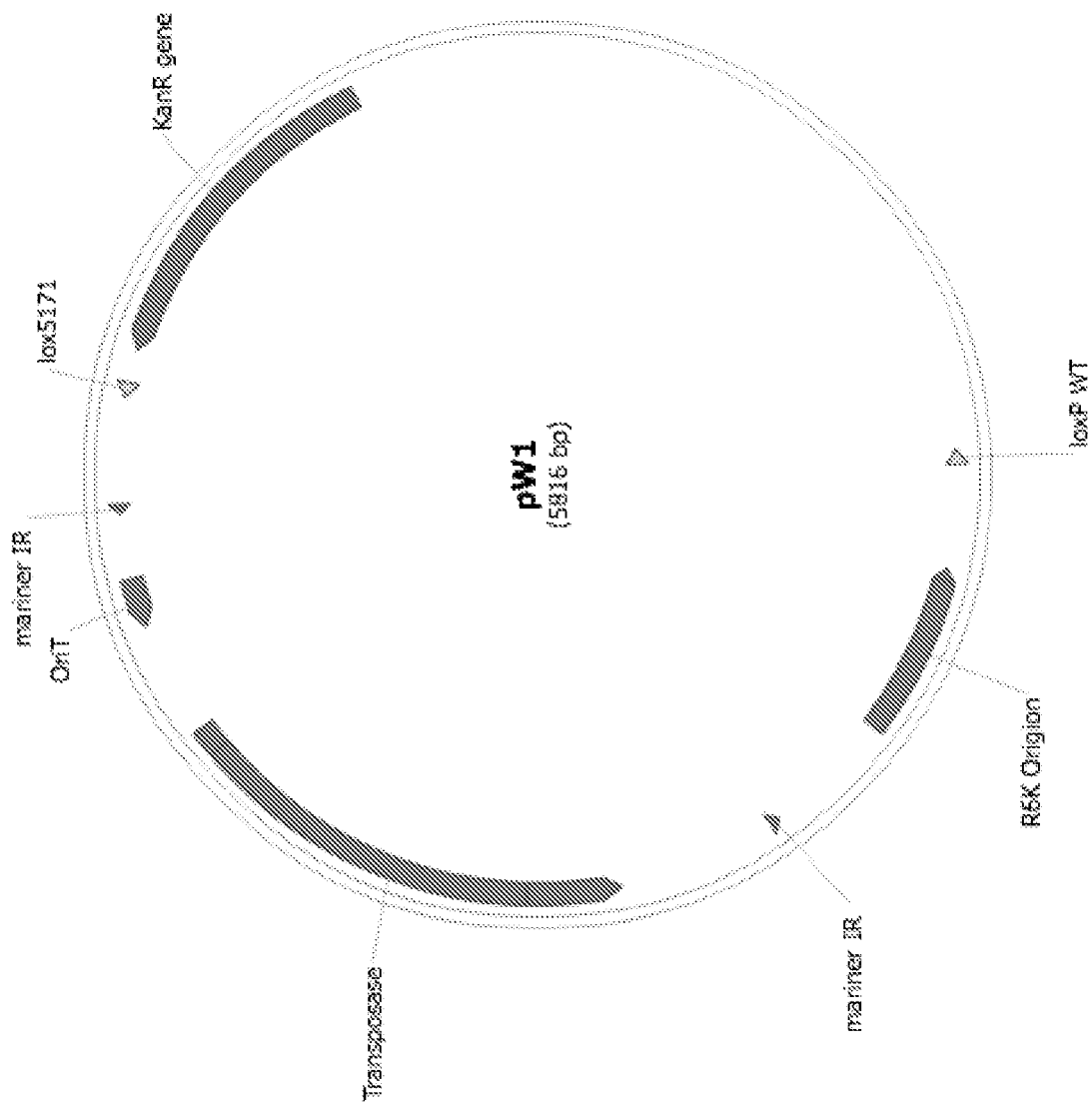
FIG. 1 is a map of the pW1 vector. The sequence between the two mariner inverted repeat ends is called the "landing pad." The landing pad contains the Kanamycin resistance gene flanked by LoxP and Lox5171 sites.

The present disclosure relates generally to a method for integrating a gene or pathway of interest into a host chromosome comprising integrating a donor sequence comprising inverted repeats flanking two lox sites into the chromosome of a host cell, and then introducing a gene or pathway of interest by recombination at the lox sites.

In particular, the present disclosure is based, at least in part, on the demonstration described herein that the present method allows engineering of a wide range of host cells stably, accurately, and efficiently. Specifically, using the Cre recombination pathway to integrate the gene or pathway of interest allows for more efficient recombination of larger pathways compared to homologous recombination, or phage transduction. Moreover, because the first step of the method described herein involves integration of a landing pad comprising two lox sites, this method can be used to easily produce a library of engineered host cells by swapping the pathways or genes contained between the Cre sites. Provided herein are studies showing successful integration and expression of pathways in 32 different strains of bacteria, demonstrating the universality of this approach and improving existing technologies (see, e.g., US PG Pub No. US20120329115).

Accordingly, certain aspects of the present disclosure relate to a method for integrating a gene of interest into a chromosome of a host cell, the method including providing a bacterial host cell comprising a donor sequence comprising a first selectable marker coding sequence flanked by a first and a second lox site, wherein the first and the second lox sites are different, and wherein the donor sequence is integrated in a chromosome of the bacterial host cell; providing a plasmid comprising the gene of interest and a second selectable marker coding sequence, wherein the gene of interest and the second selectable marker are both flanked by a first and a second lox site, wherein the first and the second lox sites are different; and introducing the plasmid into the bacterial host cell, wherein at least one of the plasmid and the donor sequence comprises a Cre recombinase coding sequence, and wherein upon introduction of the plasmid into the bacterial host cell, Cre recombinase is expressed from the Cre recombinase coding sequence, and the gene of interest is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence. Further provided herein is a method for integrating a gene of interest into a chromosome of a host cell, the method including providing a host cell comprising a donor sequence comprising a first selectable marker coding sequence flanked by a first and a second lox site, wherein the first and the second lox sites are different, and wherein the donor sequence is integrated in a chromosome of the host cell; providing a plasmid comprising the gene of interest and a second selectable marker coding sequence, wherein the gene of interest and the second selectable marker are both flanked by a first and a second lox site, wherein the first and the second lox sites are different; and introducing the plasmid into the host cell, wherein at least one of the plasmid and the donor sequence comprises a Cre recombinase coding sequence, and wherein upon introduction of the plasmid into the bacterial host cell, Cre recombinase is expressed from the Cre recombinase coding sequence, and the gene of interest is integrated into the chromosome of the host cell by the Cre recombinase through recombinase-mediated cassette exchange (RMCE) between the first lox site of the second plasmid and the first lox site of the donor sequence, and between the second lox site of the second plasmid and the second lox site of the donor sequence, wherein the host cell is a fungal, animal, or plant host cell. Further provided herein is a method for modulating expression of a gene of interest in a bacterial host cell, the method including: providing a bacterial host cell comprising a donor sequence comprising: (i) a Cre recombinase coding sequence, wherein the Cre recombinase coding sequence is flanked by a first and a second lox site, and wherein the first and the second lox sites are different; and (ii) a first selectable marker coding sequence flanked by the second lox site and a third lox site, wherein the third lox site is different from the first and second lox sites, and wherein the donor sequence is integrated in a chromosome of the bacterial host cell; providing a plasmid comprising a catalytically dead Cas9 protein coding sequence and a second selectable marker coding sequence, wherein the catalytically dead Cas9 protein coding sequence and the second selectable marker are both flanked by the second lox site and the third lox site; introducing the plasmid into the bacterial host cell, wherein upon introduction of the plasmid into the bacterial host cell, Cre recombinase is expressed from the Cre recombinase coding sequence, and the catalytically dead Cas9 protein coding sequence is integrated into the chromosome of the bacterial host cell by the Cre recombinase through recombinase-mediated cassette exchange (RMCE) between the second lox site of the plasmid and the second lox site of the donor sequence, and between the third lox site of the plasmid and the third lox site of the donor sequence; providing a second plasmid comprising a guide RNA sequence that targets a guide RNA target sequence of the gene of interest and a third selectable marker coding sequence, wherein the guide RNA sequence and the third selectable marker are both flanked by the first lox site and the second lox site; and introducing the second plasmid into the bacterial host cell, wherein upon introduction of the second plasmid into the bacterial host cell, Cre recombinase is expressed from the Cre recombinase coding sequence, and the guide RNA sequence is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest. Further provided herein is a method for modulating expression of a gene of interest in a bacterial host cell, the method including: providing a bacterial host cell comprising a donor sequence comprising: (i) a Cre recombinase coding sequence, wherein the Cre recombinase coding sequence is flanked by a first and a second lox site, and wherein the first and the second lox sites are different; and (ii) a first selectable marker coding sequence flanked by the second lox site and a third lox site, wherein the third lox site is different from the first and second lox sites, and wherein the donor sequence is integrated in a chromosome of the bacterial host cell; providing a first plasmid comprising a catalytically dead Cas9 protein coding sequence, a guide RNA sequence that targets a guide RNA target sequence of the gene of interest, and a second selectable marker coding sequence, wherein the catalytically dead Cas9 protein coding sequence, the guide RNA sequence, and the second selectable marker are flanked by the second lox site and the third lox site; introducing the first plasmid into the bacterial host cell, wherein upon introduction of the first plasmid into the bacterial host cell, Cre recombinase is expressed from the Cre recombinase coding sequence, and the catalytically dead Cas9 protein coding sequence and guide RNA sequence are integrated into the chromosome of the bacterial host cell by the Cre recombinase through recombinase-mediated cassette exchange (RMCE) between the second lox site of the first plasmid and the second lox site of the donor sequence, and between the third lox site of the first plasmid and the third lox site of the donor sequence; providing a second plasmid comprising the gene of interest and a third selectable marker coding sequence, wherein the gene of interest and the third selectable marker are both flanked by the first lox site and the second lox site; and introducing the second plasmid into the bacterial host cell, wherein upon introduction of the second plasmid into the bacterial host cell, Cre recombinase is expressed from the Cre recombinase coding sequence, and the gene of interest is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest.

Accordingly, the present disclosure provides a method for integrating a gene of interest into a chromosome of a host cell, the method including: (a) providing a first plasmid comprising: (i) a transposase coding sequence; and (ii) a donor sequence, wherein the donor sequence is flanked by inverted repeats recognized by the transposase, wherein the donor sequence includes a first selectable marker coding sequence flanked by a first and a second lox site, and wherein the first and the second lox sites are different; (b) introducing the first plasmid into the host cell, wherein upon introduction of the first plasmid into the host cell, transposase is expressed from the transposase coding sequence, and the donor sequence is integrated into a chromosome of the host cell between the inverted repeats by the transposase; (c) providing a second plasmid including the gene of interest and a second selectable marker coding sequence, wherein the gene of interest and the second selectable marker are both flanked by a first and a second lox site, wherein the first and the second lox sites are different; and (d) introducing the second plasmid into the host cell, wherein at least one of the second plasmid and the donor sequence includes a Cre recombinase coding sequence, and wherein upon introduction of the second plasmid into the bacterial host cell, Cre recombinase is expressed from the Cre recombinase coding sequence, and the gene of interest is integrated into the chromosome of the host cell by the Cre recombinase through recombinase-mediated cassette exchange (RMCE) between the first lox site of the second plasmid and the first lox site of the donor sequence, and between the second lox site of the second plasmid and the second lox site of the donor sequence.

Further provided herein is a method for integrating a gene of interest into a chromosome of a bacterial host cell, the method including: providing a first bacterial donor cell comprising a first plasmid, the first plasmid comprising: (i) a transposase coding sequence; and (ii) a donor sequence, wherein the donor sequence is flanked by inverted repeats recognized by the transposase, wherein the donor sequence includes a first selectable marker coding sequence flanked by a first and a second lox site, and wherein the first and the second lox sites are different; (b) introducing the first plasmid into the bacterial host cell by conjugation with the first bacterial donor cell, wherein upon introduction of the first plasmid into the bacterial host cell, transposase is expressed from the transposase coding sequence, and the donor sequence is integrated into the chromosome of the bacterial host cell between the inverted repeats by the transposase; (c) providing a second bacterial donor cell including a second plasmid, the second plasmid comprising the gene of interest and a second selectable marker coding sequence, wherein the gene of interest and the second selectable marker are both flanked by a first and a second lox site, wherein the first and the second lox sites are different; and (d) introducing the second plasmid into the bacterial host cell, wherein at least one of the second plasmid and the donor sequence comprises a Cre recombinase coding sequence, and wherein upon introduction of the second plasmid into the bacterial host cell, Cre recombinase is expressed from the Cre recombinase coding sequence, and the gene of interest is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence.

Also provided herein is a host cell including a chromosomally integrated donor sequence, wherein the donor sequence comprises a selectable marker coding sequence flanked by a first and a second lox site, wherein the donor sequence is flanked in a chromosome of the host cell by inverted repeats recognized by a transposase, and wherein the first and the second lox sites are different. In certain embodiments, the host cell is a bacterial host cell. Also provided herein is a vector including: (a) a transposase coding sequence; and (b) a donor sequence, wherein the donor sequence is flanked by inverted repeats recognized by the transposase, wherein the donor sequence includes a selectable marker coding sequence flanked by a first and a second lox site, and wherein the first and the second lox sites are different. Further provided herein is a method for producing a phenazine, including: (a) providing a bacterial host cell including a chromosomally integrated donor sequence, wherein the donor sequence includes a first selectable marker sequence flanked by a first and a second lox site, wherein the first and the second lox sites are different, and wherein the donor sequence is flanked by inverted repeats recognized by a transposase; (b) introducing a plasmid into the bacterial host cell, the plasmid comprising a phenazine biosynthesis pathway coding sequence and a second selectable marker coding sequence, wherein the phenazine biosynthesis pathway coding sequence and the second selectable marker coding sequence are both flanked by a first and a second lox site, wherein at least one of the chromosomally integrated donor sequence and the plasmid comprises a Cre recombinase coding sequence, and wherein upon introduction of the plasmid into the bacterial host cell, Cre recombinase is expressed from the Cre recombinase coding sequence, and the phenazine biosynthesis pathway coding sequence is integrated into the chromosome of the bacterial host cell by the Cre recombinase through recombinase-mediated cassette exchange (RMCE) between the first lox site of the plasmid and the first lox site of the donor sequence, and between the second lox site of the plasmid and the second lox site of the donor sequence; and (c) culturing the bacterial host cell comprising the chromosomally integrated phenazine biosynthesis pathway coding sequence in a culture medium under conditions whereby the phenazine biosynthesis pathway coding sequence is expressed in the cell, and whereby the phenazine biosynthesis pathway produces the phenazine. Yet further provided herein is a method for producing a class IIa bacteriocin, including: (a) providing a bacterial host cell including a chromosomally integrated donor sequence, wherein the donor sequence includes a first selectable marker sequence flanked by a first and a second lox site, wherein the first and the second lox sites are different, and wherein the donor sequence is flanked by inverted repeats recognized by a transposase; (b) introducing a plasmid into the bacterial host cell, the plasmid including a class IIa bacteriocin biosynthesis pathway coding sequence and a second selectable marker coding sequence, wherein the class IIa bacteriocin biosynthesis pathway coding sequence and the second selectable marker coding sequence are both flanked by a first and a second lox site, wherein at least one of the chromosomally integrated donor sequence and the plasmid includes a Cre recombinase coding sequence, and wherein upon introduction of the plasmid into the bacterial host cell, Cre recombinase is expressed from the Cre recombinase coding sequence, and the class IIa bacteriocin biosynthesis pathway coding sequence is integrated into the chromosome of the bacterial host cell by the Cre recombinase through recombinase-mediated cassette exchange (RMCE) between the first lox site of the plasmid and the first lox site of the donor sequence, and between the second lox site of the plasmid and the second lox site of the donor sequence; and (c) culturing the bacterial host cell including the chromosomally integrated class IIa bacteriocin biosynthesis pathway coding sequence in a culture medium under conditions whereby the class IIa bacteriocin biosynthesis pathway coding sequence is expressed in the cell, and whereby the class IIa bacteriocin biosynthesis pathway produces the class IIa bacteriocin.

I. Methods of Integration and Expression

Certain aspects of the present disclosure relate to methods of integrating one or more genes or pathways of interest into a chromosome of a host cell. Specifically, the methods described herein comprise introducing into a host cell a plasmid with a donor sequence flanked by inverted repeats, which further flank two lox sites, and a transposase coding sequence to randomly introduce the lox sites into the chromosome of the host cell to form a landing pad. In the second step, a gene of interest flanked by two lox sites in introduced into the host cell so that the gene or pathway of interest integrates into the host chromosome through Cre-lox recombination. Various methods known in the art may be used to introduce one or both of the plasmid and the gene of interest into the host cell, depending upon the specific type of host cell (e.g., transfection, electroporation, or transformation for mammalian cells; transformation in yeast, etc.).

Certain aspects of the present disclosure relate to methods of integrating one or more genes or pathways of interest into a chromosome of a bacterial host cell. Specifically, the methods described herein comprise introducing into a host cell a plasmid with a donor sequence flanked by inverted repeats, which further flank two lox sites, and a transposase coding sequence to randomly introduce the lox sites into the chromosome of the host cell to form a landing pad. In the second step, a gene of interest flanked by two lox sites in introduced into the host cell so that the gene or pathway of interest integrates into the host chromosome through Cre-lox recombination. Various methods known in the art may be used to introduce one or both of the plasmid and the gene of interest into the host cell, including without limitation conjugation, electroporation, and bacterial transformation.

Donor and Host Cells

In some embodiments, the methods of integration and expression described herein apply to donor and host cells. In some embodiments, the host cell includes unicellular organisms. A host cell may refer to a cell into which genetic material is introduced, e.g., by transposase-mediated integration or recombinase-mediated cassette exchange (RMCE), while a donor cell may refer to a cell that is introducing genetic material into a host cell (e.g., by bacterial conjugation). In some embodiments the unicellular organism can be fungus (e.g., yeast), bacteria, or a unicellular plant (e.g., algae). In other embodiments, the cell may be a cell line or cultured cell derived from an invertebrate or a vertebrate, such as a mammalian cell line.

In some embodiments, the donor and/or host cells are Alphaproteobacteria, Betaproteobacteria, Gammaproteobacteria, Deltaproteobacteria, Bacteroidetes, Cyanobacteria, Firmicutes, and Actinobacteria cells. In some embodiments, the donor and/or host cells are any of the exemplary organisms listed in Table 1.

TABLE 1

| | | |
|---|---|---|
| Proteobacteria | Alphaproteobacteria | Caulobacterales |
| | | Kiloniellales |
| | | Kordiimonadales |
| | | Magnetococcales |
| | | Parvularculales |
| | | Pelagibacterales |
| | | Rhizobiales |
| | | Rhodobacterales |
| | | Rhodospirillales |
| | | Rickettsiales |
| | | Sneathiellales |
| | | Sphingomonadales |
| | Betaproteobacteria | Burkholderiales |
| | | Ferrovales |
| | | Gallionellales |
| | | Hydrogenophilales |
| | | Methylophilales |
| | | Neisseriales |
| | | Nitrosomonadales |
| | | Rhodocyclales |
| | Deltaproteobacteria | Bdellovibrionales |
| | | Desulfarculales |
| | | Desulfobacterales |
| | | Desulfovibrionales |
| | | Desulfurellales |
| | | Desulfuromonadales |
| | | Myxococcales |
| | | Syntrophobacterales |
| | Epsilonproteobacteria | Campylobacterales |
| | | Nautiliales |
| | Gammaproteobacteria | Acidithiobacillales |
| | | Aeromonadales |
| | | Alteromonadales |
| | | Cardiobacteriales |
| | | Chromatiales |
| | | Enterobacteriales |
| | | Legionellales |
| | | Lysobacterales |
| | | Methylococcales |

TABLE 1-continued

| | | |
|---|---|---|
| | | Myoida |
| | | Oceanospirillales |
| | | Orbales |
| | | Pasteurellales |
| | | Pseudomonadales |
| | | Salinisphaerales |
| | | Thiotrichales |
| | | Vibrionales |
| | | Xanthomonadales |
| | Zetaproteobacteria | Mariprofundales |
| Firmicutes | Bacilli | Bacillales |
| | | Lactobacillales |
| | Clostridia | Clostridiales |
| | | Halanaerobiales |
| | | Natranaerobiales |
| | | Thermoanaerobacterales |
| | Erysipelotrichi | Erysipelotrichales |
| | Erysipelotrichia | Erysipelotrichales |
| | | Lactobacillales |
| | Negativicutes | Selenomonadales |
| Actinobacteria | Acidimicrobiia | Acidimicrobiales |
| | Actinobacteria | Acidimicrobiales |
| | | Actinomycetales |
| | | Actinopolysporales |
| | | Bifidobacteriales |
| | | Coriobacteriales |
| | | Corynebacteriales |
| | | Frankiales |
| | | Geodermatophilales |
| | | Jiangellales |
| | | Kineosporiales |
| | | Micrococcales |
| | | Micromonosporales |
| | | Nakamurellales |
| | | Nitriliruptorales |
| | | Propionibacteriales |
| | | Pseudonocardiales |
| | | Rubrobacterales |
| | | Solirubrobacterales |
| | | Streptomycetales |
| | | Streptosporangiales |
| | | Thermoleophilales |
| | Actinobacteria (class) | Actinomycetales |
| | Coriobacteriia | Coriobacteriales |
| Bacteroidetes | Bacteroidia | Bacteroidales |
| | Cytophagia | Cytophagales |
| | | Rhodothermales |
| | Flavobacteriia | Flavobacteriales |
| | Sphingobacteriia | Sphingobacteriales |
| Cyanobacteria | Gloeobacteria | Gloeobacterales |
| | Melainabacteria | Caenarcaniphilales |
| | | Gastranaerophilales |
| | | Obscuribacterales |

In some embodiments, where the donor and/or host cells are bacteria, the bacteria may be one of the following: *Pseudomonas fluorescens* WCS 417r, *P. fluorescens* Q8r-r, *P. putida*, KT2440, *Photorhabdus luminescens* subsp. *laumondii* TTO1, *P. luminescens* subsp. *Luminescens*, *P. temperata* subsp. *khanii*, *Xenorhabdus doucetiae*, *X. nematophila*, *X. szentirmaii*, *Serratia odorifera*, *Erwinia oleae*, *E. piriflorinigrans*, *E. pyrifoliae*, *Yersinia aldovae*, *Y. bercovieri*, *Y. mollaretii*, *Y. ruckeri*, *Dickeya dadantii* subsp. *dadantii*, *D. dadantii* subsp. *dieffenbachiae*, *D. solani*, *D. zeae*, *Pectobacterium atrosepticum*, *P. betavasculorum*, *P. carotovorum* subsp. *carotovorum*, *P. carotovorum* subsp. *odoriferum*, *P. wasabiae*, *Aeromonas encheleia*, *A. molluscorum*, *A. piscicola*, *A. salmonicida* subsp. *pectinolytica*, and *A. salmonicida* subsp. *salmonicida*. In some embodiments, the donor and/or host cells are Alphaproteobacteria, Betaproteobacteria, Gammaproteobacteria, Deltaproteobacteria, Bacteroidetes, Cyanobacteria, Firmicutes, and Actinobacteria cells (e.g., *Arthrobacter*). In certain embodiments, the Gammaproteobacteria cells are *E. coli*.

In some embodiments, a donor cell of the present disclosure is a Gammaproteobacteria or Firmicutes cell. In some embodiments, a donor cell of the present disclosure is an *E. coli* cell. Any donor cell suitable for conjugation with a host cell of the present disclosure may be used. For example, *E. coli* cells are known to conjugate with many different types of bacteria (Goessweiner-Mohr, N., et al., *Conjugation in Gram-Positive Bacteria*, Microbiol Spectr, 2014. 2(4); Mazodier, P., R. Petter, and C. Thompson, *Intergeneric Conjugation between Escherichia-Coli and Streptomyces Species*, Journal of Bacteriology, 1989. 171(6): p. 3583-3585). Conjugation assays are known in the art, such as the exemplary assays described herein.

In some embodiments, the methods of gene and pathway integration described herein apply to host cells such as fungal, plant, or mammalian cells.

In some embodiments, a host cell of the present disclosure is an invertebrate cell, e.g., an insect cell. In some embodiments, a host cell of the present disclosure is a vertebrate cell. In some embodiments, a host cell of the present disclosure is a fungal or mammalian cell. In some embodiments, the host cell is an Ascomycota, Basidiomycota, Blastocladiomycota, Chytridiomycota, Glomeromycota, Microsporidia, or Neocallimastigomycota cell. In some embodiments, the host cell is a *Saccharomyces* sp., *Saccharomyces cerevisiae*, *Saccharomyces monacensis*, *Saccharomyces bayanus*, *Saccharomyces pastorianus*, *Saccharomyces carlsbergensis*, *Saccharomyces pombe*, *Trichoderma reesei*, *Neurospora crassa*, *Neurospora* sp., *Kluyveromyces* sp., *Kluyveromyces marxiamus*, *Kluyveromyces lactis*, *Kluyveromyces fragilis*, *Pichia stipitis*, *Pichia pastoris*, *Pichia* sp., *Sporotrichum thermophile*, *Candida shehatae*, *Candida tropicalis*, or *Neurospora crassa* cell. In some embodiments, a host cell of the present disclosure is a mammalian cell line (e.g., Chinese Hamster Ovary cells, HeLa cells, or 293 cells). In some embodiments, a host cell of the present disclosure is a human or rodent cell. In some embodiments, a host cell of the present disclosure is one that is produced using a method described herein.

Certain aspects of the present disclosure relate to methods for modulating expression of a gene of interest in a bacterial host cell. Any of the host cells described herein may be selected for use by one of skill in the art. The present disclosure provides methods and techniques that allow modified CRISPR/Cas9 systems to be used to repress or activate gene expression in a targeted way. These methods include the utilization of two distinct "landing pad" sites (e.g., a first site flanked by the first and second lox sites, and a second site flanked by the second and third lox sites), allowing for the integration of more sequence into the bacterial host chromosome.

It will be appreciated by one of skill in the art that the methods for using this platform to modulate expression of a gene of interest in a bacterial host cell are multi-step processes, and thus the steps can be accomplished in a variety of orders. In some embodiments, the methods include: providing a bacterial host cell comprising a donor sequence comprising: (i) a Cre recombinase coding sequence, wherein the Cre recombinase coding sequence is flanked by a first and a second lox site, and wherein the first and the second lox sites are different; and (ii) a first selectable marker coding sequence flanked by the second lox site and a third lox site, wherein the third lox site is different from the first and second lox sites, and wherein the donor sequence is integrated in a chromosome of the bacterial host cell; providing a plasmid comprising a catalytically dead Cas9 protein coding sequence and a second selectable marker coding sequence, wherein the catalytically dead Cas9 protein coding sequence and the second selectable marker are both flanked by the second lox site and the third lox site; introducing the plasmid into the bacterial host cell, wherein upon introduction of the plasmid into the bacterial host cell, Cre recombinase is expressed from the Cre recombinase coding sequence, and the catalytically dead Cas9 protein coding sequence is integrated into the chromosome of the bacterial host cell by the Cre recombinase through recombinase-mediated cassette exchange (RMCE) between the second lox site of the plasmid and the second lox site of the donor sequence, and between the third lox site of the plasmid and the third lox site of the donor sequence; providing a second plasmid comprising a guide RNA sequence that targets a guide RNA target sequence of the gene of interest and a third selectable marker coding sequence, wherein the guide RNA sequence and the third selectable marker are both flanked by the first lox site and the second lox site; and introducing the second plasmid into the bacterial host cell, wherein upon introduction of the second plasmid into the bacterial host cell, Cre recombinase is expressed from the Cre recombinase coding sequence, and the guide RNA sequence is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest. In some embodiments, the methods include: providing a bacterial host cell comprising a donor sequence comprising: (i) a Cre recombinase coding sequence, wherein the Cre recombinase coding sequence is flanked by a first and a second lox site, and wherein the first and the second lox sites are different; and (ii) a first selectable marker coding sequence flanked by the second lox site and a third lox site, wherein the third lox site is different from the first and second lox sites, and wherein the donor sequence is integrated in a chromosome of the bacterial host cell; providing a plasmid comprising a guide RNA sequence that targets a guide RNA target sequence of the gene of interest and a second selectable marker coding sequence, wherein the guide RNA sequence and the second selectable marker are both flanked by the first lox site and the second lox site; and introducing the plasmid into the bacterial host cell, wherein upon introduction of the plasmid into the bacterial host cell, Cre recombinase is expressed from the Cre recombinase coding sequence, and the guide RNA sequence is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence; providing a second plasmid comprising a catalytically dead Cas9 protein coding sequence and a third selectable marker coding sequence, wherein the catalytically dead Cas9 protein coding sequence and the third selectable marker are both flanked by the second lox site and the third lox site; introducing the second plasmid into the bacterial host cell, wherein upon introduction of the second plasmid into the bacterial host cell, Cre recombinase is expressed from the Cre recombinase coding sequence, and the catalytically dead Cas9 protein coding sequence is integrated into the chromosome of the bacterial host cell by the Cre recombinase through recombinase-mediated cassette exchange (RMCE) between the second lox site of the second plasmid and the second lox site of the donor sequence, and between the third lox site of the second plasmid and the third lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest.

Moreover, if the dCas9 coding sequence and guide RNA are introduced in a single step (e.g., in a single "landing pad" site flanked by a pair of lox sites), the other "landing pad" site can be used to integrate a gene or pathway of interest, as described herein. In some embodiments, the methods include: providing a bacterial host cell comprising a donor sequence comprising: (i) a Cre recombinase coding sequence, wherein the Cre recombinase coding sequence is flanked by a first and a second lox site, and wherein the first and the second lox sites are different; and (ii) a first selectable marker coding sequence flanked by the second lox site and a third lox site, wherein the third lox site is different from the first and second lox sites, and wherein the donor sequence is integrated in a chromosome of the bacterial host cell; providing a first plasmid comprising a catalytically dead Cas9 protein coding sequence, a guide RNA sequence that targets a guide RNA target sequence of the gene of interest, and a second selectable marker coding sequence, wherein the catalytically dead Cas9 protein coding sequence, the guide RNA sequence, and the second selectable marker are flanked by the second lox site and the third lox site; introducing the first plasmid into the bacterial host cell, wherein upon introduction of the first plasmid into the bacterial host cell, Cre recombinase is expressed from the Cre recombinase coding sequence, and the catalytically dead Cas9 protein coding sequence and guide RNA sequence are integrated into the chromosome of the bacterial host cell by the Cre recombinase through recombinase-mediated cassette exchange (RMCE) between the second lox site of the first plasmid and the second lox site of the donor sequence, and between the third lox site of the first plasmid and the third lox site of the donor sequence; providing a second plasmid comprising the gene of interest and a third selectable marker coding sequence, wherein the gene of interest and the third selectable marker are both flanked by the first lox site and the second lox site; and introducing the second plasmid into the bacterial host cell, wherein upon introduction of the second plasmid into the bacterial host cell, Cre recombinase is expressed from the Cre recombinase coding sequence, and the gene of interest is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest.

In some embodiments, the methods include: providing a bacterial host cell comprising a donor sequence comprising: (i) a Cre recombinase coding sequence, wherein the Cre recombinase coding sequence is flanked by a first and a second lox site, and wherein the first and the second lox sites are different; and (ii) a first selectable marker coding sequence flanked by the second lox site and a third lox site, wherein the third lox site is different from the first and second lox sites, and wherein the donor sequence is integrated in a chromosome of the bacterial host cell; providing a plasmid comprising the gene of interest and a second selectable marker coding sequence, wherein the gene of interest and the second selectable marker are both flanked by the first lox site and the second lox site; and introducing the plasmid into the bacterial host cell, wherein upon introduction of the plasmid into the bacterial host cell, Cre recombinase is expressed from the Cre recombinase coding sequence, and the gene of interest is integrated into the chromosome of the bacterial host cell by the Cre recombinase through recombinase-mediated cassette exchange (RMCE) between the first lox site of the plasmid and the first lox site of the donor sequence, and between the second lox site of the plasmid and the second lox site of the donor sequence; providing a second plasmid comprising a catalytically dead Cas9 protein coding sequence, a guide RNA sequence that targets a guide RNA target sequence of the gene of interest, and a third selectable marker coding sequence, wherein the catalytically dead Cas9 protein coding sequence, the guide RNA sequence, and the third selectable marker are flanked by the second lox site and the third lox site; introducing the second plasmid into the bacterial host cell, wherein upon introduction of the second plasmid into the bacterial host cell, Cre recombinase is expressed from the Cre recombinase coding sequence, and the catalytically dead Cas9 protein coding sequence and guide RNA sequence are integrated into the chromosome of the bacterial host cell by the Cre recombinase through recombinase-mediated cassette exchange (RMCE) between the second lox site of the second plasmid and the second lox site of the donor sequence, and between the third lox site of the second plasmid and the third lox site of the donor sequence; wherein upon introduction of the second plasmid of the bacterial host cell, the catalytically dead Cas9 protein and guide RNA are expressed, form a complex, and bind the guide RNA target sequence of the gene of interest, thereby modulating expression of the gene of interest.

A variety of methods are contemplated for integrating the donor sequence into the chromosome of the bacterial host cell. In some embodiments, the donor sequence is integrated into the chromosome of the bacterial host cell by: providing a bacterial donor cell comprising a donor plasmid, the donor plasmid comprising: (i) a transposase coding sequence; and (ii) the donor sequence, wherein the donor sequence is flanked by inverted repeats recognized by the transposase; and introducing the donor plasmid into the bacterial host cell by conjugation with the bacterial donor cell, wherein upon introduction of the donor plasmid into the bacterial host cell, transposase is expressed from the transposase coding sequence, and the donor sequence is integrated into the chromosome of the bacterial host cell between the inverted repeats by the transposase. In some embodiments, the donor sequence is integrated into the chromosome of the bacterial host cell by: providing a bacterial donor cell comprising a donor plasmid, the donor plasmid comprising: (i) an integrase coding sequence; and (ii) the donor sequence, wherein the donor sequence contains an attP site; and introducing the donor plasmid into the bacterial host cell by conjugation with the bacterial donor cell, wherein upon introduction of the donor plasmid into the bacterial host cell, integrase is expressed from the integrase coding sequence, and the donor sequence is integrated into the chromosome of the bacterial host cell mediated through the recombination between the attP site and an attB site on the chromosome of the bacterial host cell (for further description of the integrase/attP/attB system, see, e.g., Hong, Y. and Hondalus, M. K. (2008) *FEBS Microbiol. Lett.* 287:63-68). In some embodiments, the donor sequence is integrated into the chromosome of the bacterial host cell by homologous recombination. In some embodiments, the donor sequence is integrated into the chromosome of the bacterial host cell by: providing a donor plasmid, the donor plasmid comprising the donor sequence, wherein the donor sequence is flanked by inverted repeats recognized by a transposase; and introducing the donor plasmid into the bacterial host cell in the presence of the transposase, wherein upon introduction of the donor plasmid into the bacterial host cell, the donor sequence is integrated into the chromosome of the bacterial host cell between the inverted repeats by the transposase (e.g., in vitro transposition).

In some embodiments, at least one of the first and the second plasmid is introduced into the host cell via conjugation. In some embodiments, at least one of the first and the second plasmid is introduced into the host cell via electroporation.

As known in the art, CRISPR-Cas9 refers to a two component ribonucleoprotein complex with guide RNA and a Cas9 endonuclease. CRISPR refers to the Clustered Regularly Interspaced Short Palindromic Repeats type II system used by bacteria and archaea for adaptive defense. This system enables bacteria and archaea to detect and silence foreign nucleic acids, e.g., from viruses or plasmids, in a sequence-specific manner (Jinek, M., et al. (2012) Science 337(6096):816-21). In type II systems, guide RNA interacts with Cas9 and directs the nuclease activity of Cas9 to target DNA sequences complementary to those present in the guide RNA. Guide RNA base pairs with complementary sequence in target DNA. Cas9 nuclease activity then generates a double-stranded break in the target DNA.

In bacteria, Cas9 polypeptides bind to two different guide RNAs acting in concert: a CRISPR RNA (crRNA) and a trans-activating crRNA (tracrRNA). The crRNA and tracrRNA ribonucleotides base pair and form a structure required for the Cas9-mediated cleavage of target DNA. However, it has recently been demonstrated that a single guide RNA (sgRNA) may be engineered to form the crRNA:tracrRNA structure and direct Cas9-mediated cleavage of target DNA (Jinek, M., et al. (2012) *Science* 337(6096):816-21). Moreover, since the specificity of Cas9 nuclease activity is determined by the guide RNA, the CRISPR-Cas9 system has been explored as a tool to direct double-stranded DNA breaks in heterologous cells, enabling customizable genome editing (Mali, P., et al. (2013) *Science* 339(6121):823-6).

The CRISPR/Cas9 system has been engineered to promote repression or activation of gene transcription. For example, a CRISPRi system has been developed to repress gene transcription through a catalytically dead Cas9 (dCas9) protein/guide RNA complex (see Qi, L. S. et al. Repurposing CRISPR as an RNA-guided platform for sequence-specific control of gene expression. Cell, 2013. 152: 1173-1183). In some embodiments, a catalytically dead Cas9 (dCas9) protein lacks endonucleolytic activity (e.g., nuclease and/or nickase activities) but retains the ability to bind DNA in a site-specific manner targeted by the complexed guide RNA. In some embodiments, the catalytically dead Cas9 (dCas9) protein comprises mutations corresponding to D10A and H840A of *S. pyogenes* Cas9. Catalytically dead Cas9 proteins have also been used to activate gene expression by introducing a transcriptional activator protein such as the *E. coli* RNA polymerase omega subunit (see Bikard, D. et al. Programmable repression and activation of bacterial gene expression using an engineered CRISPR-Cas9 system. *Nucleic Acids Res,* 2013. 41: 7429-7437). For example, a transcriptional activator protein can be fused to the N- or C-terminus of a catalytically dead Cas9 protein (thus generating aCas9). One of skill in the art can suitably select a transcriptional activator protein for use in a variety of bacterial host cells.

In some embodiments, the catalytically dead Cas9 protein/guide RNA complex mediate gene repression, e.g., by binding a guide RNA target sequence of the gene of interest and repressing expression of the gene of interest. In some embodiments, the guide RNA target sequence regulates expression of the gene of interest endogenously, e.g., in the absence of the catalytically dead Cas9 protein/guide RNA complex. In some embodiments, the guide RNA target sequence does not regulate expression of the gene of interest endogenously, but is in sufficient proximity to endogenous regulatory or coding sequences such that binding of the catalytically dead Cas9 protein/guide RNA complex represses gene transcription, e.g., by preventing binding of a transcription factor and/or RNA polymerase.

In some embodiments, the catalytically dead Cas9 protein is fused with a transcriptional activator protein, and the catalytically dead Cas9:transcriptional activator fusion protein/guide RNA complex binds the guide RNA target sequence of the gene of interest and promotes expression of the gene of interest. In some embodiments, the guide RNA target sequence regulates expression of the gene of interest endogenously, e.g., in the absence of the catalytically dead Cas9 protein/guide RNA complex. In some embodiments, the guide RNA target sequence does not regulate expression of the gene of interest endogenously, but is in sufficient proximity to endogenous regulatory or coding sequences such that binding of the catalytically dead Cas9:transcriptional activator fusion protein/guide RNA complex activates gene transcription, e.g., through the transcriptional activator.

A variety of lox sites are described herein. In some embodiments, the first lox site is a loxP2272 site. In some embodiments, the second lox site is a loxPwt site. In some embodiments, the third lox site is a loxP5171 site. In some embodiments, the first, second, and third lox sites are each different and each selected from loxP, lox5171, lox2272, lox511, lox71, lox66, M2, M3, M7, or M11.

The space between each pair of lox sites (e.g., between the first and second lox sites, and between the second and third lox sites) can be thought of as a "landing pad" for integrating one or more genetic components. In some embodiments, the dCas9 or aCas9 coding sequence is integrated into one landing pad, and the guide RNA is integrated into the other landing pad. In some embodiments, the dCas9 or aCas9 and the guide RNA are integrated into a single landing pad, and a gene or pathway of interest is integrated into the other landing pad, e.g., as described herein. This system is thought to allow for the integration of large sequences into the host chromosome, e.g., up to about 400 kb combined from the use of both landing pad sites.

A variety of Cas9 proteins are known and can be selected by one of skill in the art. In some embodiments, a Cas9 protein refers to a Cas9 protein derived from *Streptococcus pyogenes*, e.g., a protein having the sequence of the Swiss-Prot accession Q99ZW2. In some embodiments, a Cas9 protein refers to a Cas9 protein derived from *Streptococcus thermophilus*, e.g., a protein having the sequence of the Swiss-Prot accession G3ECR1. In some embodiments, a Cas9 protein refers to a Cas9 protein derived from a bacterial species within the genus *Streptococcus*. In some embodiments, a Cas9 protein refers to a Cas9 protein derived from a bacterial species within the genus *Neisseria* (e.g., GenBank accession number YP_003082577). In some embodiments, a Cas9 protein refers to a Cas9 polypeptide derived from a bacterial species within the genus *Treponema* (e.g., GenBank accession number EMB41078). In some embodiments, a Cas9 protein refers to a protein with Cas9 activity as described above derived from a bacterial or archaeal species. Methods of identifying a Cas9 protein are known in the art. For example, a putative Cas9 protein may be complexed with crRNA and tracrRNA or sgRNA and incubated with DNA bearing a target DNA sequence and a PAM motif, as described in Jinek, M., et al. (2012) Science 337(6096):816-21.

In some embodiments, the guide RNA comprises a single guide RNA (sgRNA) that forms a crRNA:tracrRNA structure. In some embodiments, the guide RNA comprises a separate CRISPR RNA (crRNA) and trans-activating crRNA (tracrRNA). In some embodiments, the guide target sequence is complementary to the guide RNA target sequence. Any desired target DNA sequence of interest may be targeted by a guide RNA target sequence. Without wishing to be bound to theory, it is thought that the only requirement for a target DNA sequence is the presence of a protospacer-adjacent motif (PAM) adjacent to the sequence complementary to the sgRNA target sequence (Mali, P., et al. (2013) Science 339(6121):823-6). Different Cas9 complexes are known to have different PAM motifs. For example, Cas9 from *Streptococcus pyogenes* has a GG dinucleotide PAM motif. For further examples, the PAM motif of *N. meningitidis* Cas9 is GATT, the PAM motif of *S. thermophilus* Cas9 is AGAA, and the PAM motif of *T. denticola* Cas9 is AAAAC.

In some embodiments, the catalytically dead Cas9 protein or catalytically dead Cas9:transcriptional activator fusion protein coding sequence is operably linked to a promoter. In some embodiments, the promoter is a constitutive promoter. In some embodiments, the promoter is an inducible or repressible promoter (e.g., can be induced or repressed by an external or internal cue, such as a metabolite). This allows control of the Cas9 protein expression. A variety of promoters are known in the art and described herein.

In some embodiments, the methods described supra are used to activate or repress expression of one or more genes of interest, e.g., a single gene, operon, or one or more, two or more, three or more, four or more, five or more, six or more, seven or more, eight or more, nine or more, or ten or more genes of interest. In some embodiments, the gene(s) of interest encode(s) one or more enzymes. In some embodiments, the one or more enzymes catalyze one or more steps in synthesis of a polysaccharide, lipopolysaccharide, nonribosomal peptide (NRP), polyketide, siderophore, terpene, lantipeptide, bacteriocin, homoserine lactone, butyrolactone, ectoine, thiopeptide, phenazine, terpenoid, alkaloid, flavonoid, amino acid, biofuel, commodity chemical, vitamin, or fatty acid.

Cre-Lox Recombination System

In certain embodiments of the present disclosure related to use of the Cre-lox recombination system. As used herein the expression "lox site" means a nucleotide sequence at which the Cre recombinase can catalyze a site-specific recombination. In some embodiments, the lox site is loxP, lox5171, lox2272, lox511, lox71, lox66, M2, M3, M7, or M11. In some embodiments, the loxP site has the sequence ATAACTTCGTATAGCATACATTATACGAAGTTAT (SEQ ID NO.:1) (Langer et al, Nucleic Acids Research, 30(14):3067-3077 (2002)). In some embodiments, the lox5171 site has the sequence ATTACTTCGTATAATGTGTACTATACGAAGTTAT (SEQ ID NO:2) (Parrish et al., J. Biomed. Biotech. 2011:

924068 (2010)). In some embodiments, various mutated sequences of lox sites can also be used so long as such sequences remain recognizable by the Cre recombinase (Lee & Saito, Gene, 216(1):55-65 (1998)). In some embodiments, the lox site comprises LoxP mutant 11, 12, 21, 22, 23, 31, 32, 33, 41, 42, 43, 51, 52, 53, 61, 62, 63, 71, 73, 81, 82, 63, 2171, 2271, 2371, 3171, 3271, 4171, 4271, 4371, 5171, 5271, 5371, 2172, 2272, 2372, 3172, 3272, 3372, 4172, 4272, 4372, 5172, 5272, 5372, 2173, 2273, 3373, 4373, or 5373 described in Lee & Saito. In some embodiments, the lox site comprises LoxP mutant 39, 33, 9, 28, 14, 29, 592, 64, 37, 25, 4, 10, 412, 7, 512, 17, 6, 21, 3, 23, 42, 20, 57, 56, 55, 38, 8, 53, 49, 51, 41, 47, 6, 30, 48, 59, 24, 19, 492, 206, 270, 271, 268, 267, 207, 269, 265, 202, 203, 208, 266, 204, 201, or 205 described in Sheren et al. (Sheren et al, NAR, 35(16):5464-73 (2007)). In some embodiments the lox site comprises LoxP mutant OW71, JT1, JT4, JT5, JT12, JT15, JT21, JT44, JT47, JT510, JT520, JT530, JT540, OW6, JTZ2, JTZ5, JTZ10, or JTZ17 as described in Thompson et al. (Thomson et al., Genesis, 36(3):162-7 (2003)). In some embodiments the lox site comprises the Lox66, Lox71, loxJTZ1, loxJTZ71, loxKR1, loxKR2, loxKR3, or loxKR4 as described in Araki et al. (Araki et al, *BMC Biotechnology*, 10:29 (2010)).

As described throughout the present disclosure (see also FIGS. 3B, 8B, 11B, 13B, and 15), Cre-lox recombination may be used to insert a gene or pathway of interest into a host cell of the present disclosure (e.g., a host cell bearing an integrated landing pad as described herein). In some embodiments, Cre-lox recombination refers to recombinase-mediated cassette exchange (RMCE) in which a genetic sequence from a host cell between two flanking lox sites is swapped with a genetic sequence from a donor cell or plasmid. Advantageously, this may be used to introduce gene(s) or pathway(s) of interest into a host cell bearing these lox sites. In some embodiments, the flanking lox sites may be heterospecific (e.g., able to recombine with each other at lesser efficiency than with other lox sites of the same type or specificity). This allows for RMCE, rather than deletion of genetic material between the lox sites.

In some embodiments, the first plasmid comprises a donor sequence, wherein the donor sequence comprises a first and second lox site, wherein the lox sites are different. In some embodiments, the second plasmid comprises a donor sequence, wherein the donor sequence comprises a first and second lox site, wherein the lox sites are different. In some embodiments, the first lox site of the second plasmid and the first lox site of the donor sequence are the same lox site. In some embodiments, the second lox site of the second plasmid and the second lox site of the donor sequence are heterospecific to the first lox site of the second plasmid and the first lox site of the donor sequence, and the second lox site of the second plasmid and the second lox site of the donor sequence are the same lox site. In some embodiments the first lox site of the first plasmid and the first lox site of the second plasmid are LoxP. In some embodiments, the second lox site of the first plasmid and the second lox site of the second plasmid are Lox5171. In some embodiments, the first lox site of the first plasmid and the first lox site of the second plasmid are LoxP and the second lox site of the first plasmid and the second lox site of the second plasmid are Lox5171.

As described herein, using the Cre recombination pathway to integrate the gene or pathway of interest allows for more efficient recombination of larger pathways, as compared to other methods such as homologous recombination or phage transduction. In some embodiments, the first and the second lox sites flank a sequence of greater than about 7 kb, greater than about 10 kb, greater than about 15 kb, greater than about 20 kb, greater than about 25 kb, greater than about 30 kb, greater than about 35 kb, greater than about 40 kb, greater than about 45 kb, greater than about 50 kb, greater than about 55 kb, greater than about 60 kb, greater than about 65 kb, greater than about 70 kb, greater than about 75 kb, greater than about 80 kb, greater than about 85 kb, greater than about 90 kb, greater than about 95 kb, greater than about 100 kb, greater than about 110 kb, greater than about 120 kb, greater than about 130 kb, greater than about 140 kb, or greater than about 150 kb. In some embodiments, the first and the second lox sites flank a sequence of less than about 200 kb, less than about 190 kb, less than about 180 kb, less than about 170 kb, less than about 160 kb, less than about 150 kb, less than about 140 kb, less than about 130 kb, less than about 120 kb, less than about 110 kb, less than about 100 kb, less than about 90 kb, less than about 80 kb, less than about 70 kb, or less than about 60 kb. In some embodiments, the first and the second lox sites flank a sequence greater than about any of the following sizes (in kb): 5, 7, 10, 15, 20, 25, 30, 35, 40, 45, 50, 55, 60, 65, 70, 75, 80, 85, 90, 95, 100, 110, 120, 130, 140, or 150. In some embodiments, the first and the second lox sites flank a sequence less than about any of the following sizes (in kb): 200, 190, 180, 170, 160, 150, 140, 130, 120, 110, 100, 95, 90, 85, 80, 75, 70, 65, 60, 59, 55, 50, 45, 40, 35, 30, 25, or 20. That is, in some embodiments, the first and the second lox sites flank a sequence having an upper limit of 200, 190, 180, 170, 160, 150, 140, 130, 120, 110, 100, 95, 90, 85, 80, 75, 70, 65, 60, 59, 55, 50, 45, 40, 35, 30, 25, or 20 kb and an independently selected lower limit of 5, 7, 10, 15, 20, 25, 30, 35, 40, 45, 50, 55, 60, 65, 70, 75, 80, 85, 90, 95, 100, 110, 120, 130, 140, or 150 kb, wherein the lower limit is less than the upper limit.

In some embodiments, the Cre coding sequence has the coding sequence of bacteriophage P1 recombinase or various mutations of this sequence such as described in (e.g., Wierzbicki et al., *J. Mol. Biol.*, 195, 785-794 (1987); Abremski et al., *J. Mol. Biol.*, 202, 59-66 (1988); Abremski et al., *J. Mol. Biol.*, 184, 211-20 (1988); Abremski et al., Protein Engineering, 5, 87-91 (1992) Hoess et al., Proc. Natl. Acad. Sci., 84, 6840-6844 (1987); Sternberg et al., J. Mol. Biol., 187, 197-212 (1986)). Further mutations of this Cre coding sequence may be employed so long as variant proteins resulting from such mutations are capable of effecting recombination at lox sites.

In certain embodiments, the gene encoding Cre recombinase is provided on a first plasmid of the present disclosure (e.g., a plasmid bearing a donor sequence flanked by inverted repeats and optionally a transposase coding sequence). In some embodiments, the gene encoding Cre recombinase is provided on a second plasmid of the present disclosure (e.g., a plasmid bearing a gene of interest). In some embodiments, the gene encoding Cre recombinase is provided on the host chromosome. In some embodiments, the gene encoding Cre recombinase is provided on the host chromosome between flanking lox sites. In some embodiments, the gene encoding Cre recombinase is provided under the control of constitutive, inducible, or developmentally-regulated promoters. In some embodiments, the Cre recombinase is under the control of the LacUV5 promoter. In some embodiments, the gene encoding Cre recombinase is under control of the Cas9 promoter. In some embodiments, the gene encoding Cre recombinase is under any promoter that functions in the host cell.

Transposition Systems

Certain aspects of the present disclosure relate to use of transposition as a means to introduce DNA into a host cell chromosome.

Transposons or transposable elements typically include a short piece of nucleic acid bounded by repeat sequences. Transposase enzymes facilitate the insertion of the transposon nucleic acid into DNA sequences. Various transposon systems (e.g., inverted repeat sequences and a transposase that acts thereupon) are known in the art and can be used in conjunction with the methods described herein. DNA transposons generally move by a cut-and-paste mechanism in which the transposon is excised from one location and reintegrated elsewhere. Most DNA transposons move through a non-replicative mechanism. DNA transposons consist of a transposase gene that is flanked by two Inverted Repeats (IRs). The transposase recognizes these IRs to perform the excision of the transposon DNA body, which is inserted into a new genomic location. Moreover, DNA transposons are generally not dependent on host factors to mediate their mobility. Thus DNA transposons are particularly useful to introduce DNA sequences across a wide array of host cells. (Lopez and Garcia-Perez, *Curr Genomics*. (2): 115-128 (2010). When used for genome engineering, the transposase gene can be provided in trans, outside of the inverted repeats that flank the transposable element, which prevents the transposon from excising from the host chromosome once it has integrated.

In some embodiments, the transposase can function across a wide range of host cells. In some embodiments, the transposase is a mariner transposase. The mariner super family of transposases, were originally discovered in *drosophila* but can function across a wide range of host cells, making them suitable for the claimed methods. (Lampe et al. *Genetics* 149:179-187 (1998); Lampe et al., *EMBO J.* 15:5470-5479 (1996)). For example, mariner transposons have also been found fungi, plants, fish and mammals. Lopez and Garcia-Perez, *Curr Genomics*, (2): 115-128 (2010). The most prominent member of the mariner transposon family is Sleeping Beauty, however other members which can be used are Frog Prince, (isolated from the Norther Leopard frog) Minos (isolated from *Drosophila hydei*), Himar1 (isolated from *Haematobia irritans*), and Mboumar-9 (isolated from ant).

Other exemplary DNA transposases that can be used include the piggyBac transposon family, which has been found in plants, fungi, and animals, including humans and hAT, transposons which have been isolated from eukaryotes. In some embodiments, the transposase is Tn1, Tn2, Tn3, Tn4, Tn6, Tn7, Tn8, Tn9, Tn10 or Tn917.

Genetic Markers

Certain aspects of the present invention related to genetic markers that allow selection of host or donor cells that have a desired DNA segment. In some embodiments, the genetic marker is a positive selection marker that confers a selective advantage to the host organisms. Examples of positive markers are genes that complement a metabolic defect (autotrophic markers) and antibiotic resistance markers.

In some embodiments, the genetic marker is an antibiotic resistance marker such as Apramycin resistance, Ampicillin resistance, Kanamycin resistance, Spectinomycin resistance, Tetracyclin resistance, Neomycin resistance, Chloramphenicol resistance, Gentamycin resistance, Erythromycin resistance, Carbenicillin resistance, Actinomycin D resistance, Neomycin resistance, Polymyxin resistance, Zeocin resistance and Streptomycin resistance. In some embodiments, the genetic marker includes a coding sequence of an antibiotic resistance protein (e.g., a beta-lactamase for certain Ampicillin resistance markers) and a promoter or enhancer element that drives expression of the coding sequence in a host cell of the present disclosure. In some embodiments, a host cell of the present disclosure is grown under conditions in which an antibiotic resistance marker is expressed and confers resistance to the host cell, thereby selected for the host cell with a successful integration of the marker. Exemplary culture conditions and media are described herein.

In some embodiments, the genetic marker is an auxotrophic marker, such that marker complements a nutritional mutation in the host cell. In some embodiments, the auxotrophic marker is a gene involved in vitamin, amino acid, fatty acid synthesis, or carbohydrate metabolism; suitable auxotrophic markers for these nutrients are well known in the art. In some embodiments, the auxotrophic marker is a gene for synthesizing an amino acid. In some embodiments, the amino acid is any of the 20 essential amino acids. In some embodiments, the auxotrophic marker is a gene for synthesizing glycine, alanine, valine, leucine, isoleucine, proline, phenylalanine, tyrosine, tryptophan, serine, threonine, cysteine, methionine, asparagine, glutamine, lysine, arginine, histidine, aspartate or glutamate. In some embodiments, the auxotrophic marker is a gene for synthesizing adenosine, biotin, thiamine, leucine, glucose, lactose, or maltose. In some embodiments, a host cell of the present disclosure is grown under conditions in which an auxotrophic resistance marker is expressed in an environment or medium lacking the corresponding nutrient and confers growth to the host cell (lacking an endogenous ability to produce the nutrient), thereby selected for the host cell with a successful integration of the marker. Exemplary culture conditions and media are described herein.

In some embodiments, the genetic marker is a screenable marker which allows distinction between cells with and without the desired DNA. In some embodiments, the screenable marker is beta galactosidase (lacZ), which results in blue colonies on X-gal plates. In some embodiments, the screenable marker is a fluorescent marker, such as GFP, YFP, or RFP.

In some embodiments, the selectable marker is the ura3 gene from yeast which can function as both a positive and negative selectable marker. The ura3 gene is required for uracil biosynthesis and can complement ura3 mutants that are auxotrophic for uracil (positive selection). The enzyme ura3 also converts 5-fluoroorotic acid (5FOA) into the toxic compound 5-fluorouracil, so any cells carrying the URA3 gene will be killed in the presence of 5FOA (negative selection).

In some embodiments, the first and second plasmids comprise different selectable markers located between the lox sites to enable counter selection. In some embodiments, the first plasmid comprises kanamycin resistance between the lox sites and the second plasmid comprises apramycin resistance between the lox sites. In some embodiments, the first plasmid comprises apramycin resistance between the lox sites and the second plasmid comprises kanamycin resistance between the lox sites.

Promoters

In some embodiments, the gene of interest, transposase, Cre recombinase, T7 RNA polymerase, and antibiotic resistance genes are under control of one or more promoters. "Under the control" refers to a recombinant nucleic acid that is operably linked to a control sequence, enhancer, or promoter. The term "operably linked" as used herein refers to a configuration in which a control sequence, enhancer, or promoter is placed at an appropriate position relative to the coding sequence of the nucleic acid sequence such that the control sequence, enhancer, or promoter directs the expression of a polypeptide.

"Promoter" is used herein to refer to any nucleic acid sequence that regulates the initiation of transcription for a particular polypeptide-encoding nucleic acid under its control. A promoter does not typically include nucleic acids that are transcribed, but it rather serves to coordinate the assembly of components that initiate the transcription of other nucleic acid sequences under its control. A promoter may further serve to limit this assembly and subsequent transcription to specific prerequisite conditions. Prerequisite conditions may include expression in response to one or more environmental, temporal, or developmental cues; these cues may be from outside stimuli or internal functions of the cell. Bacterial and fungal cells possess a multitude of proteins that sense external or internal conditions and initiate signaling cascades ending in the binding of proteins to specific promoters and subsequent initiation of transcription of nucleic acid(s) under the control of the promoters. When transcription of a nucleic acid(s) is actively occurring downstream of a promoter, the promoter can be said to "drive" expression of the nucleic acid(s). A promoter minimally includes the genetic elements necessary for the initiation of transcription, and may further include one or more genetic elements that serve to specify the prerequisite conditions for transcriptional initiation. A promoter may be encoded by the endogenous genome of a host cell, or it may be introduced as part of a recombinant, engineered polynucleotide. A promoter sequence may be taken from one host species and used to drive expression of a gene in a host cell of a different species. A promoter sequence may also be artificially designed for a particular mode of expression in a particular species, through random mutation or rational design. In recombinant engineering applications, specific promoters are used to express a recombinant gene under a desired set of physiological or temporal conditions or to modulate the amount of expression of a recombinant nucleic acid. In some embodiments, the promoters described herein are functional in a wide range of host cells.

In some embodiments, the gene of interest, transposase, Cre recombinase, and/or antibiotic resistance genes are under control of one or more constitutive promoters. In some embodiments, a constitutive promoter is defined herein as a promoter that drives the expression of nucleic acid(s) continuously and without interruption in response to internal or external cues. Constitutive promoters are commonly used in recombinant engineering to ensure continuous expression of desired recombinant nucleic acid(s). Constitutive promoters often result in a robust amount of nucleic acid expression, and, as such, are used in many recombinant engineering applications to achieve a high level of recombinant protein and enzymatic activity.

Many constitutive promoters are known and characterized in the art. Exemplary bacterial constitutive promoters include without limitation the *E. coli* promoters Pspc, Pbla, PRNAI, PRNAII, P1 and P2 from rrnB, and the lambda phage promoter PL (Liang, S. T. et al. *J Mol. Biol.* 292(1): 19-37 (1999)). In some embodiments, the constitutive promoter is functional in a wide range of host cells. In some embodiments, the constitutive promoter is the Cas9 promoter.

In some embodiments, the gene of interest, transposase, Cre recombinase, and/or antibiotic resistance genes are expressed under the control of an inducible promoter. An inducible promoter is defined herein as a promoter that drives the expression of nucleic acid(s) selectively and reliably in response to a specific stimulus. An ideal inducible promoter will drive no nucleic acid expression in the absence of its specific stimulus but drive robust nucleic acid expression rapidly upon exposure to its specific stimulus. Additionally, some inducible promoters induce a graded level of expression that is tightly correlated with the amount of stimulus received. Stimuli for known inducible promoters include, for example, heat shock, exogenous compounds (e.g., a sugar, metal, drug, or phosphate), salts or osmotic shock, oxygen, and biological stimuli (e.g., a growth factor or pheromone).

Inducible promoters are often used in recombinant engineering applications to limit the expression of recombinant nucleic acid(s) to desired circumstances. For example, since high levels of recombinant protein expression may sometimes slow the growth of a host cell, the host cell may be grown in the absence of recombinant nucleic acid expression, and then the promoter may be induced when the host cells have reached a desired density. Many inducible promoters are known and characterized in the art. Exemplary bacterial inducible promoters include without limitation the *E. coli* promoters $P_{lac}$, $P_{trp}$, $P_{tac}$, $P_{T7}$, $P_{BAD}$, and $P_{lacUV5}$ (Nocadello, S. and Swennen, E. F. *Microb Cell Fact*, 11:3 (2012)). In some preferred embodiments, the inducible promoter is a promoter that functions in a wide range of host cells. Inducible promoters that functional in a wide variety of host bacterial and yeast cells are well known in the art.

Figure 8A:
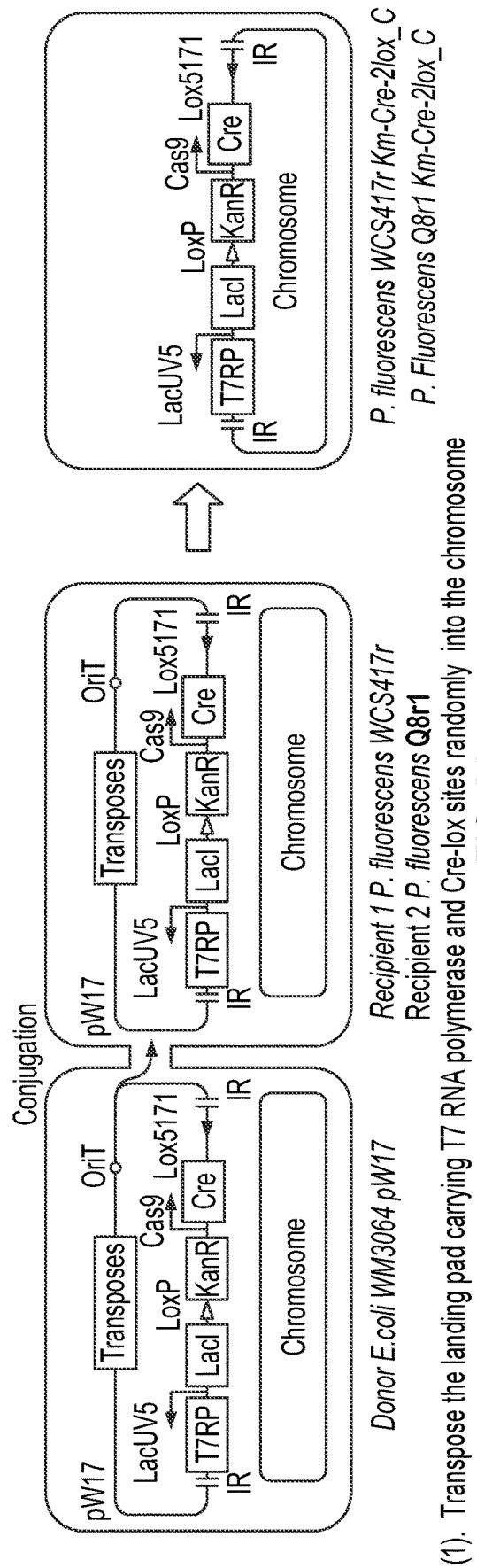
FIGS. 8A-8B show an example of the combined transposition, Cre-Lox, and T7 RNA polymerase strategy. Donor strain, E. coli WM3064 p17, which harbors the p17 plasmid, is conjugated to a recipient strain, P. fluorescens WCS514r or P. fluorescens Q8r1, resulting in random integration of the landing pad into the P. fluorescens WCS417r or P. fluorescens Q8r1 chromosome (FIG. 8A). The resulting strain is then conjugated to donor strain, E. coli WM3064 pW20 or pW21, which harbors the pW20 or pW21 plasmids (FIG. 8B). After conjugation and recombination by Cre, the PDC and Apramycin genes are integrated into the recipient strain where the PDC gene is under the control of the T7 promoter (FIG. 8B).
Figure 8B:
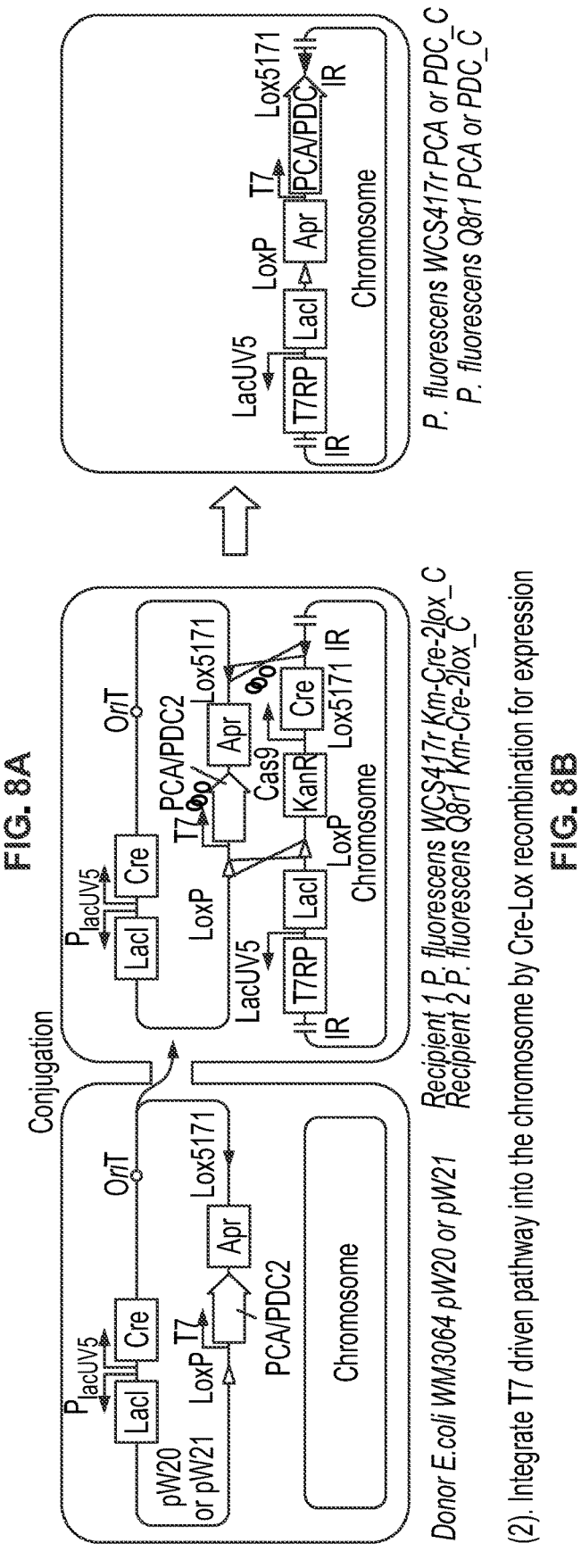
Figure 10:
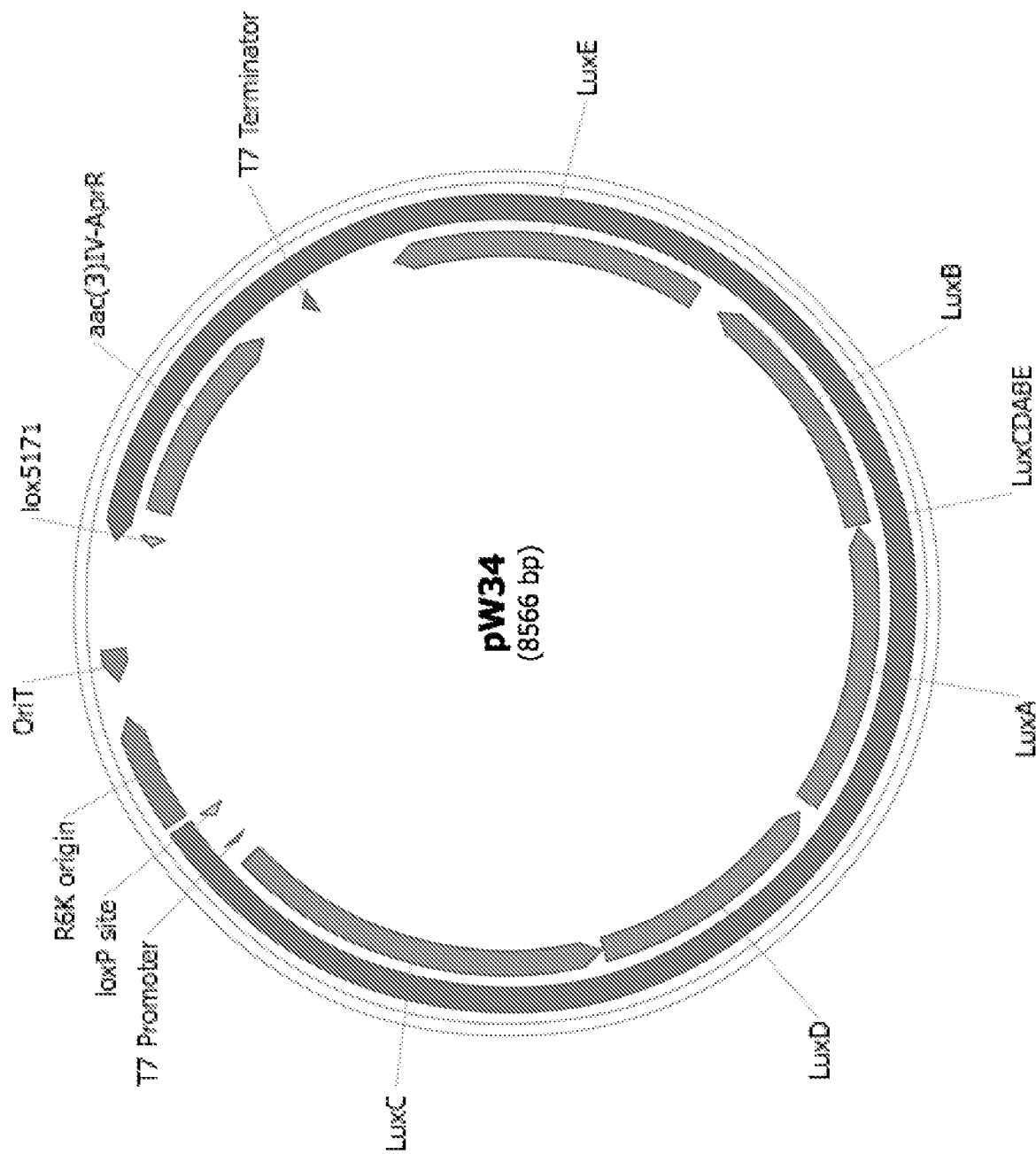
FIG. 10 is a map of the pW34 vector. The pW34 vector is composed of two parts. Part 1 is a backbone carrying OriT, the r6k replication origin, and part 2 is the T7 driven luxCDABE pathway and Apramycin resistance marker between the two lox sites. pW34 was generated by cloning the luxCDABE pathway into vector pW26 (SEQ ID NO:10).

In some embodiments, a genetic element of the present disclosure (e.g., a donor sequence) comprises a coding sequence for a protein that promotes sequence-specific gene transcription. In certain embodiments, as illustrated in FIG. 8B, the coding sequence for the protein that promotes sequence-specific gene transcription is flanked by inverted repeats but lox sites. A protein may promote sequence-specific gene transcription downstream of a promoter of the present disclosure. In some embodiments, the protein is a transcription factor active in a host cell of the present disclosure. In some embodiments, the protein is an RNA polymerase, e.g., a sequence-specific RNA polymerase.

T7 RNA polymerase is known in the art as an RNA polymerase that catalyzes transcription downstream of a specific DNA sequence, e.g., the T7 RNA polymerase promoter. In some embodiments, an inducible promoter of the present disclosure is the T7 RNA polymerase promoter. In some embodiments, the T7 RNA polymerase promoter is TAATCGACTCACTATG (SEQ ID NO:3). Advantageously, a sequence-specific RNA polymerase allows for sequence-directed transcription in nearly any host cell, since the sequence recognition and transcription machinery are the same modular unit (e.g., T7 RNA polymerase).

In some embodiments, a Cre recombinase coding sequence of the present disclosure is under control of a promoter that is functional in a wide range of hosts. One of skill in the art will recognize and be able to identify suitable promoters, based upon the desired host, for example by conducting transcriptome analysis of the desired host to identify functional promoters. In some embodiments, the Cre recombinase gene is under control of the Cas9 promoter. In some embodiments, the Cre recombinase gene is under the control of the T7 RNA polymerase promoter.

In some embodiments, the gene or pathway of interest is under the control of an inducible promoter. In some embodiments the gene or pathway of interest is under the control of universal promoter that functions in a wide range of host cells. In some embodiments, the gene or pathway of interest is under control of a sequence-specific RNA polymerase promoter. In some embodiments, the inducible promoter is controlled by a transcription factor. In some embodiments, the gene or pathway of interest is under the control of the T7 RNA polymerase promoter.

II. Vectors

Certain aspects of the present disclosure relate to vectors. In some embodiments, a vector of the present disclosure may be used, inter alia, to integrate one or more genes or pathways of interest into a chromosome of a host or donor cell. In some embodiments, the vector may be used to integrate one or more genes or pathways of interest into a chromosome of any of the cells described herein.

As used herein, the term "vector" may refer to a polynucleotide construct designed to introduce and/or express nucleic acids in one or more cell types. In some embodiments, the vector may be a plasmid. Typically plasmids include one or more selectable markers as described herein and an origin of replication. In some embodiments, the origin of replication is the pMB1 origin, the pBR322 origin, the ColE1 origin, the p15A origin, the pSC101 or the R6K origin of replication. In some embodiments, the origin of replication is the R6K origin.

A vector of the present disclosure may include one or more of the exemplary genetic elements described above. In some embodiments, a vector includes a donor sequence which is a sequence flanked by inverted repeats that can be integrated into a host chromosome. In some embodiments, the inverted repeats are recognized by a transposase. In some embodiments, the inverted repeats are recognized by the mariner transposase. In some embodiments, the donor sequence includes a selectable marker. In some embodiments, the donor sequence includes a first lox site and a second lox site. In some embodiments the donor sequence includes two different lox sites. In some embodiments, the donor sequence includes a selectable marker and a Cre gene. In some embodiments, the donor sequence includes a selectable marker, a Cre gene and a T7 RNA polymerase gene.

In some embodiments, the vector includes any of the transposase coding sequences described herein. In some embodiments, the transposase coding sequence encodes a mariner transposase. In some embodiments, the vector is a conjugative plasmid. In some embodiments, the vector has an origin of transfer (oriT). In some embodiments, the vector comprises one or more genes or pathways of interest as described herein. In some embodiments, the one or more genes or pathways of interest are flanked by two lox sites. In some embodiments, the vector comprises one or more genes under the control of a promoter described herein.

For illustrative purposes, some non-limiting examples of vectors of the present disclosure are provided below. However, it is to be appreciated that any or all of the exemplary features described below may be combined in a vector without departing from the scope of the present disclosure, and additional modifications or features known in the art are possible.

Figure 3A:
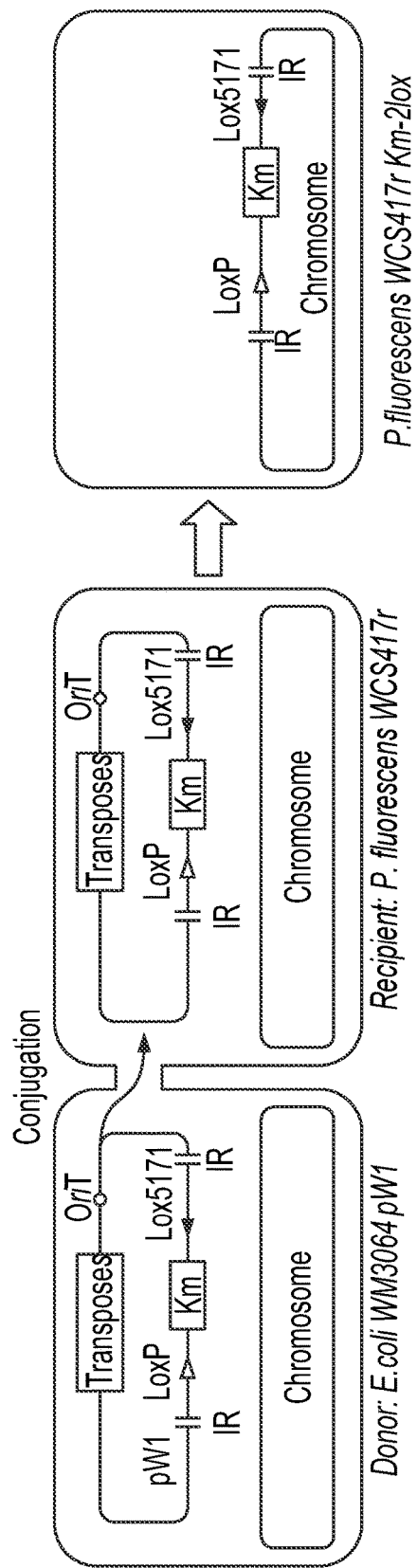
FIGS. 3A-3B show an example of the combined transposition, Cre-Lox strategy. Donor strain, E. coli WM3064 pW1, which harbors the pW1 plasmid, is conjugated to a recipient strain, P. fluorescens WCS514r, resulting in random integration of the landing pad into the P. fluorescens WCS417r chromosome (FIG. 3A). The resulting strain is then conjugated to donor strain, E. coli WM3064 pW6, which harbors the pW6 plasmid (FIG. 3B). After conjugation and recombination by Cre, the PDC and Apramycin genes are integrated into the recipient strain under the control of the T7 RNA polymerase promoter (FIG. 3B).

In some embodiments, the vector includes a transposase gene and a donor DNA sequence flanked by inverted repeats comprising a first and second lox site, wherein the first and second lox sites are different. In some embodiments the inverted repeats are mariner repeats. In some embodiments, the vector includes a LoxP site and a Lox5171 site. In some embodiments, the vector comprises a donor DNA segment further comprising a selectable marker located between the two lox sites. In some embodiments, the selectable marker is the kanamycin resistance gene. In some embodiments, the vector includes a donor DNA sequence comprising a T7 RNA polymerase gene under control of a promoter that functions in the host cell. In some embodiments, the vector includes a transposase. In some embodiments, the vector includes a transposase located at a position other than in the donor DNA sequence. In some embodiments, the vector is a conjugative vector. In some embodiments, the vector comprises an origin of transfer. In some embodiments, the vector is a medium copy plasmid. In some embodiments, the vector comprises the R6K origin. An exemplary vector with these features is illustrated in FIG. 3A.

In some embodiments, the vector includes a donor sequence flanked by inverted repeats comprising a T7 RNA polymerase gene, a LacI gene, an antibiotic resistance gene, a Cre gene, and first and second lox sites. In some embodiments, the vector includes a LoxP site and a Lox5171 site. In some embodiments, the antibiotic resistance gene and Cre gene are located between the two lox sites. In some embodiments, the antibiotic resistance gene is kanamycin resistance. In some embodiments, the Cre gene is under control of a promoter that functions in the host cell. In some embodiments, the Cre gene is under control of the Cas9 promoter. In some embodiments, the vector includes T7 RNA polymerase under control of the LacUV5 promoter. In some embodiments, the vector incudes an origin of transfer and a transposase gene. In some embodiments, the transposase gene is located in the vector other than in the donor DNA sequence. In some embodiments, the vector is a single copy plasmid. An exemplary vector with these features is illustrated in FIG. 8A.

Figure 3B:
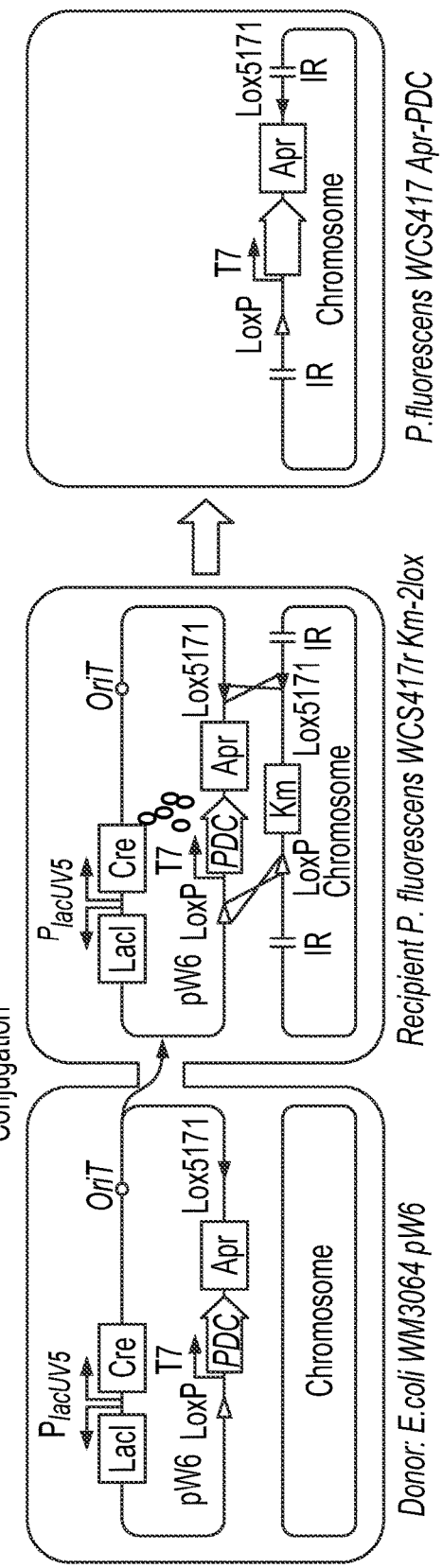
Figure 4B:
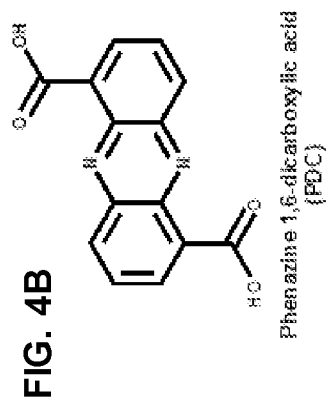
FIGS. 4A-4D show the Phenazine 1,6-dicarboxylic acid (PDC) and phenazine 1-carboxylic (PCA) pathways and chemical products.
Figure 4D:
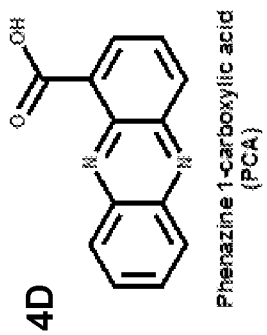
Figure 4A:
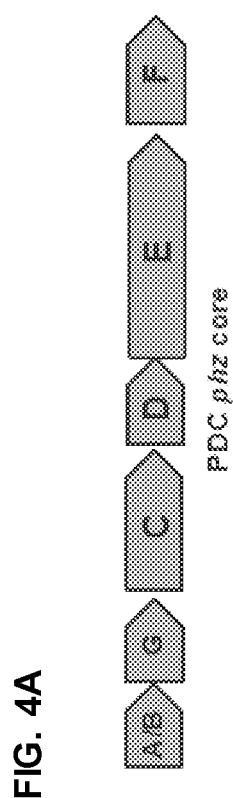
Figure 4C:
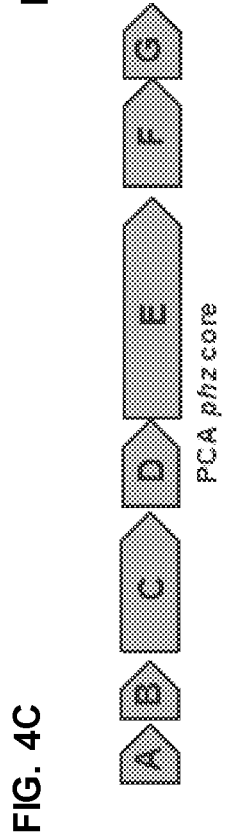
Figure 5:
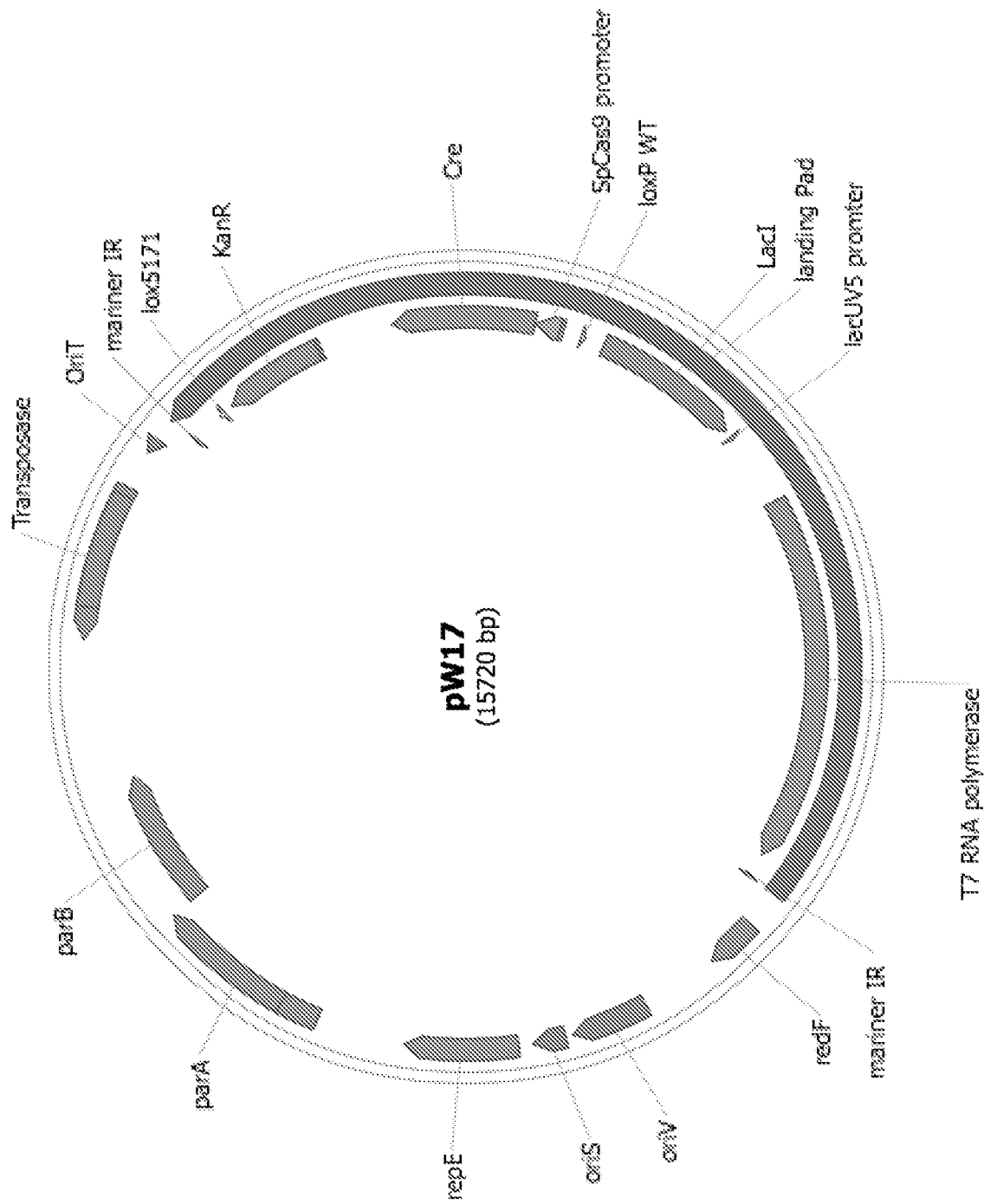
FIG. 5 is a map of the pW17 vector. The sequence between the two mariner inverted repeat (IR) ends is called the "landing pad." The landing pad includes LacI-T7 RNA polymerase to enable the T7 driven pathway expression, and also includes LoxP-Km-Cas9Cre-Lox5171 for pathway integration. pW17 is a single copy plasmid.
Figure 6:
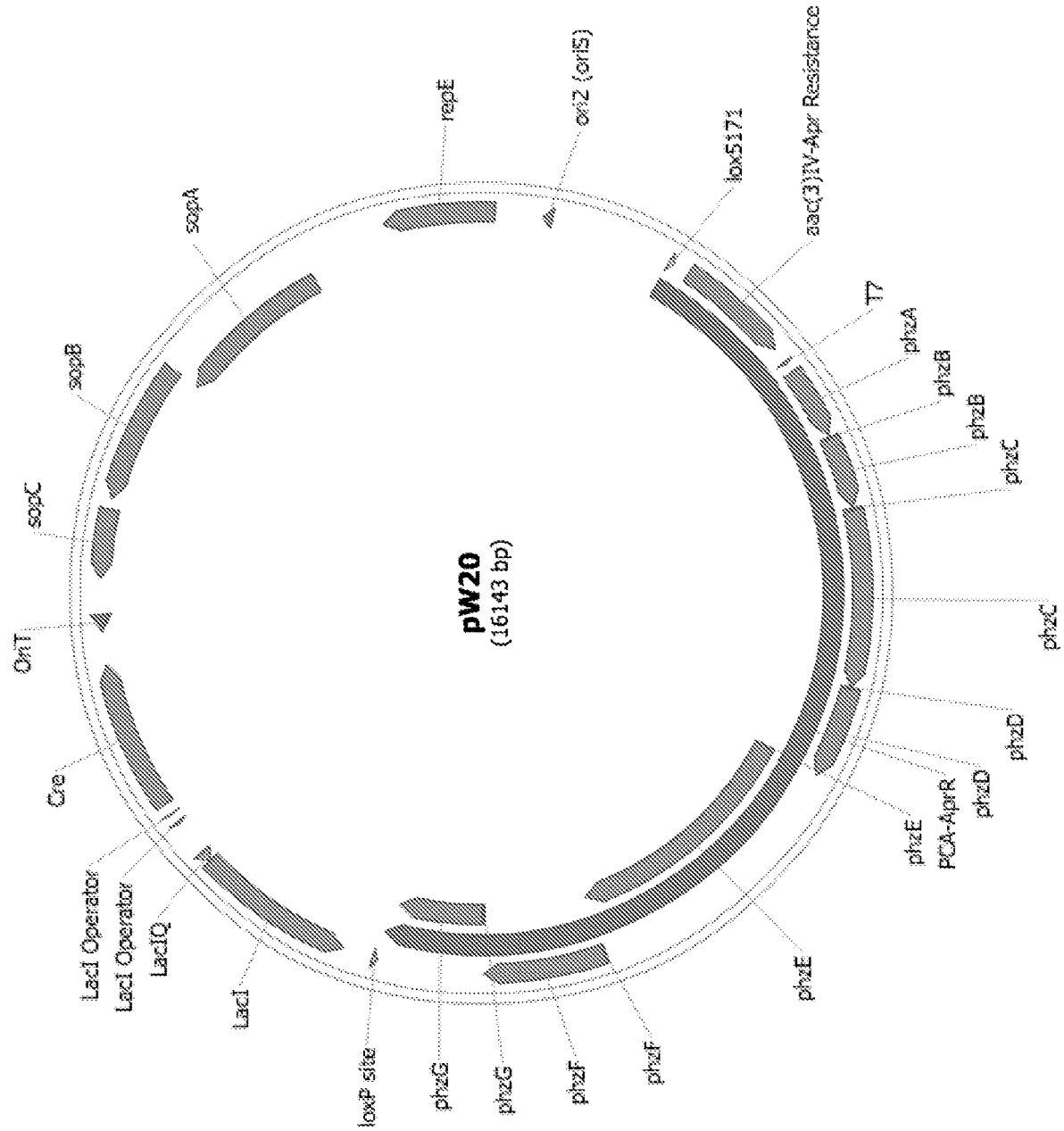
FIG. 6 is a map of the pW20 vector. The pW20 vector is composed of three parts. Part 1 is the pBeloBAC11 backbone, part 2 is the LacI and LacUV5 driven Cre recombinase, and part 3 is the T7 driven PCA and apramycin resistance marker between the two Lox sites ("PCA-AprR").
Figure 7:
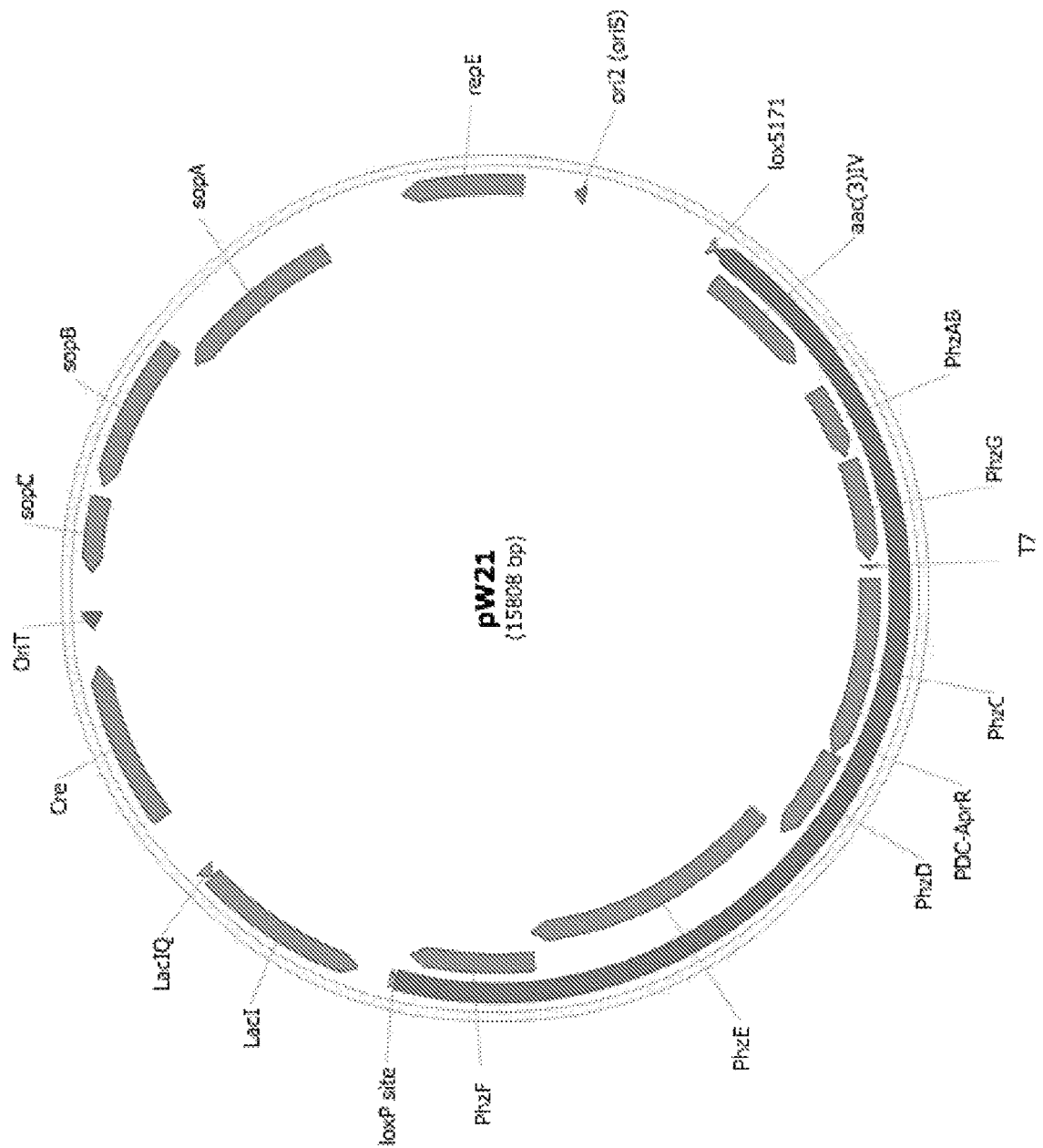
FIG. 7 is map of the pW21 vector. The pW21 vector is composed of three parts. Part 1 is the pBeloBAC11 backbone, part 2 is the LacI and LacUV5 driven Cre recombinase, and part 3 is the T7 driven PDC and Apramycin resistance marker between the two Lox sites ("PDC-AprR").

In some embodiments, the vector comprises one or more genes or pathways of interest. In some embodiments, the vector comprises one or more genes or pathways of interest located between a first and second lox site. In some embodiments, the vector comprises a LoxP site and a Lox5171 site. In some embodiments, the vector comprises a selectable marker and one or more genes or pathways of interest located between a first and second lox site. In some embodiments, the selectable marker is apramycin. In some embodiments, the vector comprises one or more genes or pathways of interest under the control of an inducible promoter. In some embodiments the vector comprises the one or more genes or pathways of interest under the control of the T7 promoter. In some embodiments the genes or pathways of interest include the bacterial luciferase operon luxCDABE. In some embodiments the gene or pathway of interest is a phenazine pathway. In some embodiments the gene or pathway of interest is the phenazine 1-carboxylic acid (PCA) pathway. In some embodiments, the pathway of interest is the phenazine 1,6-dicarboxylic acid (PDC) pathway. In some embodiments, the vector includes a LacI gene and a Cre gene. In some embodiments, the LacI and Cre genes are under control of the LacUV5 promoter. Exemplary vectors with these features are illustrated in FIGS. 3B and 8B. In some embodiments, the vector includes one or more genes or pathways of interest and a selectable marker located between a first and second lox site and does not comprise LacI or Cre genes. In some embodiments, the vector is a medium copy plasmid. In some embodiments, the vector includes the R6K replication origin. Exemplary vectors with these features are illustrated in FIG. 11B.

In some embodiments, the vector includes a transposase coding sequence and a donor sequence, wherein the donor sequence is flanked by inverted repeats recognized by the transposase, wherein the donor sequence includes a selectable marker coding sequence flanked by a first and a second lox site, and wherein the first and second lox sites are different.

Further provided herein are kits comprising the vectors of the present disclosure. In some embodiments, the vectors are supplied in lyophilized format in a container. In some embodiments, the vectors are supplied as purified vectors in a suitable buffer such as TE. In some embodiments, the vectors are supplied as bacterial or yeast stocks. In some embodiments, the kits include a first vector comprising: (i) a transposase coding sequence; and (ii) a donor sequence, wherein the donor sequence is flanked by inverted repeats recognized by the transposase, wherein the donor sequence comprises a first selectable marker coding sequence flanked by a first and a second lox site, and wherein the first and the second lox sites are different; and a second vector comprising: (i) one or more restriction or targeted cloning sites suitable for recombining a gene of interest into the second vector; and (ii) a second selectable marker, wherein the second selectable marker and the one or more restriction or targeted cloning sites are flanked by the first and the second lox sites. In some embodiments, the kits further include a third vector comprising (i) one or more restriction or targeted cloning sites suitable for recombining a gene of interest into the second vector; and (ii) a second selectable marker, wherein the second selectable marker and the one or more restriction or targeted cloning sites are flanked by the first and the second lox sites. In some embodiments, the second vector is a multiple-copy plasmid, and wherein the third vector is a single-copy plasmid. For example, the second vector (e.g., pW26) can be used for cloning relatively smaller sequences of interest (e.g., shorter genes or pathways), whereas the third vector (e.g. pW5Y) can be used to accommodate relatively longer sequences of interest (e.g., larger genes or pathways).

A variety of restriction or targeted cloning sites are known in the art and can be selected by one of skill in the art. For example, multiple cloning sites (MCSs) have been used to insert sequences of interest into a vector using restriction digest and ligation. More recently, targeted cloning sites have come into use, such as site-specific recombination using phage/bacterial attP and attB sites mediated by phage integrase. For further description of suitable cloning sites and methods, see, e.g., worldwide web address: addgene.org/plasmid-reference/cloning-choice/.

In some embodiments, the first vector comprises the polynucleotide sequence of SEQ ID NO:4. In some embodiments, the second vector comprises the polynucleotide sequence of SEQ ID NO:10. In some embodiments, the third vector comprises the polynucleotide sequence of SEQ ID NO:11. In some embodiments, the kits further include instructions for using the kit to integrate the gene of interest into a chromosome of a host cell (e.g., a bacterial host cell).

Any of the lox sites, selectable markers, origins of replication, transposase coding sequences, and so forth described herein may be selected for use in a kit of the present disclosure by one of skill in the art.

III. Methods of Pathway Engineering

Certain aspects of the present disclosure relate to methods of producing a product, e.g., using the methods, vectors, and cells described herein. For example, any of the methods of integrating one or more genes or pathways of interest into a chromosome of a bacterial host cell described herein may find use, inter alia, in generating a bacterial host cell that produces a product. As described herein, a potential application of the methods of integration and expression of the present disclosure is in the generation of host cells that produce a product of interest, e.g., using one or more of the integrated genes or pathways of interest. In some embodiments, one or more of the integrated genes or pathways of interest may produce a product of interest, or an intermediate in the synthesis thereof.

In some embodiments, methods of integration and expression described herein relate to generation of host cells comprising a phenazine pathway. In some embodiments, the phenazine pathway is introduced into a host cell to produce phenazine 1-carboxylic acid (PCA). In some embodiments the PCA phenazine core pathway is introduced into a host cell to produce PCA. In some embodiments, the PCA phenazine core pathway comprises phzABCDEFG. In some embodiments, the phenazine pathway is introduced into a host cell to produce phenazine 1,6-dicarboxylic acid (PDC). In some embodiments, the PDC phenazine core pathway is introduced into a host cell to produce PDC. In some embodiments, the PDC core pathway comprises phzABGCDEF.

In some embodiments, the methods described herein comprise generation of host cells comprising a gene or pathway of interest, wherein the gene or pathway of interest comprises a gene encoding a metabolic enzyme. In some embodiments, the metabolic enzyme comprises an enzyme involved in amino acid metabolism, biofuel production, commodity chemical production, vitamin metabolism, or fatty acid production. In some embodiments, the gene of or pathway of interest produces one or more secondary metabolites. Various secondary metabolites known in the art include without limitation lipopolysaccharides, polysaccharides, non-ribosomal peptide (NRP), polyketide, siderophore, terpene, lantipeptide, bacteriocin, homoserine lactone, butyrolactone, ectoine, thiopeptide, phenazine, terpinoids, alkanoids, and flavonoids.

Since various genes and pathways sufficient for the production of these secondary metabolites are known, it will be appreciated that the exemplary methods described supra with respect to production of phenazines could readily be adapted to produce these secondary metabolites based on the methods and techniques described herein. For example, gene clusters sufficient to produce various biofuels (Wargacki, A. J. et al. (2012) *Science* 335:308-13; Enquist-Newman, M. et al. (2014) *Nature* 505:239-43), antibiotics (Wohlleben, W. et al. (2012) *FEBS Letters* 586:2171-6), secondary metabolites (Omura, S. et al. (2001) *Proc. Natl. Acad. Sci.* 98:12215-20; Chaudhary, A. K. et al. (2013) *Biomed Res. Int.* 968518), alkaloids (Sato, F. et al. (2013) *Proc. Jpn. Acad. Ser. B Phys. Biol. Sci.* 89:165-82), and small molecule therapeutics (Arsenault, P. R. et al. (2008) *Curr. Med. Chem.* 15:2886-96) are known in the art. In some embodiments, the gene(s) and/or pathway(s) of interest may be engineered to produce non-natural products (see, e.g., Dietrich, J. A. et al. (2009) *ACS Chem. Biol.* 4:261-7).

In some embodiments, the gene or pathway of interest is an orphan pathway. In some embodiments, the gene or pathway of interest is any of those described in Fu, J., et al., at *Nat. Biotechnol.*, 2012. 30(5):440-6 (2012). In some embodiments, the gene or pathway of interest is a pathway involved in terpene or terpenoid synthesis. In some embodiments the gene or pathway of interest includes a gene or pathway involved in vanillin, benzaldehyde (bitter almond, cherry) and 4-(R)-decanolide (fruity±fatty) synthesis. In certain embodiments that may be combined with any of the preceding embodiments, the method comprises expressing a gene or pathway involved in benzaldehyde, butyric acid, 2,3-butanedione, citronellal, (+)-curcumene, γ-decalactone, δ-decalactone, (+)-dehydro-curcumene, (−)-isopulegol, (−)-methol, nor-patchoulenol, (+)-nuciferal, phenolethanol, β-binene, raspberry ketone, thaumatin, monellin, or (+)-turmerone as described in Gupta et al., Biotechnological Approach to Microbial Based Perfumes and Flavours. *Journal of Microbiology & Experimentation,* 2015 or Krigs et al., *Applied Micribio. and Biotech.,* 49(1):1-8 (1998).

In some embodiments, the gene or pathway of interest is involved in bacteriocin synthesis. In some embodiments, the bacteriocin is a class IIa bacteriocin. In some embodiments the bacteriocin is Leucin A, MesentericinY105, Mundticin, Piscicolin 126, Bavaricin A, Sakacin P, Pediocin PA-1, Bavaricin MN, Divercin V41, Enterocin A, Enterocin P, Carnobacteriocin BM1, Sakacin A, Carnobacterocin B2, Bacteriocin 31, or Acidocin A, as described in Ennahar, S., et al., FEMS Microbiol Rev, 24(1):85-106 (2000). Non-limiting examples of bacteriocins, and their corresponding biosynthesis pathways, include Sakacin A and sapAKRTE; Sakacin P and sppKRTE; Leucocin A and lcaBAECD; Mesentericin Y105 and mesIYCDE; Pediocin AcH and papABCD; Divercin V41 and dvnAT1T2IRK; Enterocin A and entFAI; Enterocin P and entP; and Curvacin A and curA (see, e.g., Ennahar, S., et al., FEMS Microbiol Rev, 24(1): 85-106 (2000) for additional descriptions and references describing these pathways and products). In some embodiments, the bacteriocin may be purified, e.g., from the host cell and/or culture medium. Efficient protocols for purification of these peptides are standard in the art (see, e.g., Ennahar, S., et al., FEMS Microbiol Rev, 24(1):85-106 (2000)).

In some embodiments, the gene or pathway of interest is involved in production of a polysaccharide, siderophore, lantipeptide, homoserine lactone, butyrolactone, ectoine, thiopeptide alkaloids, flavonoid, commodity chemical or a vitamin.

In some embodiments, the gene or pathway of interest is involved in omega-3 or omaga-6 fatty acid synthesis. In certain embodiments that may be combined with any of the preceding embodiments, the gene of interest is any of Δ6-desaturase (D6D), fatty acid desaturase 2 (FADS2), Δ5-desaturase (D5D).

In some embodiments, the gene or pathway of interest is involved in lipopolysaccharide synthesis. A non-limiting list of genes and pathways involved in lipopolysaccharide synthesis may be found, e.g., at worldwide web address: genome.jp/kegg-bin/show_pathway?map00540.

In some embodiments, the methods of the present disclosure include culturing a host cell of the present disclosure comprising a gene or pathway coding sequence (e.g., chromosomally integrated using any of the methods described herein) in a culture medium under conditions whereby the gene or pathway coding sequence is expressed in the cell, and whereby the gene or pathway produces a product, such as the exemplary secondary metabolites described above. Exemplary culture media and conditions are described herein.

In some embodiments, the gene or pathway of interest is an orphan pathway, which is integrated into a host cell to determine its function in vivo. For example, a gene or pathway may be integrated into a host cell of the present disclosure (e.g., using the methods described herein), cultured, and one or more products of the gene or pathway may be detected and/or identified as a product of the cell, e.g., using standard methods known in the art including without limitation mass spectrometry or liquid/gas chromatography.

Cell Culture Media and Methods

Certain aspects of the present disclosure relate to methods of culturing a cell. As used herein, "culturing" a cell refers to introducing an appropriate culture medium, under appropriate conditions, to promote the growth of a cell. Methods of culturing various types of cells are known in the art. Culturing may be performed using a liquid or solid growth medium. Culturing may be performed under aerobic or anaerobic conditions where aerobic, anoxic, or anaerobic conditions are preferred based on the requirements of the microorganism and desired metabolic state of the microorganism. In addition to oxygen levels, other important conditions may include, without limitation, temperature, pressure, light, pH, and cell density.

In some embodiments, a culture medium is provided. A "culture medium" or "growth medium" as used herein refers to a mixture of components that supports the growth of cells. In some embodiments, the culture medium may exist in a liquid or solid phase. A culture medium of the present disclosure can contain any nutrients required for growth of microorganisms. In certain embodiments, the culture medium may further include any compound used to reduce the growth rate of, kill, or otherwise inhibit additional contaminating microorganisms, preferably without limiting the growth of a host cell of the present disclosure (e.g., an antibiotic, in the case of a host cell bearing an antibiotic resistance marker of the present disclosure). The growth medium may also contain any compound used to modulate the expression of a nucleic acid, such as one operably linked to an inducible promoter (for example, when using a yeast cell, galactose may be added into the growth medium to activate expression of a recombinant nucleic acid operably linked to a GAL1 or GAL10 promoter). In further embodiments, the culture medium may lack specific nutrients or components to limit the growth of contaminants, select for microorganisms with a particular auxotrophic marker, or induce or repress expression of a nucleic acid responsive to levels of a particular component.

In some embodiments, the methods of the present disclosure may include culturing a host cell under conditions sufficient for the production of a product, such as one or more of the secondary metabolites or other products described herein. In certain embodiments, culturing a host cell under conditions sufficient for the production of a product entails culturing the cells in a suitable culture medium. Suitable culture media may differ among different microorganisms depending upon the biology of each microorganism. Selection of a culture medium, as well as selection of other parameters required for growth (e.g., temperature, oxygen levels, pressure, etc.), suitable for a given microorganism based on the biology of the microorganism are well known in the art. Examples of suitable culture media may include, without limitation, common commercially prepared media, such as Luria Bertani (LB) broth, Sabouraud Dextrose (SD) broth, or Yeast medium (YM) broth. In other embodiments, alternative defined or synthetic culture media may also be used.

Purification of Products from Host Cells

In some aspects, the methods described herein can be used to engineer cells to express one or more genes or pathways of interest to produce a chemical or biological product, such as a chemical, small molecule, protein, peptide, nucleic acid, fuel, perfume, or secondary metabolite, for example. In some embodiments, the methods described herein involve introducing a gene or pathway of interest into a host cell and culturing the host cell under conditions where the gene or pathway of interest is expressed to produce a desired product. In some embodiments, the method comprises purifying the product produced by the host cell.

A variety of methods known in the art may be used to purify a product from a host cell or host cell culture. In some embodiments, one or more products may be purified continuously, e.g., from a continuous culture. In other embodiments, one or more products may be purified separately from fermentation, e.g., from a batch or fed-batch culture. One of skill in the art will appreciate that the specific purification method(s) used may depend upon, inter alia, the host cell, culture conditions, and/or particular product(s).

EXAMPLES

The present disclosure will be more fully understood by reference to the following examples. They should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Chromosomal Integration of a 7.0 kb Pathway

This study shows the integration of pathways to bacterial chromosome using a combined transposition and Cre-Lox P strategy (FIGS. 3A, 3B). In this study, a 7.0-kb PDC pathway was integrated into the strain *P. fluorescens* WCS417r.

Phenazines are nitrogen containing heterocyclic secondary metabolites of bacterial origin. Almost all phenazines exhibit broad antibacterial and antifungal bioactivity due to their redox activity. Phenazine biosynthesis proceeds via a core pathway (phzABCDEFG) that is found in all phenazine-producing bacteria and is responsible for producing the phenazine tricycle nucleus (FIGS. 4A-4D). Phenazine 1,6-dicarboxylic acid (PDC) is a core phenazine structure from which many phenazine derivatives may be formed. The 7kbPDC core pathway (FIG. 4A) is used in this study to test for integration.

Materials and Methods
Strains

Figure 2:
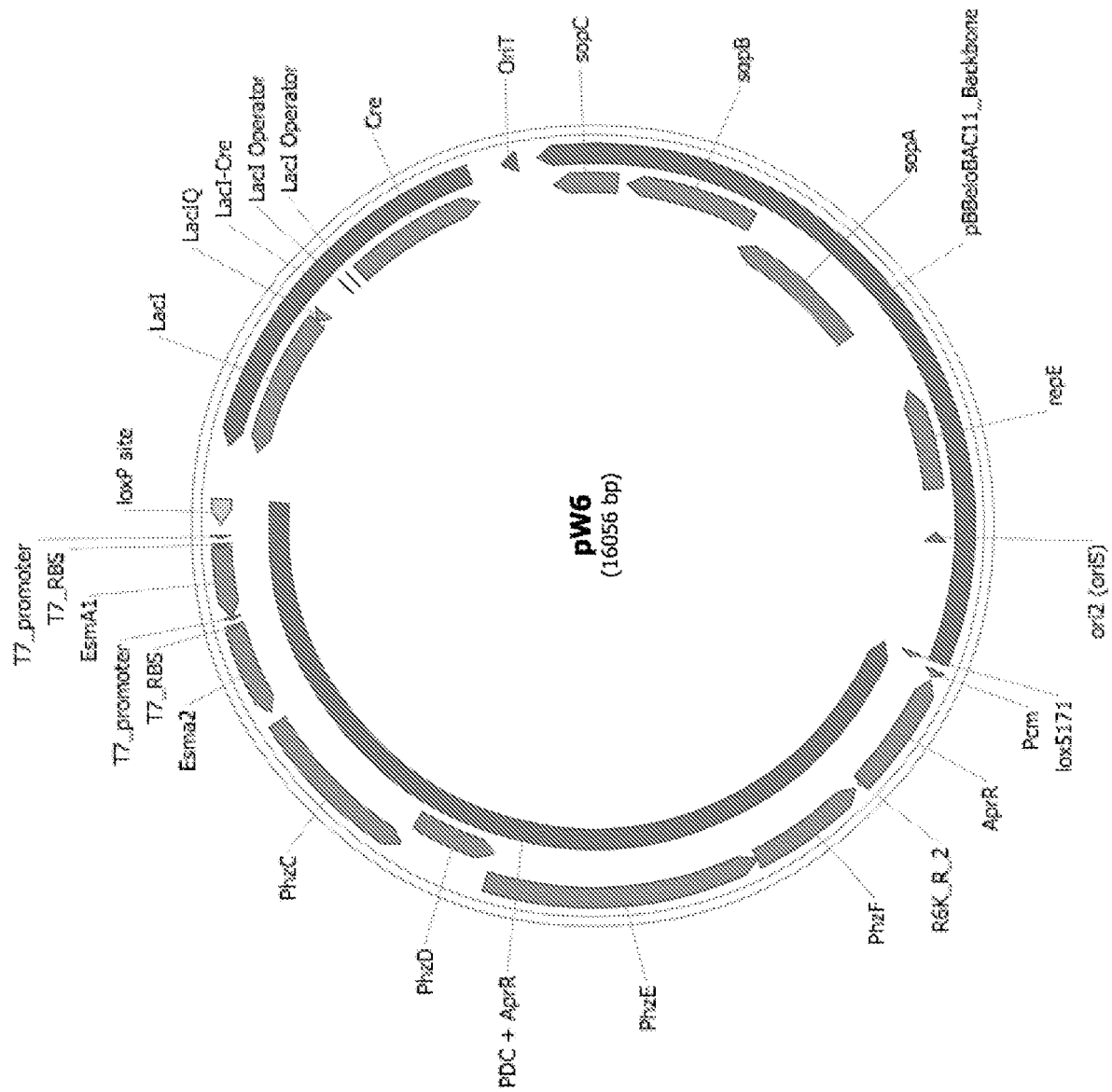
FIG. 2 is a map of the pW6 vector. The pW6 vector is comprised of three parts. Part 1 is the pBeloBAC11 backbone, part 2 is the LacI and lac UV5 driven Cre recombinase, and part 3 is the PDC pathway and Apramycin resistance marker between the two lox sites ("PDC+AprR").

Strains used in this study are listed in Table 2. Plasmids pW1 and pW6 were constructed in this study. Vector maps are shown in FIG. 1 and FIG. 2.

TABLE 2

Strains and Plasmids Used in Example 1

| Names | Features |
|---|---|
| Strains | |
| *E. coli* WM3064 | Conjugation donor, derived from *E. coli* B2155, auxotrophic to 2,3-Diaminopropionic Acid (DAP) |
| *P. fluorescens* WCS417r | Wild type, root colonizer of *Arabidopsis* |
| *P. fluorescens* WCS417r Km-2lox | A wild type strain with landing pad insertion, Kanamycin resistant |
| *P. fluorescens* WCS417r Apr-PDC | PDC integrated to the chromosome, Apramycin resistant |
| Plasmids | |
| pKMW2 | r6k replication origin, carrying OriT for conjugation, Kanamycin resistant, contain marine transposon |
| pW1 | pKMW2 with loxP and lox5171 within the transposon sequence |
| pW6 | Single copy plasmid, constructed based on pBeloBAC-11, carrying LacI driven Cre recombinase, carrying T7-PDC between loxP and lox5171 sites. |

Conjugation was conducted as follows. Donor *E. coli* bacterial strain, WM3064 is derived from B2155 and is auxotrophic for Diaminopimelic acid (DAP). DAP is an amino acid, representing an epsilon-carboxy derivative of lysine. This strain can be used for conjugation experiments (by mobilizing plasmids with RP4) and for the replication of plasmids with the R6K origin of replication (WM3064 has the pir gene). WM3064 was developed by William Metcalf at UIUC. Strain APA752 contains the plasmid pKMW5 in WM3064. pKMW5 is a mariner class transposon vector that confers resistance to kanamycin and is DNA barcoded with a 20mer. Strain APA766 contains the plasmid pKMW7 in WM3064. pKMW7 is a Tn5 class transposon vector that confers resistance to kanamycin and is DNA barcoded with a 20mer.

Different ratios of acceptor to donor (WM3064 with transposon vector) were tested to determine the optimal ratio for maximizing the number of mutants.

On day 1, 10 mL of media was inoculated with the acceptor or recipient strain and the cells were grown to late log phase. 10 mL of LB/Kan/DAP was inoculated with donor strain and grown at 37° C. with shaking until late log phase.

On day 2, the donor cells were pelleted by spinning at 4,000 rpm for 5 minutes. The pellet was washed twice by resuspending in 10 mL of LB and spinning at 4,000 rpm for 5 minutes. The pellet was then resuspended in 10 mL LB. The OD of the washed donor and recipient cultures was determined.

Conjugation was performed with different ratios of donor to recipient cells, for example 4:1, 1:1, and 1:4 (donor: recipient). After the cultures were mixed together, the cells were centrifuged and the supernatant was removed. The cells were then resuspended in 100 ul of the media required for the recipient supplemented with DAP. Three Millipore filters were placed on recipient media with DAP. 40 uL of cell suspension was added to each filter. The conjugation was incubated for 6 to 8 hours at a temperature appropriate for both the donor and recipient.

Filters were placed in 15 mL falcon tube with 2 mL donor media and vortexed to resuspend the cells. $10^{-1}$, $10^{-2}$ and $10^{-3}$ dilutions were plated on recipient media plus kanamycin to select mutants.

Results

*E. coli* WM3064pW1 was conjugated to *P. fluorescence* WCS417r (FIG. 3A). After conjugation, thousands of colonies were obtained on LB Kanamycin (150 ug/ml) plate, and only one colony (*P. fluorescens* 417r Km-2lox 2.2.2) was selected for subsequent pathway integration. The selected *P. fluorescens* 417r Km-2lox grew well on M9 minimum medium, and the landing pad (sequence between two IRs) was detected in it by colony PCR. Since the r6k replication origin is not functional in *P. fluorescens*, the plasmid was not able to replicate in the *P. fluorescens* strain. Therefore, the colony PCR results show the landing pad was successfully inserted into the chromosome of *P. fluorescence* WCS417r (FIG. 3A, right).

*E. coli* WM3064pW6 was conjugated to *P. fluorescence* WCS417r Km-2lox, and colonies were selected by LB Apramycin (50 ug/ml) (FIG. 3B). In this conjugation, IPTG was added to the mixture of donor and recipient cells on the membrane filter during conjugation to induce the expression of Cre recombinase. After conjugation, thousands of colonies were obtained on LB Apramycin (50 ug/ml) plate. 16 colonies were separately streaked on LB Apramycin (50 ug/ml) and LB Kanamycin (150 ug/ml) plates. This counter selection showed that 100% of the colonies grew on LB Apramycin (50 ug/ml), and none of them grew on LB Kanamycin (150 ug/ml). In addition, the PDC pathway between the two lox sites was detected by colony PCR and colony PCR also confirmed the PDC integration occurred at the loxP and lox5171 sites (FIG. 3B, right).

The pW6 backbone outside the loxP and lox5171 region was not detected by colony PCR, indicating that the pW6 was not able to replicate in *P. fluorescens* WCS 417r. This study demonstrates successful integration of the 7.0 kb PDC pathway in the *P. fluorescens* 417r chromosome.

Example 2: Chromosomal Integration of the PCA and PDC Pathways

This study shows the integration and expression of pathways to bacterial chromosomes using the combined transposition, Cre-Lox P, and T7 RNA polymerase strategy. Specifically, in this study, integration and expression of the PCA and the PDC pathways in the chromosome of both *P. fluorescens* WCS417r and *P. fluorescens* Q8r1 was demonstrated.

TABLE 3

Strains and Plasmids used in Example 2

| Names | Features |
|---|---|
| Strains | |
| *E. coli* WM3064 | Conjugation donor, derived from *E. coli* B2155, auxotrophic to 2,3-Diaminopropionic Acid (DAP) |
| *P. fluorescens* WCS417r | Wild type, root colonizer of *Arabidopsis* |
| *P. fluorescens* Q8r1 | Wild type, root colonizer of wheat and corn |
| *P. fluorescens* WCS417r Km-Cre-2lox__C | Mixture of colonies obtained after pW17 conjugated to *P. fluorescens* WCS417r, Kanamycin resistant |
| *P. fluorescens* Q8r1 Km-Cre-2lox__C | Mixture of colonies obtained after pW17 conjugated to *P. fluorescens* Q8r1, Kanamycin resistant |
| *P. fluorescens* 417r Apr-PCA | *P. fluorescens* 417r with PCA pathway integrated to the chromosome |
| *P. fluorescens* Q8r1 Apr-PCA | *P. fluorescens* Q8r1 with PCA pathway integrated to the chromosome |
| *P. fluorescens* Q8r1 Apr-PDC | *P. fluorescens* 417r with PDC2 pathway integrated to the chromosome |
| *P. fluorescens* 417r Apr-PDC | *P. fluorescens* Q8r1 with PDC2 pathway integrated to the chromosome |
| Plasmids | |
| pW17 | Plasmid carrying transposable landing pad, landing pad contains lacI-T7RP, LoxP, Lxo5171 Cas9-driven Cre and Kanamycin resistance |
| pW20 | Single copy plasmid, constructed based on pBeloBAC-11, carrying LacI driven Cre recombinase, carrying T7-PCA between loxP and lox5171 sites. |
| pW21 | Single copy plasmid, constructed based on pBeloBAC-11, carrying LacI driven Cre recombinase, carrying T7-PDC2 between loxP and lox5171 sites. |

*E. coli* WM3064pW17 was conjugated to *P. fluorescence* WCS417r and *P. fluorescens* Q8r1 (FIG. 8A). After conjugation, thousands of colonies were obtained on LB Kanamycin (150 ug/ml) plate, and all colonies on the plates were pooled to make a *P. fluorescens* 417r Km-Cre-2lox consortia and *P. fluorescens* Q8r1 Km-Cre-2lox consortia. The landing pad randomly integrated into the genomes of these two strains, and the presence of the landing pad was detected by colony PCR using each consortium as the template. These two consortia were used for the following experiments.

*E. coli* WM3064pW20 and *E. coli* WM3064pW21 was conjugated to *P. fluorescens* 417r Km-Cre-2lox consortia and *P. fluorescens* Q8r1 Km-Cre-2lox consortia (FIG. 8B). Colonies were selected by LB Apramycin (50 ug/ml). After conjugation, thousands of colonies were obtained on LB Apramycin (50 ug/ml) plate. Four colonies of each combination were picked out and sub-cultured. The rest of the colonies in this conjugation were pulled together and sub-cultured (marked as consortia). The sub-cultured consortia and single colonies were fermented separately downstream for PCA or PDC production detection.

In this conjugation, IPTG was not added to the mixture of donor and recipient cells on the membrane filter during conjugation. However, the Cre-lox recombination efficiency was very high. This could be because of the leaky expression of Cre in the pW20 or pW21 plasmids or due to the Cas9 promoter driven Cre expression in the landing pad.

Engineered strains were cultivated in Luria-Bertani (LB) broth at 28° C. for 72 hrs. Antibiotic supplements were used at the following concentrations: ampicillin: 50 µg/ml, kanamycin 100 µg/ml, rifampicin 50 µg/ml. Cultures were induced for expression with 0.1 mM Isopropyl-β-D-thiogalactopyranoside (IPTG) when they reached of 0.6 OD 600. Cultures were centrifuged and 1.5 ml of supernatant was used for extraction. Supernatants were extracted with 0.5 ml 1.25% TFA and 1.5 ml of ethyl acetate. The ethyl acetate was removed and dried via speed vacuum. Extracts were suspended in acetonitrile and filtered using 0.2 m PTFE filters. Filtered extracts were analyzed via LCMS using an Agilent HPLC and Thermo Q Exactive detector. Separation via HPLC was completed using a C-18 reverse phase column with a 2 µl injection volume. Phenazines were detected and confirmed using comparisons of exact mass, ms/ms fragmentation, and retention time to authentic standards.

The production of PCA or PDC from the consortia or from single colonies was detected qualitatively by LCMS analysis (FIGS. 9A-9E and Table 3). Since PCA is the precursor of PDC, to detect PDC production, both PCA and PDC should be present (FIGS. 9A-9D). The expression of phenazine pathways in the consortia and in the single colonies was successfully detected. All strains exhibited PCA production, indicating that both core phenazine pathways are functional in the recombinant strains and the T7 promoter is functionally driving expression of the pathway. Representative LCMS data were shown in FIGS. 9A-9E only for *P. fluorescens* Q8R1.

TABLE 4

Conjugation Scheme and Compound Production

| | | | Production | |
|---|---|---|---|---|
| Donor | Recipient | Obtained Strain | PCA | PDC |
| *E. coli* WM3064pW20 | *P. fluorescens* 417r Km-Cre-2lox__C | *P. fluorescens* 417r Apr-PCA__consortia | Yes | No |
| | | *P. fluorescens* 417r Apr-PCA | Yes | No |
| *E. coli* WM3064pW20 | *P. fluorescens* Q8r1 Km-Cre-2lox__C | *P. fluorescens* Q8r1 Apr-PCA__consortia | Yes | No |
| | | *P. fluorescens* Q8r1 Apr-PCA | Yes | No |
| *E. coli* WM3064pW21 | *P. fluorescens* 417r Km-Cre-2lox__C | *P. fluorescens* 417r Apr-PDC2 consortia | Yes | Yes |
| | | *P. fluorescens* 417r Apr-PDC2 | Yes | Yes |
| *E. coli* WM3064pW21 | *P. fluorescens* Q8r1 Km-Cre-2lox__C | *P. fluorescens* Q8r1 Apr-PDC2 consortia | Yes | Yes |
| | | *P. fluorescens* Q8r1 Apr-PDC2 #1 | Yes | Yes |

This study showed successful integration and expression of the PCA and PDC pathways in the *P. fluorescens* 417r and *P. fluorescens* Q8r1 chromosomes.

Example 3: Chromosomal Integration and Expression of Bacterial Luciferase Pathways in Two *Pseudomonas fluorescens* Strains This study shows the chromosomal integration and expression of pathways using the transposition, Cre-Lox P, and T7 RNA polymerase combined strategy. Specifically, this study demonstrates integration and expression bacterial luciferase luxCDABE pathway in the chromosome of both *P. fluorescens* WCS417r and *P. fluorescens* Q8r1.

TABLE 5

Strains and Plasmids Used in Example 3

| Names | Features |
|---|---|
| Strains | |
| *E. coli* WM3064 | Conjugation donor, derived from *E. coli* B2155, auxotrophic to 2,3-Diaminopropionic Acid (DAP) |
| *P. fluorescens* WCS417r | Wild type, root colonizer of *Arabidopsis* |
| *P. fluorescens* Q8r1 | Wild type, root colonizer of wheat and corn |
| *P. fluorescens* WCS417r Km-Cre-2lox | Obtained after pW17 conjugated to *P. fluorescens* WCS417r, Kanamycin resistant |
| *P. fluorescens* Q8r1 Km-Cre-2lox | Obtained after pW17 conjugated to *P. fluorescens* Q8r1, Kanamycin resistant |
| *P. fluorescens* 417r Apr-lux | *P. fluorescens* 417r with luxCDABE pathway integrated to the chromosome |
| *P. fluorescens* Q8r1 Apr-lux | *P. fluorescens* Q8r1 with luxCDABE pathway integrated to the chromosome |
| Plasmids | |
| pW17 | Plasmid carrying transposable landing pad, landing pad contains lacI-T7RP, LoxP, Lxo5171 Cas9-driven Cre and Kanamycin resistance |
| pW34 | Medium copy plasmid, carrying T7-luxCDABE between loxP and lox5171 sites. |

Figure 11A:
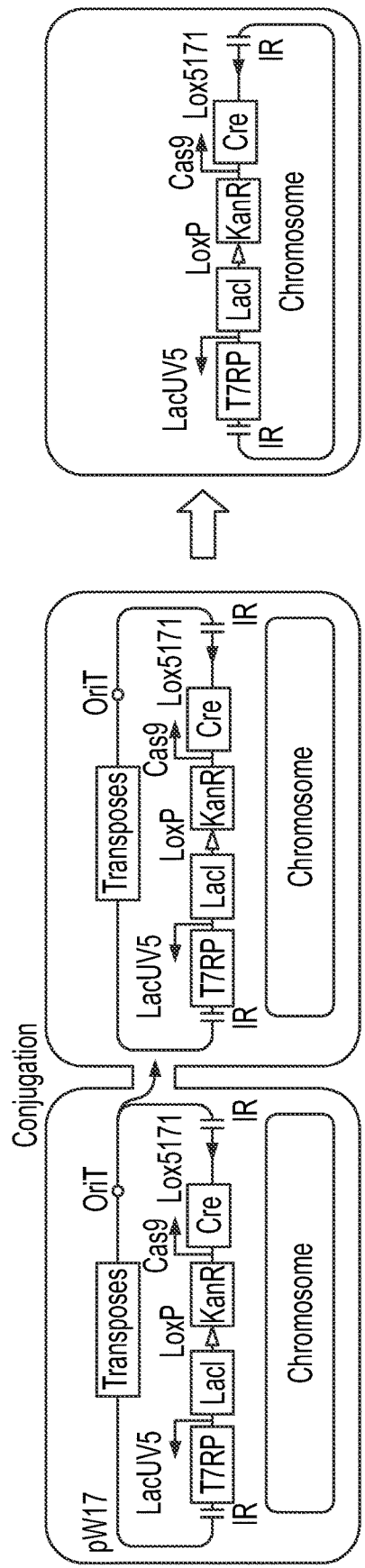
FIGS. 11A-11B show an example of the combined transposition, Cre-LoxP, and T7 RNA polymerase strategy. Donor strain, E. coli WM3064 p17, which harbors the p17 plasmid, is conjugated to a recipient strain, P. fluorescens WCS514r or P. fluorescens Q8r1 resulting in random integration of the landing pad into the P. fluorescens WCS417r or P. fluorescens Q8r1 chromosome (FIG. 11A). The resulting strain is then conjugated to donor strain, E. coli WM3064 pW34, which harbors the pW34 plasmid. After conjugation and recombination by Cre, the Lux pathway and Apramycin gene are integrated into the recipient strain where the Lux pathway is under the control of the T7 RNA polymerase promoter (FIG. 11B).
Figure 11B:
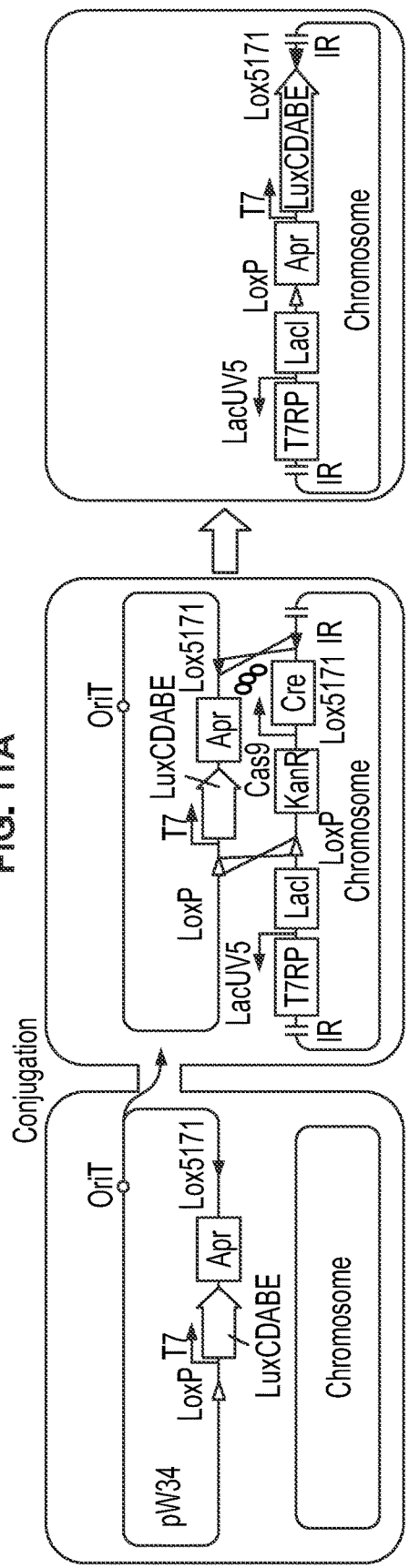

*E. coli* WM3064pW17 was conjugated to *P. fluorescence* WCS417r and *P. fluorescens* Q8r1 (FIG. 11A). After conjugation, thousands of colonies were obtained on LB Kanamycin (150 ug/ml) plate. One single colony from each group was selected and it was confirmed that the landing pad has inserted to these two colonies by colony PCR. These two strains *P. fluorescens* 417r Km-Cre-2lox and *P. fluorescens* Q8r1 Km-Cre-2lox were used for following study.

*E. coli* WM3064pW34 (SEQ ID NO:5) was conjugated to *P. fluorescens* 417r Km-Cre-2lox and *P. fluorescens* Q8r1 Km-Cre-2lox (FIG. 11B). Colonies were selected by LB Apramycin (50 ug/ml). After conjugation, thousands of colonies were obtained on LB Apramycin (50 ug/ml) plate. Three colonies of each combination were picked out and sub-cultured for bioluminescence assay.

*P. fluorescens* strains with the landing pad or with luxCD-ABE were inoculated to 1 mL of LB Kanamycin (150 ug/ml) or LB Apramycin (50 ug/ml). After overnight growth at 28° C. overnight with shaking at 220 rpm, each culture was diluted to OD600 of 0.1. IPTG was added to each well at a final concentration of 0 mM, 0.01 mM, 0.1 mM, and 1.0 mM. Luminescence and OD600 was read at 0, 0.17, 1, 2, 3, 5, and 10 hours using a Synergy H1 Micro-plate reader.

Figure 12A:
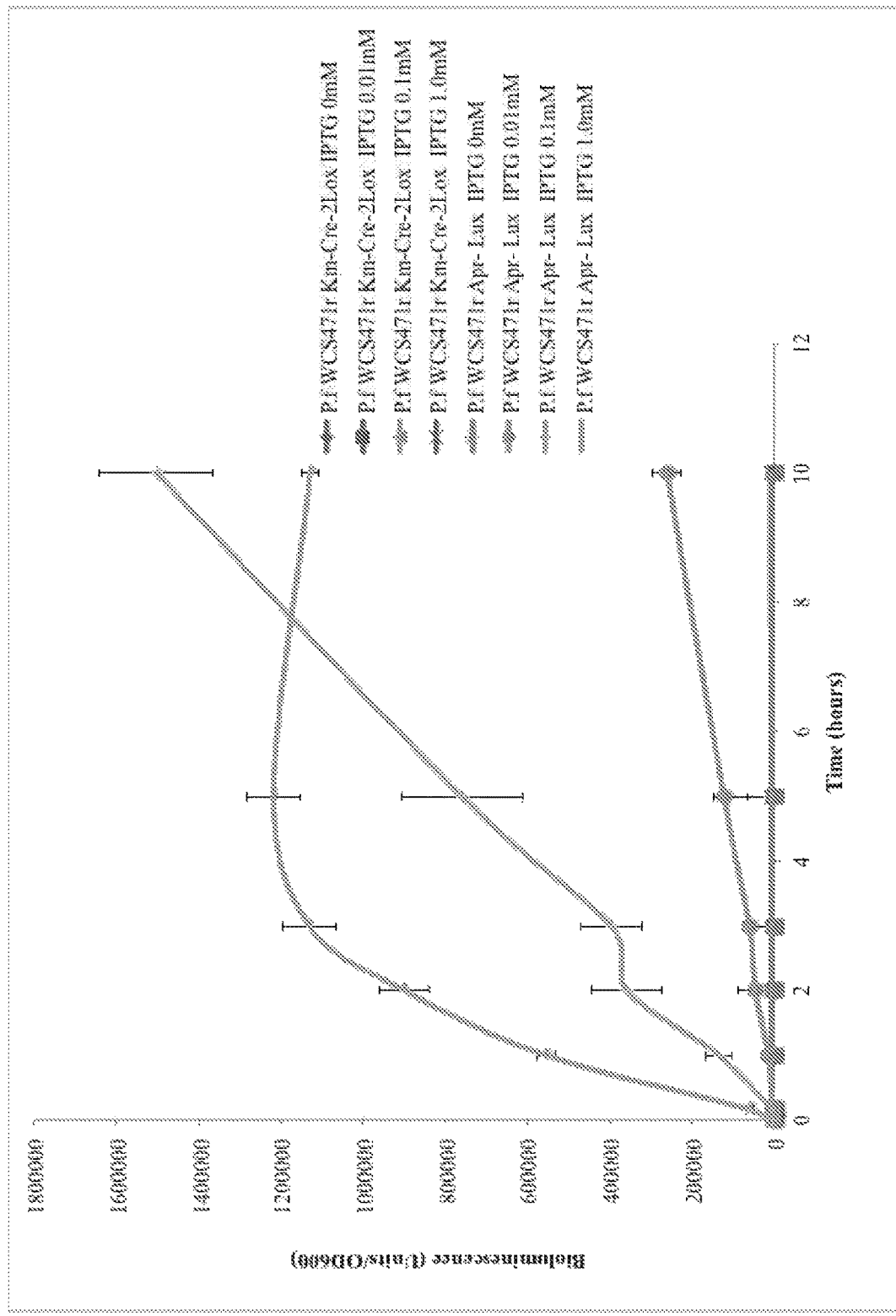
FIGS. 12A-12B show the bioluminescence of P. fluorescence WCS417r Km-Cre-2lox and P. fluorescence WCS417r Apr-Lux (FIG. 12A) and P. fluorescence Q8r1 Km-Cre-2lox and P. fluorescence Q8r1 Apr-lux (FIG. 12B) strains with 0, 0.01, 0.1, and 1 mM IPTG.
Figure 12B:
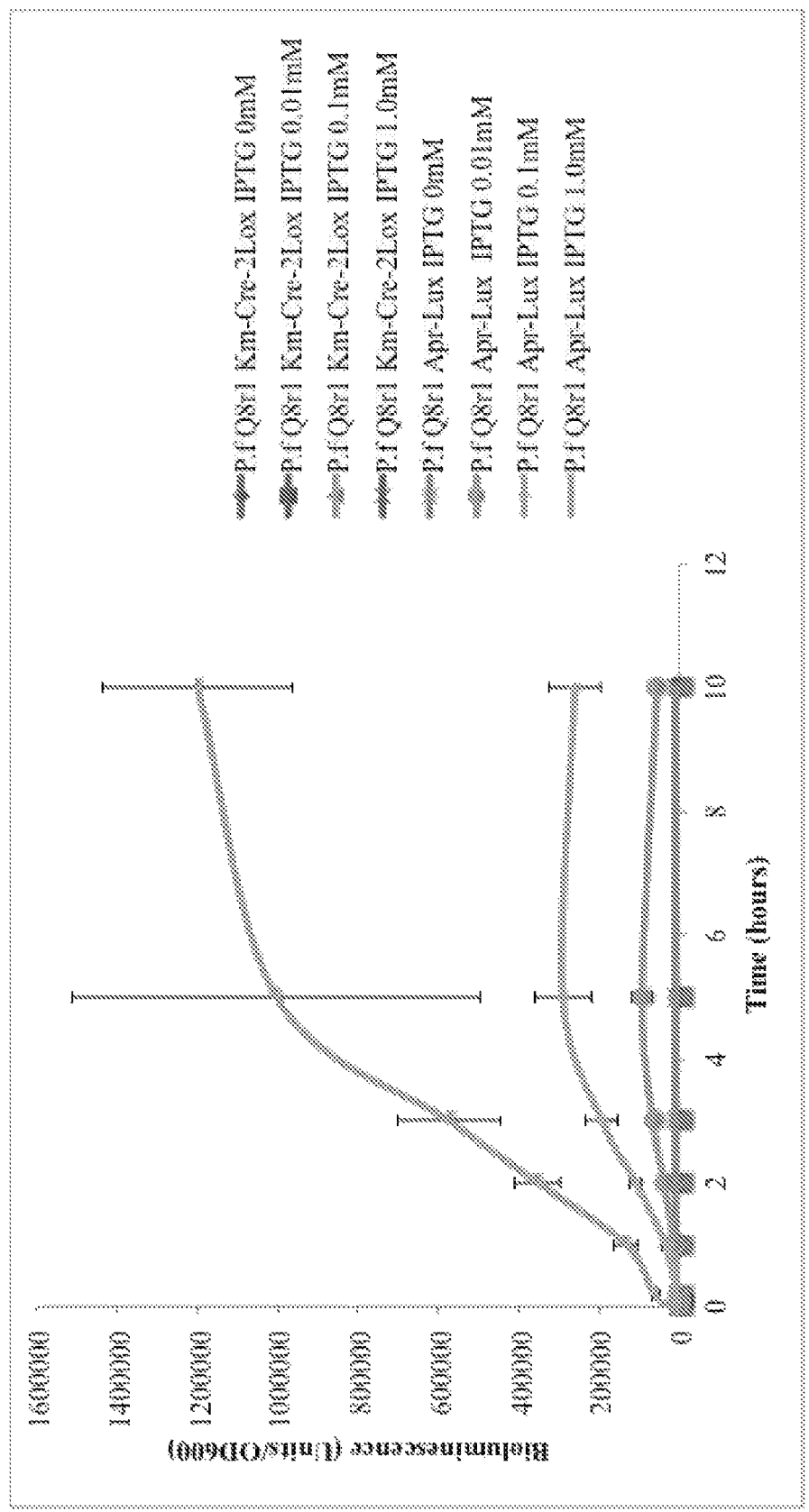

Three independent colonies of *P. fluorescens* WCS417r lux and *P. fluorescens* Q8r1 lux were tested for Bioluminescence. *P. fluorescens* WCS417r Km-Cre-2lox and *P. fluorescens* Q8r1 Km-Cre-2lox were used as control. The results in FIGS. 12A-12B show that the within 5 hours after IPTG induction, the intensity of bioluminescence increased with time. High IPTG induction caused faster increase of the bioluminescence signals.

This study showed the successfully integration and expression of the bacterial luciferase luxCDABE pathway into the *P. fluorescens* 417r and *P. fluorescens* Q8r1 chromosomes. The Cre in the landing pad expressed by the Cas promoter, thus enabling the recombination.

The Cas9 promoter that drives Cre expression in the landing pad is known in the art as a broad host promoter. Therefore, this landing pad could be used in many other strains. Moreover, the pW34 donor vector is constructed from a medium copy vector of about 2 kb, which is easy to construct and can be used to engineer other pathways.

Example 4: Chromosomal Integration and Expression in 32 Strains of Proteobacteria This study was conducted to show that the combined transposition, Cre-LoxP, and T7 RNA polymerase strategy is effective across a wide range of bacterial species.
Materials and Methods Bacterial strains used in this study are listed in Table 5. *E. coli* TOP10 was used to construct pBeloBAC11 based plasmid pW17. *E. coli* EC100D pir+ was used to construct pW34 with r6k replication of origin. 32 strains of γ-proteobacteria to be engineered were purchased from DSMZ (Germany), ATCC, or a gift from David Weller (USDA-ARS) and Jeff Dangl (UNC, Chapel Hill).

TABLE 6

Strains Used in Example 4

| Strain name | Features |
|---|---|
| *E. coli* TOP10 | Cloning host for construction pW17 |
| *E. coli* EC100D pir+ | Constitutively express the π protein (the pir gene product) for replication of plasmids containing the R6Kγ origin of replication; cloning host for constructing pW34 |
| *E. coli* WM3064 | Conjugation donor, derived from *E. coli* B2155, auxotrophic to 2,3-diaminopropionic acid (DAP) |

TABLE 6-continued

Strains Used in Example 4

| Strain name | Features |
| --- | --- |
| *Pseudomonas fluorescens* WCS 417r | γ-proteobacteria to be engineered in this study; conjugation recipients |
| *P. fluorescens* Q8r-r1 | |
| *P. putida* KT2440 ATCC_47054 | |
| *Photorhabdus luminescens* subsp. *laumondii* TTO1 DSM_15139 | |
| *P. luminescens* subsp. *Luminescens* DSM_3368 | |
| *P. temperata* subsp. *khanii* DSM_3369 | |
| *Xenorhabdus doucetiae* DSM_17909 | |
| *X. nematophila* DSM_3370 | |
| *X. szentirmaii* DSM_16338 | |
| *Serratia odorifera* DSM_4582 | |
| *Erwinia oleae* DSM_23398 | |
| *E. piriflorinigrans* DSM_26166 | |
| *E. pyrifoliae* DSM_12163 | |
| *Yersinia aldovae* DSM_18303 | |
| *Y. bercovieri* DSM_18528 | |
| *Y. mollaretii* DSM_18520 | |
| *Y. ruckeri* DSM_18270 | |
| *Y. ruckeri* DSM_18506 | |
| *Dickeya dadantii* subsp. *dadantii* DSM_18020 | |
| *D. dadantii* subsp. *dieffenbachiae* DSM_18013 | |
| *D. solani* DSM_28711 | |
| *D. zeae* DSM_18068 | |
| *Pectobacterium atrosepticum* DSM_18077 | |
| *P. betavasculorum* DSM_18076 | |
| *P. carotovorum* subsp. *carotovorum* DSM_30168 | |
| *P. carotovorum* subsp. *odoriferum* DSM_22556 | |
| *P. wasabiae* DSM_18074 | |
| *Aeromonas encheleia* DSM_11577 | |
| *A. molluscorum* DSM_17090 | |
| *A. piscicola* DSM_23451 | |
| *A. salmonicida* subsp. *pectinolytica* DSM_12609 | |
| *A. salmonicida* subsp. *salmonicida* DSM_19634 | |

Figure 13A:
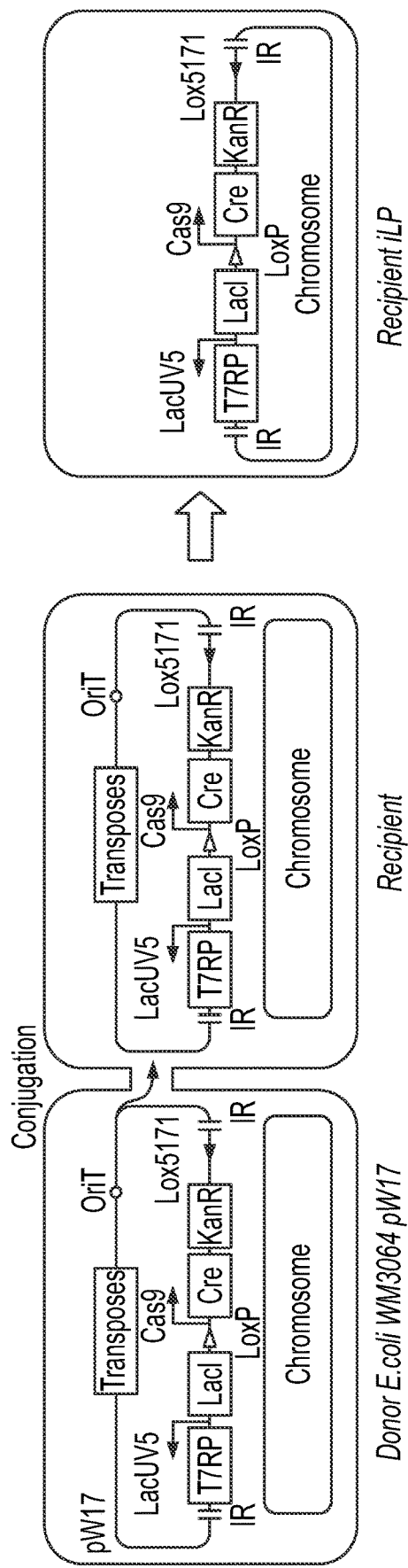
FIGS. 13A-13B show an example of the transposition, Cre-LoxP, and T7 RNA polymerase combined strategy. Donor strain, E. coli WM3064 p17, which harbors the pW17 plasmid, is conjugated to a recipient strain, resulting in random integration of the landing pad into the recipient chromosome (FIG. 13A). The resulting strain is then conjugated to donor strain, E. coli WM3064 pW34, which harbors the pW34 plasmid. After conjugation and recombination by Cre, the Lux pathway and Apramycin gene are integrated into the recipient strain under the control of the T7 RNA polymerase promoter (FIG. 13B).

Conjugation was conducted as described above. Colony PCR was performed using KAPA HiFi PCR kits (KAPA Biosystems, MA) according to standard protocol.

pW17 was transformed to *E. coli* WM3064 by electroporation. Conjugation was established between the donor strain *E. coli* WM3064pW17 and each of the 32 γ-proteobacteria recipients. After pW17 was conjugated to the recipients, the landing pad (sequence between two IRs in pW17) was expected to transpose randomly into the recipient chromosome (FIG. 13A). As a result, lawn of colonies were obtained on LB Kanamycin (50~ 200 ug/ml) plate for 20 strains, hundreds of colonies appeared for 7 strains and less than 100 colonies were obtained for 5 strains. Among them, only 8 and 9 colonies were obtained for *Photorhabdus luminescens* subsp. *laumondii* TTO1 and *P. luminescens* subsp. *luminescens*, suggesting low but detectable conjugation efficiency for those two strains.

After conjugation, 4 to 40 single colonies on the LB Km plates for each of the 32 proteobacteria were randomly selected and screened by colony PCR to detect the landing pad existence. 2 to 24 colonies of each strain carried the landing pad (number varies for each strain). 2 to 10 colonies for each strain with landing pad were inoculated to M9 medium with appropriate kanamycin concentration and their growth were compared with the wild type in M9 medium. At least 2 colonies with landing pad insertion in 28 strains of the 32 strains grew as well as the wild type. Neither wild type nor landing pad insertion colonies of *Photorhabdus temperata* subsp. *khanii*, *Xenorhabdus doucetiae*, *X. nematophila* and *Aeromonas salmonicida* subsp. *salmonicida* grew in M9 medium. As an alternative, 5 to 7 landing pad insertion colonies of those four strains in LB with antibiotics were compared with their wild type in LB medium. All 4 of them grew similarly to wild type.

Figure 13B:
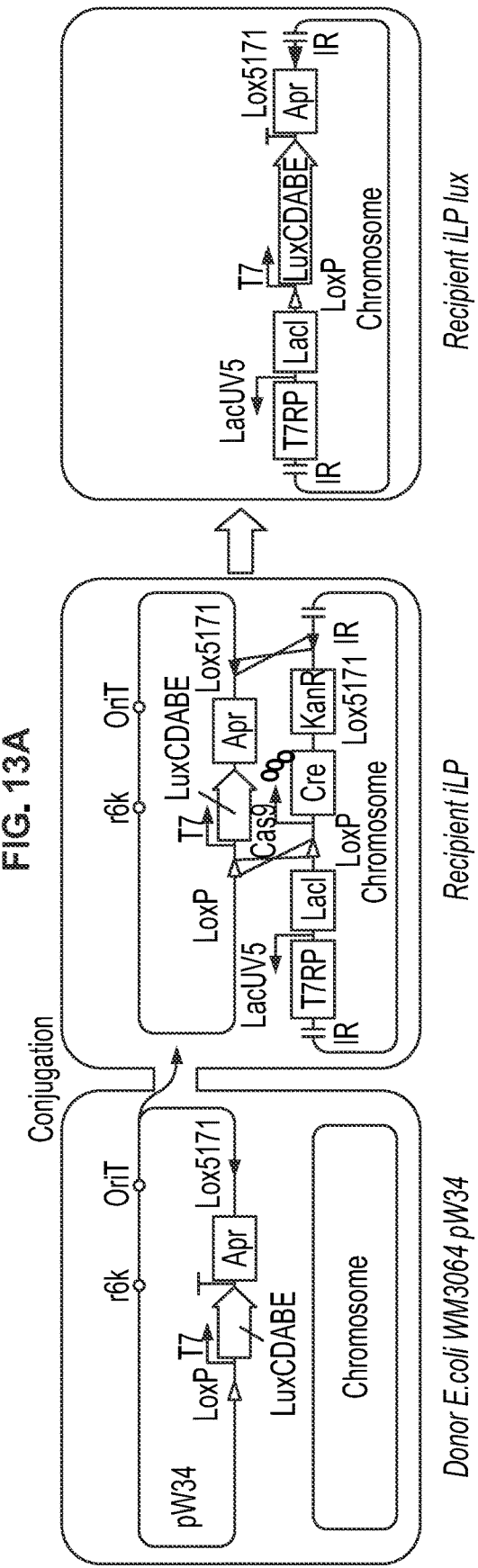

Finally, two colonies (recipient iLP_1 and recipient iLP_2) of each strain with positive testing results were subcultured for subsequent luxCDABE pathway integration experiment (FIG. 13B). These two colonies were thought to most probably contain landing pad insertions into different locations of the bacterial chromosome, and the insertion of landing pad did not affect normal growth of the bacteria. In addition, two lines of each strain were sent to MiSeq sequencing to identify the landing pad insertion locations.

Results pW34 was transformed to *E. coli* WM3064 by electroporation. *E. coli* WM3064pW34 was conjugated to each of the two variants of each recipient carrying the landing pad. LuxCDABE was expected to be integrated into the landing pad at the loxP and lox5171 sites (FIG. 13B). After conjugation, a spot of mixed cultures on the filter was taken with a sterile inoculation loop and streaked on LB apramycin plates (50 or 100 ug/ml) or the mixture were totally plated out on LB apramycin plates (50 or 100 ug/ml). Many colonies were obtained for 30 of the 32 strains. Only a few colonies were obtained for *P. luminescens* subsp. *laumondii* TTO1 and *P. luminescens* subsp. *luminescens*. The second conjugation efficiencies for *P. temperata* subsp. *khanii*, *X. doucetiae*, *X. nematophila*, *X. szentirmaii*, *Erwinia oleae*, *P. carotovorum* subsp. *carotovorum*, *P. carotovorum* subsp. *odoriferum*, *P. wasabiae*, *A. molluscorum* and *A. piscicola* were higher than the first conjugation efficiencies. Ten single colonies were randomly picked and streaked on LB Apr and LB Km plates for counter selection. If the Apr-luxCDABE was successfully integrated to the chromosome under Cre-lox recombination, the resulted colonies were expected to grow and exhibit luminescence LB Apr plates, but show no growth or luminescence on LB Km plates.

The counter selection results showed that among all the 32 strains tested, 22, 4, 1, 1, and 3 of the strains showed 100%, 95%, 90.0%, 80.0%, and 50%, respectively, of the expected antibiotic resistance and luminescence patterns (Table 6). No colony of *Yersinia rohdei* showed the expected pattern. This indicated that 96.9% of the selected strains were able to be engineered, at a very high success rate (87.5% of them have a >80% success rate).

In this plate luminescence assay, no IPTG was added. The leaky expression of T7 RNA polymerase drove the expression of the weak expression of luxCDABE, and therefore images were taken after 20 min of exposure to ensure strong signal. Leaky expression of luxCDABE significantly shortened the screening time and increased the efficiency.

Five colonies of each recipient with luxCDABE integrated into the landing pads in both insertion locations were selected for further luminescent assays in LB under the induction of IPTG. Two sets of 5 colonies were tested for each strain, except *Y. ruckeri* and *Erwinia oleae* which only have one set. The recipient strains with landing pads were used as controls. Single colonies were inoculated to 1 ml LB with appropriate antibiotics and incubated at 28° C. overnight with shaking. Cultures were diluted to OD600 of 0.1-0.2 and added to 96 well black plates with clear bottoms. IPTG was added to the cultures at a final concentration of 0 mM or 1 mM.

Without adding IPTG in the solid media, plates with (or without obvious) bacterial cultures were placed in the Gel Documentation System (BioRad, CA) to collect bioluminescent signals. Images were taken after 20 min of exposure.

Figure 14A:
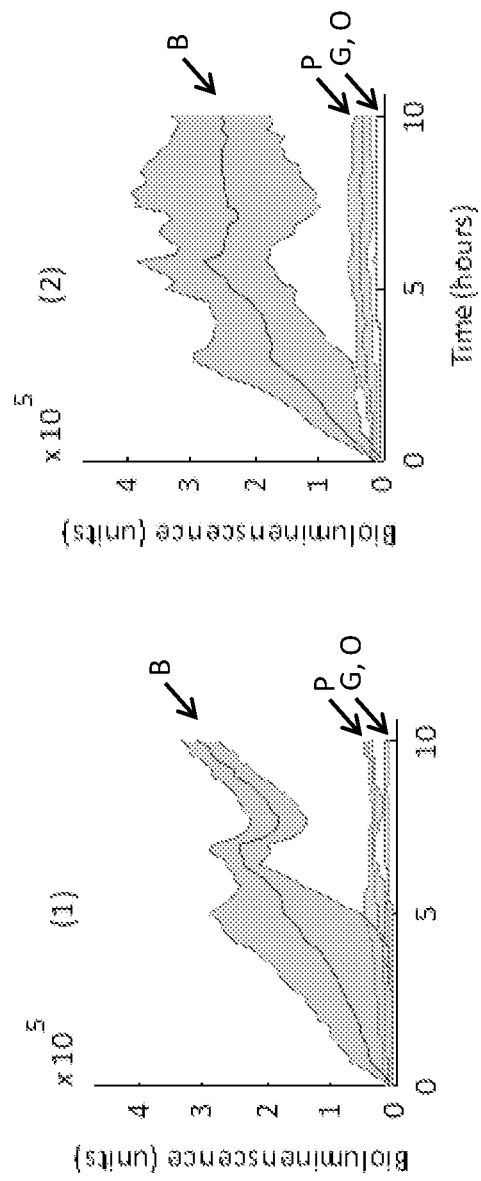
FIGS. 14A-14BB show bioluminescence of 31 strains with the landing pad (control) and with the luxCDABE pathway integrated in the chromosome in two potentially different locations. In each figure, the shaded center line shows the average bioluminescence of 4 to 5 colonies with luxCDABE under 1 mM IPTG induction ("B"). The outside shaded lines show the average plus and average minus standard deviation under 1 mM IPTG induction, with these entire areas shaded. Green ("G") and orange ("O") lines show bioluminescence of strains with the landing pad only and pink lines ("P") show bioluminescence of the mutant strains with 0 mM IPTG induction. Bioluminescence was measured for Photorhabdus luminescens subsp. Laumondii TTO1 (FIG. 14A), P. luminescens subsp. Luminescens (FIG. 14B), Photorhabdus temperate subsp. khanii (FIG. 14C), Xenorhabdus doucetia (FIG. 14D) X. nematophila (FIG. 14E), X. szentirmaii (FIG. 14F), Serratia odorifera (FIG. 14G), Erwinia oleae (FIG. 14H), E. piriflorinigrans (FIG. 14I), E. pyrifoliae (FIG. 14J), Yersinia aldovae (FIG. 14K), Y. bercovieri (FIG. 14L), Y. mollaretii (FIG. 14M), Y. ruckeri (FIG. 14N), Dickeya dadantii subsp. Dadantii (FIG. 14O), D. dadantii subsp. Dieffenbachiae (FIG. 14P), D. solani (FIG. 14Q), D. zeae (FIG. 14R), Pectobacterium atrosepticum (FIG. 14S), P. betavasculorum (FIG. 14T), P. carotovorum subsp. carotovorum (FIG. 14U), P. carotovorum subsp. odoriferum (FIG. 14V), P. wasabiae (FIG. 14W), Aeromonas encheleia (FIG. 14X), A. molluscorum (FIG. 14Y), A. piscicola (FIG. 14Z), A. salmonicida subsp. pectinolytica (FIG. 14AA), A. salmonicida subsp. salmonicida (FIG. 14BB). A. pisciola (FIG. 14Z) and A. salmonicida subsp. pectinolytica (FIG. 14AA) were induced with 0.1 or 0 mM IPTG rather than 1 or 0 mM.
Figure 14B:
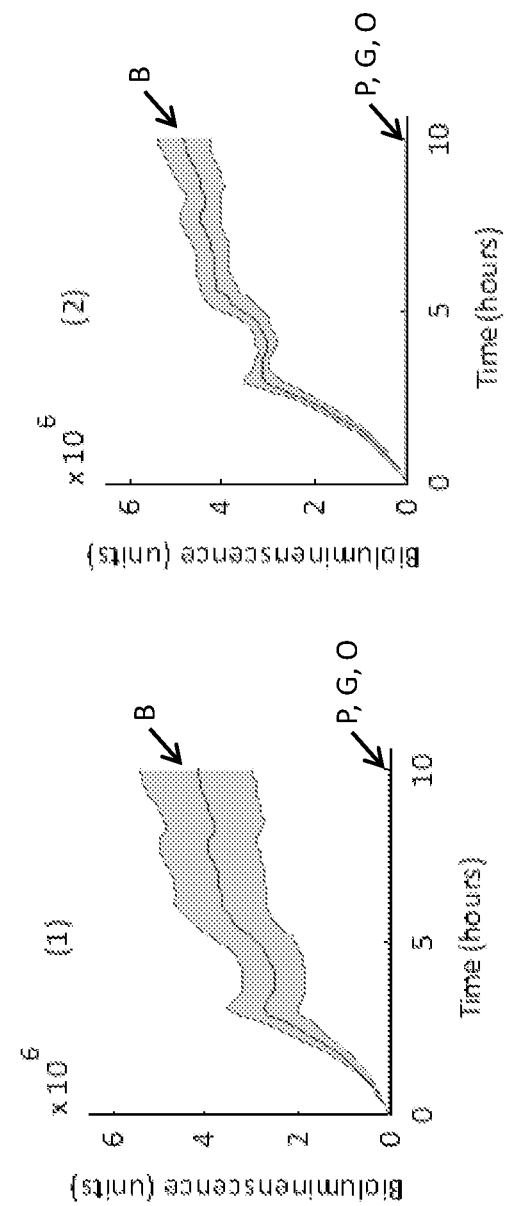
Figure 14E:
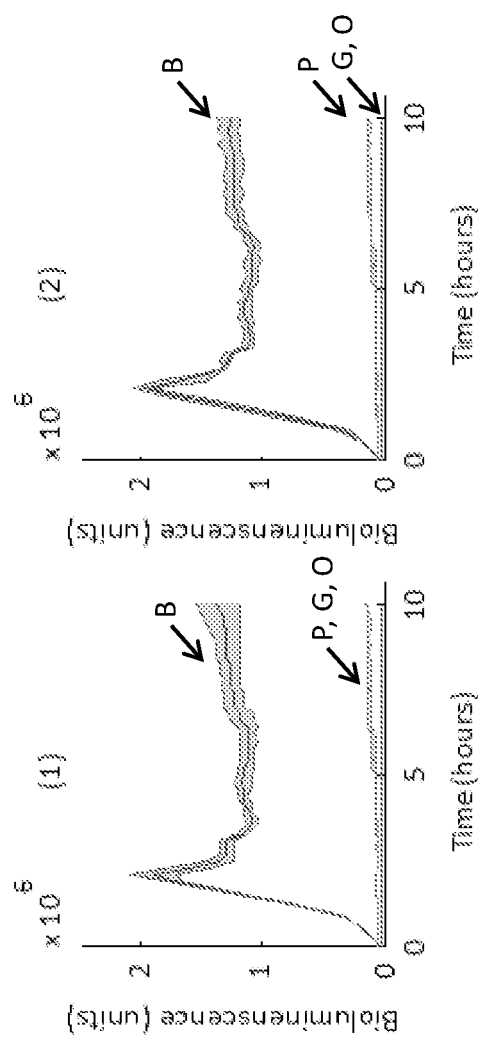
Figure 14F:
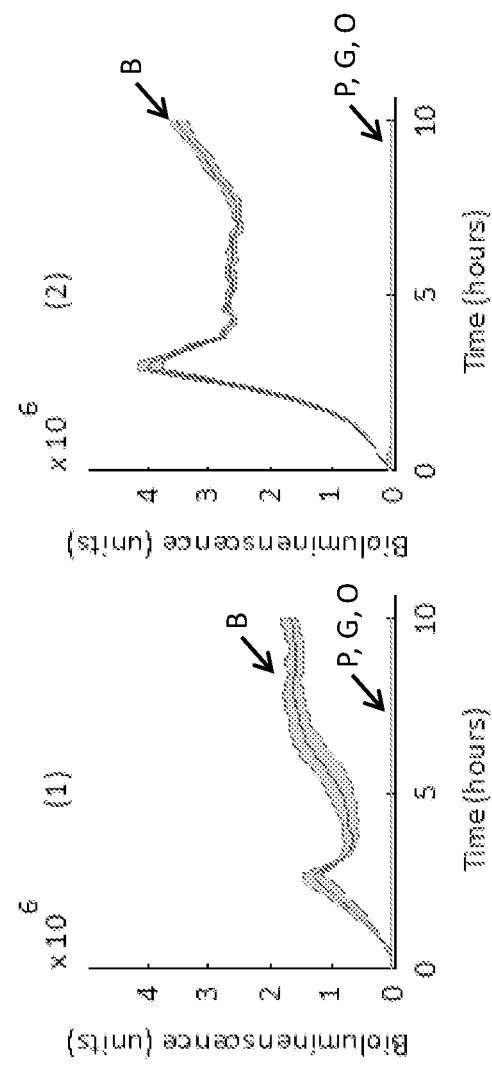
Figure 14G:
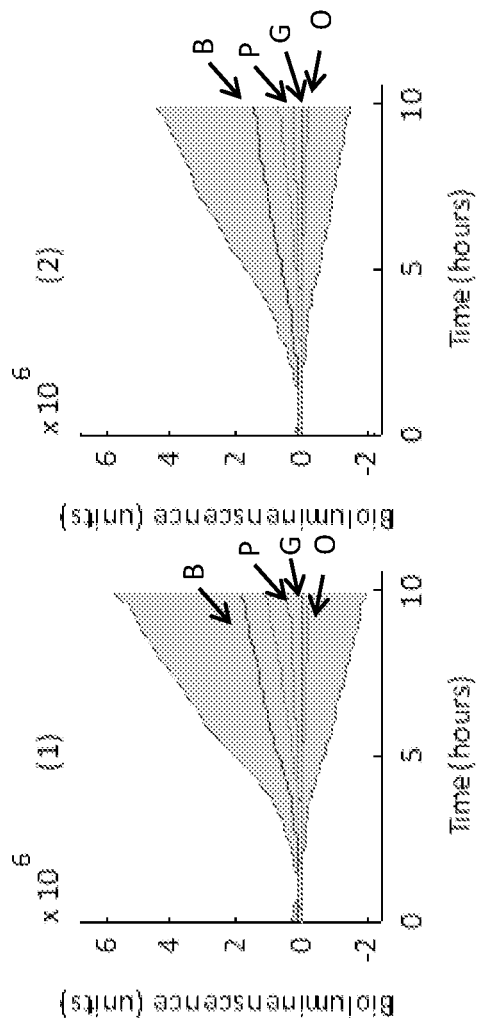
Figure 14H:
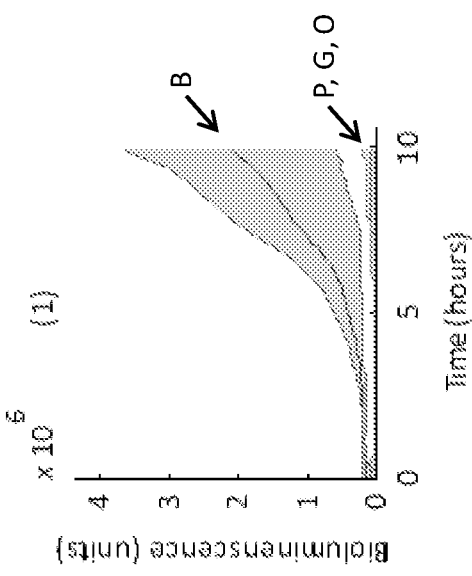
Figure 14I:
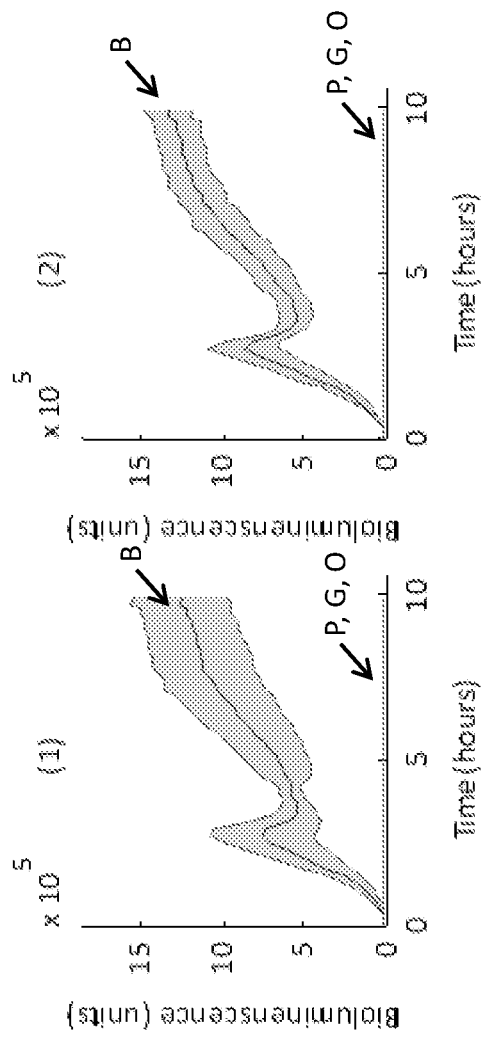
Figure 14J:
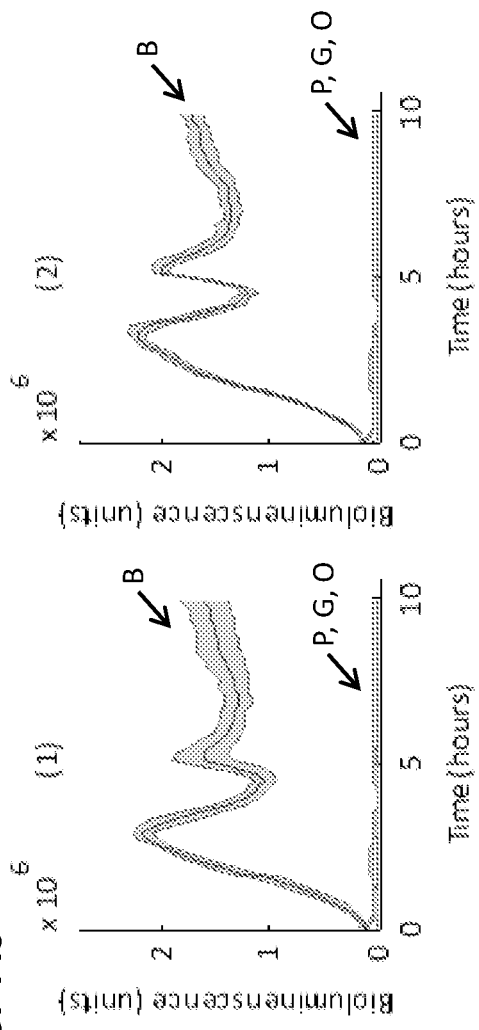
Figure 14K:
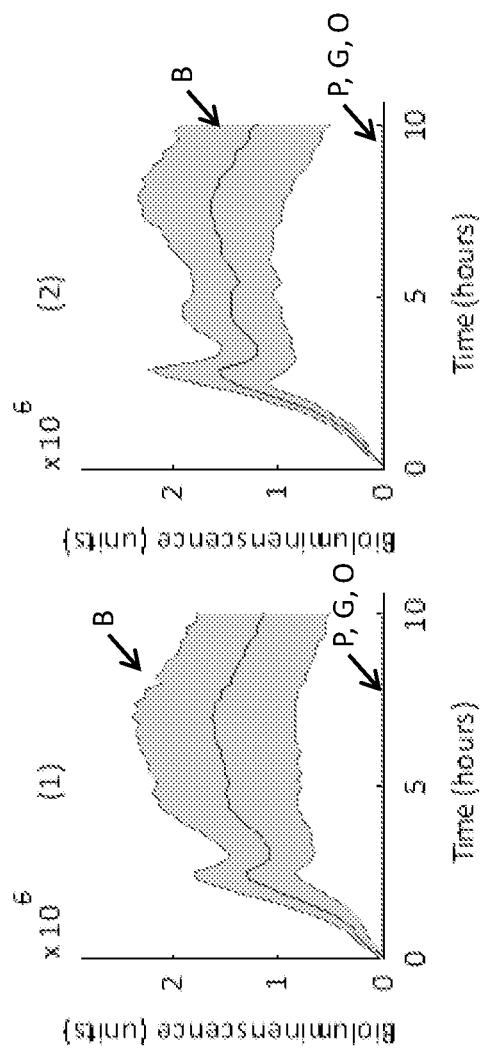
Figure 14L:
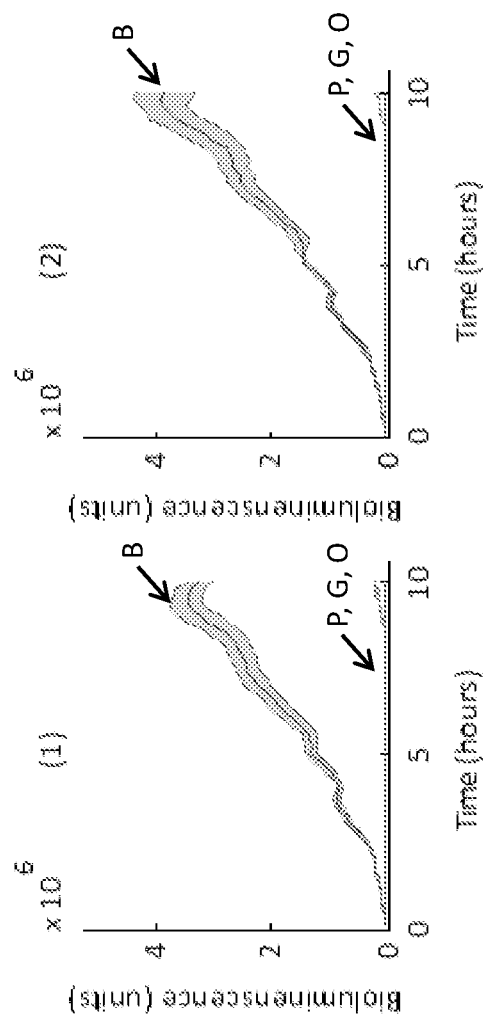
Figure 14M:
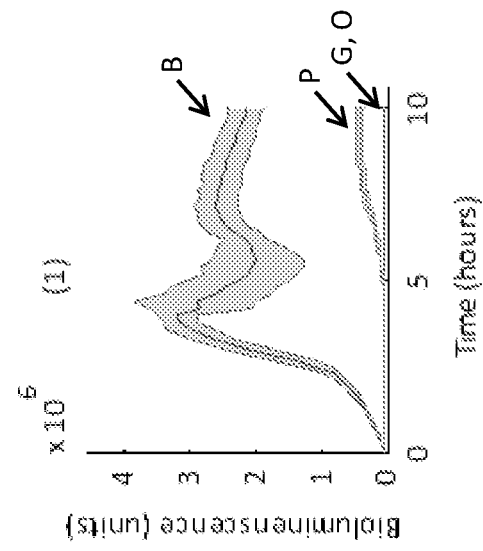
Figure 14N:
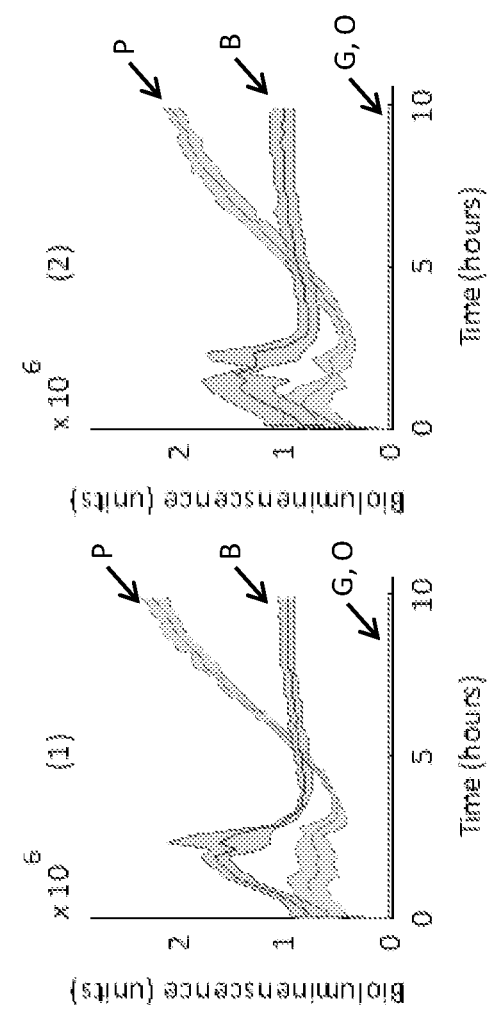
Figure 14O:
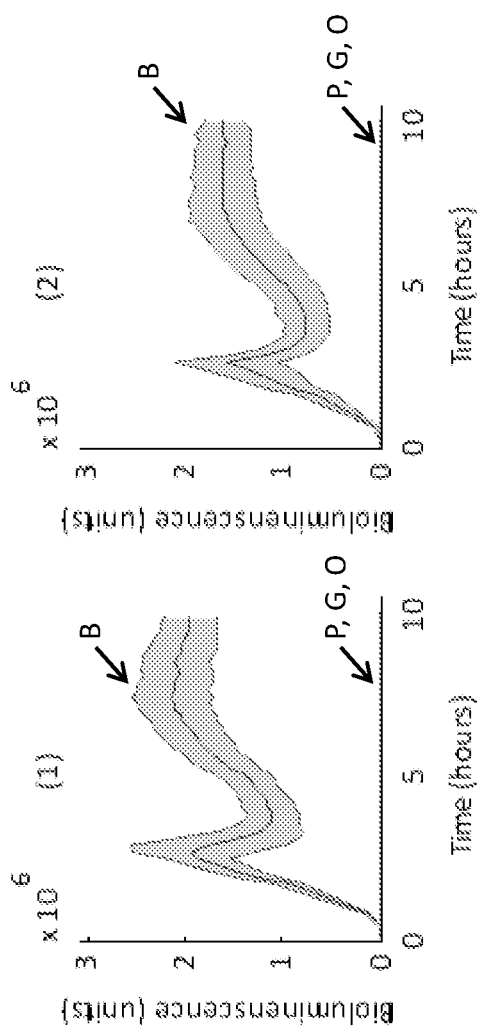
Figure 14P:
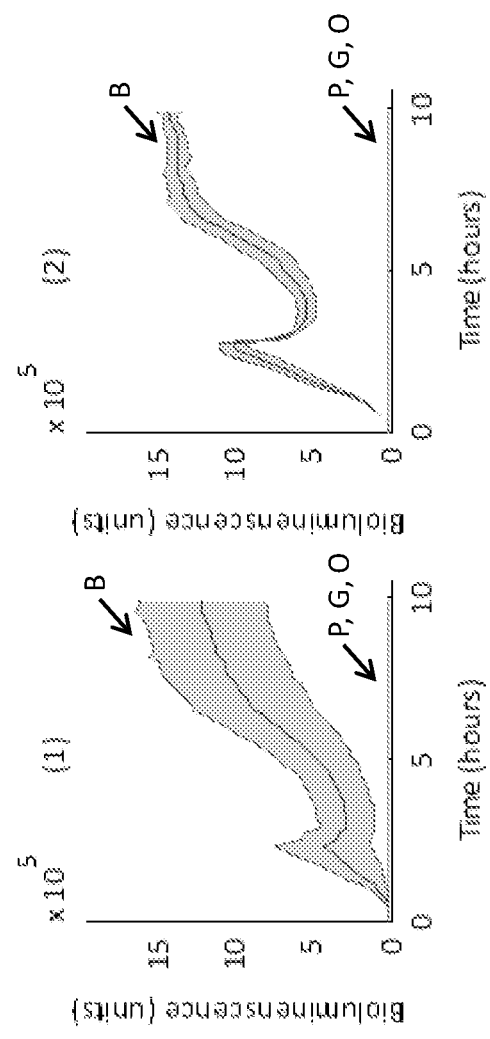
Figure 14Q:
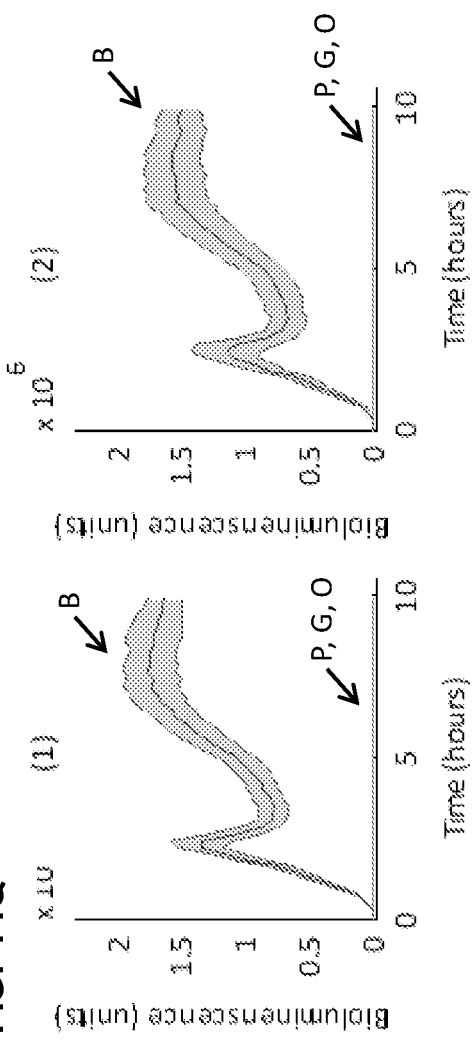
Figure 14R:
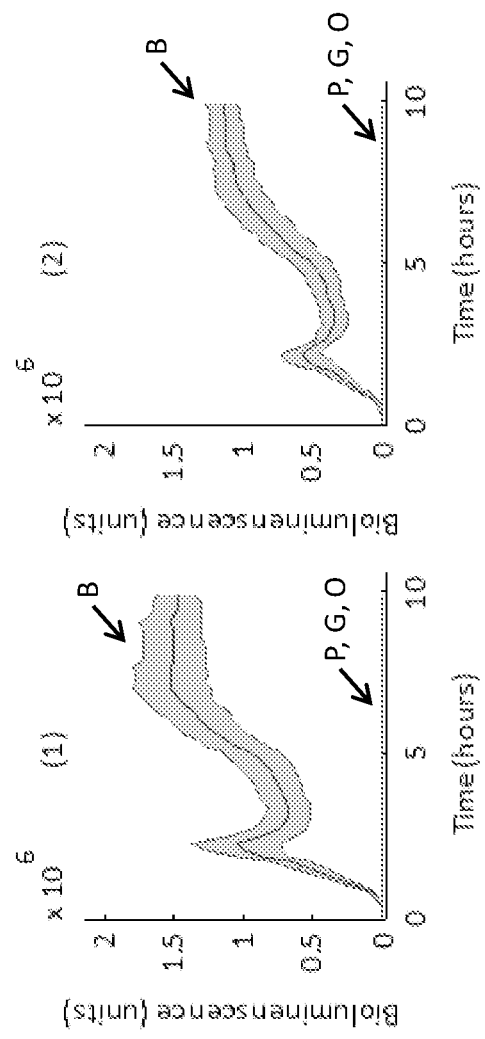
Figure 14S:
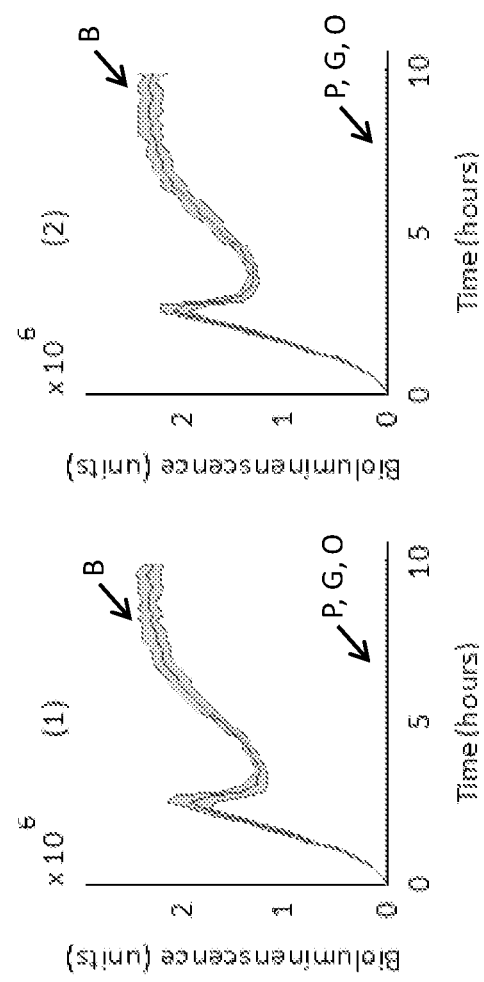
Figure 14T:
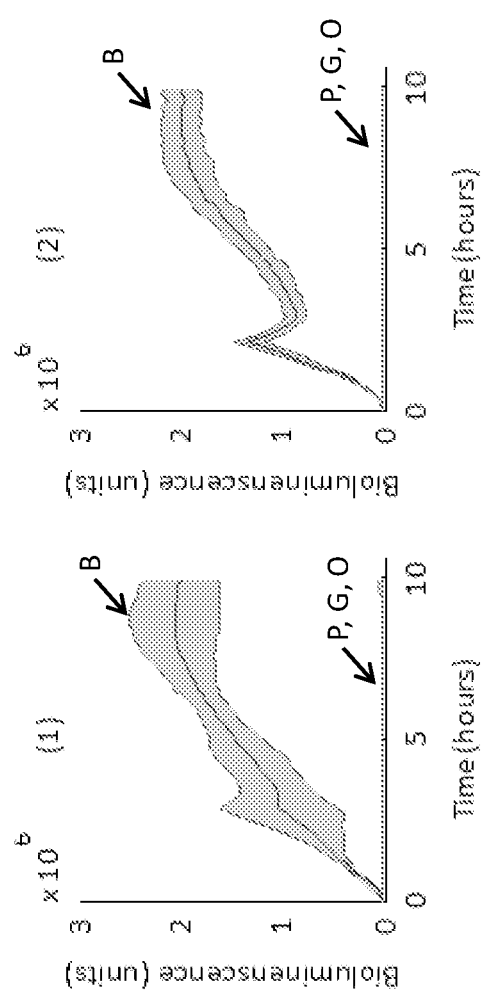
Figure 14U:
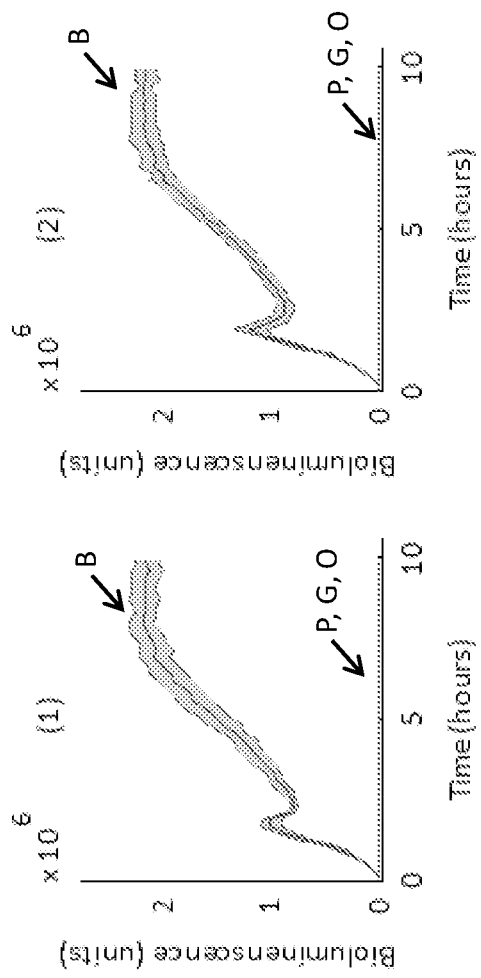
Figure 14V:
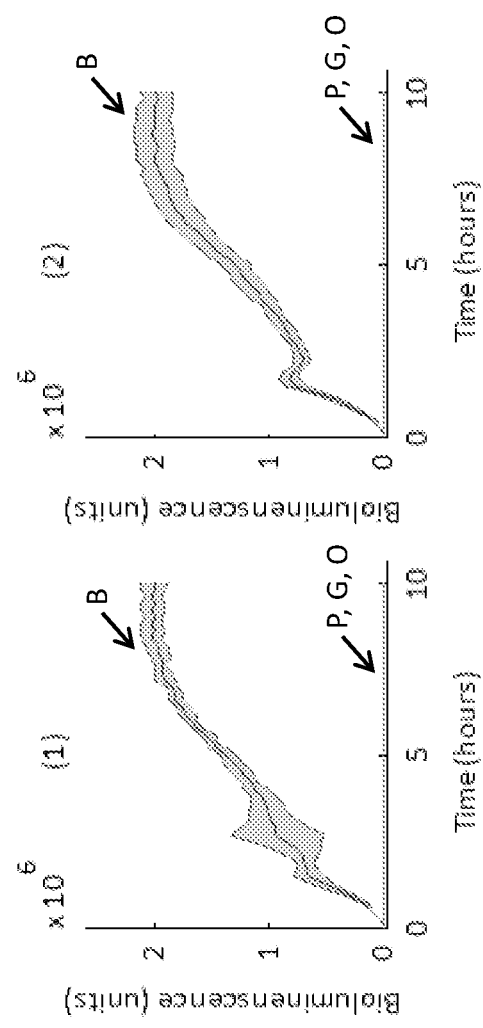
Figure 14W:
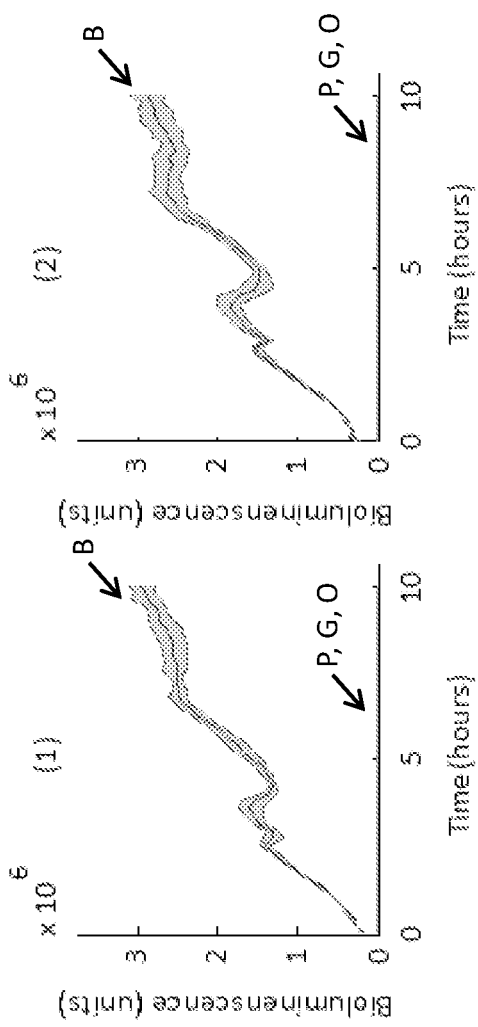
Figure 14X:
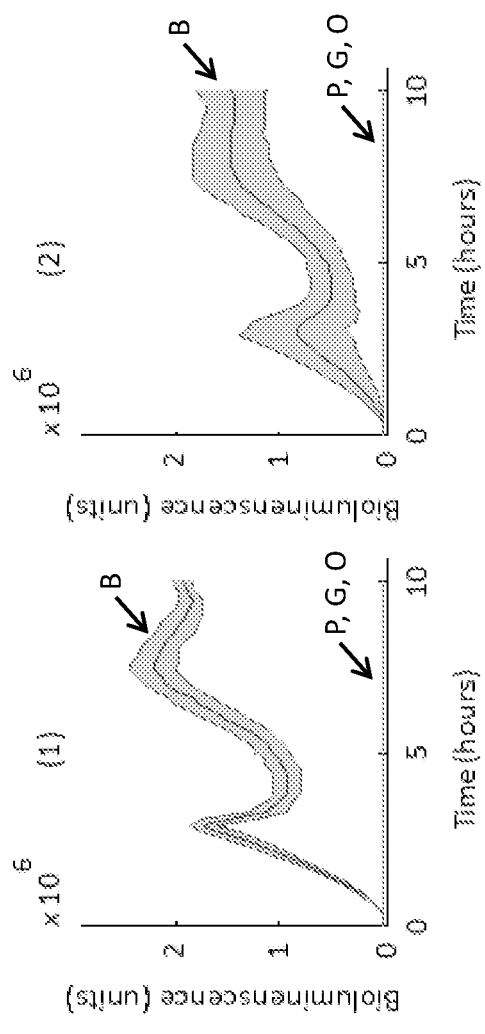
Figure 14Y:
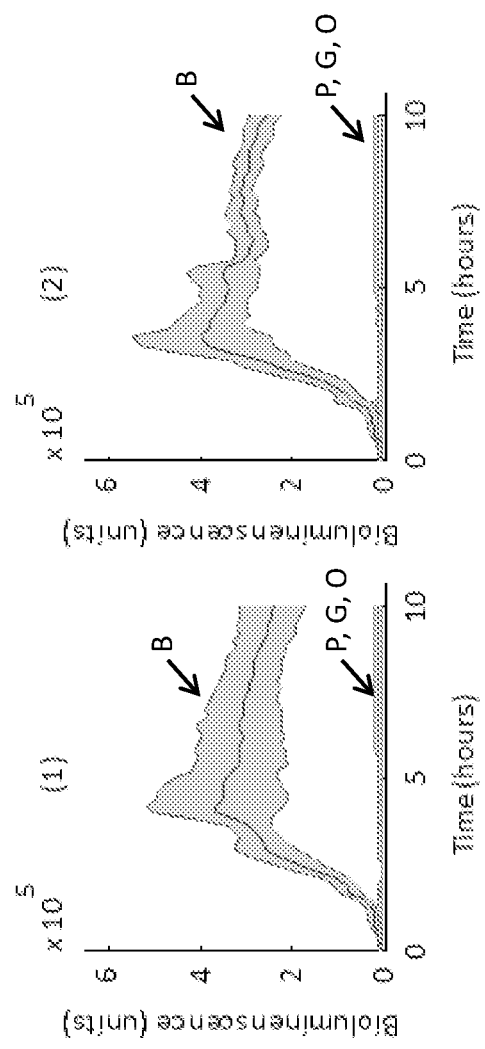
Figure 14Z:
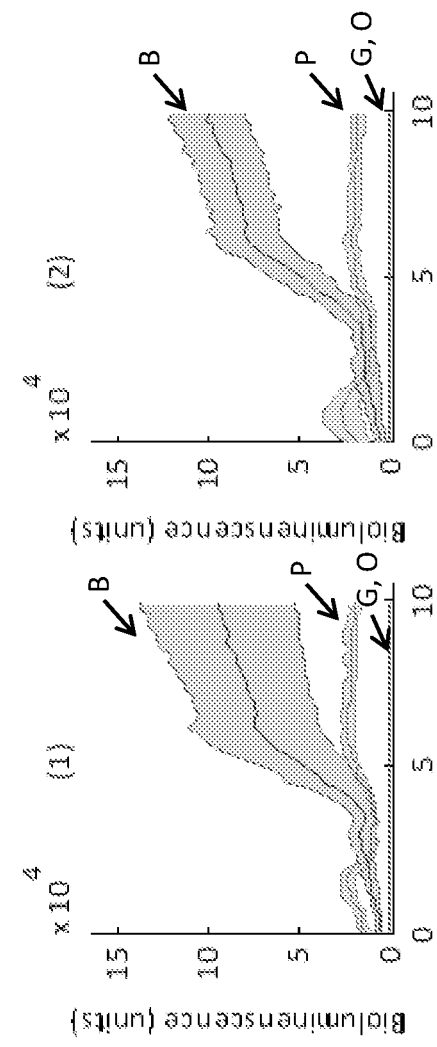
Figure 14A:
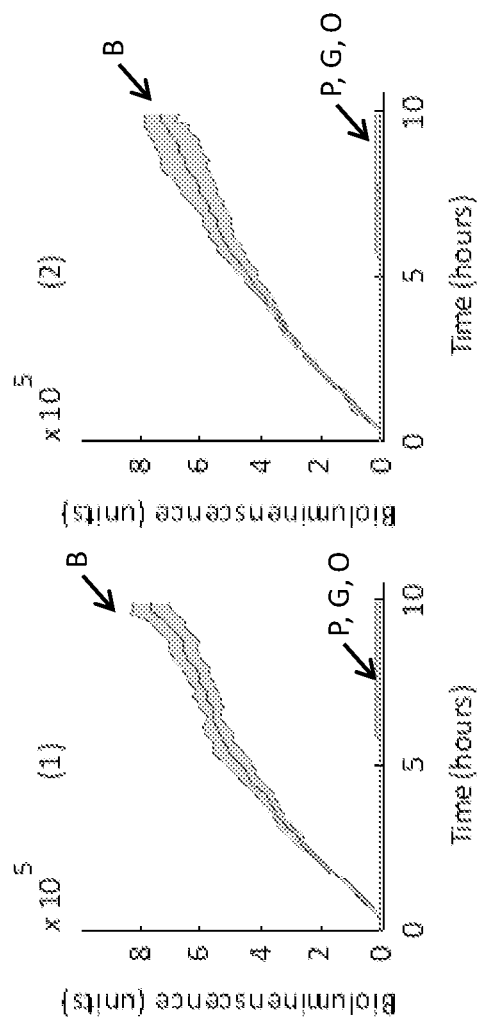
Figure 14B:
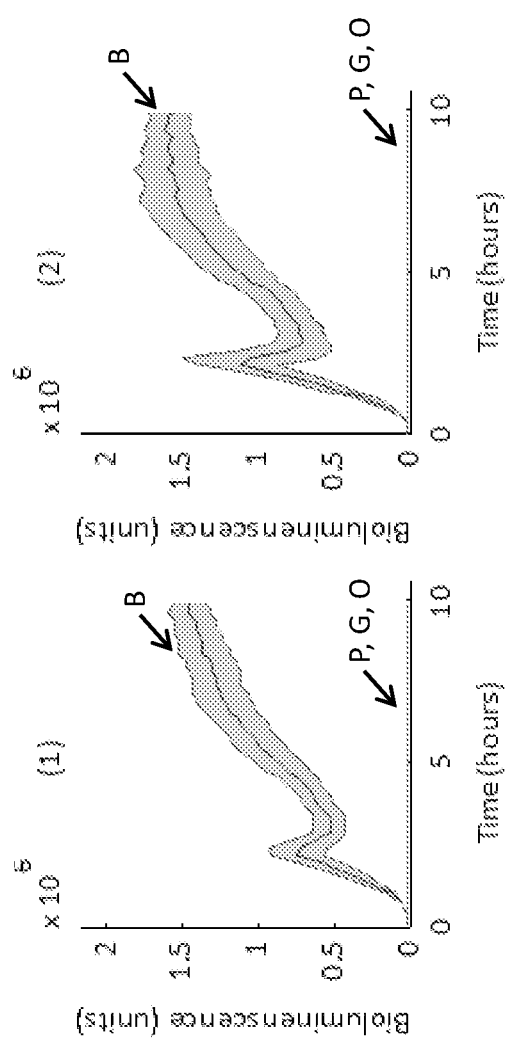

Bioluminescence of the culture was measured using a Synergy H1 Micro-plate reader at intervals of 12 min for up to 10 hours. All of the 1 mM IPTG induced recipients with luxCDABE showed significant higher luminescence than uninduced cells and the controls (except Dickeya dadantii subsp. dadantii and *Serratia odorifera*) (FIGS. 14A-14BB).

TABLE 7

Bioluminescent Plate Bioassay and Counter Selection Results

| | iLP_1-lux | | | | iLP_2-lux | | | |
|---|---|---|---|---|---|---|---|---|
| | Apr | | Kan | | Apr | | Kan | |
| Bacterial strain | Groww+* | Lum+* | Grow+ | Lum+ | Grow+ | Lum+ | Grow+ | Lum+ |
| *Photorhabdus luminescens* subsp. *laumondii* TTO1 | 10 | 10 | 1 | 0 | 10 | 10 | 0 | 0 |
| *P. luminescens* subsp. *Luminescens* | 10 | 10 | 0 | 0 | 10 | 10 | 0 | 0 |
| *P. temperata* subsp. Khanii | 10 | 10 | 0 | 0 | 10 | 10 | 0 | 0 |
| *Xenorhabdus doucetiae* | 10 | 9 | 4 | 0 | 10 | 10 | 0 | 0 |
| *X. nematophila* | 10 | 10 | 0 | 0 | 10 | 10 | 0 | 0 |
| *X. szentirmaii* | 10 | 10 | 0 | 0 | 10 | 10 | 1 | 1 |
| *Serratia odorifera* | 10 | 10 | 0 | 0 | 10 | 10 | 0 | 0 |
| *Erwinia oleae* | 10 | 10 | 10 | 10 | 10 | 10 | 0 | 0 |
| *E. pirifloriinigrans* | 10 | 10 | 0 | 0 | 10 | 10 | 0 | 0 |
| *E. pyrifoliae* | 10 | 10 | 0 | 0 | 10 | 10 | 0 | 0 |
| *Yersinia aldovae* | 10 | 10 | 0 | 0 | 10 | 0 | 0 | 0 |
| *Y. bercovieri* | 10 | 10 | 0 | 0 | 10 | 10 | 0 | 0 |
| *Y. mollaretii* | 10 | 10 | 0 | 0 | 10 | 10 | 0 | 0 |
| *Y. rohdei* | 10 | 0 | 10 | 0 | 10 | 0 | 10 | 0 |
| *Y. ruckeri* | 10 | 10 | 10 | 10 | 10 | 10 | 0 | 0 |
| *Dickeya dadantii* subsp. *Dadantii* | 10 | 10 | 0 | 0 | 10 | 10 | 0 | 0 |
| *D. dadantii* subsp. *Dieffenbachiae* | 10 | 10 | 0 | 0 | 10 | 10 | 0 | 0 |
| *D. solani* | 10 | 10 | 0 | 0 | 10 | 10 | 0 | 0 |
| *D. zeae* | 10 | 10 | 0 | 0 | 10 | 10 | 0 | 0 |
| *Pectobacterium atrosepticum* | 10 | 10 | 0 | 0 | 10 | 10 | 0 | 0 |
| *P. betavasculorum* | 10 | 10 | 0 | 0 | 10 | 10 | 0 | 0 |
| *P. carotovorum* subsp. *carotovorum* | 10 | 10 | 0 | 0 | 10 | 10 | 0 | 0 |
| *P. carotovorum* subsp. *odoriferum* | 10 | 10 | 0 | 0 | 10 | 10 | 0 | 0 |
| *P. wasabiae* | 10 | 10 | 0 | 0 | 10 | 10 | 0 | 0 |
| *Aeromonas encheleia* | 10 | 10 | 0 | 0 | 10 | 10 | 1 | 1 |
| *A. molluscorum* | 10 | 10 | 1 | 0 | 10 | 10 | 0 | 0 |
| *A. piscicola* | 10 | 10 | 2 | 2 | 10 | 10 | 0 | 0 |
| *A. salmonicida* subsp. *pectinolytica* | 10 | 10 | 0 | 0 | 10 | 10 | 0 | 0 |
| *A. salmonicida* subsp. *salmonicida* | 10 | 10 | 0 | 0 | 10 | 10 | 0 | 0 |
| *P. fluorescence* WCS 417r | 10 | 10 | 0 | 0 | 10 | 10 | 0 | 0 |
| *P. putida* KT2440 | 10 | 10 | 0 | 0 | 10 | 10 | 0 | 0 |
| *P. fluorescence* Q8-R1 | 10 | 10 | 0 | 0 | 10 | 10 | 0 | 0 |

*grow+ indicates the streaked culture from single colonies grow well on LB plates corresponding antibiotics.
*lum+ indicates the streaked culture from single colonies exhibited luminescence on LB plates with corresponding antibiotics.

Discussion

These results demonstrate that a ~7 kb bacterial luciferase gene cluster luxCDABE was successfully integrated into the genome of 31 gamma-proteobacteria, and the gene cluster was successfully expressed under IPTG induction. Interestingly, the conjugation efficiency for pathway integration was generally higher than in the first conjugation for landing pad transposition. Without being bound by theory, it is possible that the Cre-lox recombination is more efficient than the landing pad insertion after the plasmid was conjugated into the recipient cells. In this study, we selected two variants that contain the landing pad after the first conjugation for following pathway integration. Since those two variants grew as robustly as the wild type in M9 minimum medium, without being bound by theory, we hypothesize that the insertions of the landing pads are likely in non-essential regions in the genome that do not cause detrimental effects on the host.

This strategy can provide a universal means to engineer bacteria across all phyla, since it does not depend on traditional plasmid expression systems or homologous recombination. This strategy uses conjugation to transfer DNA from *E. coli* to different bacteria, which has been previously demonstrated between *E. coli* to many bacteria (Goessweiner-Mohr, N., et al., *Conjugation in Gram-Positive Bacteria*, Microbiol Spectr, 2014. 2(4); Mazodier, P., R. Petter, and C. Thompson, Intergeneric Conjugation between *Escherichia-Coli* and *Streptomyces Species*, Journal of Bacteriology, 1989. 171(6): p. 3583-3585), or even yeast (Hayman, G. T. and P. L. Bolen, *Movement of Shuttle Plasmids from Escherichia coli into Yeasts Other Than Saccharomyces cerevisiae Using Trans-kingdom Conjugation*. Plasmid, 1993. 30(3): p. 251-257). Mariner transposon (Himar1) also has a broad distribution, and its horizontal transfer does not require species-specific host factors, because it binds to the inverted terminal repeat sequences of its cognate transposon and mediates 5' and 3' cleavage of the element termini (Lampe, D. J., M. E. A. Churchill, and H. M. Robertson, *Purified mariner transposase is sufficient to mediate transposition in vitro*, Embo Journal, 1996. 15(19): p. 5470-5479). It has been reported to transpose into a very broad host range that includes various species of Proteobacteria, Bacteroidetes, Firmicutes, Actinobacteria and Spirochaetes (Ongley, S. E., et al., *Recent advances in the heterologous expression of microbial natural product biosynthetic pathways*, Natural Product Reports, 2013. 30(8): p. 1121-1138), even in vitro (Pelicic, V., et al., *Mutagenesis of Neisseria meningitidis by in vitro transposition of Himar1 mariner*, Journal of Bacteriology, 2000. 182(19): p. 5391-5398. and mammalian cells Zhang, L. N., et al., *The Himar1 mariner transposase cloned in a recombinant adenovirus vector is functional in mammalian cells*. Nucleic Acids Research, 1998. 26(16): p. 3687-3693).

Meanwhile, the Cre-lox recombination strategy has already allowed implementation of large pathways comprising at least ~59 kb in some species of γ-proteobacteria with high efficiency, accuracy, and precision (Santos, C. N., D. D. Regitsky, and Y. Yoshikuni, *Implementation of stable and complex biological systems through recombinase-assisted genome engineering*, Nat Commun, 2013. 4: p. 2503). In addition, both the Cre-lox recombination and T7 drive gene or pathways expression have been demonstrated to function in vitro (Qin, M. M., et al., *Site-Specific Cleavage of Chromosomes in-Vitro through Cre-Lox Recombination*, Nucleic Acids Research, 1995. 23(11): p. 1923-1927; Kohrer, C., et al., *Use of T7 RNA polymerase in an optimized Escherichia coli coupled in vitro transcription-translation system—Application in regulatory studies and expression of long transcription units*, European Journal of Biochemistry, 1996. 236(1): p. 234-239.), and in various bacteria (Marx, C. J. and M. E. Lidstrom, *Broad-host- range cre-lox system for antibiotic marker recycling in Gram-negative bacteria*, Biotechniques, 2002. 33(5): p. 1062-1067; Lussier, F. X., F. Denis, and F. Shareck, *Adaptation of the highly productive T7 expression system to Streptomyces lividans*, Appl Environ Microbiol, 2010. 76(3): p. 967-70; Conrad, B., et al., *A T7 promoter-specific, inducible protein expression system for Bacillus subtilis*, Mol Gen Genet, 1996. 250(2): p. 230-6), or even yeast (Ribeiro, O., et al., *Application of the Cre-loxP system for multiple gene disruption in the yeast Kluyveromyces marxianus*, J Biotechnol, 2007. 131(1): p. 20-6; Pinkham, J. L., A. M. Dudley, and T. L. Mason, *T7 RNA polymerase-dependent expression of COXI in yeast mitochondria*, Mol Cell Biol, 1994. 14(7): p. 4643-52) and mammalian cells (Yu, Y. and A. Bradley, *Engineering chromosomal rearrangements in mice*, Nat Rev Genet, 2001. 2(10): p. 780-90; Lieber, A., U. Kiessling, and M. Strauss, *High level gene expression in mammalian cells by a nuclear T7-phase RNA polymerase*, Nucleic Acids Res, 1989. 17(21): p. 8485-93). Since each of the steps functions in a broad range of hosts, the technology describe herein could represent a universal strategy. Besides the γ-proteobacteria, this technology can be applied, for example, to α-proteobacteira, β-proteobacteria, Bacteroidetes, Firmicutes, and Actinobacteria.

Successful engineering of broad hosts of bacteria would allow generation of a host library, which would be a powerful tool in pharmaceutical and chemical industries. The diverse collection of bacteria provides diverse metabolic environments (for example, transcription, translation, post-translational modification, tolerance to products and availability of substrates and co-factors, etc.), which can improve the likelihood of expression of orphan pathways. For example, these results demonstrated that expressing the same pathway in different hosts under same IPTG induction resulted in dramatic different production levels (FIGS. 14A-14BB). This strategy may also lead to breakthroughs in engineering plant root microbiome and human gut microbiome, providing means to agricultural and health (including pharmaceutical) industries to enhance sustainable crop production for food, chemicals and energy and health.

This study demonstrated successful integration and expression of bacterial luciferase luxCDABE in 31 strains of gamma-proteobacteria, but can be expanded to a broader range of bacterial hosts, thereby providing a common toolbox for microbe and microbiome engineering in the field of synthetic biology.

Example 5: Chromosomal Integration an Expression of Bacterial Luciferase Pathways in *E. coli*

Figure 15:
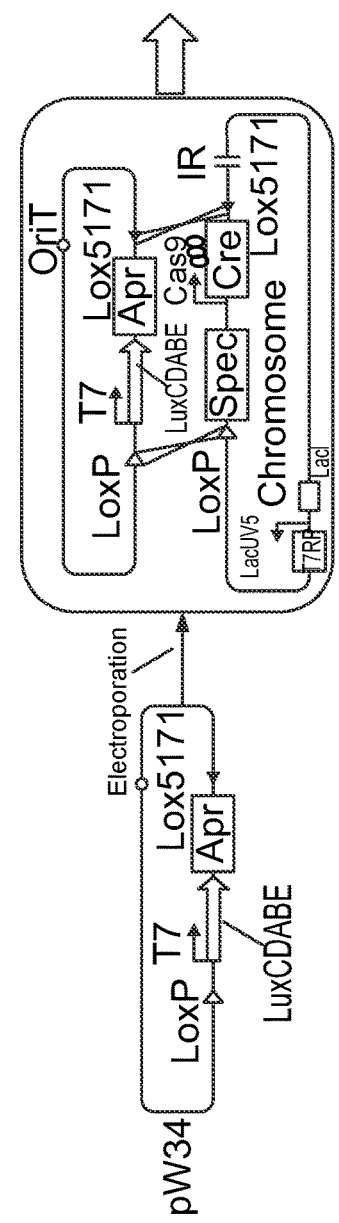
FIG. 15 shows an example of the combined transposition, Cre-LoxP, and T7 RNA polymerase strategy. pW34, is introduced into E. coli MG1655 cells by electroporation. After recombination by Cre, the Lux pathway and Apramycin gene are integrated into the recipient strain where the Lux pathway is under the control of the T7 RNA polymerase promoter.

This study shows the integration and expression of pathways to bacterial chromosome using the transposition, Cre-Lox, and T7 RNA polymerase combined strategy (FIG. 15). Specifically, in this study, integration and expression bacterial luciferase luxCDABE pathway in the chromosome of *E. coli* str. K-12 substr. MG1655 (DE3) is shown.

*E. coli* MG1655 Spec-Cre-2lox was previously constructed by Jan-Fang Chen. pW34 was transformed into *E. coli* MG1655 Spec-Cre-2lox. 3 transformants on the LB Apramycin (50 ug/ml) plate were observed.

Figure 16:
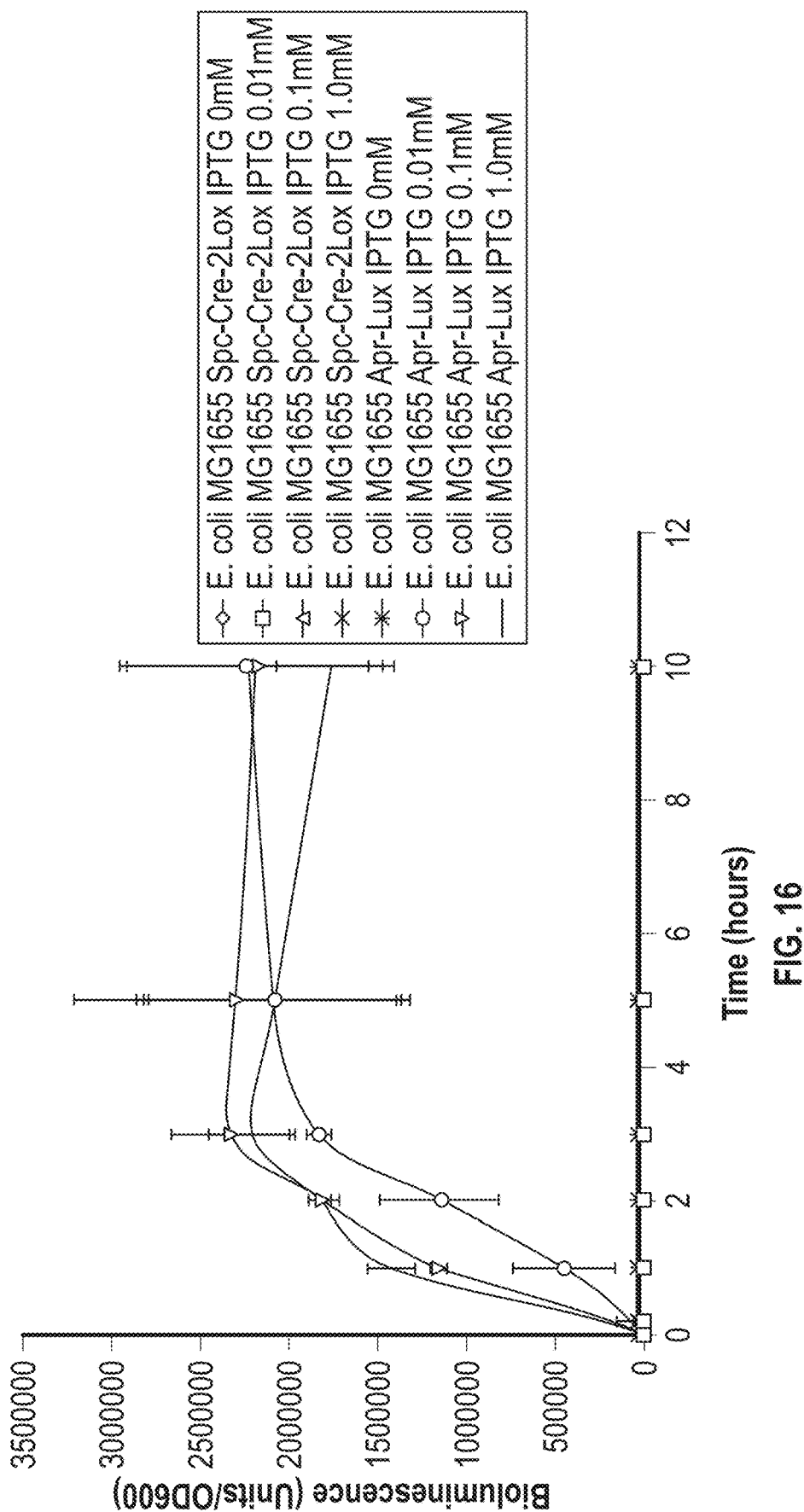
FIG. 16 shows bioluminescence of E. coli MG1655 Spec-Cre-2lox and E. coli MG1655 Apr-lux upon induction with 0, 0.01, 0.1, and 1.0 mM IPTG.

To test for integration and expression of the lux pathway, *E. coli* MG1655 with the landing pad or with luxCDABE were inoculated to 1 ml of LB Spectinomycin (50 ug/ml) or LB Apramycin (50 ug/ml). After overnight growth at 28° C. overnight with shaking at 220 rpm, each culture were diluted to OD600 of 0.1. IPTG was added to each well at a final concentration of 0 mM, 0.01 mM, 0.1 mM, and 1.0 mM. Luminescence and OD600 were read at 0, 0.17, 1, 2, 3, 5, 10 hours using Synergy H1 Micro-plate reader. The cells transformed with pW34 showed bioluminescence when induced with IPTG (FIG. 16).

TABLE 8

Strains and Plasmids Used in Example 5

| Names | Features |
|---|---|
| *Strains* | |
| E. coli str. K-12 substr. MG1655 (DE3) | Genotype is F- ilvG- rfb-50 rph-1 (λ DE3) |
| E. coli MG1655 Spec-Cre-2lox | Landing pad containing Cre and speR were introduced into the genome near the atpI gene using the Cas9-CRISPR editing method. |
| E. coli MG1655 Apr-lux | LuxCDABE and Apr resistance gene integrated to E. coli MG1655 genome |
| *Plasmids* | |
| pW34 | Medium copy plasmid, carrying T7-luxCDABE between loxP and lox5171 sites. |

This study demonstrates successful integration and expression of bacterial luciferase luxCDABE in the *E. coli* MG1655 chromosome.

Example 6: Pathway Integration and Expression in 23 Gamma Proteobacteria Strains This study shows the chromosomal integration and expression of pathways using the transposition, Cre-Lox P, and T7 RNA polymerase combined strategy. Specifically, this study demonstrates integration and expression of the bacterial luciferase operon luxCDABE and orphan secondary metabolite biosynthetic pathways Plu3263 and Plu0897-Plu0899 in 23 gamma proteobacteria strains.

Materials and Methods

Bacterial strains used in this study are listed in Table 9. *E. coli* WM3064 was the conjugation donor developed by William Metcalf (UIUC). *E. coli* WM3064 was derived from *E. coli* B2155 and was auxotrophic to 2,3-diaminopropionic acid (DAP). *E. coli* BL21 sfp+ was used as a control strain.

TABLE 9

Strains Used in Example 6.

| Bacterial Strain | Landing pad insertion location** | Counter Selection*** |
|---|---|---|
| Pseudomonas flourescens Q8r1 | 2945409 | 10/10 |
| Pseudomonas simiae WCS417 | 5480832 | 10/10 |
| Photorhabdus luminescens subsp. laumondii TTO1 | 1716132 | 10/10 |
| Photorhabdus luminescens subsp. luminescens | 1739259 | 10/10 |
| Photorhabdus temperata subsp. khanii | 3819789 | 10/10 |
| Xenorhabdus doucetiae | 559513 | 8/8 |
| Serratia odorifera | 4691627 | 10/10 |
| Erwinia oleae | 1475937 | 10/10 |
| Erwinia pyrifoliae | 2063242 | 10/10 |
| Yersinia bercovieri | 1776696 | 10/10 |
| Yersinia mollaretii | 479824 | 10/10 |
| Dickeya dadantii subsp. dadantii | 3060401 | 10/10 |
| Dickeya dadantii subsp. dieffenbachiae | 2594266 | 10/10 |
| Dickeya solani | 1635144 | 10/10 |
| Dickeya zeae | 3297764 | 10/10 |
| Aeromonas encheleia | 3673285 | 10/10 |
| Aeromonas piscicola | 3518388 | 10/10 |
| Aeromonas salmonicida subsp. pectinolytica | 489248 | 10/10 |
| Aeromonas salmonicida subsp. salmonicida | 2218778 | 10/10 |
| Pantoea agglomerans | 5029470 | 10/10 |
| Pseudomonas putida KT2440 | 5256355 | 10/10 |
| Pectobacterium carotovorum subsp. odoriferum | Not Determined | 10/10 |
| Aeromonas molluscorum | 3673285 | 10/10 |
| E. coli BL21 sfp+* | Not applicable | Not Applicable |

*E. coli BL21 sfp+ is a control strain.
**Indicates the location of insertion in each strain's genome.
***Indicates the luminescent, Apr resistant, Kan sensitive colonies over the totally colonies assayed.

The plasmid pW17 (SEQ ID NO:4) contained a landing pad. The plasmid pW34 contained LuxCDABE and the plasmid pT7_Plu3263 contained a 15.651 kb orphan secondary metabolite pathway (Plu3263) from *Photorhabdus luminescens* TTO1. This pathway started from position 3880777 and ended in position 3865127 in the genome (Fu, J., et al., *Full-length RecE enhances linear-linear homologous recombination and facilitates direct cloning for bioprospecting. Nat Biotechnol*, 2012. 30(5): p. 440-6). Plu3263 was previously reported to produce secondary metabolites luminmide A and luminmide B with the m/z [M+H]$^+$ of 586.3963 and 552.4117 (Fu, J., et al., *Full-length RecE enhances linear-linear homologous recombination and facilitates direct cloning for bioprospecting*. Nat Biotechnol, 2012. 30(5): p. 440-6); (Bian, X. Y., et al., *Rational and efficient site-directed mutagenesis of adenylation domain alters relative yields of luminmide derivatives in vivo*. Biotechnology and Bioengineering, 2015. 112(7): p. 1343-1353). This plasmid was assembled using a yeast TAR cloning method. pW5Y (SEQ ID NO:11) was also constructed using a pBeloBAC11 backbone as a single copy plasmid useful for accommodating larger sequences of interest (e.g., pathways). pW5Y can be PCR cloned in 3 pieces, the sequence of interest can also be cloned via PCR, and all 4 PCR fragments can be put into yeast and assembled into pW5Y bearing the sequence of interest between two lox sites.

pT7_Plu0897-Plu0899 contained a 14.262 kb orphan secondary metabolite pathway (Plu0897-Plu0899) from *Photorhabdus luminescens* TTO1. This pathway started from position 1021625 and ended in position 1035887 in the genome (Fu, J., et al., *Full-length RecE enhances linear-linear homologous recombination and facilitates direct cloning for bioprospecting*. Nat Biotechnol, 2012. 30(5): p. 440-6). This plasmid was assembled using the yeast TAR cloning method.

The method was demonstrated in FIG. 17 wherein: (1) an engineered mariner transposon carrying an inducible T7 RNA polymerase, a Cre recombinase and two mutually exclusive lox sites was transposed to the desired bacterial chromosome and (2) a pathway under the control of the T7 promoter flanked by two mutually exclusive lox sites was integrated to the bacterial genome mediated by the Cre-lox recombination, leading to Lac inducible expression of the pathway in the chromosome.

Conjugation was conducted as described in Example 1. In each conjugation reaction, some variations were made regarding to the amount of donor and/or recipient cultures, incubation temperature, and/or incubation time to optimize the reaction conditions and/or to increase transformation efficiency.

For counter selection, the same single colony was streaked on a LB plate with Kanamycin and on a LB plate with Apramycin; slightly above the minimal inhibitory concentration of 100% was used for each strain. These plates were incubated at 28° C. for two days to check growth.

Whole genome sequencing analysis was performed using an Illumina MiSeq sequencing system. Reads were mapped to the landing pad sequence using Geneious software. The flanking sequences were mapped to the genome sequence of each corresponding host to identify the insertion location of the landing pad.

For bioluminescence assays, single colonies were inoculated to 1 ml of LB with appropriate antibiotics and incubated at 28° C. overnight with shaking. Cultures were diluted to OD600 0.1-0.2 and were added to a 96 well black plate with clear bottom. IPTG was added to the cultures at final concentrations of 0, 0.01, 0.1 and 1.0 mM, respectively. Bioluminescence of the culture was measured using Synergy H1 Micro-plate reader (Biotek) at an interval of 12 minutes.

Fermentation and Extraction techniques were performed as follows. On day 1, all strains were streaked onto an LB Apr50 plate and incubated at 28° C. for 2 days. On day 2, glycerol stock or colonies were seeded on plates to 3 mL LB Apr10 at 28° C. in 15 mL tubes and incubated at 28° C. for 2 days at 200 rpm. On day 3, cultures were diluted 20x, OD was measured on a 96-well plate, and the amount of culture needed for seeding 25 mL medium was calculated. This amount of bacteria was centrifuged at 3000 g for 5 minutes, supernatant discarded, and pellets were resuspended in 25 ml special M9 medium to the final OD 600 nm of 0.1. Special M9 medium with Apr10 was made as shown in Table 10.

TABLE 10

Recipe for special M9 medium with Apr10

| | Chemicals | Volunm (ml) |
|---|---|---|
| 1 | 5* M9 | 200 ml |
| 2 | 1M MgSO4 | 2.0 ml |
| 3 | 20% glucose | 20 ml |
| 4 | 1M CaCl2 | 0.1 ml |
| 5 | 25 g/L Yeast Extract | 200 ml |
| 6 | Vitamin Solution | 2.5 ml |
| 7 | Trace Metal Solution | 2.5 ml |
| 8 | 0.1M Citric Acid solution | 100 ml |
| 9 | 50 mg/ml Apr | 0.2 ml |
| | Fill water to 1 L | |
| | Filter Sterilize | |

Cultures were incubated at 28° C. at 200 rpm for 5-6 hours. 5 mL culture from each strain was distributed into each of 4 tubes. 100 μL of 0, 0.5, 5, or 50 mM IPTG was added into each tube. Cultures were incubated at 28° C. at 200 rpm for 3 days. On day 6, 2.10 mL of each culture was transferred into 2 ml tubes, and another 2.10 ml was transferred to 48 well plate as backup. 100 μl was taken from each tube and diluted 10 times, OD was measured using 96 well plate. Cultures were centrifuged at 3300*g for 10 min at room temperature, then supernatant was discarded. On day 7, for acetone extraction, pellets were vibrated to loosen, and 1.0 mL acetone was added to each tube. Tubes were placed in an ultrasonic bath for 15 minutes, then rotated for 2 hours at room temperature. For ethyl acetate extraction, tubes were centrifuged at 5000*g (4° C.) for 15 min. Supernatants were transferred into new tubes, then extracts were dried by speed-vac (~-40-60 mins). Dried solids were resuspended with 1.0 mL ethyl acetate and pipetted up and down to homogenize. Tubes were rotated overnight for extraction. On day 8, for filtration, tubes were centrifuged at 16000 g 4° C. for 15 min. Supernatants were transferred into new tubes, then extracts were dried by speed-vac (~-40-60 mins). 0.1 mL internal standard ABMBA (200 fold) was mixed with 19.9 mL methanol. Dried solids were resuspended in 100 μL methanol with internal standard ABMBA. This was transferred to a 96-well filter with a 96-well plate (solvent resistant) downside. The plate was centrifuged at 2500 rpm at 15° C. for 3 minutes to collect filtrate, then plate was sealed and stored at −20° C. for LCMS analysis.

HPLC-MS/MS analyses were performed for each sample, and the data were analyzed using a Maven software package.
Results pW17 was conjugally transformed into 23 gamma proteobacteria strains from the donor E. coli strain WM3064. The landing pad within a Mariner transposon was randomly integrated into the chromosome of each strain. After the conjugation, colonies for each strain were obtained from the LB agar plate with appropriate kanamycin concentration. Colony PCR was used to identify the colonies for each strain containing the landing pad. Preliminary assessment suggested that pW17 is sometimes maintained in the transformants. Therefore, colony PCR was used to screen transformants with the chromosomally integrated landing pad (positive to the landing pad and negative to the pW17 plasmid backbone). For those transformants for which the correct colony PCR patterns could not be determined initially, serial culture and screening was performed until a transformant demonstrating the correct colony PCR patterns was identified. To identify the genomic location where the landing pad was inserted, low coverage (10-100) whole-genome sequencing was carried out for these transformants. The insertion location in the genome of each strain is listed on Table 9.

LuxCDABE integration was performed by conjugation. Specifically, donor strain E. coli WM3064 pW34 was conjugated to the 23 strains containing landing pad. After conjugation, colonies were obtained on LB agar plate with the appropriate Apramycin concentration. About 10 colonies were spotted both on LB agar Kanamycin and LB agar Apramycin for counter section. Most colonies grew only on LB agar Apramycin, which indicated that the pathway successfully replaced the landing pad within the genome, and the pW34 backbone is cured from the transformants. The bioluminescence was measured in triplicate for all strains containing the landing pad with luxCDABE (without the Lux operon as a control) at 8 hours after induction with various concentrations of IPTG (FIG. 18A). These engineered strains produced significantly higher bioluminescence compared to the control strains. In general, the bioluminescence production was induced by the addition of IPTG.

Integration of pathways T7-Plu3263 and T7-Plu0897-Plu0899 was performed by conjugation. The donor strains, E. coli WM3064 harboring pT7_Plu3263 or T7-Plu0897-Plu0899, were conjugated to the 23 strains with landing pads. After the conjugation, colonies were obtained from a LB agar plate with appropriate Apramycin concentration. Subsequent counter-selection with Km and Apr identified successful transformants of this pathway. E. coli BL21 sfp+pT7_Plu3263 or T7-Plu0897-Plu0899 were included as controls. For each strain, the engineered variant containing only the landing pad (control) and the landing pad replaced with the pathways, T7-Plu3263 and T7-Plu0897-Plu0899, were fermented for 3 days. During the fermentation, these cultures were induced by 0, 0.01, 0.1, and 1.0 mM of IPTG at 5 hours after inoculation respectively. Secondary metabolites were extracted and analyzed by HPLC-MS/MS.

Figure 18B:
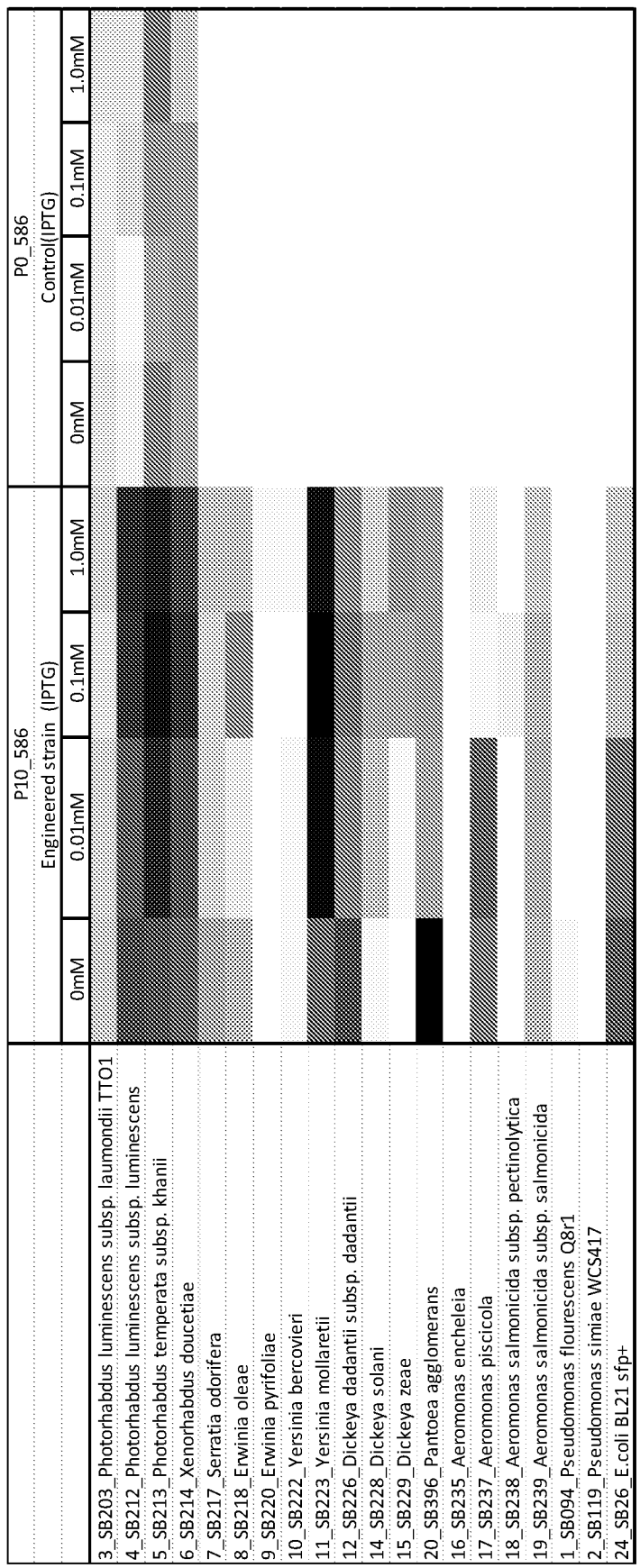
Figure 18C:
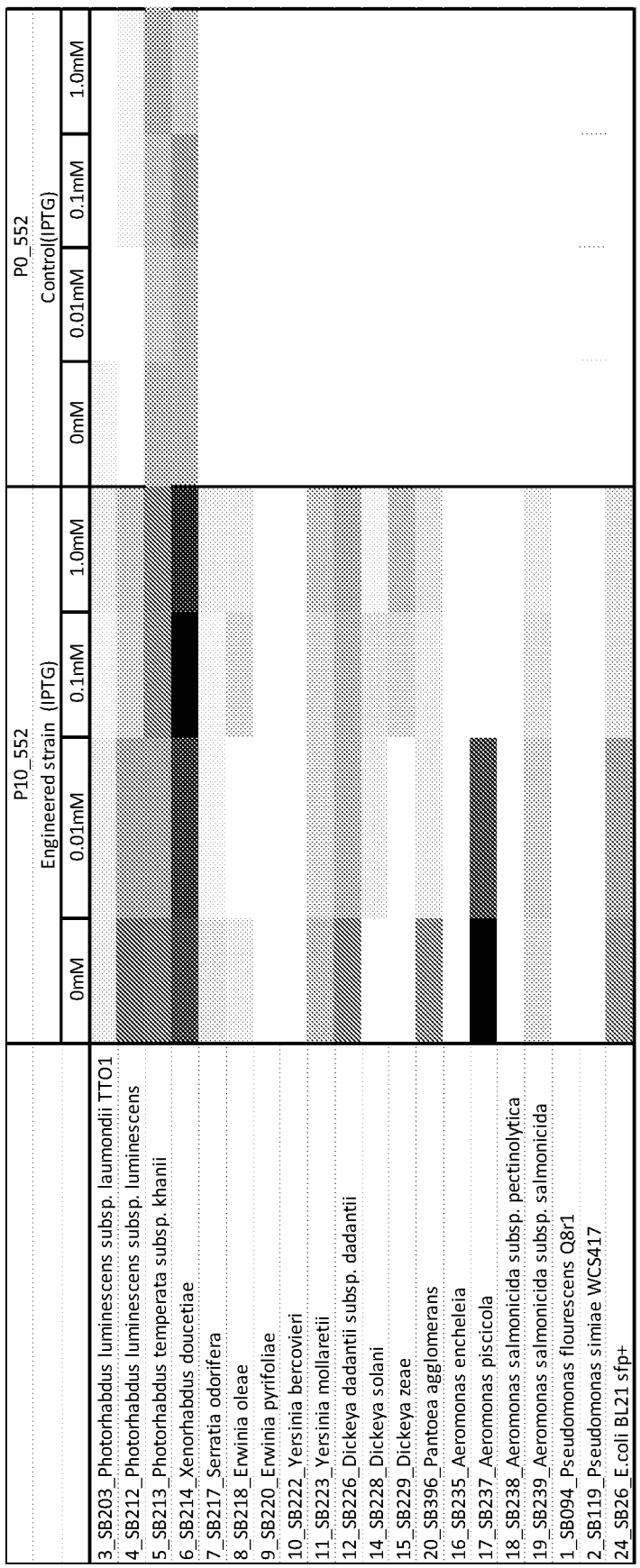
Figures 19A, 19B:
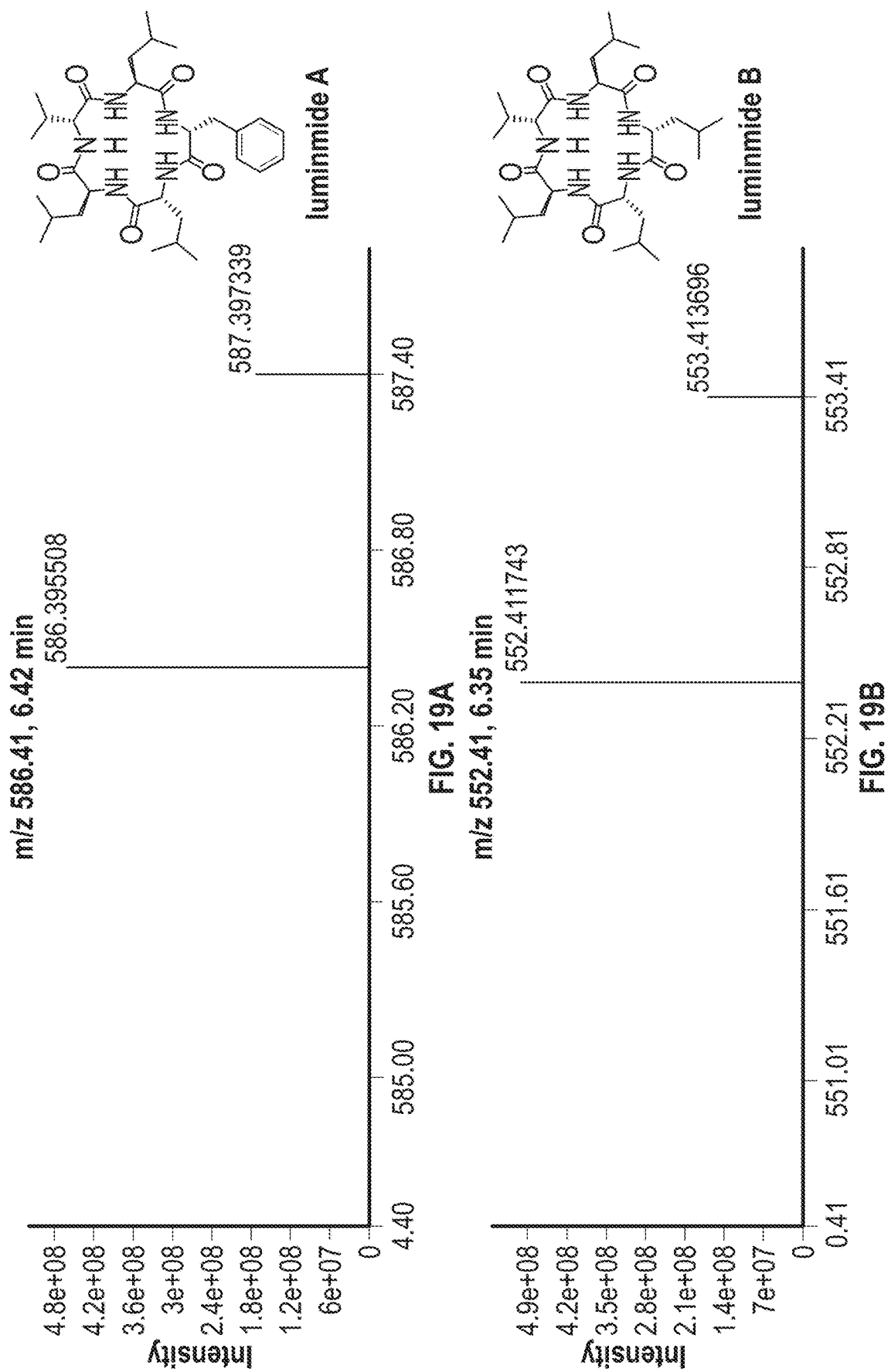
FIGS. 19A-19B show the MS/MS spectra and structures of luminmide A (FIG. 19A) and luminmide B (FIG. 19B) (Fu, J., et al., Full-length RecE enhances linear-linear homologous recombination and facilitates direct cloning for bioprospecting. Nat Biotechnol, 2012. 30(5): p. 440-6).
Figure 19C:
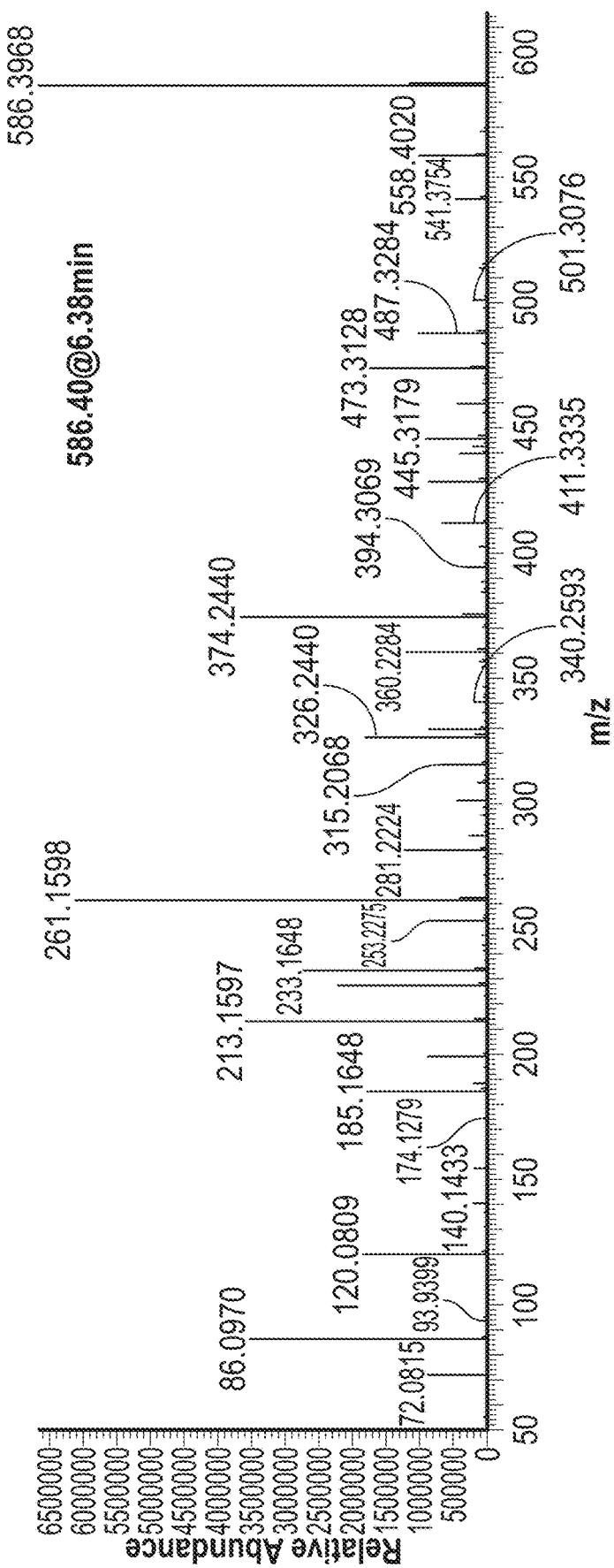
FIGS. 19C-19D show the LC-MS/MS spectra and structures of luminmide A (FIG. 19C) and luminmide B (FIG. 19D).
Figure 19D:
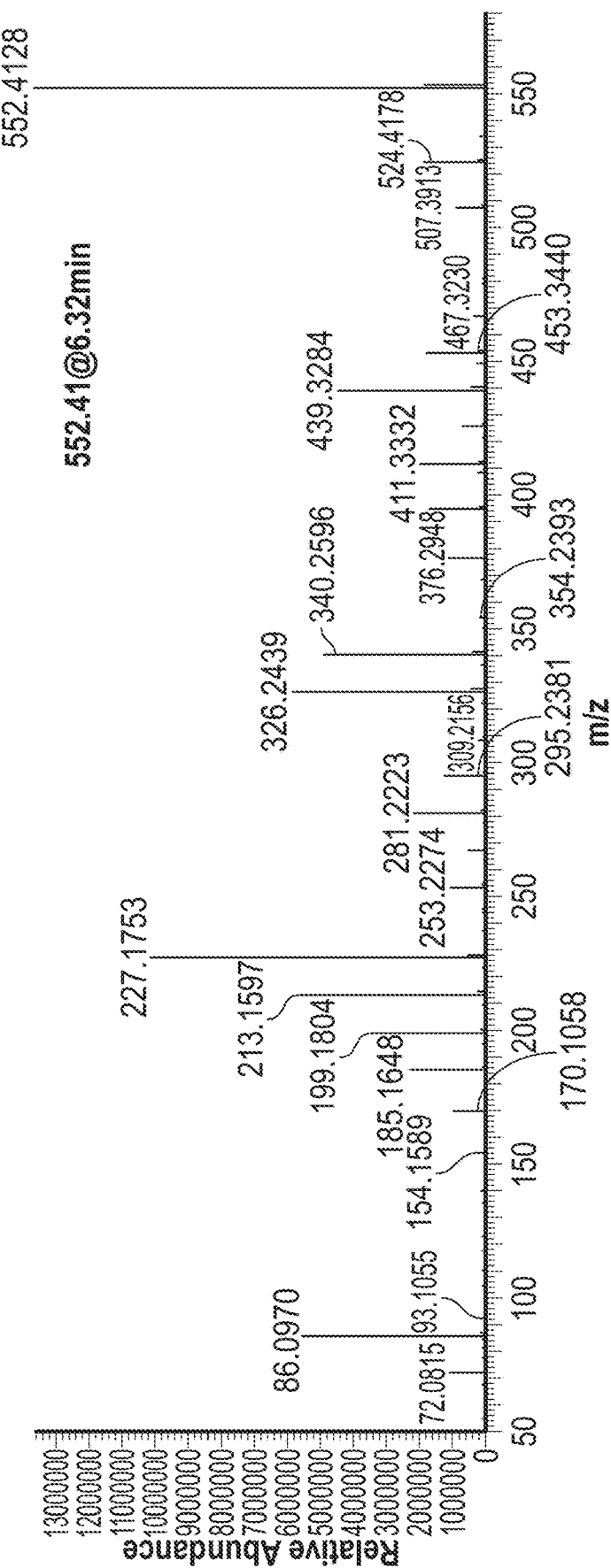
Figure 20:
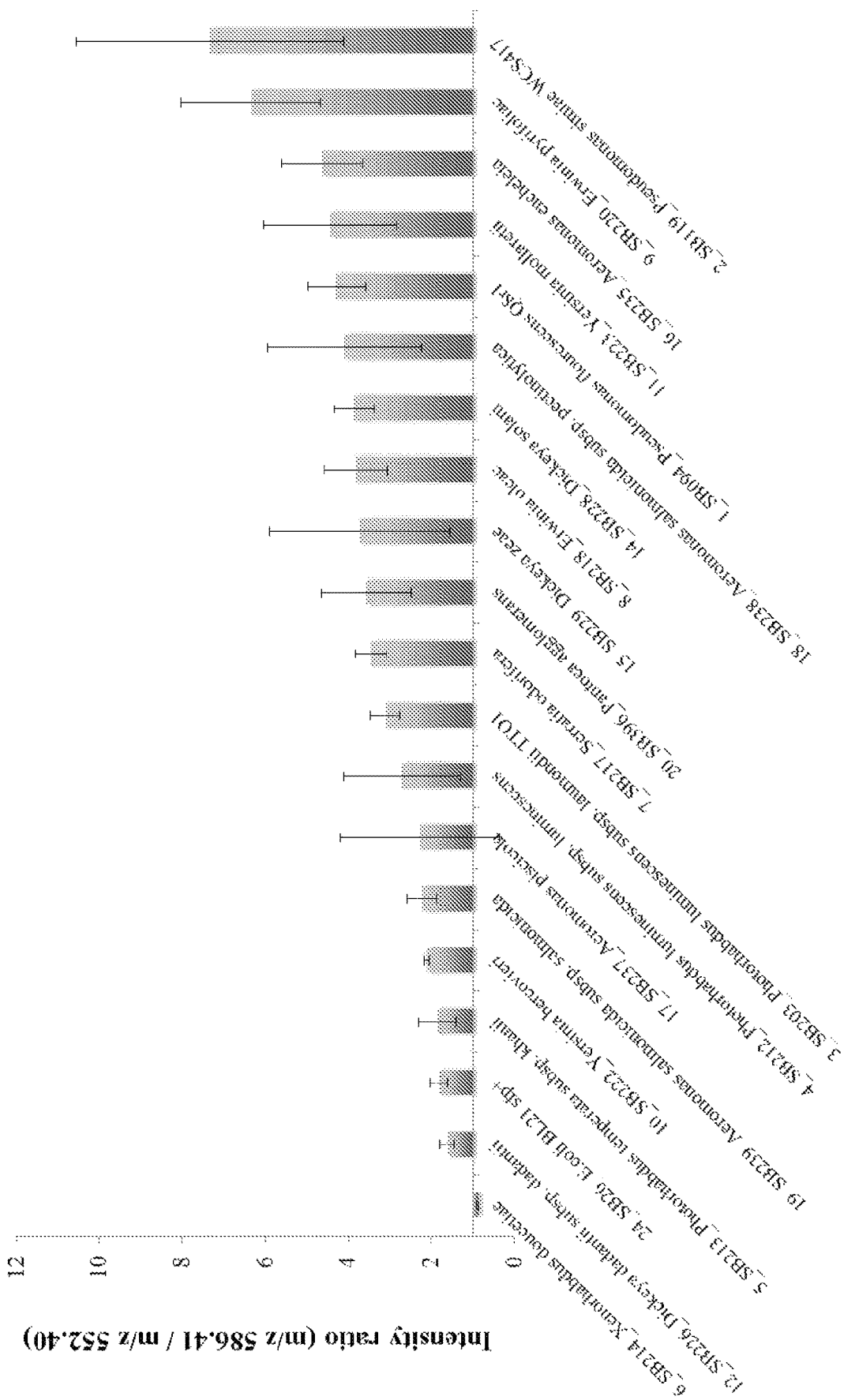
FIG. 20 shows the ratio of luminmide A (m/z 586.41) to luminmide B (m/z 552.40) production in engineered bacterial strains expressing the orphan secondary metabolite T7-Plu3263 pathway.

In addition to the native producers, *Photorhabdus* and *Xenorhabdus* species, luminmide A (m/z 586.40) and luminmide B (m/z 552.41) at the retention times of 6.42 min and 6.35 min, respectively, were only produced by strains expressing Plu3263 (FIGS. 18B-18C). The MS/MS and structure of luminmide A (FIG. 19A & FIG. 19C) and B (FIG. 19B & FIG. 19D) are indicated. While *P. agglomerans* and *Y. mollaretii* showed the highest level of luminmide A production, *X. doucetiae* and *A. piscicola* showed the highest level of luminmide B production, suggesting that this approach could provide a rapid means to identify more suitable strains for production of secondary metabolites than traditional model hosts such as *E. coli*. Also, the ratio of luminmide A to B production varies ~10-fold from *X. doucetiae* to *P. simiae* WCS417 (FIG. 20), suggesting that this approach may provide a means to activate hidden functions of pathways.

Figure 21C:
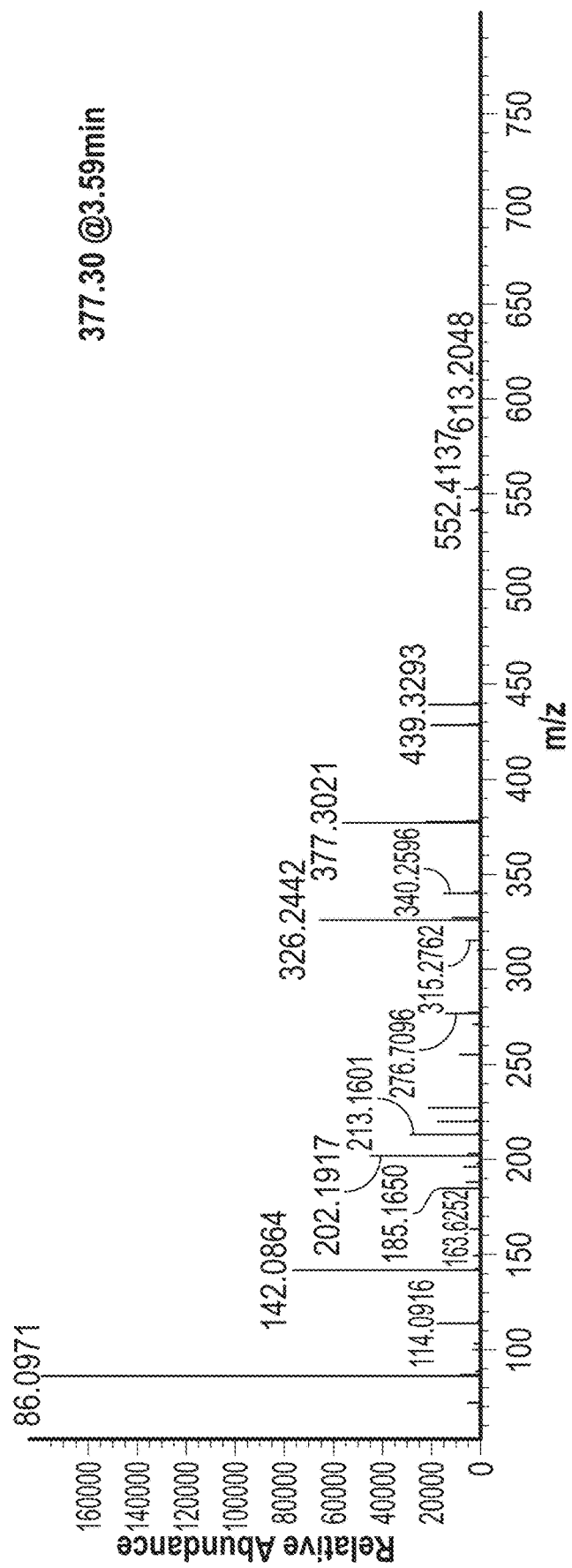
FIG. 21C shows the LC-MS/MS spectra and structure of the secondary metabolite.

Several strains expressing Plu0897-Plu0899 showed the production of a secondary metabolite with m/z 377.30 at the retention time 3.64 min (FIG. 21A). This secondary metabolite was most highly produced by *Yersinia mollaretii* among the panel of strains examined (FIG. 21B) and further analyzed by LC-MS/MS (FIG. 21C). Interestingly, this secondary metabolite was not produced by *P. luminescens* sp. *Luminescens* TTO1 (both a wild type strain with the landing pad and the strain expressing Plu0897-Plu0899), suggesting that this approach provides a means to activate the function of orphan secondary metabolite biosynthetic pathways.

Discussion

This study showed successful integration and expression of bacterial luciferase luxCDABE, and orphan secondary metabolite biosynthetic pathways Plu3263 and Plu0897-Plu0899 in 23 gamma proteobacteria strains. Because one or more strains produced secondary metabolites which are not found in the respective native strain, this approach may prove to be an effective strategy to activate and characterize the function of orphan biosynthetic pathways and to identify novel bioactive secondary metabolites. Additionally, since the abundance and ratio of secondary metabolite production (e.g., luminmide A and B) varied significantly among the examined strains, this approach may offer an effective strategy to identify more commercially suitable production host strains compared to traditional model strains.

Example 7: Pathway Integration and Expression in Two Alpha Proteobacteria Strains and One Beta Proteobacteria Strain This study was conducted to show integration and expression of pathways to bacterial chromosomes using the combined transposition, Cre-Lox P, and T7 RNA polymerase strategy. Specifically, integration and expression of the luxCDABE pathway in the chromosome of two representative alpha proteobacteria and one representative beta proteobacteria was demonstrated.

Materials and Methods

*E. coli* WM3064 was the conjugation donor. *Rhizobium mongolense* and *Brevundimonas* sp. 374 were the alpha proteobacteria recipients. *Ralstonia* sp. UNC404CL21Col was the beta proteobacteria recipient. For culture medium, R2A was used for *Rhizobium mongolense* and LB was used for all other strains. The plasmids pW17 and pW34 were used to engineer the bacterial chromosomes. The integration and expression methodology, including conjugation, counter selection, MiSeq analysis and bioluminescence assays, is described in Example 6.

Results

Landing pad transposition was achieved by conjugation. Specifically, donor strain *E. coli* WM3064pW17 was conjugated to the alpha proteobacteria or beta proteobacteria strains. The landing pad insertion to the chromosomes was confirmed via colony PCR and MiSeq analysis.

For luxCDABE integration, the donor strain *E. coli* WM3064pW34 was conjugated to the alpha proteobacteria or beta proteobacteria strains containing the landing pads. After conjugation, colonies were obtained on selection plate with appropriate Apramycin concentrations. Integration of the Lux operon was confirmed through antibiotic counter selection (resistant to Apramycin; sensitive to Kanamycin).

Figure 22A:
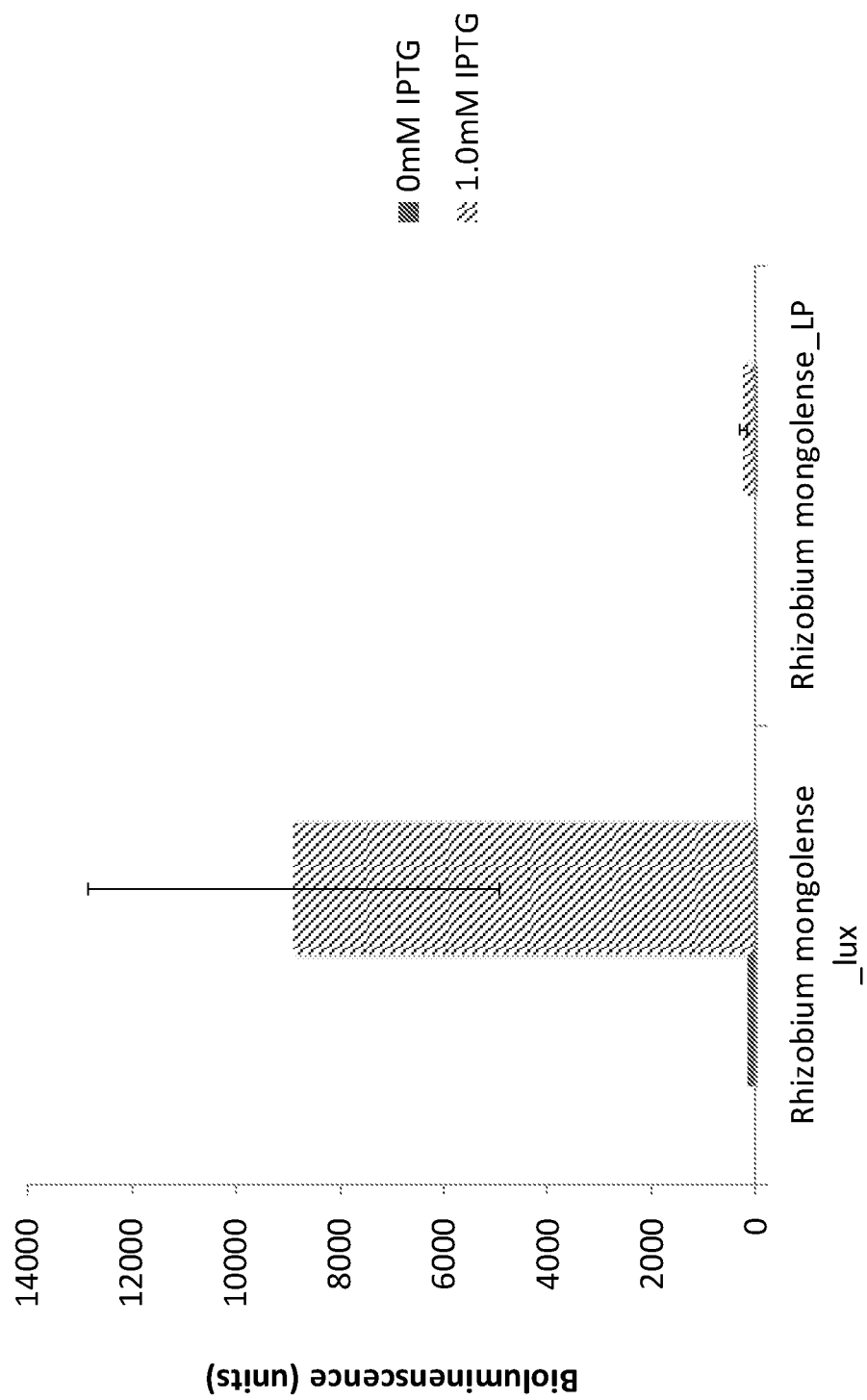
FIG. 22A shows bioluminescence of an engineered Rhizobium mongolense (alpha proteobacteria) strain expressing luxCDADBE versus the landing pad alone (control) upon induction with 0 and 1.0 mM IPTG.
Figure 22B:
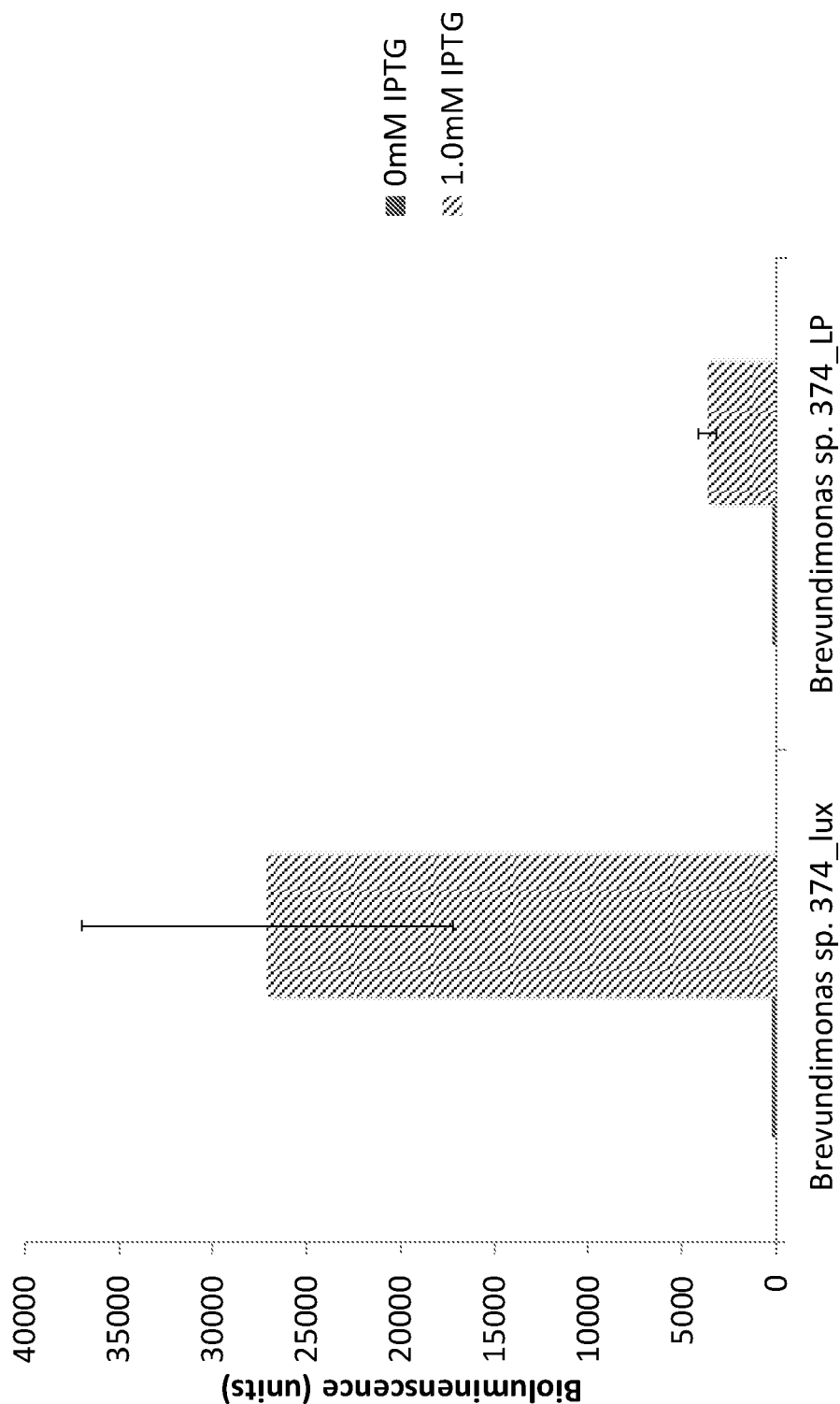
FIG. 22B shows bioluminescence of an engineered Brevundimonas sp. 374 (alpha proteobacteria) strain expressing luxCDADBE versus the landing pad alone (control) upon induction with 0 and 1.0 mM IPTG.
Figure 22C:
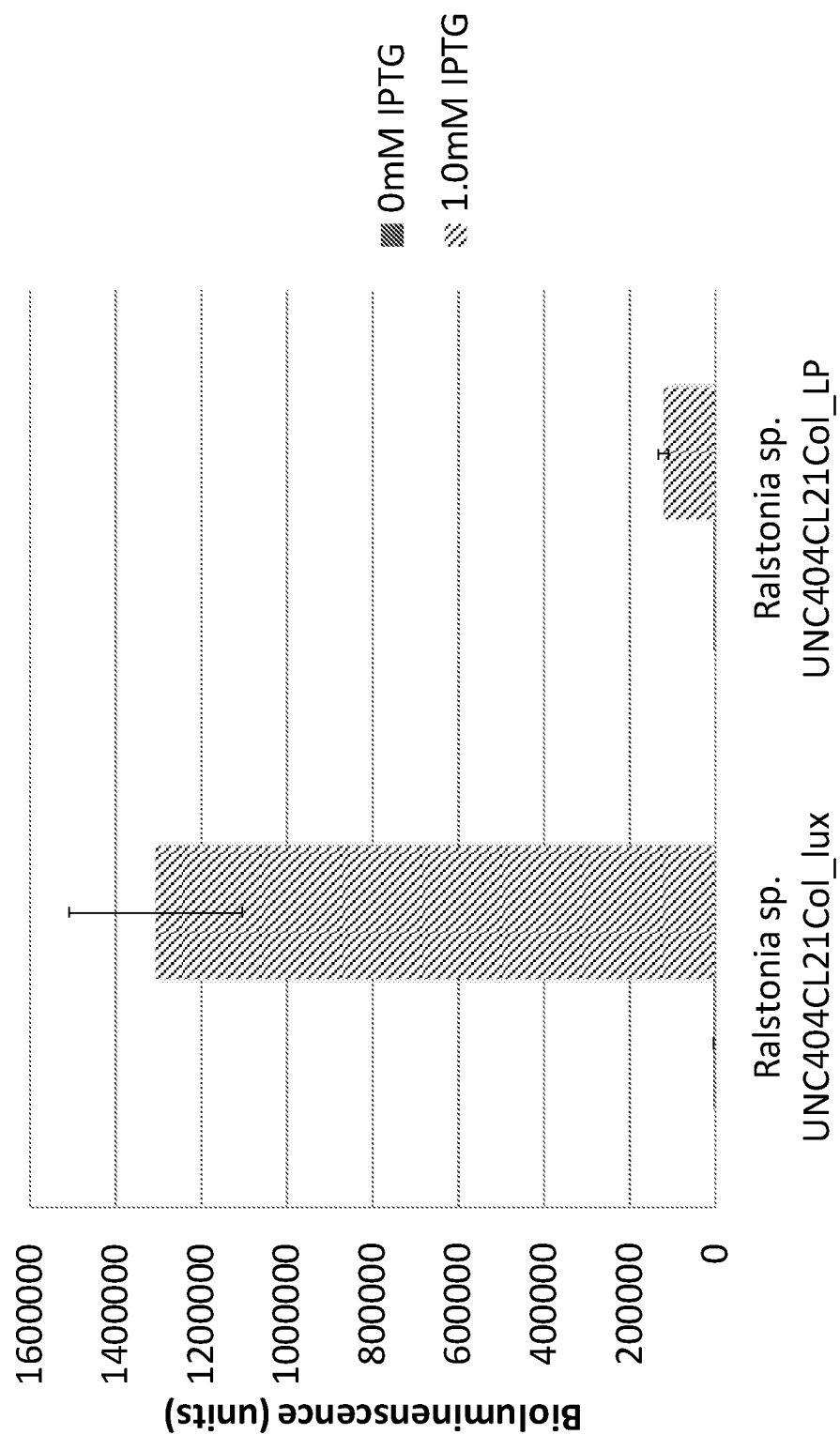
FIG. 22C shows bioluminescence of an engineered Ralstonia sp. UNC404CL21Col (beta proteobacteria) strain expressing luxCDADBE versus the landing pad alone (control) upon induction with 0 and 1.0 mM IPTG.
Figure 23:
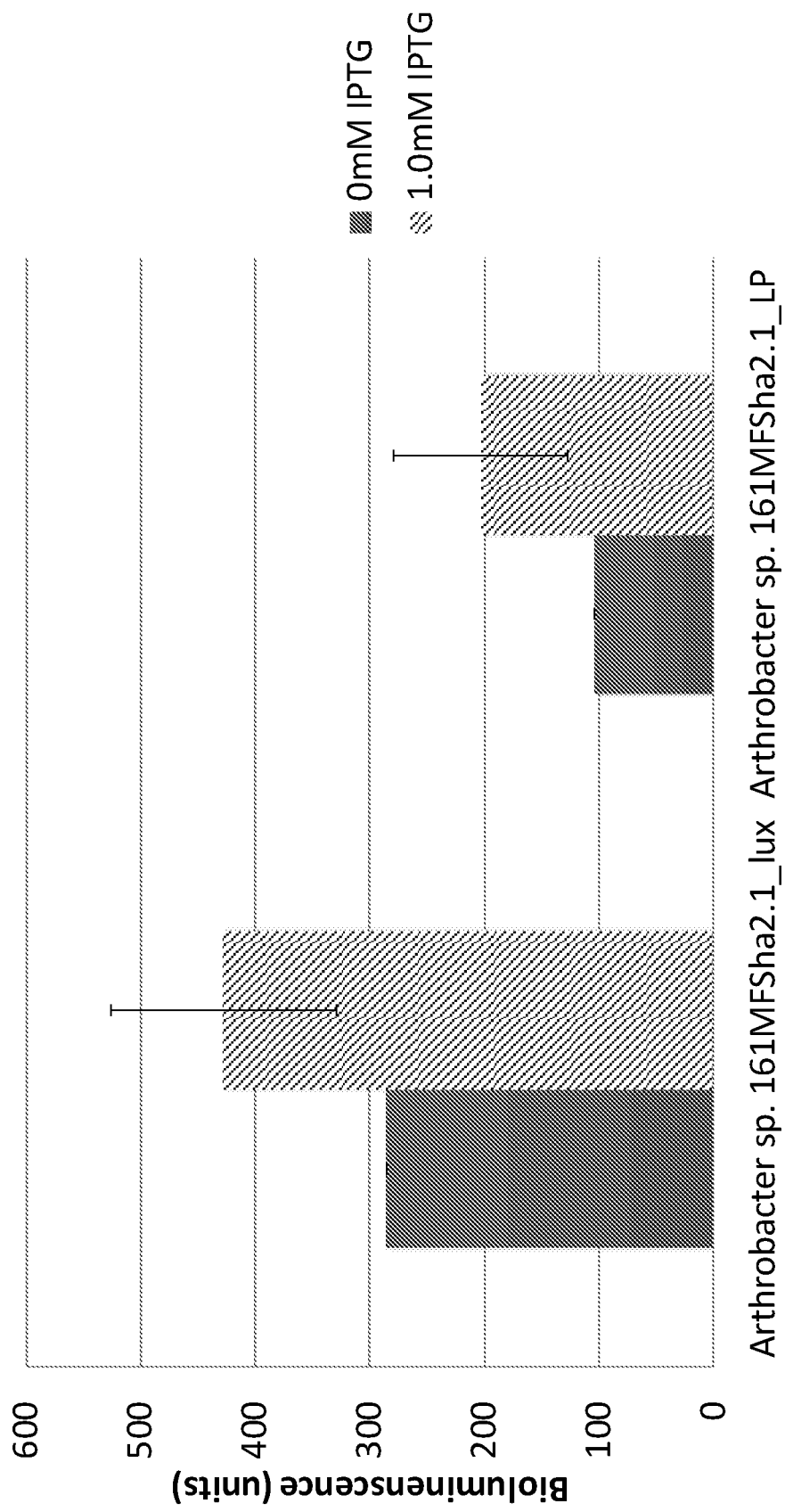
FIG. 23 shows bioluminescence of an engineered Arthrobacter sp. 161MFSha2.1 (actinobacteria) strain expressing luxCDADBE versus the landing pad alone (control) upon induction with 0 and 1.0 mM IPTG.

Bioluminescence assays demonstrated that alpha proteobacteria *Rhizobium mongolense* containing luxCDABE (10 replicates) showed higher bioluminescence than its landing pad counterpart (1 replicate) as shown in FIG. 22A. Alpha proteobacteria *Brevundimonas* sp. 374 containing luxCDABE (3 replicates) showed higher bioluminescence than its landing pad counterpart (1 replicate) as shown in FIG. 22B Beta Proteobacteria *Ralstonia* sp. UNC404CL21Col containing luxCDABE (3 replicates) showed higher bioluminescence than its landing pad counterpart (1 replicate) as shown in FIG. 22C. Actinobacteia *Arthrobacter* sp. 161MFSha2.1 containing luxCDABE (3 replicates) showed higher bioluminescence than its landing pad counterpart (1 replicate) as shown in FIG. 23. These results indicated that under IPTG induction, engineered strains produced significantly higher bioluminescent signals than strains only containing landing pad in all three strains.

This study showed that the combined transposition, Cre-LoxP, and T7 RNA polymerase strategy is effective in engineering a broad range of gram negative bacteria, particularly in the phylum of proteobacteria.

Example 8: Pathway Integration and Expression in One Actinobacteria Strain

This study was conducted to show that the combined transposition, Cre-LoxP, and T7 RNA polymerase strategy is effective for chromosomal integration and expression of pathways in one strain of Actinobacteria.

Materials and Methods

*E. coli* WM3064 was the conjugation donor. *Arthrobacter* sp. 161MFSha2.1 was the recipient. The plasmids pW17 and pW34 were used to engineer the actinobacterium. The integration and expression methodology, including conjugation and bioluminescence assays, is described in Example 6.

Results

Transposition of the landing pad was achieved by conjugation. Specifically, donor strain *E. coli* WM3064pW17 was conjugated to the *Arthrobacter* sp. 161MFSha2.1 strain. PCR confirmed the landing pad insertion.

For luxCDABE integration, donor strain *E. coli* WM3064 pW34 was conjugated to the actinobacterium containing the landing pad. After conjugation, colonies were obtained on a selection plate with appropriate Apramycin concentration, suggesting that $Apr^R$-Lux operon is successfully integrated into the landing pad. One colony was picked as it demonstrated acquired Apramycin resistance (Figure not shown here). Colonies containing luxCDABE showed higher bioluminenscence than colonies containing only landing pad as shown in FIG. 23.

This study indicated that combined transposition, Cre-LoxP, and T7 RNA polymerase strategy is effective in engineering a broad range of bacteria including both gram-positive bacteria, particularly in the phylum of actinobacteria.

Example 9: Three LoxP Landing Pad and Applications in Photorhabdus luminescens This study was conducted to show that the combined transposition and Cre-LoxP strategy is effective for pathway integration and expression in proteobacteria. In particular, Photorhabdus luminescens subsp. laumondii TTO1 was engineered with a landing pad containing three lox sites, and the landing pad was replaced with dCas9 or aCas9 to modulate gene expression in a targeted manner.

The additional loxP site created the ability to insert a second piece of DNA fragment into the host genome adjacent to the first inserted fragment. Using this modified landing pad in combination with the CRISPR-Cas9 technology, the operon responsible for generating bioluminescence in Photorhabdus luminescens subsp. laumondii TTO1 was repressed or activated through insertion of a set of sgRNA fragments into the second site on the landing pad. The Cas9 proteins used in this example were the catalytically defective Cas9 (dCas9) and the activating Cas9 (aCas9), which is a fusion protein containing the catalytically defective Cas9 fused with the omega subunit of RNA polymerase. These Cas9 variants were shown to repress or activate gene expression in prokaryotes and eukaryotes (aCas9: Bikard, D. et al. Programmable repression and activation of bacterial gene expression using an engineered CRISPR-Cas9 system. *Nucleic Acids Res,* 2013. 41: 7429-7437); (dCas9: Qi, L. S. et al. Repurposing CRISPR as an RNA-guided platform for sequence-specific control of gene expression. *Cell,* 2013. 152: 1173-1183).

Materials and Methods

Figure 24:
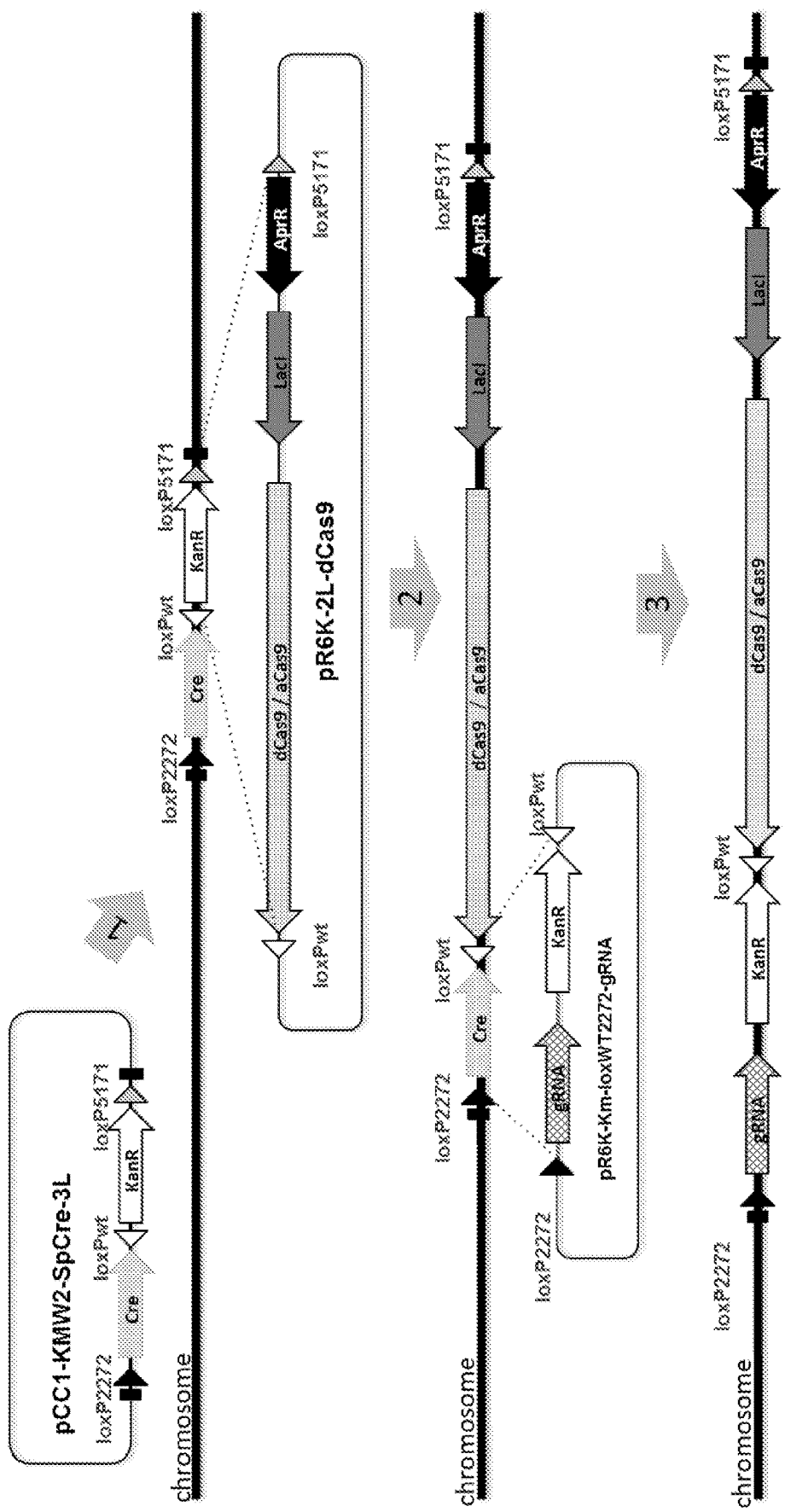
FIG. 24 shows an example of the stepwise methodology involving transposition and Cre-LoxP recombination wherein the landing pad is modified to include three loxP sites: (1) the landing pad is inserted to genome, (2) KanR is replaced by dCas9-LacI-Apr or aCas9-LacI-Apr, and (3) Cre is replaced by gRNA-KanR. Subsequently, dCas9 or aCas9 is directed to bind to the LuxA gene and regulate bioluminescence.

E. coli WM3064 was the conjugation donor developed by William Metcalf (UIUC). E. coli WM3064 was derived from E. coli B2155 and was auxotrophic to 2,3-diaminopropionic acid (DAP). The plasmids used in the study were pCC1-KMW2-SpCre-3L (SEQ ID NO:6), pR6K-2L-dCas9 (SEQ ID NO:7), pR6K-2L-aCas9 (SEQ ID NO:8), and pR6K-Km-loxWT2272-gRNA (SEQ ID NO:9). As shown in FIG. 24, the landing pad contained three lox sites: loxPwt, loxP5171, and loxP2272. The integration and expression methodology, including conjugation, counter selection, and bioluminescence assays, is described in Example 6.

Results

The landing pad transposition was achieved by conjugation (FIG. 24, step 1). Specifically, the donor strain was E. coli WM3064 pCC1-KMW2-SpCre-3L and recipient was Photorhabdus luminescens subsp. laumondii TTO1. PCR analysis was used to confirm that the landing pad was inserted into the P. luminescens chromosome For dCas9 or aCas9 integration, the donor strain E. coli WM3064 containing the pR6K-2L-dCas9 or the pR6K-2L-aCas9 plasmid was conjugated with the recipient containing the three loxP landing pad (FIG. 24, step 2). After conjugation, colonies were obtained on selection plate with appropriate Apramycin. Counter selection confirmed that those colonies lost Kanamycin resistance, which indicated the kanamycin resistant marker has been replaced.

Figure 25A:
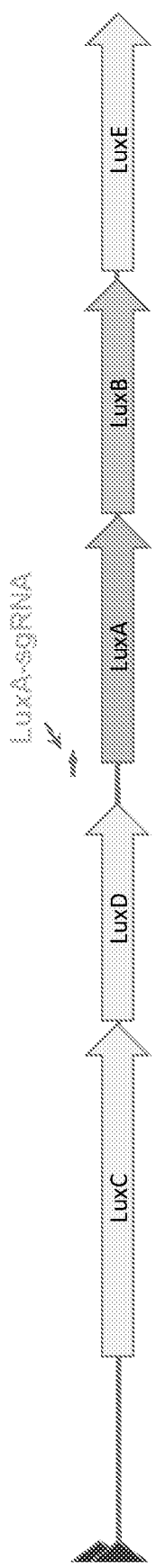
FIGS. 25A-25D show bioluminescence of Photorhabdus luminescens subsp. laumondii TTO1 engineered with the three loxP landing pad under 1 mM IPTG induction.
Figure 25B:
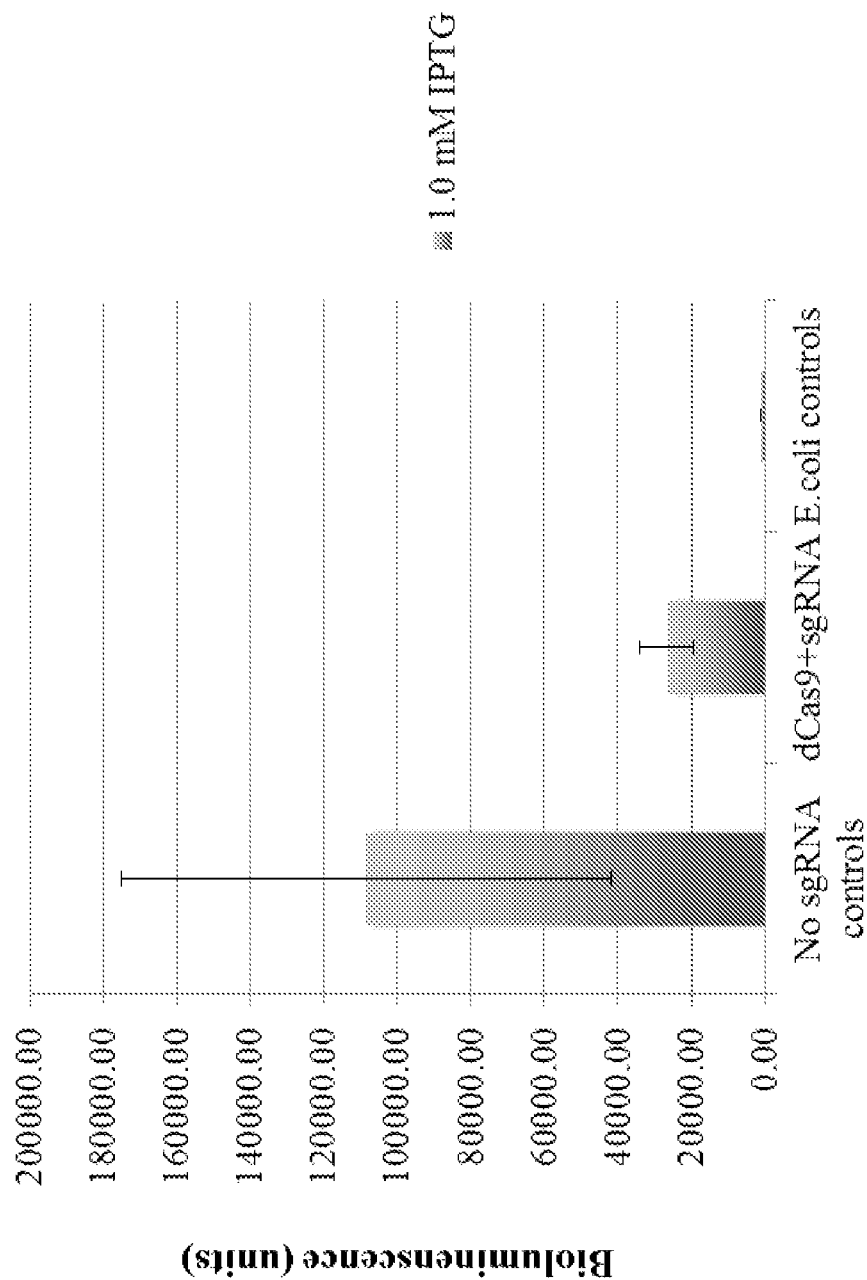
Figure 25C:
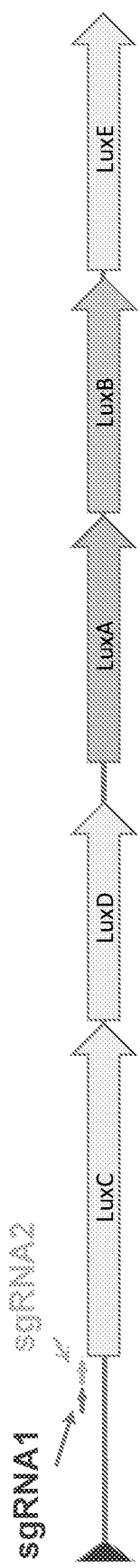

For sgRNA integration, the donor strain E. coli WM3064 containing the sgRNA plasmid, pR6K-Km-loxWT2272-gRNA, was conjugated with the recipient containing dCas9 (FIG. 24, step 3). After conjugation, colonies were obtained on a selection plate with an appropriate Kanamycin concentration. The sgRNAs were designed such that dCas9+sgRNA was directed to bind to the promoter and RBS region of the luxCDABE operon in the recipient genome, thereby repressing the production of bioluminescence (FIG. 25A). In contrast, the aCas9+sgRNA was directed to bind to the promoter region of the luxCDABE operon, thereby activating the production of bioluminescence (FIG. 25C).

Figure 25D:
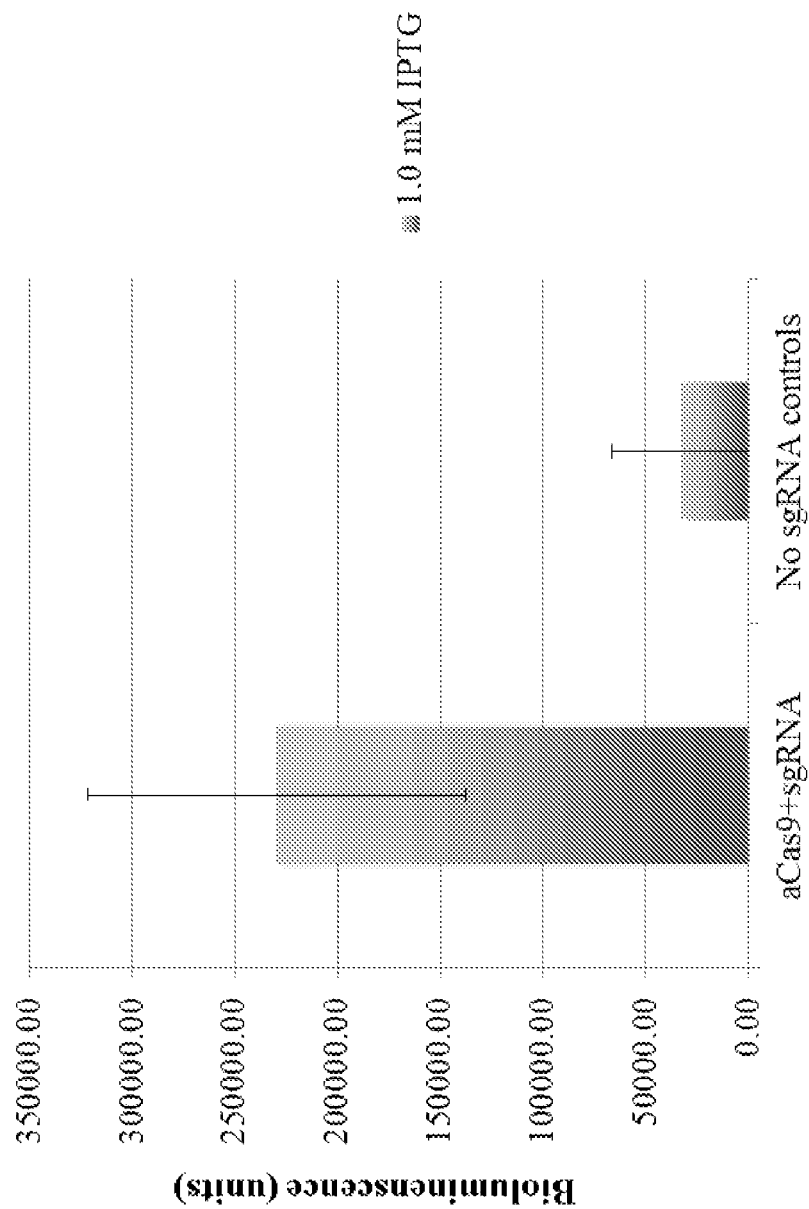

The engineered strains were inoculated for bioluminescent assays in liquid as described in Example 6. The results showed that the engineered strains containing the dCas9 integrated into the first landing pad location and the sgRNA in the second location produced significantly lower bioluminescent signals than the wild type strain (FIG. 25B). In contrast, the strains containing the aCas9+sgRNA produced significantly higher bioluminescence than controls lacking the sgRNA (FIG. 25D).

This study showed that the combined transposition, Cre-LoxP, and T7 RNA polymerase strategy with the three loxP landing pad worked well in Photorhabdus luminescens subsp. laumondii TTO1.

Example 10: Pathway Integration and Expression in Delta Proteobacteria

This study is conducted to show that the combined transposition and Cre-LoxP strategy is effective for pathway integration and expression in the delta proteobacteria strain Myxococcus xanthus TM-12. In particular, using the same methodology as described in Example 9, the delta proteobacterium is engineered with a landing pad containing three loxP sites and the landing pad is replaced with dCas9 or aCas9.

Materials and Methods

E. coli WM3064 is selected as the conjugation donor, which was developed by William Metcalf (UIUC). E. coli WM3064 was derived from E. coli B2155 and was auxotrophic to 2,3-diaminopropionic acid (DAP). The delta proteobacteria Myxococcus xanthus TM-12 is selected as the recipient. The plasmid pCC1-KMW2-SpCre-3L is used to engineer the delta proteobacterium. The integration and expression methodology, including conjugation, counter selection, and MiSeq analysis, is described in Example 6.

Results

The landing pad transposition is achieved by conjugation. Specifically, the donor strain is E. coli WM3064 pCC1-KMW2-SpCre-3L and the recipient is the delta proteobacteria strain Myxococcus xanthus TM-12. Additionally, the landing pad is replaced with dCas9 and aCas9 to provide greater versatility.

---

What is claimed is:

1. A method for integrating a gene of interest into a chromosome of a bacterial host cell, the method comprising:
   (a) providing a bacterial donor cell comprising a donor plasmid, the donor plasmid comprising: a transposase coding sequence; and a donor sequence, wherein the donor sequence is flanked by inverted repeats recognized by the transposase, wherein the donor sequence comprises a first selectable marker coding sequence and a first and a second lox site, and wherein the first selectable marker coding sequence is flanked by the first and the second lox sites;
   (b) introducing the donor plasmid into a bacterial host cell by conjugation with the bacterial donor cell, wherein upon introduction of the donor plasmid into the bacterial host cell, transposase is expressed from the transposase coding sequence, and the donor sequence is integrated into a chromosome of the bacterial host cell between the inverted repeats by the transposase;
   (c) providing a second plasmid comprising the gene of interest and a second selectable marker coding sequence, wherein the gene of interest and the second selectable marker are both flanked by a first lox site of the second plasmid and a second lox site of the second plasmid, wherein the first and the second lox sites of the second plasmid are different; and
   (d) introducing the second plasmid into the bacterial host cell,
   wherein the donor sequence comprises a Cre recombinase coding sequence, and wherein upon introduction of the second plasmid into the bacterial host cell, Cre recombinase is expressed from the Cre recombinase coding sequence, and the gene of interest is integrated into the chromosome of the bacterial host cell by the Cre recombinase through recombinase-mediated cassette exchange (RMCE) between the first lox site of the second plasmid and the first lox site of the donor sequence, and between the second lox site of the second plasmid and the second lox site of the donor sequence.

2. The method of claim 1, wherein the bacterial host cell is not an *E. coli* cell.

3. The method of claim 1, wherein the bacterial host cell is a Proteobacteria cell.

4. The method of claim 1, wherein the bacterial host cell is a cell selected from the group consisting of Bacteroidetes, Cyanobacteria, Firmicutes, and Actinobacteria.

5. The method of claim 1, wherein the first lox site of the second plasmid and the first lox site of the donor sequence are the same lox site selected from the group consisting of loxP, lox5171, lox2272, lox511, loxm2, loxm3, loxm7, loxm11, lox71, and lox66.

6. The method of claim 5, wherein the second lox site of the second plasmid and the second lox site of the donor sequence are heterospecific to the first lox site of the second plasmid and the first lox site of the donor sequence, and wherein the second lox site of the second plasmid and the second lox site of the donor sequence are the same lox site selected from the group consisting of loxP, lox5171, lox2272, lox511, loxm2, loxm3, loxm7, loxm11, lox71, and lox66.

7. The method of claim 1, wherein the donor sequence further comprises a coding sequence for a protein that promotes sequence-specific gene transcription, and wherein the coding sequence for the protein that promotes sequence-specific gene transcription is not flanked by the first and the second lox sites.

8. The method of claim 7, wherein the protein that promotes sequence-specific gene transcription promotes transcription downstream of a first promoter sequence, wherein the gene of interest is operably linked to the first promoter sequence, and wherein the first promoter sequence is flanked by the first and the second lox sites.

9. The method of claim 1, wherein the gene of interest comprises a coding sequence of one or more enzymes.

10. The method of claim 1, wherein the first and the second lox sites of the second plasmid flank a sequence of greater than 7 kb and less than 200 kb.

11. A bacterial host cell comprising a chromosomally integrated donor sequence, wherein the donor sequence comprises a selectable marker coding sequence and a first and a second lox site, wherein the selectable marker coding sequence is flanked by the first and the second lox site, wherein the donor sequence is flanked in the chromosome of the bacterial host cell by inverted repeats recognized by a transposase, wherein the first and the second lox sites are different; wherein the donor sequence further comprises a Cre recombinase coding sequence, and wherein the Cre recombinase coding sequence is flanked by the first and the second lox sites.

12. The bacterial host cell of claim 11, wherein the donor sequence further comprises a coding sequence for a protein that promotes sequence-specific gene transcription, and wherein the coding sequence for the protein that promotes sequence-specific gene transcription is flanked by the inverted repeats but not by the first and the second lox sites.

13. The bacterial host cell of claim 11, wherein the Cre recombinase coding sequence is operably linked to a promoter active when integrated into the host cell.

14. The bacterial host cell of claim 11, wherein the bacterial host cell is a Proteobacteria cell.

15. The bacterial host cell of claim 11, wherein the bacterial host cell is a cell selected from the group consisting of Bacteroidetes, Cyanobacteria, Firmicutes, and Actinobacteria.

16. The bacterial host cell of claim 11, wherein the bacterial host cell is not an *E. coli* cell.

17. The bacterial host cell of claim 11, wherein the first lox site of the plasmid and the first lox site of the donor sequence are the same lox site selected from the group consisting of loxP, lox5171, lox2272, lox511, loxm2, loxm3, loxm7, loxm11, lox71, and lox66.

18. The bacterial host cell of claim 17, wherein the second lox site of the plasmid and the second lox site of the donor sequence are heterospecific to the first lox site of the plasmid and the first lox site of the donor sequence, and wherein the second lox site of the plasmid and the second lox site of the donor sequence are the same lox site selected from the group consisting of loxP, lox5171, lox2272, lox511, loxm2, loxm3, loxm7, loxm11, lox71, and lox66.

19. The bacterial host cell of claim 11, wherein the first and the second lox sites flank a sequence of greater than 7 kb and less than 200 kb.

20. A kit, comprising:
   (a) a first vector comprising:
      (i) a transposase coding sequence; and
      (ii) a donor sequence, wherein the donor sequence is flanked by inverted repeats recognized by the transposase, wherein the donor sequence comprises: (1) a first selectable marker coding sequence flanked by a first and a second lox site, wherein the first and the second lox sites are different, and (2) a Cre recombinase coding sequence flanked by the first and the second lox sites; and (b) a second vector comprising:
- (i) one or more restriction or targeted cloning sites suitable for recombining a gene of interest into the second vector; and
- (ii) a second selectable marker, wherein the second selectable marker and the one or more restriction or targeted cloning sites are flanked by the first and the second lox sites.

21. The kit of claim 20, further comprising a third vector comprising (i) one or more restriction or targeted cloning sites suitable for recombining a gene of interest into the second vector; and (ii) a third selectable marker, wherein the third selectable marker and the one or more restriction or targeted cloning sites are flanked by the first and the second lox sites.

22. The kit of claim 21, wherein the third vector comprises the polynucleotide sequence of SEQ ID NO:11.

23. The kit of claim 20, wherein the first vector comprises the polynucleotide sequence of SEQ ID NO:4.

24. The kit of claim 20, wherein the second vector comprises the polynucleotide sequence of SEQ ID NO:10.

* * * * *

SEQUENCE LISTING

<160> NUMBER OF SEQ ID NOS: 11

<210> SEQ ID NO 1
<211> LENGTH: 34

```
<212> TYPE: DNA
<213> ORGANISM: Artificial Sequence
<220> FEATURE:
<223> OTHER INFORMATION: Synthetic Construct

<400> SEQUENCE: 1
ataacttcgt atagcataca ttatacgaag ttat                                    34

<210> SEQ ID NO 2
<211> LENGTH: 34
<212> TYPE: DNA
<213> ORGANISM: Artificial Sequence
<220> FEATURE:
<223> OTHER INFORMATION: Synthetic Construct

<400> SEQUENCE: 2
attacttcgt ataatgtgta ctatacgaag ttat                                    34

<210> SEQ ID NO 3
<211> LENGTH: 16
<212> TYPE: DNA
<213> ORGANISM: Artificial Sequence
<220> FEATURE:
<223> OTHER INFORMATION: Synthetic Construct

<400> SEQUENCE: 3
taatcgactc actatg                                                        16

<210> SEQ ID NO 4
<211> LENGTH: 15720
<212> TYPE: DNA
<213> ORGANISM: Artificial Sequence
<220> FEATURE:
<223> OTHER INFORMATION: Synthetic Construct

<400> SEQUENCE: 4
cgcaaaaaag ggaataaggg cgacacggaa atgttgaata ctcatactct tccttttca       60 atccatcaca ctggcggccg ctcgagcatg catctagtaa cggccgccag tgtgctggaa      120
ttctgcagat ccggtctaac aaagaaaaac acatttttt gtgaaaattc gttttatta       180 ttcaacatag ttcccttcaa gagcgataca acgattataa cgaccttcca atttttgat      240 accattttgg tagtactcct tcggttttgc ctcaaaatag gcctcagttt cggcgatcac      300
ctcttcattg cagccaaatt ttttccctgc gagcatcctt tgaggtctg agaacaagaa      360 aaagtcgctg ggggccagat ctggagaata cggcgggtgg ggaagcaatt cgaagcccaa      420
ttcatgaatt tttgccatcg ttctcaatga cttgtggcac ggtgcgttgt cttggtggaa      480
caacactttt ttcttcttca tgtggggccg ttttgccgcg atttcgacct tcaaacgctc      540
caataacgcc atataatagt cactgttgat ggttttccc ttctcaagat aatcgataaa      600
aattattcca tgcgcatccc aaaaaacaga ggccattact ttgccagcgg acttttgagt      660
ctttccacgc ttcggagacg gttcaccggt cgctgtccac tcagccgact gtcgattgga      720
ctcaggagtg tagtgatgga gccatgtttc atccattgtc acatatcgac ggaaaaactc      780
gggtgtatta cgagttaaca gctgcaaaca ccgctcagaa tcatcaacac gttgttgttt      840
ttggtcaaat gtgagctcgc gcggcaccca ttttgcacag agcttccgca tatccaaata      900
ttgatgaatg atatgaccaa cacgttcctt tgatatcttt aaggcctctg ctatctcgat      960
caacttcatt ttacggtcat tcaaaatcat tttgtggatt ttttttgatgt tttcgtcggt    1020 aaccacctct ttcgggcgtc cactgcgttc accgtcctcc gtgctcatt caccacgctt    1080
```

```
gaattttgca taccaatcaa ttattgttga tttccctggg gcagagtccg gaaactcatt   1140
atcaagccaa gttttttgctt ccactgtatt ttttcccttc agaaaacagt attttatcaa   1200
aacacgaaat tccttttttt ccatatgtgt ttcctgtgtg aaattgttat ccgctcacaa   1260
ttccacacaa catacgagcc ggaagcataa agtgtaaagc ctggggtgcc taatgagtga   1320
gctaactcac attaattgcg ttgcgctcac ccgctgcata accctgcttc ggggtcatta   1380
tagcgatttt ttcggtatat ccatcctttt tcgcacgata tacaggattt tgccaaaggg   1440
ttcgtgtaga ctttccttgg tgtatccaac ggcgtcagcc gggcaggata ggtgaagtag   1500
gcccacccgc gagcgggtgt tccttcttca ctgtcccta ttcgcacctg gcggtgctca   1560
acgggaatcc tgctctgcga ggctggccga taagctctaa gaaaccatta ttatcatgac   1620
attaacctat aaaaataggc gtatcacgag gccctttcgt cttcaagaat taattcactg   1680
gccgtcgttt tacaacgtcg tgactgggaa accctggcg ttacccaaca cataacaggt   1740
tggctgataa gtccccggtc tggccggccc attgcatcct gcaggggcgta atgctctgcc   1800 agtgtcgcga accccagagt cgtcgacacg cgcagaccaa aacgatctca agaagatcat   1860
cttattaatc agataaaata tttctaggca ccaataactg ccttaaaaaa attacgcccc   1920
gccctgccac tcatcgcagt actgttgata ccgggaagtc ctgggccaac ttttggcgaa   1980
aatgagacgt tgaataactt cgtatagtac acattatacg aagttattcg gcacgtaaga   2040
ggttccaact ttcacccggg ccgctcagaa gaactcgtca agaaggcgat agaaggcgat   2100
gcgctgcgaa tcgggagcgg cgataccgta aagcacgagg aagcggtcag cccattcgcc   2160
gccaagctct tcagcaatat cacgggtagc caacgctatg tcctgatagc ggtccgccac   2220
acccagccgg ccacagtcga tgaatccaga aaagcggcca ttttccacca tgatattcgg   2280
caagcaggca tcgccatggg tcacgacgag atcctcgccg tcgggcatcc gcgccttgag   2340
cctggcgaac agttcggctg gcgcgagccc ctgatgctct tcgtccagat catcctgatc   2400
gacaagaccg gcttccatcc gagtacgtgc tcgctcgatg cgatgtttcg cttggtggtc   2460
gaatgggcag gtagccggat caagcgtatg cagccgccgc attgcatcag ccatgatgga   2520
tactttctcg gcaggagcaa ggtgagatga caggagatcc tgccccggca cttcgcccaa   2580
tagcagccag tcccttcccg cttcagtgac aacgtcgagc acagctgcgc aaggaacgcc   2640
cgtcgtggcc agccacgata gccgcgctgc ctcgtcttgg agttcattca gggcaccgga   2700
caggtcggtc ttgacaaaaa gaaccgggcg cccctgcgct gacagccgga acacggcggc   2760
atcagagcag ccgattgtct gttgtgccca gtcatagccg aatagcctct ccacccaagc   2820
ggccggagaa cctgtgtgca atccatcttg ttcaatcatg cgaaacgatc ctcatcctgt   2880
ctcttgatca gatcttgatc ccctgcgcca tcagatcctt ggcggcaaga aagccatcca   2940
gtttactttg cagggcttcc caaccttacc agagggcgcc ccagctggca attccggttc   3000
gcttgctgtc cataaaaccg cccagtctag ctatcgccat gtaagcccac tgcaagctac   3060
ctgctttctc tttgcgcttg cgttttccct tgtccagata gcccagtagc tgacattcat   3120
ccggggtcag caccgtttct gcggactggc tttctacgtg ttccgcttcc tttagcagcc   3180
cttgcgccct gagtgcttgc ggcagcgtga actagttaag gttcagcagt cctgccctc   3240 tgattttcca gtctgaccac ttcggattat cccgtgacag gtcattcaga ctggctaatg   3300
cacccagtaa ggcagcggta tcatcaacag gcttacccgt cttactgtct cgagttttgt   3360
tcaaaaaaaa gcccgctcat taggcgggct gggctaatcg ccatcttcca gcaggcgcac   3420
cattgcccct gtttcactat ccaggttacg gatatagttc atgacaatat ttacattggt   3480
```

```
ccagccacca gcttgcatga tctccggtat tgaaactcca gcgcgggcca tatctcgcgc      3540
ggctccgaca cgggcactgt gtccagacca ggccaggtat ctctgaccag agtcatcctt      3600
agcgccgtaa atcaatcgat gagttgcttc aaaaatccct tccagggcgc gagttgatag      3660
ctggctggtg gcagatggcg cggcaacacc attttttctg acccggcaaa acaggtagtt      3720
attcggatca tcagctacac cagagacgga aatccatcgc tcgaccagtt tagttacccc      3780
caggctaagt gccttctcta cacctgcggt gctaaccagc gttttcgttc tgccaatatg      3840
gattaacatt ctcccaccgt cagtacgtga gatatcttta accctgatcc tggcaatttc      3900
ggctatacgt aacagggtgt tataagcaat ccccagaaat gccagattac gtatatcctg      3960
gcagcgatcg ctattttcca tgagtgaacg aacctggtcg aaatcagtgc gttcgaacgc      4020
tagagcctgt tttgcacgtt caccggcatc aacgttttct tttcggatcc gccgcataac      4080
cagtgaaaca gcattgctgt cacttggtcg tggcagcccg gaccgacgat gaagcatgtt      4140
tagctggccc aaatgttgct ggatagtttt tactgccaga ccgcgcgcct gaagatatag      4200
aagataatcg cgaacatctt caggttctgc gggaaaccat ttccggttat tcaacttgca      4260
ccatgccgcc cacgaccggc aaacggacag aagcattttc caggtatgct cagaaaacgc      4320
ctggcgatcc ctgaacatgt ccatcaggtt cttgcgaacc tcatcactcg ttgcatcgac      4380
cggtaatgca ggcaaatttt ggtgtacggt cagtaaattg acattttg cctcctaaaa        4440 taaaagttt aaattaaatc cataatgagt ttgatgattt caataatagt tttaatgacc       4500
tccgaaatta gtttaatatg ctttaatttt tcttttcaa aatatctctt caaaaaatat       4560
tacccaatac ttaataataa atagattata acacaaaatt cttttaaaaa agtagtttat      4620
tttgttatca ttcggtaccg ggccccccct cgaggtcgac ggtatcgata agcttgatat      4680
cgaattcctg cagcccgggg gatccactag ttctagagcg gccgccaccg cggtggagct      4740
cactcaaagg cggtaatacg gttatcataa cttcgtataa tgtatgctat acgaagttat      4800
cctttgcact ggattgcgag gctttgcacg atgcgtccgg cgtagaggat ccagatcccg      4860
gacaccatcg aatggcgcaa aacctttcgc ggtatggcat gatagcgccc ggaagagagt      4920
caattcaggg tggtgaatgt gaaaccagta acgttatacg atgtcgcaga gtatgccggt      4980
gtctcttatc agaccgtttc ccgcgtggtg aaccaggcca gccacgtttc tgcgaaaacg      5040
cgggaaaaag tggaagcggc gatggcgag ctgaattaca ttcccaaccg cgtggcacaa       5100
caactggcgg gcaaacagtc gttgctgatt ggcgttgcca cctccagtct ggccctgcac      5160
gcgccgtcgc aaattgtcgc ggcgattaaa tctcgcgccg atcaactggg tgccagcgtg      5220
gtggtgtcga tggtagaacg aagcggcgtc gaagcctgta aagcggcggt gcacaatctt      5280
ctcgcgcaac gcgtcagtgg gctgatcatt aactatccgc tggatgacca ggatgccatt      5340
gctgtggaag ctgcctgcac taatgttccg gcgttatttc ttgatgtctc tgaccagaca      5400
cccatcaaca gtattatttt ctcccatgaa gacggtacgc gactgggcgt ggagcatctg      5460
gtcgcattgg gtcaccagca aatcgcgctg ttagcgggcc cattaagttc tgtctcggcg      5520
cgtctgcgtc tggctggctg gcataaatat ctcactcgca atcaaattca gccgatagcg      5580
gaacgggaag gcgactggag tgccatgtcc ggttttcaac aaaccatgca aatgctgaat      5640
gagggcatcg ttcccactgc gatgctggtt gccaacgatc agatggcgct gggcgcaatg      5700
cgcgccatta ccgagtccgg gctgcgcgtt ggtgcggata tctcggtagt gggatacgac      5760
gataccgaag acagctcatg ttatatcccg ccgttaacca ccatcaaaca ggattttcgc      5820
```

```
ctgctggggc aaaccagcgt ggaccgcttg ctgcaactct ctcagggcca ggcggtgaag    5880
ggcaatcagc tgttgcccgt ctcactggtg aaaagaaaaa ccaccctggc gcccaatacg    5940
caaaccgcct ctccccgcgc gttggccgat tcattaatgc agctggcacg acaggtttcc    6000
cgactggaaa gcgggcagtg agcgcaacgc aattaatgta agttagctca ctcattaggc    6060
accccaggct ttacacttta tgcttccggc tcgtataatg tgtggaattg tgagcggata    6120
acaatttcac acaggaaaca gctatgacca tgattacgga ttcactggcc gtcgttttac    6180
aacgtcgtga ctgggaaaac cctggcgtta cccaacttaa tcgccttgca gcacatcccc    6240
ctttcgccag ctggcgtaat agcgaagagg cccgcaccga tcgcccttcc caacagttgc    6300
gcagcctgaa tggcgaatgg cgctttgcct ggtttccggc accagaagcg gtgccggaaa    6360
gctggctgga gtgcgatctt cctgaggccg atactgtcgt cgtccsctca aactggcaga    6420
```

```
cgctggcgtt tgacgggtct tgctctggca tccagcactt ctccgcgatg ctccgagatg   8280
aggtaggtgg tcgcgcggtt aacttgcttc ctagtgaaac cgttcaggac atctacggga   8340
ttgttgctaa gaaagtcaac gagattctac aagcagacgc aatcaatggg accgataacg   8400
aagtagttac cgtgaccgat gagaacactg gtgaaatctc tgagaaagtc aagctgggca   8460
ctaaggcact ggctggtcaa tggctggctt acggtgttac tcgcagtgtg actaagcgtt   8520
cagtcatgac gctggcttac gggtccaaag agttcggctt ccgtcaacaa gtgctggaag   8580
ataccattca gccagctatt gattccggca agggtctgat gttcactcag ccgaatcagg   8640
ctgctggata catggctaag ctgatttggg aatctgtgag cgtgacggtg gtagctgcgg   8700
ttgaagcaat gaactggctt aagtctgctg ctaagctgct ggctgctgag gtcaaagata   8760
agaagactgg agagattctt cgcaagcgtt gcgctgtgca ttgggtaact cctgatggtt   8820
tccctgtgtg gcaggaatac aagaagccta ttcagacgcg cttgaacctg atgttcctcg   8880
gtcagttccg cttacagcct accattaaca ccaacaaaga tagcgagatt gatgcacaca   8940
aacaggagtc tggtatcgct cctaactttg tacacagcca agacggtagc caccttcgta   9000
agactgtagt gtgggcacac gagaagtacg gaatcgaatc ttttgcactg attcacgact   9060
ccttcggtac cattccggct gacgctgcga acctgttcaa agcagtgcgc gaaactatgg   9120
ttgacacata tgagtcttgt gatgtactgg ctgatttcta cgaccagttc gctgaccagt   9180
tgcacgagtc tcaattggac aaaatgccag cacttccggc taaaggtaac ttgaacctcc   9240
gtgacatctt agagtcggac ttcgcgttcg cgtaacgcca atcaatacg actccggatc   9300
cacaggacgg gtgtggtcgc gaccgagata gggttgagtg ttgttccagt ttgagatctg   9360
ggaatcattt gaaggttggt actatataaa aataatatgc atttaatact agcgacgcca   9420
tctatgtgtc agaccgggga cttatcagcc aacctgttag cagaacttta aaagtgctca   9480
tcattggaaa acgttcttcg gggcgaaaac tctcaaggat cttaccgctg ttgagatcca   9540
gttcgatgta acccactcgt gcacccaact gatcttcagc atcttttact ttcaccagcg   9600
tttctgggtg agcaaaaaca ggaaggcaaa atgcacaggg acaccaggat ttatttattc   9660
tgcgaagtga tcttccgtca caggtattta ttcgcgataa gctcatggag cggcgtaacc   9720
gtcgcacagg aaggacagag aaagcgcgga tctgggaagt gacggacaga acggtcagga   9780
cctggattgg ggaggcggtt gccgccgctg ctgctgacgg tgtgacgttc tctgttccgg   9840
tcacaccaca tacgttccgc cattcctatg cgatgcacat gctgtatgcc ggtataccgc   9900
tgaaagttct gcaaagcctg atgggacata agtccatcag ttcaacggaa gtctacgaca   9960
aggttttgc gctggatgtg gctgcccggc accgggtgca gtttgcgatg ccggagtctg   10020
atgcggttgc gatgctgaaa caattatcct gagaataaat gccttggcct ttatatgaa   10080
atgtggaact gagtggatat gctgttttg tctgttaaac agagaagctg ctgttatcc   10140
actgagaagc gaacgaaaca gtcgggaaaa tctcccatta tcgtagagat ccgcattatt   10200
aatctcagga gcctgtgtag cgtttatagg aagtagtgtt ctgtcatgat gcctgcaagc   10260
ggtaacgaaa acgatttgaa tatgccttca ggaacaatag aaatcttcgt gcggtgttac   10320
gttgaagtga agcggattat gtcagcaatg gacagaacaa cctaatgaac acagaaccat   10380
gatgtggtct gtccttttac agccagtagt gctcgccgca gtcgagcgac agggcgaagc   10440
cctcggctgt tgccctcgc cgctgggctg cggccgtct atgggccctgc aaacgcgcca   10500
gaaacgccgt cgaagccgtg tgcgagacac cgcggccggc cgccggcgtt gtggatacct   10560
```

```
cgcggaaaac ttggccctca ctgacagatg aggggcggac gttgacactt gagggccga    10620
ctcacccggc gcggcgttga cagatgaggg gcaggctcga tttcggccgg cgacgtggag    10680
ctggccagcc tcgcaaatcg gcgaaaacgc ctgattttac gcgagtttcc cacagatgat    10740
gtggacaagc ctggggataa gtgccctgcg gtattgacac ttgaggggcg cgactactga    10800
cagatgaggg gcgcgatcct tgacacttga ggggcagagt gctgacagat gagggcgca    10860
cctattgaca tttgaggggc tgtccacagg cagaaaatcc agcatttgca agggtttccg    10920
cccgttttc ggccaccgct aacctgtctt ttaacctgct tttaaaccaa tatttataaa     10980
ccttgttttt aaccagggct gcgccctgtg cgcgtgaccg cgcacgccga aggggggtgc    11040
ccccccttct cgaaccctcc cggtcgagtg agcgaggaag caccagggaa cagcacttat    11100
atattctgct tacacacgat gcctgaaaaa acttcccttg gggttatcca cttatccacg    11160
gggatatttt tataattatt tttttatag tttttagatc ttctttttta gagcgccttg     11220
taggccttta tccatgctgg ttctagaaa ggtgttgtga caaattgccc tttcagtgtg     11280
acaaatcacc ctcaaatgac agtcctgtct gtgacaaatt gcccttaacc ctgtgacaaa    11340
ttgccctcag aagaagctgt tttttcacaa agttatccct gcttattgac tcttttttat    11400
ttagtgtgac aatctaaaaa cttgtcacac ttcacatgga tctgtcatgg cggaaacagc    11460
ggttatcaat cacaagaaac gtaaaaatag cccgcgaatc gtccagtcaa acgacctcac    11520
tgaggcggca tatagtctct cccgggatca aaaacgtatg ctgtatctgt tcgttgacca    11580
gatcagaaaa tctgatggca ccctacagga acatgacggt atctgcgaga tccatgttgc    11640
taaatatgct gaaatattcg gattgacctc tgcggaagcc agtaaggata tacggcaggc    11700
attgaagagt ttcgcgggga aggaagtggt tttttatcgc cctgaagagg atgccggcga    11760
tgaaaaggc tatgaatctt tccttggtt tatcaaacgt gcgcacagtc catccagagg     11820
gctttacagt gtacatatca acccatatct cattcccttc tttatcgggt tacagaaccg    11880
gtttacgcag tttcggctta gtgaaacaaa agaaatcacc aatccgtatg ccatgcgttt    11940
atacgaatcc ctgtgtcagt atcgtaagcc ggatggctca ggcatcgtct ctctgaaaat    12000
cgactggatc atagagcgtt accagctgcc tcaaagttac cagcgtatgc ctgacttccg    12060
ccgccgcttc ctgcaggtct gtgttaatga gatcaacagc agaactccaa tgcgcctctc    12120
atacattgag aaaagaaag gccgccagac gactcatatc gtattttcct tccgcgatat    12180
cacttccatg acgacaggat agtctgaggg ttatctgtca cagatttgag ggtggttcgt    12240
cacatttgtt ctgacctact gagggtaatt tgtcacagtt ttgctgtttc cttcagcctg    12300
catggatttt ctcatacttt ttgaactgta atttttaagg aagccaaatt tgagggcagt    12360
ttgtcacagt tgatttcctt ctctttccct tcgtcatgtg acttgatatc ggggttagt     12420
tcgtcatcat tgatgagggt tgattatcac agtttattac tctgaattgg ctatccgcgt    12480
gtgtacctct acctggagtt ttttcccacg tggatatttc ttcttgcgct gagcgtaaga    12540
gctatctgac agaacagttc ttctttgctt cctcgccagt tcgctcgcta tgctcggtta    12600
cacggctgcg gcgagcgcta gtgataataa gtgactgagg tatgtgctct tcttatctcc    12660
ttttgtagtg ttgctcttat tttaaacaac tttgcggttt tttgatgact ttgcgatttt    12720
gttgttgctt tgcagtaaat tgcaagattt aataaaaaaa cgcaaagcaa tgattaaagg    12780
atgttcagaa tgaaactcat ggaaacactt aaccagtgca taaacgctgg tcatgaaatg    12840
acgaaggcta tcgccattgc acagtttaat gatgacagcc ggaagcgag gaaaataacc     12900
cggcgctgga gaataggtga agcagcggat ttagttgggg tttcttctca ggctatcaga    12960
```

```
gatgccgaga aagcagggcg actaccgcac ccggatatgg aaattcgagg acgggttgag   13020
caacgtgttg gttatacaat tgaacaaact aatcatatgc gtgatgtgtt tggtacgcga   13080
ttgcgacgtg ctgaagacgt atttccaccg gtgatcgggg ttgctgccca taaaggtggc   13140
gtttacaaaa cctcagtttc tgttcatctt gctcaggatc tggctctgaa ggggctacgt   13200
gttttgctcg tggaaggtaa cgaccccag ggaacagcct caatgtatca cggatgggta    13260
ccagatcttc atattcatgc agaagacact ctcctgcctt tctatcttgg ggaaaaggac   13320
gatgtcactt atgcaataaa gcccacttgc tggccggggc ttgacattat tccttcctgt   13380
ctggctctgc accgtattga aactgagtta atgggcaaat ttgatgaagg taaactgccc   13440
accgatccac acctgatgct ccgactggcc attgaaactg ttgctcatga ctatgatgtc   13500
atagttattg acagcgcgcc taacctgggt atcggcacga ttaatgtcgt atgtgctgct   13560
gatgtgctga ttgttcccac gcctgctgag ttgtttgact acacctccgc actgcagttt   13620
ttcgatatgc ttcgtgatct gctcaagaac gttgatctta aagggttcga gcctgatgta   13680
cgtattttgc ttaccaaata cagcaatagt aatggctctc agtccccgtg gatggaggag   13740
caaattcggg atgcctgggg aagcatggtt ctaaaaaatg ttgtacgtga aacggatgaa   13800
gttggtaaag gtcagatccg gatgagaact gttttttgaac aggccattga tcaacgctct   13860
tcaactggtg cctggagaaa tgctctttct atttgggaac ctgtctgcaa tgaaattttc   13920
gatcgtctga ttaaaccacg ctgggagatt agataatgaa gcgtgcgcct gttattccaa   13980
aacatacgct caatactcaa ccggttgaag atacttcgtt atcgacacca gctgccccga   14040
tggtggattc gttaattgcg cgcgtaggag taatggctcg cggtaatgcc attactttgc   14100
ctgtatgtgg tcgggatgtg aagtttactc ttgaagtgct ccggggtgat agtgttgaga   14160
agacctctcg ggtatggtca ggtaatgaac gtgaccagga gctgcttact gaggacgcac   14220
tggatgatct catcccttct tttctactga ctggtcaaca gacaccggcg ttcggtcgaa   14280
gagtatctgg tgtcatagaa attgccgatg ggagtcgccg tcgtaaagct gctgcactta   14340
ccgaaagtga ttatcgtgtt ctggttggcg agctggatga tgagcagatg gctgcattat   14400
ccagattggg taacgattat cgcccaacaa gtgcttatga acgtggtcag cgttatgcaa   14460
gccgattgca gaatgaattt gctggaaata ttctgcgct ggctgatgcg gaaaatattt    14520
cacgtaagat tattacccgc tgtatcaaca ccgccaaatt gcctaaatca gttgttgctc   14580
ttttttctca ccccggtgaa ctatctgccc ggtcaggtga tgcacttcaa aaagccttta   14640
cagataaaga ggaattactt aagcagcagg catctaacct tcatgagcag aaaaaagctg   14700
gggtgatatt tgaagctgaa gaagttatca ctcttttaac ttctgtgctt aaaacgtcat   14760
ctgcatcaag aactagttta agctcacgac atcagtttgc tcctggagcg acagtattgt   14820
ataagggcga taaatggtg cttaacctgg acaggtctcg tgttccaact gagtgtatag    14880
agaaaattga ggccattctt aaggaacttg aaaagccagc ccctgatgc gaccacgttt    14940 tagtctacgt ttatctgtct ttacttaatg tcctttgtta caggccagaa agcataactg   15000
gcctgaatat tctctctggg cccactgttc cacttgtatc gtcggtctga taatcagact   15060
gggaccatgg tcccactcgt atcgtcggtc tgattattag tctgggacca cggtcccact   15120
cgtatcgtcg gtctgattat tagtctggga ccacggtccc actcgtatcg tcggtctgat   15180
aatcagactg ggaccacggt cccactcgta tcgtcggtct gattattagt ctgggaccat   15240
ggtcccactc gtatcgtcgg tctgattatt agtctgggac cacggtccca ctcgtatcgt   15300
```

```
cggtctgatt attagtctgg aaccacggtc ccactcgtat cgtcggtctg attattagtc    15360
tgggaccacg gtcccactcg tatcgtcggt ctgattatta gtctgggacc acgatcccac    15420
tcgtgttgtc ggtctgatta tcggtctggg accacggtcc cacttgtatt gtcgatcaga    15480
ctatcagcgt gagactacga ttccatcaat gcctgtcaag gcaagtatt gacatgtcgt     15540 cgtaacctgt agaacggagt aacctcggtg tgcggttgta tgcctgctgt ggattgctgc    15600
tgtgtcctgc ttatccacaa cattttgcgc acggttatgt ggacaaaata cctggttacc    15660
caggccgtgc cggcacgtta accgggctgc atccgatgca agtgtgtcgc tgtcgacgag    15720
```

<210> SEQ ID NO 5
<211> LENGTH: 8578
<212> TYPE: DNA
<213> ORGANISM: Artificial Sequence
<220> FEATURE:
<223> OTHER INFORMATION: Synthetic Construct
<400> SEQUENCE: 5

```
aattttgcg gccgctatgt gttgggtaac gccagggttt tcccagtcac gacgttgtaa      60
aacgacggcc agtgaattaa ttcttgaaga cgaaagggcc tcgtgatacg cctatttta    120 taggttaatg tcatgataat aatggttct tagagcttat cggccagcct cgcagagcag    180
gattcccgtt gagcaccgcc aggtgcgaat aagggacagt gaagaaggaa cacccgctcg    240 cggtgggcc tacttcacct atcctgcccg gctgacgccg ttggatacac caaggaaagt     300
ctacacgaac cctttggcaa atcctgtat atcgtgcgaa aaaggatgga tataccgaaa     360
aaatcgctat aatgacccg aagcaggtt atgcagcgaa gatccgcagt tcaacctgtt      420
gatagtacgt actaagctct catgtttcac gtactaagct ctcatgttta acgtactaag    480
ctctcatgtt taacgaacta aaccctcatg gctaacgtac taagctctca tggctaacgt    540
actaagctct catgtttcac gtactaagct ctcatgtttg aacaataaaa ttaatataaa    600
tcagcaactt aaatagcctc taaggtttta agttttataa gaaaaaaaag aatatataag    660
gcttttaaag cttttaaggt ttaacggttg tggacaacaa gccagggatg taacgcactg    720
agaagccctt agagcctctc aaagcaattt tgagtgacac aggaacactt aacggctgac    780
atgggaatta gccatggcaa agcctcgcaa tccagtgcaa aggataactt cgtatagcat    840
acattatacg aagttatgat aaccgtatta ccgcctttga gtgagctcca ccgcggtggc    900
ggccgctcta gaactagtgg atccccatgc gtccggcgta gaggatcgag atcgatctcg    960
atcccgcgaa attaatacga ctcactatag ggaattgtg agcggataac aattcccctc    1020
tagaaataat tttgtttaac tttaagaagg agatatacat atgactaaaa aaatttcatt    1080
cattattaac ggccaggttg aaatctttcc cgaaggtgat gatttagtgc aatccattaa    1140
ttttggtgat aatagtgttt acctgccaat attgaatgac tctcatgtaa aaaacattat    1200
tgattgtaat ggaaataacg aattacggtt gcataacatt gtcaattttc tctatacggt    1260
agggcaaaga tggaaaaatg aagaatactc aagacgcagg acatacattc gtgacttaaa    1320
aaaatatatg ggatattcag aagaaatggc taagctagag gccaattgga tatctatgat    1380
tttatgttct aaaggcggcc tttatgatgt tgtagaaaat gaacttggtt ctcgccatat    1440
catggatgaa tggctacctc aggatgaaag ttatgttcgg gcttttccga aggtaaatc     1500 tgtacatctg ttggcaggta atgttccatt atctgggatc atgtctatat acgcgcaat    1560 tttaactaag aatcagtgta ttataaaaac atcgtcaacc gatcctttta ccgctaatgc    1620
attagcgtta agttttatt atgtagaccc taatcatccg ataacgcgct ctttatctgt    1680
```

```
tatatattgg ccccaccaag gtgatacatc actcgcaaaa gaaattatgc aacatgcgga   1740
tgttattgtc gcttgggag ggccagatgc gattaattgg gcggtagagc atgcgccatc    1800
ttatgctgat gtgattaaat ttggttctaa aaagagtctt tgcattatcg ataatcctgt   1860
tgatttgacg tccgcagcga caggtgcggc tcatgatgtt tgtttttacg atcagcgagc   1920 ttgttttttct gcccaaaaca tatattacat gggaaatcat tatgaggaat ttaagttagc  1980
gttgatagaa aaacttaatc tatatgcgca tatattaccg aatgccaaaa aagatttga    2040 tgaaaaggcg gcctattctt tagttcaaaa agaaagcttg tttgctggat taaaagtaga   2100
ggtggatatt catcaacgtt ggatgattat tgagtcaaat gcaggtgtgg aatttaatca   2160
accacttggc agatgtgtgt accttcatca cgtcgataat attgagcaaa tattgcctta   2220
tgttcaaaaa aataagacgc aaaccatatc tatttttcct tgggagtcat catttaaata   2280
tcgagatgcg ttagcattaa aaggtgcgga aaggattgta gaagcaggaa tgaataacat   2340
atttcgagtt ggtggatctc atgacggaat gagaccgttg caacgattag tgacatatat   2400
ttctcatgaa aggccatcta actatacggc taaggatgtt gcggttgaaa tagaacagac   2460
tcgattcctg gaagaagata agttccttgt atttgtccca taataggtaa aaagtatgga   2520
aaatgaatca aaatataaaa ccatcgacca cgttatttgt gttgaaggaa ataaaaaaat   2580
tcatgtttgg gaaacgctgc cagaagaaaa cagcccaaag agaaagaatg ccattattat   2640
tgcgtctggt tttgcccgca ggatggatca ttttgctggt ctggcggaat atttatcgcg   2700
gaatggattt catgtgatcc gctatgattc gcttcaccac gttggattga gttcagggac   2760
aattgatgaa tttacaatgt ctataggaaa gcagagcttg ttagcagtgg ttgattggtt   2820
aactacacga aaaataaata acttcggtat gttggcttca agcttatctg cgcggatagc   2880
ttatgcaagc ctatctgaaa tcaatgcttc gttttttaatc accgcagtcg gtgttgttaa   2940
cttaagatat tctcttgaaa gagctttagg gttttgattat ctcagtctac ccattaatga   3000
attgccgaat aatctagatt ttgaaggcca taaattgggt gctgaagtct ttgcgagaga   3060
ttgtcttgat tttggttggg aagatttagc ttctacaatt aataacatga tgtatcttga   3120
tataccgttt attgctttta ctgcaaataa cgataattgg gtcaagcaag atgaagttat   3180
cacattgtta tcaaatattc gtagtaatcg atgcaagata tattctttgt taggaagttc   3240
gcatgacttg agtgaaaatt tagtggtcct gcgcaatttt tatcaatcgg ttacgaaagc   3300
cgctatcgcg atggataatg atcatctgga tattgatgtt gatattactg aaccgtcatt   3360
tgaacattta actattgcga cagtcaatga acgccgaatg agaattgaga ttgaaaatca   3420
agcaatttct ctgtcttaaa atctattgag atattctatc actcaaatag caatataagg   3480
actctctatg aaatttggaa acttttttgct tacataccaa cctccccaat tttctcaaac   3540
agaggtaatg aaacgtttgg ttaaattagg tcgcatctct gaggagtgtg ttttgatac    3600 cgtatggtta ctggagcatc atttcacgga gtttggtttg cttggtaacc cttatgtcgc   3660
tgctgcatat ttacttggcg cgactaaaaa attgaatgta ggaactgccg ctattgttct   3720
tcccacagcc catccagtac gccaacttga agatgtgaat ttattggatc aaatgtcaaa   3780
aggacgattt cggtttggta tttgccgagg gctttacaac aaggactttc gcgtattcgg   3840
cacagatatg aataacagtc gcgccttagc ggaatgctgg tacgggctga taaagaatgg   3900
catgacagag ggatatatgg aagctgataa tgaacatatc aagttccata aggtaaaagt   3960
aaaccccgcg gcgtatagca gaggtggcgc accggtttat gtggtggctg aatcagcttc   4020
```

-continued

```
gacgactgag tgggctgctc aatttggcct accgatgata ttaagttgga ttataaatac    4080
taacgaaaag aaagcacaac ttgagctttta taatgaagtg gctcaagaat atgggcacga    4140
tattcataat atcgaccatt gcttatcata taacatct gtagatcatg actcaattaa    4200
agcgaaagca atttgccgga aatttctggg gcattggtat gattcttatg tgaatgctac    4260
gactattttt gatgattcag accaaacaag aggttatgat ttcaataaag ggcagtggcg    4320
tgactttgta ttaaaaggac ataaagatac taatcgccgt attgattaca gttacgaaat    4380
caatcccgtg ggaacgccgc aggaatgtat tgacataatt caaaaagaca ttgatgctac    4440
aggaatatca aatatttgtt gtggatttga agctaatgga acagtagacg aaattattgc    4500
ttccatgaag ctcttccagt ctgatgtcat gccatttctt aaagaaaaac aacgttcgct    4560
attatattag ctaaggagaa agaaatgaaa tttggattgt tcttccttaa cttcatcaat    4620
tcaacaactg ttcaagaaca agtatagtt cgcatgcagg aaataacgga gtatgttgat    4680
aagttgaatt ttgaacagat tttagtgtat gaaaatcatt tttcagataa tggtgttgtc    4740
ggcgctcctc tgactgtttc tggttttctg ctcggtttaa cagagaaaat taaaattggt    4800
tcattaaatc acatcattac aactcatcat cctgtccgca tagcggagga agcttgctta    4860
ttggatcagt taagtgaagg gagatttatt ttagggttta gtgattgcga aaaaaaagat    4920
gaaatgcatt tttttaatcg cccggttgaa tatcaacagc aactatttga agagtgttat    4980
gaaatcatta acgatgcttt aacaacaggc tattgtaatc cagataacga ttttatagc    5040 ttccctaaaa tatctgtaaa tccccatgct tatacgccag gcggacctcg gaaatatgta    5100
acagcaacca gtcatcatat tgttgagtgg gcggccaaaa aaggtattcc tctcatcttt    5160
aagtgggatg attctaatga tgttagatat gaatatgctg aaagatataa agccgttgcg    5220
gataaatatg acgttgacct atcagagata gaccatcagt taatgatatt agttaactat    5280
aacgaagata gtaataaagc taaacaagag acgcgtgcat ttattagtga ttatgttctt    5340
gaaatgcacc ctaatgaaaa tttcgaaaat aaacttgaag aaataattgc agaaaacgct    5400
gtcggaaatt atacggagtg tataactgcg gctaagttgg caattgaaaa gtgtggtgcg    5460
aaaagtgtat tgctgtcctt tgaaccaatg aatgatttga tgagccaaaa aaatgtaatc    5520
aatattgttg atgataatat taagaagtac cacatggaat atacctaata gatttcgagt    5580
tgcagcgagg cggcaagtga acgaatcccc aggagcatag ataactatgt gactggggtg    5640
agtgaaagca gccaacaaag cagcagcttg aaagatgaag ggtataaaag agtatgacag    5700
cagtgctgcc atactttcta atattatctt gaggagtaaa acaggtatga cttcatatgt    5760
tgataaacaa gaaattacag caagctcaga aattgatgat ttgattttt cgagcgatcc    5820 attagtgtgg tcttacgacg agcaggaaaa aatcagaaaa aaacttgtgc ttgatgcatt    5880
tcgtaatcat tataaacatt gtcgagaata tcgtcactac tgtcaggcac acaaagtaga    5940
tgacaatatt acgaaattg atgacatacc tgtattccca acatcggttt ttaagtttac    6000
tcgcttatta acttctcagg aaaacgagat tgaaagttgg tttaccagta gcggcacgaa    6060
tggtttaaaa agtcaggtgg cgcgtgacag attaagtatt gagagactct taggctctgt    6120
gagttatggc atgaaatatg ttggtagttg gtttgatcat caaatagaat tagtcaattt    6180
gggaccagat agatttaatg ctcataatat ttggttttaaa tatgttatga gtttggtgga    6240
attgttatat cctacgacat ttaccgtaac agaagaacga atagattttg ttaaaacatt    6300
gaatagtctt gaacgaataa aaaatcaagg gaaagatctt tgtcttattg gttcgccata    6360
cttattttat ttactctgcc attatatgaa agataaaaaa atctcatttt ctggagataa    6420
```

```
aagcctttat atcataaccg gaggcggctg gaaaagttac gaaaaagaat ctctgaaacg    6480
tgatgatttc aatcatcttt tatttgatac tttcaatctc agtgatatta gtcagatccg    6540
agatatattt aatcaagttg aactcaacac ttgtttcttt gaggatgaaa tgcagcgtaa    6600
acatgttccg ccgtgggtat atgcgcgagc gcttgatcct gaaacgttga aacctgtacc    6660
tgatggaacg ccggggttga tgagttatat ggatgcgtca gcaaccagtt atccagcatt    6720
tattgttacc gatgatgtcg ggataattag cagagaatat ggtaagtatc ccggcgtgct    6780
cgttgaaatt ttacgtcgcg tcaatacgag gacgcagaaa gggtgtgctt taagcttaac    6840
cgaagcgttt gatagttgca ggcatgagct tgacggccgc gggccccatg gatcgatagc    6900
tggtcgacac aatctgccct ttcgaaagat cccaacgaaa agcgtgacca catggtcctt    6960
cttgagtttg taactgctgc tgggattaca catggcatgg atgagctcta caaataatga    7020
gctagcccgc ctaatgagcg ggcttttttt tctcggccta ggagatactt aacagggaag    7080
tgagagggcc gcggcaaagc cgttttcca taggctccgc cccctgaca agcatcacga    7140 aatctgacgc tcaaatcagt ggcaaagccc gaaaggaagc tgagttggct gctgccaccg    7200
ctgagcaata actagcataa ccccttgggg cctctaaacg ggtcttgagg ggttttttgc    7260
tgaaaggagg aactatatcc ggattggcga atgggacgcg ccctgtagcg gcgcattaag    7320
gctgcaggaa ttcgatatca agcttatcga taccgtcgac ctcgaggggg ggcccggtac    7380
cctccacgtg ttgccccagc aatcagcgcg accttgcccc tccaacgtca tctcgttctc    7440
cgctcatgag ctcagccaat cgactggcga gcggcatcgc attcttcgca tcccgcctct    7500
ggcggatgca ggaagatcaa cggatctcgg cccagttgac ccagggctgt cgccacaatg    7560
tcgcgggagc ggatcaaccg agcaaaggca tgaccgactg gaccttcctt ctgaaggctc    7620
ttctccttga gccacctgtc cgccaaggca aagcgctcac agcagtggtc attctcgaga    7680
taatcgacgc gtaccaactt gccatcctga agaatggtgc agtgtctcgg caccccatag    7740
ggaacctttg ccatcaactc ggcaagatgc agcgtcgtgt tggcatcgtg tcccacgccg    7800
aggagaagta cctgcccatc gagttcatgg acacgggcga ccgggcttgc aggcgagtga    7860
ggtggcaggg gcaatggatc agagatgatc tgctctgcct gtggccccgc tgccgcaaag    7920
gcaaatggat gggcgctgcg ctttacattt ggcaggcgcc agaatgtgtc agagacaact    7980
ccaaggtccg gtgtaacggg cgacgtgca ggatcgaacg gctcgtcgtc cagacctgac    8040
cacgagggca tgacgagcgt ccctcccgga cccagcgcag cacgcagggc ctcgatcagt    8100
ccaagtggcc catcttcgag gggccggacg ctacggaagg agctgtggac cagcagcaca    8160
ccgccggggg taaccccaag gttgagaagc tgaccgatga gctcggcttt tcgccattcg    8220
tattgcattt tagcttcctt agctcctgaa aatctcgata actcaaaaaa tacgcccggt    8280
agtgatctta tttcattatg gtgaaagttg gaacctctta cgtgccgaat aacttcgtat    8340
aatgtgtact atacgaagtt attcaacgtc tcatttcgc caaaagttgg cccagggctt    8400
cccggtatca acagggacac caggatttat ttattctgcg aagtgatctt ccgtcacagg    8460
tatttattcg cgataagctc atggagcggc gtaaccgtcg cacaggaagg acagagaaag    8520
cgcggatctg ggaagtgacg gacagaacgg tcaggacctg gagcggccgc tttttttcc    8578
```

<210> SEQ ID NO 6
<211> LENGTH: 11201
<212> TYPE: DNA
<213> ORGANISM: Artificial Sequence
<220> FEATURE:

<223> OTHER INFORMATION: Synthetic Construct

<400> SEQUENCE: 6

```
ctcgtcgaca gcgacacact tgcatcggat gcagcccggt taacgtgccg gcacggcctg      60
ggtaaccagg tattttgtcc acataaccgt gcgcaaaatg ttgtggataa gcaggacaca     120
gcagcaatcc acagcaggca tacaaccgca caccgaggtt actccgttct acaggttacg     180
acgacatgtc aatacttgcc cttgacaggc attgatggaa tcgtagtctc acgctgatag     240
tctgatcgac aatacaagtg ggaccgtggt cccagaccga taatcagacc gacaacacga     300
gtgggatcgt ggtcccagac taataatcag accgacgata cgagtgggac cgtggtccca     360
gactaataat cagaccgacg atacgagtgg gaccgtggtt ccagactaat aatcagaccg     420
acgatacgag tgggaccgtg gtcccagact aataatcaga ccgacgatac gagtgggacc     480
gtggtcccag actaataatc agaccgacga tacgagtggg accgtggtcc cagtctgatt     540
atcagaccga cgatacgagt gggaccgtgg tcccagacta ataatcagac cgacgatacg     600
agtgggaccg tggtcccaga ctaataatca gaccgacgat acgagtggga ccgtggtccc     660
agtctgatta tcagaccgac gatacaagtg aacagtgggc ccagagaga atattcaggc     720
cagttatgct ttctggcctg taacaaagga cattaagtaa agacagataa acgtagacta     780
aaacgtggtc gcatcagggt gctggctttt caagttcctt aagaatggcc tcaattttct     840
ctatacactc agttggaaca cgagacctgt ccaggttaag caccatttta tcgcccttat     900
acaatactgt cgctccagga gcaaactgat gtcgtgagct taaactagtt cttgatgcag     960
atgacgtttt aagcacagaa gttaaaagag tgataacttc ttcagcttca aatatcaccc    1020
cagcttttt ctgctcatga aggttagatg cctgctgctt aagtaattcc tctttatctg    1080
taaaggcttt ttgaagtgca tcacctgacc gggcagatag ttcaccgggg tgagaaaaaa    1140
gagcaacaac tgatttaggc aatttggcgg tgttgataca gcgggtaata atcttacgtg    1200
aaatatttc cgcatcagcc agcgcagaaa tatttccagc aaattcattc tgcaatcggc    1260
ttgcataacg ctgaccacgt tcataagcac ttgttgggcg ataatcgtta cccaatctgg    1320
ataatgcagc catctgctca tcatccagct cgccaaccag aacacgataa tcactttcgg    1380
taagtgcagc agctttacga cggcgactcc catcggcaat ttctatgaca ccagatactc    1440
ttcgaccgaa cgccggtgtc tgttgaccag tcagtagaaa agaagggatg agatcatcca    1500
gtgcgtcctc agtaagcagc cctggtcac gttcattacc tgaccatacc cgagaggtct    1560
tctcaacact atcaccccgg agcacttcaa gagtaaactt cacatcccga ccacatacag    1620
gcaaagtaat ggcattaccg cgagccatta ctcctacgcg cgcaattaac gaatccacca    1680
tcggggcagc tggtgtcgat aacgaagtat cttcaaccgg ttgagtattg agcgtatgtt    1740
ttggaataac aggcgcacgc ttcattatct aatctcccag cgtggtttaa tcagacgatc    1800
gaaaatttca ttgcagacag gttcccaaat agaaagagca tttctccagg caccagttga    1860
agagcgttga tcaatggcct gttcaaaaac agttctcatc cggatctgac ctttaccaac    1920
ttcatccgtt tcacgtacaa catttttttag aaccatgctt ccccaggcat cccgaatttg    1980
ctcctccatc cacggggact gagagccatt actattgctg tatttggtaa gcaaaatacg    2040
tacatcaggc tcgaacccctt taagatcaac gttcttgagc agatcacgaa gcatatcgaa    2100
aaactgcagt gcggaggtgt agtcaaacaa ctcagcaggc gtgggaacaa tcagcacatc    2160
agcagcacat acgacattaa tcgtgccgat acccaggtta ggcgcgctgt caataactat    2220
gacatcatag tcatgagcaa cagtttcaat ggccagtcgg agcatcaggt gtggatcggt    2280
```

```
gggcagttta ccttcatcaa atttgcccat taactcagtt tcaatacggt gcagagccag    2340
acaggaagga ataatgtcaa gccccggcca gcaagtgggc tttattgcat aagtgacatc    2400
gtccttttcc ccaagataga aaggcaggag agtgtcttct gcatgaatat gaagatctgg    2460
tacccatccg tgatacattg aggctgttcc ctggggtcg ttaccttcca cgagcaaaac     2520
acgtagcccc ttcagagcca gatcctgagc aagatgaaca gaaactgagg ttttgtaaac    2580
gccaccttta tgggcagcaa ccccgatcac cggtggaaat acgtcttcag cacgtcgcaa    2640
tcgcgtacca aacacatcac gcatatgatt aatttgttca attgtataac caacacgttg    2700
ctcaacccgt cctcgaattt ccatatccgg gtgcggtagt cgccctgctt tctcggcatc    2760
tctgatagcc tgagaagaaa ccccaactaa atccgctgct tcacctattc tccagcgccg    2820
ggttattttc ctcgcttccg ggctgtcatc attaaactgt gcaatggcga tagccttcgt    2880
catttcatga ccagcgttta tgcactggtt aagtgtttcc atgagtttca ttctgaacat    2940
cctttaatca ttgctttgcg ttttttatt aaatcttgca atttactgca aagcaacaac     3000
aaaatcgcaa agtcatcaaa aaccgcaaa gttgtttaaa ataagagcaa cactacaaaa     3060
ggagataaga agagcacata cctcagtcac ttattatcac tagcgctcgc cgcagccgtg    3120
taaccgagca tagcgagcga actggcgagg aagcaaagaa gaactgttct gtcagatagc    3180
tcttacgctc agcgcaagaa gaaatatcca ccgtgggaaa aactccaggt agaggtacac    3240
acgcggatag ccaattcaga gtaataaact gtgataatca accctcatca atgatgacga    3300
actaaccccc gatatcaggt cacatgacga agggaaagag aaggaaatca actgtgacaa    3360
actgccctca aatttggctt ccttaaaaat tacagttcaa aaagtatgag aaaatccatg    3420
caggctgaag gaaacagcaa aactgtgaca aattaccctc agtaggtcag aacaaatgtg    3480
acgaaccacc ctcaaatctg tgacagataa ccctcagact atcctgtcgt catggaagtg    3540
atatcgcgga aggaaaatac gatatgagtc gtctggcggc ctttcttttt ctcaatgtat    3600
gagaggcgca ttggagttct gctgttgatc tcattaacac agacctgcag gaagcggcgg    3660
cggaagtcag gcatacgctg gtaactttga ggcagctggt aacgctctat gatccagtcg    3720
attttcagag agacgatgcc tgagccatcc ggcttacgat actgacacag ggattcgtat    3780
aaacgcatgg catacggatt ggtgatttct tttgtttcac taagccgaaa ctgcgtaaac    3840
cggttctgta acccgataaa gaagggaatg agatatgggt tgatatgtac actgtaaagc    3900
cctctggatg gactgtgcgc acgtttgata aaccaaggaa aagattcata gccttttttca   3960 tcgccggcat cctcttcagg gcgataaaaa accacttcct tccccgcgaa actcttcaat    4020
gcctgccgta tatccttact ggcttccgca gaggtcaatc cgaatatttc agcatattta    4080
gcaacatgga tctcgcagat accgtcatgt tcctgtaggg tgccatcaga ttttctgatc    4140
tggtcaacga acagatacag catacgtttt tgatcccggg agagactata tgccgcctca    4200
gtgaggtcgt tgactggac gattcgcggg ctatttttac gtttcttgtg attgataacc     4260
gctgtttccg ccatgacaga tccatgtgaa gtgtgacaag ttttagatt gtcacactaa     4320 ataaaaaaga gtcaataagc agggataact ttgtgaaaaa acagcttctt ctgagggcaa    4380
tttgtcacag ggttaagggc aatttgtcac agacaggact gtcatttgag ggtgatttgt    4440
cacactgaaa gggcaatttg tcacaacacc ttctctagaa ccagcatgga taaggccta    4500 caaggcgctc taaaaagaa gatctaaaaa ctataaaaa aataattata aaatatccc       4560 cgtggataag tggataaccc caagggaagt tttttcaggc atcgtgtgta agcagaatat    4620
```

```
ataagtgctg ttccctggtg cttcctcgct cactcgaccg ggagggttcg agaagggggg    4680
gcaccccct  tcggcgtgcg cggtcacgcg cacaggcgc  agccctggtt aaaaacaagg    4740
tttataaata ttggtttaaa agcaggttaa aagacaggtt agcggtggcc gaaaaacggg    4800
cggaaaccct tgcaaatgct ggattttctg cctgtggaca gccctcaaa  tgtcaatagg    4860
tgcgcccctc atctgtcagc actctgcccc tcaagtgtca aggatcgcgc ccctcatctg    4920
tcagtagtcg cgccctcaa  gtgtcaatac cgcaggcac  ttatcccag  gcttgtccac    4980
atcatctgtg ggaaactcgc gtaaaatcag gcgttttcgc cgatttgcga ggctggccag    5040
ctccacgtcg ccggccgaaa tcgagcctgc ccctcatctg tcaacgccgc gccgggtgag    5100
tcggcccctc aagtgtcaac gtccgcccct catctgtcag tgagggccaa gttttccgcg    5160
aggtatccac aacgccggcg gccggccgcg gtgtctcgca cacggcttcg acggcgtttc    5220
tggcgcgttt gcagggccat agacggccgc cagcccagcg gcgagggcaa ccagccgagg    5280
gcttcgccct gtcgctcgac tgcggcgagc actactggct gtaaaaggac agaccacatc    5340
atggttctgt gttcattagg ttgttctgtc cattgctgac ataatccgct ccacttcaac    5400
gtaacaccgc acgaagattt ctattgttcc tgaaggcata ttcaaatcgt tttcgttacc    5460
gcttgcaggc atcatgacag aacactactt cctataaacg ctacacaggc tcctgagatt    5520
aataatgcgg atctctacga taatgggaga ttttcccgac tgtttcgttc gcttctcagt    5580
ggataacagc cagcttctct gtttaacaga caaaaacagc atatccacat ggaaatgtgg    5640
aactgaataa aggccaaggc atttattctc aggataattg tttcagcatc gcaaccgcat    5700
cagactccgg catcgcaaac tgcacccggt gccgggcagc cacatccagc gcaaaaacct    5760
tcgtgtagac ttccgttgaa ctgatggact tatgtcccat caggctttgc agaactttca    5820
gcggtatacc ggcatacagc atgtgcatcg cataggaatg gcggaacgta tgtggtgtga    5880
ccggaacaga gaacgtcaca ccgtcagcag cagcggcggc aaccgcctcc ccaatccagg    5940
tcctgaccgt tctgtccgtc acttcccaga tccgcgcttt ctctgtcctt cctgtgcgac    6000
ggttacgccg ctccatgagc ttatcgcgaa taaatacctg tgacggaaga tcacttcgca    6060
gaataaataa atcctggtgt ccctgtgcat tttgccttcc tgtttttgct cacccagaaa    6120
cgctggtgaa agtaaaagat gctgaagatc agttgggtgc acgagtgggt tacatcgaac    6180
tggatctcaa cagcggtaag atccttgaga gttttcgccc cgaagaacgt tttccaatga    6240
tgagcacttt taaagttctg ctaacaggtt ggctgataag tccccggtct gacacataga    6300
tggcgtcgct agtattaaat gcatattatt tttatatagt accaaccttc aaatgattcc    6360
cagatctcaa actggaacaa cactcaaccc tatctcggtc gcgaccacac ccgtcctgtg    6420
gcaaagcctc gcaatccagt ggctagccaa aggataactt cgtataaagt atcctatacg    6480
aagttatgat aaccgtatta ccgcctttga gtgagctcct aggggaatga taacaaaata    6540
aactactttt taaagaatt  ttgtgttata atctatttat tattaagtat tgggtaatat    6600
tttttgaaga gatattttga aaagaaaaa  ttaaagcata ttaaactaat ttcggaggtc    6660
attaaaacta ttattgaaat catcaaactc attatggatt taatttaaac ttttttatttt   6720
aggaggcaaa aatgtccaat ttactgaccg tacaccaaaa tttgcctgca ttaccggtcg    6780
atgcaacgag tgatgaggtt cgcaagaacc tgatggacat gttcagggat cgccaggcgt    6840
tttctgagca tacctggaaa atgcttctgt ccgtttgccg gtcgtggggcg gcatggtgca    6900
agttgaataa ccggaaatgg tttcccgcag aacctgaaga tgttcgcgat tatcttctat    6960
atcttcaggc gcgcggtctg gcagtaaaaa ctatccagca acatttgggc cagctaaaca    7020
```

```
tgcttcatcg tcggtccggg ctgccacgac caagtgacag caatgctgtt tcactggtta   7080
tgcggcggat ccgaaaagaa aacgttgatg ccggtgaacg tgcaaaacag gctctagcgt   7140
tcgaacgcac tgatttcgac caggttcgtt cactcatgga aaatagcgat cgctgccagg   7200
atatacgtaa tctggcattt ctggggattg cttataacac cctgttacgt atagccgaaa   7260
ttgccaggat cagggttaaa gatatctcac gtactgacgg tgggagaatg ttaatccata   7320
ttggcagaac gaaaacgctg gttagcaccg caggtgtaga aaggcactt agcctggggg    7380
taactaaact ggtcgagcga tggatttccg tctctggtgt agctgatgat ccgaataact   7440
acctgttttg ccgggtcaga aaaaatggtg ttgccgcgcc atctgccacc agccagctat   7500
caactcgcgc cctggaaggg attttgaag caactcatcg attgatttac ggcgctaagg     7560
atgactctgg tcagagatac ctggcctggt ctggacacag tgcccgtgtc ggagccgcgc   7620
gagatatggc ccgcgctgga gtttcaatac cggagatcat gcaagctggt ggctggacca   7680
atgtaaatat tgtcatgaac tatatccgta acctggatag tgaaacaggg gcaatggtgc   7740
gcctgctgga agatggcgat tagcccagcc cgcctaatga gcgggctttt ttttgaacaa   7800
aactcgagac agtaagacgg gtaagcctgt tgatgatacc gctgccttac tgggtgcatt   7860
agccagtctg aatgacctgt cacgggataa tccgaagtgg tcagactgga aaatcagagg   7920
gcaggaactg ctgaacccta gggctctaga actagtggat cccccgataa cttcgtatag   7980
catacattat acgaagttat ggctgcagga attcgatatc aagcttatcg ataccgtcga   8040
cctcgagggg ttaactagtt cacgctgccg caagcactca gggcgcaagg gctgctaaag   8100
gaagcggaac acgtagaaag ccagtccgca gaaacggtgc tgaccccgga tgaatgtcag   8160
ctactgggct atctggacaa gggaaaacgc aagcgcaaag agaaagcagg tagcttgcag   8220
tgggcttaca tggcgatagc tagactgggc ggttttatgg acagcaagcg aaccggaatt   8280
gccagctggg gcgccctctg gtaaggttgg gaagccctgc aaagtaaact ggatggcttt   8340
cttgccgcca aggatctgat ggcgcagggg atcaagatct gatcaagaga caggatgagg   8400
atcgtttcgc atgattgaac aagatggatt gcacgcaggt tctccggccg cttgggtgga   8460
gaggctattc ggctatgact gggcacaaca gacaatcggc tgctctgatg ccgccgtgtt   8520
ccggctgtca gcgcaggggc gcccggttct ttttgtcaag accgacctgt ccggtgccct   8580
gaatgaactc caagacgagg cagcgcggct atcgtggctg gccacgacgg gcgttccttg   8640
cgcagctgtg ctcgacgttg tcactgaagc gggaagggac tggctgctat tgggcgaagt   8700
gccggggcag gatctcctgt catctcacct tgctcctgcc gagaaagtat ccatcatggc   8760
tgatgcaatg cggcggctgc atacgcttga tccggctacc tgcccattcg accaccaagc   8820
gaaacatcgc atcgagcgag cacgtactcg gatggaagcc ggtcttgtcg atcaggatga   8880
tctggacgaa gagcatcagg ggctcgcgcc agccgaactg ttcgccaggc tcaaggcgcg   8940
gatgcccgac ggcgaggatc tcgtcgtgac ccatggcgat gcctgcttgc cgaatatcat   9000
ggtggaaaat ggccgctttt ctggattcat cgactgtggc cggctgggtg tggcggaccg   9060
ctatcaggac atagcgttgg ctacccgtga tattgctgaa gagcttggcg gcgaatgggc   9120
tgaccgcttc ctcgtgcttt acggtatcgc cgctcccgat tcgcagcgca tcgccttcta   9180
tcgccttctt gacgagttct tctgagcggc ccgggtgaaa gttggaacct cttacgtgcc   9240
gaataacttc gtataatgtg tactatacga agttattcaa cgtctcattt tcgccaaaag   9300
ttggcccagg gcttcccggt atcaacagta ctgcgatgag tggcagggcg gggcgtaatt   9360
```

| | |
|---|---|
| tttttaaggc agttattggt gcctagaaat attttatctg attaataaga tgatcttctt | 9420 |
| gagatcgttt tggtctgcgc gtgtcgacca cgtggactct gggggttcgcg acactggcag | 9480 |
| agcattacgc cctgcaggat gcaatgggcc ggccagaccg gggacttatc agccaacctg | 9540 |
| ttatgtgttg ggtaacgcca gggttttccc agtcacgacg ttgtaaaacg acggccagtg | 9600 |
| aattaattct tgaagacgaa agggcctcgt gatacgccta ttttataggt taatgtcat | 9660 |
| gataataatg gtttcttaga gcttatccag tcacgacgtt gtaaaacgac ggccagtgaa | 9720 |
| ttactgacgc cgttggatac accaaggaaa gtctacacga acccttggc aaaatcctgt | 9780 |
| atatcgtgcg aaaaaggatg gatataccga aaaaatcgct ataatgaccc cgaagcaggg | 9840 |
| ttatgcagcg ggtgagcgca acgcaattaa tgtgagttag ctcactcatt aggcacccca | 9900 |
| ggctttacac tttatgcttc cggctcgtat gttgtgtgga attgtgagcg ataacaatt | 9960 |
| tcacacagga aacacatatg aaaaaaagg aatttcgtgt tttgataaaa tactgttttc | 10020 |
| tgaagggaaa aaatacagtg gaagcaaaaa cttggcttga taatgagttt ccggactctg | 10080 |
| ccccagggaa atcaacaata attgattggt atgcaaaatt caagcgtggt gaaatgagca | 10140 |
| cggaggacgg tgaacgcagt ggacgcccga agaggtggt taccgacgaa acatcaaaa | 10200 |
| aaatccacaa aatgattttg aatgaccgta aatgaagtt gatcgagata gcagaggcct | 10260 |
| taaagatatc aaaggaacgt gttggtcata tcattcatca atatttggat atgcggaagc | 10320 |
| tctgtgcaaa atgggtgccg cgcgagctca catttgacca aaaacaacaa cgtgttgatg | 10380 |
| attctgagcg gtgtttgcag ctgttaactc gtaatacacc cgagttttc cgtcgatatg | 10440 |
| tgacaatgga tgaaacatgg ctccatcact acactcctga gtccaatcga cagtcggctg | 10500 |
| agtggacagc gaccggtgaa ccgtctccga agcgtggaaa gactcaaaag tccgctggca | 10560 |
| aagtaatggc ctctgttttt tgggatgcgc atggaataat ttttatcgat tatcttgaga | 10620 |
| agggaaaaac catcaacagt gactattata tggcgttatt ggagcgtttg aaggtcgaaa | 10680 |
| tcgcggcaaa acggcccac atgaagaaga aaaagtgtt gttccaccaa gacaacgcac | 10740 |
| cgtgccacaa gtcattgaga acgatggcaa aaattcatga attgggcttc gaattgcttc | 10800 |
| cccacccgcc gtattctcca gatctggccc ccagcgactt tttcttgttc tcagacctca | 10860 |
| aaaggatgct cgcagggaaa aaatttggct gcaatgaaga ggtgatcgcc gaaactgagg | 10920 |
| cctattttga ggcaaaaccg aaggagtact accaaaatgg tatcaaaaaa ttggaaggtc | 10980 |
| gttataatcg ttgtatcgct cttgaaggga actatgttga ataataaaa cgaatttca | 11040 |
| caaaaaatg tgttttctt tgttagaccg gatctgcaga attccagcac actggcggcc | 11100 |
| gttactagat gcatgctcga gcggccgcca gtgtgatgga ttgaaaaagg aagagtatga | 11160 |
| gtattcaaca tttccgtgtc gcccttattc cctttttgc g | 11201 |

<210> SEQ ID NO 7
<211> LENGTH: 8223
<212> TYPE: DNA
<213> ORGANISM: Artificial Sequence
<220> FEATURE:
<223> OTHER INFORMATION: Synthetic Construct

<400> SEQUENCE: 7

| | |
|---|---|
| tatgtgttgg gtaacgccag ggttttccca gtcacgacgt tgtaaaacga cggccagtga | 60 |
| attaattctt gaagacgaaa gggcctcgtg atacgcctat ttttataggt taatgtcatg | 120 |
| ataataatgg tttcttagag cttatcgcc agcctcgcag agcaggattc ccgttgagca | 180 |
| ccgccaggtg cgaataaggg acagtgaaga aggaacaccc gctcgcgggt gggcctactt | 240 |

```
cacctatcct gcccggctga cgccgttgga tacaccaagg aaagtctaca cgaacccttt    300
ggcaaaatcc tgtatatcgt gcgaaaaagg atggatatac cgaaaaaatc gctataatga    360
ccccgaagca gggttatgca gcgcaaagcc tcgcaatcca gtgcaaagga taacttcgta    420
tagcatacat tatacgaagt tatgataacc gtattaccgc ctttgagtga gctccacggc    480
cgctctagaa ctagtggatc ccccggtatt taccacaaca gtacgccaac cagccatcag    540
tcacctccta gctgactcaa atcaatgcgt gtttcataaa gaccagtgat ggattgatgg    600
ataagagtgg catctaaaac ttcttttgta gacgtatatc gtttacgatc aattgttgta    660
tcaaaatatt taaaagcagc gggagctcca agattcgtca acgtaaataa atgaataata    720
ttttctgctt gttcacgtat tggtttgtct ctatgtttgt tatatgcact aagaacttta    780
tctaaattgg catctgctaa aataacacgc ttagaaaatt cactgatttg ctcaataatc    840
tcatctaaat aatgcttatg ctgctccaca aacaattgtt tttgttcgtt atcttctgga    900
ctacccttca acttttcata atgactagct aaatataaaa aattcacata tttgcttggc    960
agagccagct catttccttt ttgtaattct ccggcactag ccagcatccg tttacgaccg   1020
ttttctaact caaaaagact atatttaggt agtttaatga ttaagtcttt tttaacttcc   1080
ttatatcctt tagcttctaa aaagtcaatc ggattttttt caaggaact tctttccata   1140 attgtgatcc ctagtaactc tttaacggat tttaacttct tcgatttccc ttttttccacc   1200 ttagcaacca ctaggactga ataagctacc gttggactat caaaaccacc atatttttt   1260 ggatcccagt ctttttttacg agcaataagc ttgtccgaat ttcttttggg taaaattgac   1320
tccttggaga atccgcctgt ctgtacttct gttttcttga caatattgac ttggggcatg   1380
gacaatactt tgcgcactgt ggcaaaatct cgccctttat cccagacaat ttctccagtt   1440
tccccattag tttcgattag agggcgtttg cgaatctctc catttgcaag tgtaatttct   1500
gttttgaaga agttcatgat attagagtaa aagaaatatt ttgcggttgc tttgcctatt   1560
tcttgctcag acttagcaat cattttacga acatcataaa ctttataatc accatagaca   1620
aactccgatt caagttttgg atatttctta atcaaagcag ttccaacgac ggcatttaga   1680
tacgcatcat gggcatgatg gtaattgtta atctcacgta ctttatagaa ttggaaatct   1740
tttcggaagt cagaaactaa tttagatttt aaggtaatca ctttaacctc tcgaataagt   1800
ttatcatttt catcgtattt agtattcatg cgactatcca aaatttgtgc cacatgctta   1860
gtgatttggc gagtttcaac caattggcgt ttgataaaac cagctttatc aagttcactc   1920
aaacctccac gttcagcttt cgttaaatta tcaaacttac gttgagtgat taacttggcg   1980
tttagaagtt gtctccaata gttttttcatc tttttgacta cttcttcact tggaacgtta   2040
tccgatttac cacgattttt atcagaacgc gttaagacct tattgtctat tgaatcgtct   2100
ttaaggaaac tttgtggaac aatggcatcg acatcataat cacttaaacg attaatatct   2160
aattcttggt ccacatacat gtctcttcca ttttggagat aatagagata gagcttttca   2220
ttttgcaatt gagtattttc aacaggatgc tctttaagaa tctgacttcc taattctttg   2280
ataccttctt cgattcgttt catacgctct cgcgaatttt tctggcccct ttgagttgtc   2340
tgattttcac gtgccatttc aataacgata ttttctggct tatgccgccc cattactttg   2400
accaattcat caacaacttt tacagtctgt aaaatacctt ttttaatagc agggctacca   2460
gctaaatttg caatatgttc atgtaaacta tcgccttgtc cagacacttg tgcttttga   2520 atgtcttctt taaatgtcaa actatcatca tggatcagct gcataaaatt gcgattggca   2580
```

-continued

```
aaaccatctg atttcaaaaa atctaatatt gttttgccag attgcttatc cctaatacca    2640
ttaatcaatt ttcgagacaa acgtccccaa ccagtataac ggcgacgttt aagctgtttc    2700
atcaccttat catcaaagag gtgagcatat gttttaagtc tttcctcaat catctcccta    2760
tcttcaaata aggtcaatgt taaaacaata tcctctaaga tatcttcatt ttcttcatta    2820
tccaaaaaat ctttatcttt aataattttt agcaaatcat ggtaggtacc taatgaagca    2880
ttaaatctat cttcaactcc tgaaatttca acactatcaa acattctat ttttttgaaa     2940 taatcttctt ttaattgctt aacggttact tttcgatttg ttttgaagag taaatcaaca    3000
atggctttct tctgttcacc tgaaagaaat gctggttttc gcattccttc agtaacatat    3060
ttgacctttg tcaattcgtt ataaaccgta aaatactcat aaagcaaact atgttttggt    3120
agtacttttt catttggaag atttttatca agtttgtca tgcgttcaat aaatgattga     3180
gctgaagcac ctttatcgac aacttcttca aaattccatg gggtaattgt ttcttcagac    3240
ttccgagtca tccatgcaaa acgactattg ccacgcgcca atggaccaac ataataagga    3300
attcgaaaag tcaagatttt ttcaatcttc tcacgattgt cttttaaaaa tggataaaag    3360
tcttcttgtc ttctcaaaat agcatgcagc tcacccaagt gaatttgatg gggaatagag    3420
ccgttgtcaa aggtccgttg cttgcgcagc aaatcttcac gatttagttt caccaataat    3480
tcctcagtac catccatttt ttctaaaatt ggtttgataa atttataaaa ttcttcttgg    3540
ctagctcccc catcaatata acctgcatat ccgtttttg attgatcaaa aaagatttct     3600
ttatactttt ctggaagttg ttgtcgaact aaagcttta aaagagtcaa gtcttgatga     3660
tgttcatcgt agcgtttaat cattgaagct gataggggag ccttagttat ttcagtattt    3720
actcttagga tatctgaaag taaaatagca tctgataaat tcttagctgc caaaacaaa     3780 tcagcatatt gatctccaat ttgcgccaat aaattatcta atcatcatc gtaagtatct     3840 tttgaaagct gtaatttagc atcttctgcc aaatcaaaat ttgatttaaa attaggggtc    3900
aaacccaatg acaaagcaat gagattccca ataagccat ttttcttctc accgggagc      3960 tgagcaatga gattttctaa tcgtcttgat ttactcaatc gtgcagaaag aatcgcttta    4020
gcatctactc cacttgcgtt aatagggttt tcttcaaata attgattgta ggtttgtacc    4080
aactggataa atagtttgtc cacatcacta ttatcaggat ttaaatctcc ctcaatcaaa    4140
aaatgaccac gaaacttaat catatgcgct aaggccaaat agattaagcg caaatccgct    4200
ttatcagtag aatctaccaa ttttttttcgc agatgataga tagttggata tttctcatga   4260
taagcaactt catctactat atttccaaaa ataggatgac gttcatgctt cttgtcttct    4320
tccaccaaaa aagactcttc aagtcgatga agaaactat catctacttt cgccatctca    4380
tttgaaaaaa tctcctgtag ataacaaata cgattcttcc gacgtgtata ccttctacga    4440
gctgtccgtt tgagacgagt cgcttccgct gtctctccac tgtcaaataa aagagcccct    4500
ataagatttt ttttgatact gtggcggtct gtatttccca gaaccttgaa cttttttagac   4560 ggaaccttat attcatcagt gatcaccgcc catccgacgc tatttgtgcc gatagctaag    4620
cctattgagt atttcttatc cattttgcc tcctaaaata aaagtttaa attaaatcca      4680 taatgagttt gatgatttca ataatagttt taatgacctc cgaaattagt ttaatatgct    4740 ttaattttc ttttcaaaa tatctcttca aaaatatta cccaatactt aataataaat       4800
agattataac acaaaattct tttaaaaagt agtttatttt gttatcattc tatagtatta    4860
agtattgttt tatggctgat aaatttcttt gaatttctcc ttgattattt gttataaaag    4920
ttataaaata atcttgttgg aaccattcaa aacagcatag caagttaaaa taaggctagt    4980
```

```
ccgttatcaa cttgaaaaag tggcaccgag tcggtgcttt ttttgatact tctattctac    5040
tctgactgca aaccaaaaaa acaagcgctt tcaaaacgct tgttttatca ttttaggga     5100 aattaatctc ttaatccttt tatcattcta catttaggcg ctgccatctt gctaaaccta   5160
ctaagctcag gtgatttctc atggattctt cgtctgtttc tactggtatt ggcacaaacc   5220
tgattccaat ttgagcaagg cgcctggggt gcctaatgag tgagctaact tacattaatt   5280
gcgttgcgct cactgcccgc tttccagtcg ggaaacctgt cgtgccagct gcattaatga   5340
atcggccaac gcgcggggag aggcggtttg cgtattgggc gccagggtgg ttttctttt    5400 caccagtgag acgggcaaca gctgattgcc cttcaccgcc tggccctgag agagttgcag    5460
caagcggtcc acgctggttt gccccagcag gcgaaaatcc tgtttgatgg tggttaacgg    5520
cgggatataa catgagctgt cttcggtatc gtcgtatccc actaccgaga tatccgcacc    5580
aacgcgcagc ccggactcgg taatggcgcg cattgcgccc agcgccatct gatcgttggc    5640
aaccagcatc gcagtgggaa cgatgccctc attcagcatt tgcatggttt gttgaaaacc    5700
ggacatggca ctccagtcgc cttcccgttc cgctatcggc tgaatttgat tgcgagtgag    5760
atatttatgc cagccagcca gacgcagacg cgccgagaca gaacttaatg ggcccgctaa    5820
cagcgcgatt tgctggtgac ccaatgcgac cagatgctcc acgcccagtc gcgtaccgtc    5880
ttcatgggag aaaataatac tgttgatggg tgtctggtca gagacatcaa gaaataacgc    5940
cggaacatta gtgcaggcag cttccacagc aatggcatcc tggtcatcca gcggatagtt    6000
aatgatcagc ccactgacgc gttgcgcgag aagattgtgc accgccgctt tacaggcttc    6060
gacgccgctt cgttctacca tcgacaccac cacgctggca cccagttgat cggcgcgaga    6120
tttaatcgcc gcgacaattt gcgacggcgc gtgcagggcc agactggagg tggcaacgcc    6180
aatcagcaac gactgtttgc ccgccagttg ttgtgccacg cggttgggaa tgtaattcag    6240
ctccgccatc gccgcttcca cttttttcccg cgttttcgca gaaacgtggc tggcctggtt    6300
caccacgcgg gaaacggtct gataagagac accggcatac tctgcgacat cgtataacgt    6360
tactggtttc acattcacca ccctgaattg actctcttcc gggcgctatc atgccatacc    6420
gcgaaaggtt ttgcgccatt cgatggtgtc cgggatctgg atcctctacg ggctgcagga    6480
attcgatatc aagcttatcg ataccgtcga cctcgagggg gggcccggta ccctccacgt    6540
gttgccccag caatcagcgc gaccttgccc ctccaacgtc atctcgttct ccgctcatga    6600
gctcagccaa tcgactggcg agcggcatcg cattcttcgc atcccgcctc tggcggatgc    6660
aggaagatca acgatctcg gcccagttga cccaggctg tcgccacaat gtcgcggag      6720 cggatcaacc gagcaaaggc atgaccgact ggaccttcct tctgaaggct cttctccttg    6780
agccacctgt ccgccaaggc aaagcgctca cagcagtggt cattctcgag ataatcgacg    6840
cgtaccaact tgccatcctg aagaatggtg cagtgtctcg gcaccccata gggaaccttt    6900
gccatcaact cggcaagatg cagcgtcgtg ttggcatcgt gtcccacgcc gaggagaagt    6960
acctgcccat cgagttcatg gacacgggcg accgggcttg caggcgagtg aggtggcagg    7020
ggcaatggat cagagatgat ctgctctgcc tgtggcccg ctgccgcaaa ggcaaatgga     7080
tgggcgctgc gctttacatt tggcaggcgc cagaatgtgt cagagacaac tccaaggtcc    7140
ggtgtaacgg gcgacgtggc aggatcgaac ggctcgtcgt ccagacctga ccacgagggc    7200
atgacgagcg tccctcccgg acccagcgca gcacgcaggg cctcgatcag tccagtggc     7260 ccatcttcga ggggccggac gctacggaag gagctgtgga ccagcagcac accgccgggg   7320
```

```
gtaaccccaa ggttgagaag ctgaccgatg agctcggctt ttcgccattc gtattgcatt    7380
ttagcttcct tagctcctga aaatctcgat aactcaaaaa atacgcccgg tagtgatctt    7440
atttcattat ggtgaaagtt ggaacctctt acgtgccgaa taacttcgta taatgtgtac    7500
tatacgaagt tattcaacgt ctcatttttcg ccaaaagttg gcccagggct tcccggtatc    7560
aacagggaca ccaggattta tttattctgc gaagtgatct tccgtcacag gtatttattc    7620
gcgataagct catggagcgg cgtaaccgtc gcacaggaag gacagagaaa gcgcggatct    7680
gggaagtgac ggacagaacg gtcagcgtaa ttttttttaag gcggaagtga cggacagaac    7740
ggtcaggacc tggagcggcc gcttttttcc aattttttgcg gccgcaagat ccgcagttca    7800
acctgttgat agtacgtact aagctctcat gtttcacgta ctaagctctc atgtttaacg    7860
tactaagctc tcatgtttaa cgaactaaac cctcatggct aacgtactaa gctctcatgg    7920
ctaacgtact aagctctcat gtttcacgta ctaagctctc atgtttgaac aataaaatta    7980
atataaatca gcaacttaaa tagcctctaa ggttttaagt tttataagaa aaaaagaat    8040 atataaggct tttaaagctt ttaaggttta acgttgtgg acaacaagcc agggatgtaa    8100
cgcactgaga agcccttaga gcctctcaaa gcaattttca gtgacacagg aacacttaac    8160
ggctgacatg ggaattagcc atggcaaagc ctcgcaatcc agtgcaaagg caatacgcaa    8220
acc                                                                 8223

<210> SEQ ID NO 8
<211> LENGTH: 8536
<212> TYPE: DNA
<213> ORGANISM: Artificial Sequence
<220> FEATURE:
<223> OTHER INFORMATION: Synthetic Construct

<400> SEQUENCE: 8
ggtttgcgta ttgcctttgc actggattgc gaggctttgc catggctaat tcccatgtca      60
gccgttaagt gttcctgtgt cactcaaaat tgctttgaga ggctctaagg gcttctcagt     120
gcgttacatc cctggcttgt tgtccacaac cgttaaacct taaaagcttt aaaagcctta     180
tatattcttt tttttcttat aaaacttaaa accttagagg ctatttaagt tgctgattta     240
tattaatttt attgttcaaa catgagagct tagtacgtga acatgagag cttagtacgt     300 tagccatgag agcttagtac gttagccatg agggtttagt tcgttaaaca tgagagctta     360
gtacgttaaa catgagagct tagtacgtga acatgagag cttagtacgt actatcaaca     420
ggttgaactg ctgatcttca gatcctctac gccggacgca tcgtggccgg atcttgcggc     480
cgcaaaaatt ggaaaaaagc ggccgctcca ggtcctgacc gttctgtccg tcacttccgc     540
cttaaaaaaa ttacgctgac cgttctgtcc gtcacttccc agatccgcgc tttctctgtc     600
cttcctgtgc gacggttacg ccgctccatg agcttatcgc gaataaatac ctgtgacgga     660
agatcacttc gcagaataaa taaatcctgg tgtccctgtt gataccggga agccctgggc     720
caacttttgg cgaaaatgag acgttgaata acttcgtata gtacacatta tacgaagtta    780
ttcggcacgt aagaggttcc aactttcacc ataatgaaat aagatcacta ccgggcgtat    840
tttttgagtt atcgagattt tcaggagcta aggaagctaa aatgcaatac gaatggcgaa    900
aagccgagct catcggtcag cttctcaacc ttggggttac cccggcggt gtgctgctgg    960 tccacagctc cttccgtagc gtccggcccc tcgaagatgg gccacttgga ctgatcgagg   1020
ccctgcgtgc tgcgctgggt ccgggaggga cgctcgtcat gccctcgtgg tcaggtctgg   1080
acgacgagcc gttcgatcct gccacgtcgc ccgttacacc ggaccttgga gttgtctctg   1140
```

```
acacattctg gcgcctgcca aatgtaaagc gcagcgccca tccatttgcc tttgcggcag    1200
cggggccaca ggcagagcag atcatctctg atccattgcc cctgccacct cactcgcctg    1260
caagcccggt cgcccgtgtc catgaactcg atgggcaggt acttctcctc ggcgtgggac    1320
acgatgccaa cacgacgctg catcttgccg agttgatggc aaaggttccc tatggggtgc    1380
cgagacactg caccattctt caggatggca agttggtacg cgtcgattat ctcgagaatg    1440
accactgctg tgagcgcttt gccttggcgg acaggtggct caaggagaag agccttcaga    1500
aggaaggtcc agtcggtcat gcctttgctc ggttgatccg ctcccgcgac attgtggcga    1560
cagccctggg tcaactgggc cgagatccgt tgatcttcct gcatccgcca gaggcgggat    1620
gcgaagaatg cgatgccgct cgccagtcga ttggctgagc tcatgagcgg agaacgagat    1680
gacgttggag gggcaaggtc gcgctgattg ctggggcaac acgtggaggg taccgggccc    1740
cccctcgagg tcgacggtat cgataagctt gatatcgaat tcctgcagcc cgtagaggat    1800
ccagatcccg gacaccatcg aatggcgcaa aaccttcgc ggtatggcat gatagcgccc    1860
ggaagagagt caattcaggg tggtgaatgt gaaaccagta acgttatacg atgtcgcaga    1920
gtatgccggt gtctcttatc agaccgtttc ccgcgtggtg aaccaggcca gccacgtttc    1980
tgcgaaaacg cgggaaaaag tggaagcggc gatggcggag ctgaattaca ttcccaaccg    2040
cgtggcacaa caactggcgg gcaaacagtc gttgctgatt ggcgttgcca cctccagtct    2100
ggccctgcac gcgccgtcgc aaattgtcgc ggcgattaaa tctcgcgccg atcaactggg    2160
tgccagcgtg gtggtgtcga tggtagaacg aagcggcgtc gaagcctgta aagcggcggt    2220
gcacaatctt ctcgcgcaac gcgtcagtgg gctgatcatt aactatccgc tggatgacca    2280
ggatgccatt gctgtggaag ctgcctgcac taatgttccg gcgttatttc ttgatgtctc    2340
tgaccagaca cccatcaaca gtattatttt ctcccatgaa gacggtacgc gactgggcgt    2400
ggagcatctg gtcgcattgg gtcaccagca atcgcgctg ttagcgggcc cattaagttc    2460
tgtctcggcg cgtctgcgtc tggctggctg gcataaatat ctcactcgca atcaaattca    2520
gccgatagcg gaacgggaag gcgactggag tgccatgtcc ggttttcaac aaaccatgca    2580
aatgctgaat gagggcatcg ttcccactgc gatgctggtt gccaacgatc agatggcgct    2640
gggcgcaatg cgcgccatta ccgagtccgg gctgcgcgtt ggtgcggata tctcggtagt    2700
gggatacgac gataccgaag acagctcatg ttatatcccg ccgttaacca ccatcaaaca    2760
ggattttcgc ctgctggggc aaaccagcgt ggaccgcttg ctgcaactct ctcagggcca    2820
ggcggtgaag ggcaatcagc tgttgcccgt ctcactggtg aaaagaaaaa ccaccctggc    2880
gcccaatacg caaaccgcct ctccccgcgc gttggccgat tcattaatgc agctggcacg    2940
acaggtttcc cgactggaaa gcgggcagtg agcgcaacgc aattaatgta agttagctca    3000
ctcattaggc accccaggcg ccttgctcaa attggaatca ggtttgtgcc aataccagta    3060
gaaacagacg aagaatccat gagaaatcac ctgagcttag taggtttagc aagatggcag    3120
cgcctaaatg tagaatgata aaaggattaa gagattaatt tccctaaaaa tgataaaaca    3180
agcgttttga aagcgcttgt ttttttggtt tgcagtcaga gtagaataga agtatcaaaa    3240
aaagcaccga ctcggtgcca cttttttcaag ttgataacgg actagcctta ttttaacttg    3300
ctatgctgtt ttgaatggtt ccaacaagat tatttataa cttttataac aaataatcaa    3360
ggagaaattc aaagaaattt atcagccata aacaaatact taatactata gaatgataac    3420
aaaataaact acttttttaaa agaattttgt gttataatct atttattatt aagtattggg    3480
```

```
taatatttt  tgaagagata  ttttgaaaaa  gaaaaattaa  agcatattaa  actaatttcg    3540
gaggtcatta  aaactattat  tgaaatcatc  aaactcatta  tggatttaat  ttaaacttt     3600 tattttagga  ggcaaaaatg  gataagaaat  actcaatagg  cttagctatc  ggcacaaata    3660
gcgtcggatg  ggcggtgatc  actgatgaat  ataaggttcc  gtctaaaaag  ttcaaggttc    3720
tgggaaatac  agaccgccac  agtatcaaaa  aaatcttat   aggggctctt  ttatttgaca    3780
gtggagagac  agcggaagcg  actcgtctca  aacggacagc  tcgtagaagg  tatacacgtc    3840
ggaagaatcg  tatttgttat  ctacaggaga  ttttttcaaa  tgagatggcg  aaagtagatg    3900
atagtttctt  tcatcgactt  gaagagtctt  ttttggtgga  agaagacaag  aagcatgaac    3960
gtcatcctat  ttttggaaat  atagtagatg  aagttgctta  tcatgagaaa  tatccaacta    4020
tctatcatct  gcgaaaaaaa  ttggtagatt  ctactgataa  agcggatttg  cgcttaatct    4080
atttggcctt  agcgcatatg  attaagttc   gtggtcattt  tttgattgag  ggagatttaa    4140
atcctgataa  tagtgatgtg  gacaaactat  ttatccagtt  ggtacaaacc  tacaatcaat    4200
tatttgaaga  aaaccctatt  aacgcaagtg  gagtagatgc  taaagcgatt  ctttctgcac    4260
gattgagtaa  atcaagacga  ttagaaaatc  tcattgctca  gctccccggt  gagaagaaaa    4320
atggcttatt  tgggaatctc  attgctttgt  cattgggttt  gacccctaat  tttaaatcaa    4380
attttgattt  ggcagaagat  gctaaattac  agctttcaaa  agatacttac  gatgatgatt    4440
tagataattt  attggcgcaa  attggagatc  aatatgctga  tttgttttg   gcagctaaga    4500 atttatcaga  tgctatttta  ctttcagata  tcctaagagt  aaatactgaa  ataactaagg    4560
ctcccctatc  agcttcaatg  attaaacgct  acgatgaaca  tcatcaagac  ttgactcttt    4620
taaaagcttt  agttcgacaa  caacttccag  aaaagtataa  agaaatcttt  tttgatcaat    4680
caaaaaacgg  atatgcaggt  tatattgatg  ggggagctag  ccaagaagaa  ttttataaat    4740
ttatcaaacc  aatttagaa   aaaatggatg  gtactgagga  attattggtg  aaactaaatc    4800
gtgaagattt  gctgcgcaag  caacggacct  ttgacaacgg  ctctattccc  catcaaattc    4860
acttgggtga  gctgcatgct  attttgagaa  gacaagaaga  cttttatcca  ttttttaaaag   4920 acaatcgtga  gaagattgaa  aaaatcttga  cttttcgaat  tccttattat  gttggtccat    4980
tggcgcgtgg  caatagtcgt  tttgcatgga  tgactcggaa  gtctgaagaa  acaattaccc    5040
catgaatttt  tgaagaagtt  gtcgataaag  gtgcttcagc  tcaatcattt  attgaacgca    5100
tgacaaactt  tgataaaaat  cttccaaatg  aaaaagtact  accaaaacat  agtttgctt    5160 atgagtattt  tacggtttat  aacgaattga  caaaggtcaa  atatgttact  gaaggaatgc    5220
gaaaaccagc  atttctttca  ggtgaacaga  agaaagccat  tgttgattta  ctcttcaaaa    5280
caaatcgaaa  agtaaccgtt  aagcaattaa  aagaagatta  tttcaaaaaa  atagaatgtt    5340
ttgatagtgt  tgaaatttca  ggagttgaag  atagatttaa  tgcttcatta  ggtacctacc    5400
atgatttgct  aaaaattatt  aaagataaag  attttttgga  taatgaagaa  atgaagata     5460 tcttagagga  tattgttta   acattgacct  tatttgaaga  tagggagatg  attgaggaaa    5520
gacttaaaac  atatgctcac  ctctttgatg  ataaggtgat  gaaacagctt  aaacgtcgcc    5580
gttatactgg  ttggggacgt  ttgtctcgaa  aattgattaa  tggtattagg  gataagcaat    5640
ctggcaaaac  aatattagat  ttttgaaat   cagatggttt  tgccaatcgc  aattttatgc    5700
agctgatcca  tgatgatagt  ttgacattta  aagaagacat  tcaaaagca   caagtgtctg    5760 gacaaggcga  tagtttacat  gaacatattg  caaattagc   tggtagccct  gctattaaaa    5820
aaggtatttt  acagactgta  aaagttgttg  atgaattggt  caaagtaatg  ggcggcata     5880
```

```
agccagaaaa tatcgttatt gaaatggcac gtgaaaatca gacaactcaa aagggccaga   5940
aaaattcgcg agagcgtatg aaacgaatcg aagaaggtat caaagaatta ggaagtcaga   6000
ttcttaaaga gcatcctgtt gaaaatactc aattgcaaaa tgaaaagctc tatctctatt   6060
atctccaaaa tggaagagac atgtatgtgg accaagaatt agatattaat cgtttaagtg   6120
attatgatgt cgatgccatt gttccacaaa gtttccttaa agacgattca atagacaata   6180
aggtcttaac gcgttctgat aaaaatcgtg gtaaatcgga taacgttcca agtgaagaag   6240
tagtcaaaaa gatgaaaaac tattggagac aacttctaaa cgccaagtta atcactcaac   6300
gtaagtttga taatttaacg aaagctgaac gtggaggttt gagtgaactt gataaagctg   6360
gttttatcaa acgccaattg gttgaaactc gccaaatcac taagcatgtg gcacaaattt   6420
tggatagtcg catgaatact aaatacgatg aaaatgataa acttattcga gaggttaaag   6480
tgattacctt aaaatctaaa ttagtttctg acttccgaaa agatttccaa ttctataaag   6540
tacgtgagat taacaattac catcatgccc atgatgcgta tctaaatgcc gtcgttggaa   6600
ctgctttgat taagaaatat ccaaaacttg aatcggagtt tgtctatggt gattataaag   6660
tttatgatgt tcgtaaaatg attgctaagt ctgagcaaga aataggcaaa gcaaccgcaa   6720
aatatttctt ttactctaat atcatgaact tcttcaaaac agaaattaca cttgcaaatg   6780
gagagattcg caaacgccct ctaatcgaaa ctaatgggga aactggagaa attgtctggg   6840
ataaagggcg agattttgcc acagtgcgca agtattgtc catgccccaa gtcaatattg   6900
tcaagaaaac agaagtacag acaggcggat tctccaagga gtcaattta ccaaaaagaa   6960 attcggacaa gcttattgct cgtaaaaaag actgggatcc aaaaaaatat ggtggttttg   7020
atagtccaac ggtagcttat tcagtcctag tggttgctaa ggtggaaaaa gggaaatcga   7080
agaagttaaa atccgttaaa gagttactag ggatcacaat tatggaaaga agttcctttg   7140
aaaaaaatcc gattgacttt ttagaagcta aaggatataa ggaagttaaa aaagacttaa   7200
tcattaaact acctaaatat agtcttttg agttagaaaa cggtcgtaaa cggatgctgg   7260
ctagtgccgg agaattacaa aaaggaaatg agctggctct gccaagcaaa tatgtgaatt   7320
ttttatattt agctagtcat tatgaaaagt tgaagggtag tccagaagat aacgaacaaa   7380
aacaattgtt tgtggagcag cataagcatt atttagatga gattattgag caaatcagtg   7440
aattttctaa gcgtgttatt ttagcagatg ccaatttaga taaagttctt agtgcatata   7500
acaaacatag agacaaacca atacgtgaac aagcagaaaa tattattcat ttatttacgt   7560
tgacgaatct tggagctccc gctgctttta aatattttga tacaacaatt gatcgtaaac   7620
gatatacgtc tacaaaagaa gttttagatg ccactcttat ccatcaatcc atcactggtc   7680
tttatgaaac acgcattgat ttgagtcagc taggaggtga cgcagctgca cgcgtaactg   7740
ttcaggacgc tgtagagaaa attggtaacc gttttgacct ggtactggtc gccgcgcgtc   7800
gcgctcgtca gatgcaggta ggcggaaagg atccgctggt accggaagaa aacgataaaa   7860
ccactgtaat cgcgctgcgc gaaatcgaag aaggtctgat caacaaccag atcctcgacg   7920
ttcgcgaacg ccaggaacag caagagcagg aagccgctga attacaagcc gttaccgcta   7980
ttgctgaagg tcgtcgttga tggctggttg gcgtactgtt gtggtaaata ccggggggatc   8040 cactagttct agagcggccg tggagctcac tcaaaggcgg taatacggtt atcataactt   8100
cgtataatgt atgctatacg aagttatcct ttgcactgga ttgcgaggct ttgcgctgca   8160
taaccctgct tcggggtcat tatagcgatt ttttcggtat atccatcctt tttcgcacga   8220
```

| | | | | |
|---|---|---|---|---|
| tatacaggat | tttgccaaag | ggttcgtgta | gactttcctt | ggtgtatcca acggcgtcag | 8280 |
| ccgggcagga | taggtgaagt | aggcccaccc | gcgagcgggt | gttccttctt cactgtccct | 8340 |
| tattcgcacc | tggcggtgct | caacgggaat | cctgctctgc | gaggctggcc gataagctct | 8400 |
| aagaaaccat | tattatcatg | acattaacct | ataaaaatag | gcgtatcacg aggccctttc | 8460 |
| gtcttcaaga | attaattcac | tggccgtcgt | tttacaacgt | cgtgactggg aaaaccctgg | 8520 |
| cgttacccaa | cacata | | | | 8536 |

<210> SEQ ID NO 9
<211> LENGTH: 2968
<212> TYPE: DNA
<213> ORGANISM: Artificial Sequence
<220> FEATURE:
<223> OTHER INFORMATION: Synthetic Construct

<400> SEQUENCE: 9

| | | | | | |
|---|---|---|---|---|---|
| caggaactgc | tgaaccctag | ggctctagaa | ctagtggatc | ccccgataac ttcgtatagc | 60 |
| atacattata | cgaagttatg | gctgcaggaa | ttcgatatca | agcttatcga taccgtcgac | 120 |
| ctcgagggct | taacggtcag | cgtaattttt | ttaaggcgga | agtgacggac agaacggtca | 180 |
| ggacctggag | cggccgcttt | tttccaattt | ttgcggccgc | aagatccggc cacgatgcgt | 240 |
| ccggcgtaga | ggatctgaag | atcagcagtt | caacctgttg | atagtacgta ctaagctctc | 300 |
| atgtttcacg | tactaagctc | tcatgtttaa | cgtactaagc | tctcatgttt aacgaactaa | 360 |
| accctcatgg | ctaacgtact | aagctctcat | ggctaacgta | ctaagctctc atgtttcacg | 420 |
| tactaagctc | tcatgtttga | caataaaat | taatataaat | cagcaactta atagcctct | 480 |
| aaggttttaa | gttttataag | aaaaaaaaga | atatataagg | cttttaaagc ttttaaggtt | 540 |
| taacggttgt | ggacaacaag | ccagggatgt | aacgcactga | gaagccctta gagcctctca | 600 |
| aagcaattt | gagtgacaca | ggaacactta | acggctgaca | tgggaattag ccatggcaaa | 660 |
| gcctcgcaat | ccagtgcaaa | ggcaatacgc | aaacctatgt | gttgggtaac gccagggttt | 720 |
| tcccagtcac | gacgttgtaa | aacgacggcc | agtgaattaa | ttcttgaaga cgaaagggcc | 780 |
| tcgtgatacg | cctatttta | taggttaatg | tcatgataat | aatggtttct tagagcttat | 840 |
| cggccagcct | cgcagagcag | gattcccgtt | gagcaccgcc | aggtgcgaat aagggacagt | 900 |
| gaagaaggaa | cacccgctcg | cgggtgggcc | tacttcacct | atcctgcccg gctgacgccg | 960 |
| ttggatacac | caaggaaagt | ctacacgaac | cctttggcaa | aatcctgtat atcgtgcgaa | 1020 |
| aaaggatgga | tataccgaaa | aaatcgctat | aatgaccccg | aagcagggtt atgcagcgac | 1080 |
| aacactcaac | cctatctcgg | tcgcgaccac | acccgtcctg | tggcaaagcc tcgcaatcca | 1140 |
| gtggctagcc | aaaggataac | ttcgtataaa | gtatcctata | cgaagttatg ataaccgtat | 1200 |
| taccgccttt | gagtgagctc | ctaggggaat | gataacaaaa | taaacgaccg aatggattct | 1260 |
| ttttgtaatt | aaatgcttgc | cagcgtcaaa | gaacgcccta | atgcgcca ccactgaccg | 1320 |
| acacaacgct | gataaacatt | gtgaggtcgg | gcagagaaag | cgataatcag tgcttgactc | 1380 |
| tgcgggcgaa | cagcgtagta | tacgcagccc | ggctgaacga | gaatattatt ttttatgtca | 1440 |
| gcctgctctt | taacaattaa | tcagacaatc | tgtgtgggca | ctcacaagac cgtatcacaa | 1500 |
| aaaaatacgt | tttaaagtct | tgaagagtga | acaacagtta | attcattacg aaataattag | 1560 |
| tcagaattct | ttgagcatca | aactaaaata | caagaagcaa | atatgtttta gagctagaaa | 1620 |
| tagcaagtta | aaataaggct | agtccgttat | caacttgaaa | aagtggcacc gagtcggtgg | 1680 |
| tgctttattt | tgaaacaaaa | aggccaccct | tctgggtggc | cttttgcat taacaaaga | 1740 |

```
actaacttag ttttccaact gttttccacg cctgtcttaa ctagttcacg ctgccgcaag    1800
cactcagggc gcaagggctg ctaaaggaag cggaacacgt agaaagccag tccgcagaaa    1860
cggtgctgac cccggatgaa tgtcagctac tgggctatct ggacaaggga aaacgcaagc    1920
gcaaagagaa agcaggtagc ttgcagtggg cttacatggc gatagctaga ctgggcggtt    1980
ttatggacag caagcgaacc ggaattgcca gctgggcgc cctctggtaa ggttgggaag    2040
ccctgcaaag taaactggat ggctttcttg ccgccaagga tctgatggcg caggggatca    2100
agatctgatc aagagacagg atgaggatcg tttcgcatga ttgaacaaga tggattgcac    2160
acaggttctc cggccgcttg ggtggagagg ctattcggct atgactgggc acaacagaca    2220
atcggctgct ctgatgccgc cgtgttccgg ctgtcagcgc agggggcgccc ggttctttt    2280 gtcaagaccg acctgtccgg tgccctgaat gaactccaag acgaggcagc gcggctatcg    2340
tggctggcca cgacgggcgt tccttgcgca gctgtgctcg acgttgtcac tgaagcggga    2400
agggactggc tgctattggg cgaagtgccg gggcaggatc tcctgtcatc tcaccttgct    2460
cctgccgaga aagtatccat catggctgat gcaatgcggc ggctgcatac gcttgatccg    2520
gctacctgcc cattcgacca ccaagcgaaa catcgcatcg agcgagcacg tactcggatg    2580
gaagccggtc ttgtcgatca ggatgatctg gacgaagagc atcaggggct cgcgccagcc    2640
gaactgttcg ccaggctcaa ggcgcggatg cccgacggcg aggatctcgt cgtgacccat    2700
ggcgatgcct gcttgccgaa tatcatggtg gaaaatggcc gcttttctgg attcatcgac    2760
tgtggccggc tgggtgtggc ggaccgctat caggacatag cgttggctac ccgtgatatt    2820
gctgaagagc ttggcggcga atgggctgac cgcttcctcg tgctttacgg tatcgccgct    2880
cccgattcgc agcgcatcgc cttctatcgc cttcttgacg agttcttctg agcggcccgg    2940
gtgaaagttg gaacctctta cgtgccga                                      2968
```

<210> SEQ ID NO 10
<211> LENGTH: 2649
<212> TYPE: DNA
<213> ORGANISM: Artificial Sequence
<220> FEATURE:
<223> OTHER INFORMATION: Synthetic Construct

<400> SEQUENCE: 10

```
aattttgcg gccgctatgt gttgggtaac gccagggttt tcccagtcac gacgttgtaa     60
aacgacggcc agtgaattaa ttcttgaaga cgaaagggcc tcgtgatacg cctattttta    120
taggttaatg tcatgataat aatggtttct tagagcttat cggccagcct cgcagagcag    180
gattcccgtt gagcaccgcc aggtgcgaat aagggacagt gaagaaggaa cacccgctcg    240
cgggtgggcc tacttcacct atcctgcccg gctgacgccg ttggatacac caaggaaagt    300
ctacacgaac cctttggcaa aatcctgtat atcgtgcgaa aaaggatgga tataccgaaa    360
aaatcgctat aatgaccccg aagcagggtt atgcagcgaa gatccgcagt caacctgtt    420 gatagtacgt actaagctct catgtttcac gtactaagct ctcatgttta acgtactaag    480
ctctcatgtt taacgaacta aaccctcatg gctaacgtac taagctctca tggctaacgt    540
actaagctct catgtttcac gtactaagct ctcatgtttg aacaataaaa ttaatataaa    600
tcagcaactt aaatagcctc taaggtttta agttttataa gaaaaaaaag aatatataag    660
gcttttaaag cttttaaggt ttaacggttg tggacaacaa gccagggatg taacgcactg    720
agaagccctt agagcctctc aaagcaattt tgagtgacac aggaacactt aacggctgac    780
```

| | |
|---|---:|
| atgggaatta gccatggcaa agcctcgcaa tccagtgcaa aggataactt cgtatagcat | 840 |
| acattatacg aagttatgat aaccgtatta ccgcctttga gtgagctcca ccgcggtggc | 900 |
| ggccgctcta gaactagtgg atccccatgc gtccggcgta gaggatcgag atcgatctcg | 960 |
| atcccgcgaa attaatacga ctcactatag gggaattgtg agcggataac aattcccctc | 1020 |
| tagaaataat tttgtttaac tttaagaagg agatatacat atgaaagaaa ccgctgctgc | 1080 |
| taaattcgaa cgccagcaca tggacagccc agatctgggt accctggtgc cacgcggttc | 1140 |
| catggcgata tcggatccga attcgagctc cgtcgacaag cttgcggccg cactcgagca | 1200 |
| ccaccaccac caccactgag atccggctgc taacaaagcc cgaaaggaag ctgagttggc | 1260 |
| tgctgccacc gctgagcaat aactagcata accccttggg gcctctaaac gggtcttgag | 1320 |
| gggttttttg ctgaaaggag gaactatatc cggattggcg aatgggacgc gccctgtagc | 1380 |
| ggcgcattaa gcctgcagga attcgatatc aagcttatcg ataccgtcga cctcgagggg | 1440 |
| gggcccggta ccctcacgt gttgcccag caatcagcgc gaccttgccc ctccaacgtc | 1500 |
| atctcgttct ccgctcatga gctcagccaa tcgactggcg agcggcatcg cattcttcgc | 1560 |
| atcccgcctc tggcggatgc aggaagatca acggatctcg gcccagttga cccagggctg | 1620 |
| tcgccacaat gtcgcgggag cggatcaacc gagcaaaggc atgaccgact ggaccttcct | 1680 |
| tctgaaggct cttctccttg agccacctgt ccgccaaggc aaagcgctca cagcagtggt | 1740 |
| cattctcgag ataatcgacg cgtaccaact tgccatcctg aagaatggtg cagtgtctcg | 1800 |
| gcacccata gggaaccttt gccatcaact cggcaagatg cagcgtcgtg ttggcatcgt | 1860 |
| gtcccacgcc gaggagaagt acctgcccat cgagttcatg gacacgggcg accgggcttg | 1920 |
| caggcgagtg aggtggcagg gcaatggat cagagatgat ctgctctgcc tgtggccccg | 1980 |
| ctgccgcaaa ggcaaatgga tgggcgctgc gctttacatt tggcaggcgc cagaatgtgt | 2040 |
| cagagacaac tccaaggtcc ggtgtaacgg gcgacgtggc aggatcgaac ggctcgtcgt | 2100 |
| ccagacctga ccacgagggc atgacgacg tccctcccgg acccagcgca gcacgcaggg | 2160 |
| cctcgatcag tccaagtggc ccatcttcga ggggccggac gctacggaag gagctgtgga | 2220 |
| ccagcagcac accgccgggg gtaaccccaa ggttgagaag ctgaccgatg agctcggctt | 2280 |
| ttcgccattc gtattgcatt ttagcttcct tagctcctga aaatctcgat aactcaaaaa | 2340 |
| atacgcccgg tagtgatctt atttcattat ggtgaaagtt ggaacctctt acgtgccgaa | 2400 |
| taacttcgta taatgtgtac tatacgaagt tattcaacgt ctcattttcg ccaaaagttg | 2460 |
| gcccagggct tccccggtatc aacagggaca ccaggattta tttattctgc gaagtgatct | 2520 |
| tccgtcacag gtatttattc gcgataagct catggagcgg cgtaaccgtc gcacaggaag | 2580 |
| gacagagaaa gcgcggatct gggaagtgac ggacagaacg tcaggacct ggagcggccg | 2640 |
| ctttttcc | 2649 |

<210> SEQ ID NO 11
<211> LENGTH: 11652
<212> TYPE: DNA
<213> ORGANISM: Artificial Sequence
<220> FEATURE:
<223> OTHER INFORMATION: Synthetic Construct

<400> SEQUENCE: 11

| | |
|---|---:|
| tatgtgttgg gtaacgccag ggttttccca gtcacgacgt tgtaaaacga cggccagtga | 60 |
| attaattctt gaagacgaaa gggcctcgtg atacgcctat ttttataggt taatgtcatg | 120 |
| ataataatgg tttcttagag cttatcggcc agcctcgcag agcaggattc ccgttgagca | 180 |

```
ccgccaggtg cgaataaggg acagtgaaga aggaacaccc gctcgcgggt gggcctactt      240
cacctatcct gcccggctga cgccgttgga tacaccaagg aaagtctaca cgaacccttt      300
ggcaaaatcc tgtatatcgt gcgaaaaagg atggatatac cgaaaaaatc gctataatga      360
ccccgaagca gggttatgca gcgaccgtta catatcaaag gaaaactgt ccatacccat       420 gggctagctg atcagccagt gccaagcttg ctcaatcaat caccggatcc ccgggaattc      480
ttactaatcg ccatcttcca gcaggcgcac cattgcccct gtttcactat ccaggttacg      540
gatatagttc atgacaatat ttacattggt ccagccacca gcttgcatga tctccggtat      600
tgaaactcca gcgcgggcca tatctcgcgc ggctccgaca cgggcactgt gtccagacca      660
ggccaggtat ctctgaccag agtcatcctt agcgccgtaa atcaatcgat gagttgcttc      720
aaaaatccct tccagggcgc gagttgatag ctggctggtg gcagatggcg cggcaacacc      780 atttttctg acccggcaaa acaggtagtt attcggatca tcagctacac cagagacgga       840
aatccatcgc tcgaccagtt tagttacccc caggctaagt gccttctcta cacctgtggt      900
gctaaccagc gttttcgttc tgccaatatg gattaacatt ctcccaccgt cagtacgtga      960
gatatcttta accctgatcc tggcaatttc ggctatacgt aacagggtgt tataagcaat     1020
ccccagaaat gccagattac gtatatcctg gcagcgatcg ctattttcca tgagtgaacg     1080
aacctggtcg aaatcagtgc gttcgaacgc tagagcctgt tttgcacgtt caccggcatc     1140
aacgttttct tttcggatcc gccgcataac cagtgaaaca gcattgctgt cacttggtcg     1200
tggcagcccg gaccgacgat gaagcatgtt tagctggccc aaatgttgct ggatagtttt     1260
tactgccaga ccgcgcgcct gaagatatag aagataatcg cgaacatctt caggttctgc     1320
gggaaaccat ttccggttat tcaacttgca ccatgccgcc cacgaccggc aaacggacag     1380
aagcattttc caggtatgct cagaaaacgc ctggcgatcc ctgaacatgt ccatcaggtt     1440
cttgcgaacc tcatcactcg ttgcatcgac cggtaatgca ggcaaatttt ggtgtacggt     1500
cagtaaattg gacatgtcaa cggtacctgc agtctagagt cgaggcctgt tcctgtgtg      1560 aaattgttat ccgctcacaa ttccacacat tatacgagcc ggaagcataa agtgtaaagc     1620
ctggggtgcc taatgagtga gctgtttcct gtgtgaaatt gttatccgct cacaattcca     1680
cacattatac gagccggaag cataaagtgt aaagcctggg gtgcctaatg agtgagctgc     1740
ctcgcgcgtt tcggtgatga cggtgaaaac ctctgacaca tgcagctccc ggagacggtc     1800
acagcttgtc tgtaagcgga tgccgggagc agacaagccc gtcagggcgc gtcagcgggt     1860
gttggcgggt gtcggggcgc agccatgacc cagtcacgta gcgatagcgg agtgtatccg     1920
acaccatcga atggtgcaaa acctttcgcg gtatggcatg atagcgcccg gaagagagtc     1980
aattcagggt ggtgaatgtg aaaccagtaa cgttatacga tgtcgcagag tatgccggtg     2040
tctcttatca gaccgtttcc cgcgtggtga accaggccag ccacgtttct gcgaaaacgc     2100
gggaaaaagt ggaagcggcg atggcggagc tgaattacat tcccaaccgc gtggcacaac     2160
aactggcggg caaacagtcg ttgctgattg gcgttgccac ctccagtctg gccctgcacg     2220
cgccgtcgca aattgtcgcg gcgattaaat ctcgcgccga tcaactgggt gccagcgtgg     2280
tggtgtcgat ggtagaacga gcggcgtcg aagcctgtaa agcggcggtg cacaatcttc      2340
tcgcgcaacg cgtcagtggg ctgatcatta actatccgct ggatgaccag gatgccattg     2400
ctgtggaagc tgcctgcact aatgttccgg cgttatttct tgatgtctct gaccagacac     2460
ccatcaacag tattattttc tcccatgaag acggtacgcg actgggcgtg gagcatctgg     2520
```

```
tcgcattggg tcaccagcaa atcgcgctgt tagcgggccc attaagttct gtctcggcgc    2580
gtctgcgtct ggctggctgg cataaatatc tcactcgcaa tcaaattcag ccgatagcgg    2640
aacgggaagg cgactggagt gccatgtccg gttttcaaca aaccatgcaa atgctgaatg    2700
agggcatcgt tcccactgcg atgctggttg ccaacgatca gatggcgctg ggcgcaatgc    2760
gcgccattac cgagtccggg ctgcgcgttg gtgcggatat ctcggtagtg ggatacgacg    2820
ataccgaaga cagctcatgt tatatcccgc cgttaaccac catcaaacag gattttcgcc    2880
tgctggggca aaccagcgtg gaccgcttgc tgcaactctc tcagggccag gcggtgaagg    2940
gcaatcagct gttgcccgtc tcactggtga aaagaaaaac caccctggcg cccaatacgc    3000
aaaccgcctc tccccgcgcg ttggccgatt cattaatgca gctggcacga caggtttccc    3060
gactggaaag cgggcagtga gcgcaacgca attaatgtaa gttagctcac tcattaggca    3120
ccccaggctt tacactttat gcttccgacc atactggctt aactatgcgg catcagagct    3180
gaaaagaaag gaaacgacag gtgctgaaag cgagcttttt ggcctctgtc gtttcctttc    3240 tctgttttg tccgtggaat gaacaatgga agtccgagct catcgctaat aacttcgtat    3300
agcatacatt atacgaagtt atggataacc gtattaccgc ctttgagtga gctccaccgc    3360
ggtggcggcc gctctagaac tagtggatcc cccgggctgc aggaattcga tatcaagctt    3420
atcgataccg tcgacctcga ggggggggcc ggtaccagcc ggcgtcccgg aaaacgattc    3480
cgaagcccaa cctttcatag aaggtttaaa caccgcctcc acgtgttgcc ccagcaatca    3540
gcgcgacctt gccccctccaa cgtcatctcg ttctccgctc atgagctcag ccaatcgact    3600
ggcgagcggc atcgcattct tcgcatcccg cctctggcgg atgcaggaag atcaacggat    3660
ctcggcccag ttgacccagg gctgtcgcca caatgtcgcg ggagcggatc aaccgagcaa    3720
aggcatgacc gactggacct tccttctgaa ggctcttctc cttgagccac ctgtccgcca    3780
aggcaaagcg ctcacagcag tggtcattct cgagataatc gacgcgtacc aacttgccat    3840
cctgaagaat ggtgcagtgt ctcggcaccc catagggaac cttttgccatc aactcggcaa    3900 gatgcagcgt cgtgttggca tcgtgtccca cgccgaggag aagtacctgc ccatcgagtt    3960
catggacacg ggcgaccggg cttgcaggcg agtgaggtgg caggggcaat ggatcagaga    4020
tgatctgctc tgcctgtggc cccgctgccg caaaggcaaa tggatgggcg ctgcgcttta    4080
catttggcag cgccagaat gtgtcagaga caactccaag gtccggtgta acgggcgacg    4140
tggcaggatc gaacggctcg tcgtccagac ctgaccacga gggcatgacg agcgtccctc    4200
ccggacccag cgcagcacgc agggcctcga tcagtccaag tggcccatct tcgaggggcc    4260
ggacgctacg gaaggagctg tggaccagca gcacaccgcc ggggggtaacc ccaaggttga    4320 gaagctgacc gatgagctcg gcttttcgcc attcgtattg cattttagct tccttagctc    4380
ctgaaaatct cgataactca aaaaatacgc ccggtagtga tcttatttca ttatggtgaa    4440
agttggaacc tcttacgtgc cgaataactt cgtataatgt gtactatacg aagttattca    4500
acgtctcatt ttcgccaaaa gttggcccag ggcttcccgg tatcaacagg gacaccagga    4560
tttatttatt ctgcgaagtg atcttccgtc acaggtattt attcgcgata agctcatgga    4620
gcggcgtaac cgtcgcacag gaaggacaga gaagcgcgga tctgggaagt gacgacagaa    4680
acggtcagga cctggattgg ggaggcggtt gccgccgctg ctgctgacgg tgtgacgttc    4740
tctgttccgg tcacaccaca tacgttccgc cattcctatg cgatgcacat gctgtatgcc    4800
ggtataccgc tgaaagttct gcaaagcctg atgggacata agtccatcag ttcaacggaa    4860
gtctacacga aggttttgc gctggatgtg gctgcccggc accgggtgca gtttgcgatg    4920
```

```
ccggagtctg atgcggttgc gatgctgaaa caattatcct gagaataaat gccttggcct    4980
ttatatggaa atgtggaact gagtggatat gctgttttg tctgttaaac agagaagctg      5040
gctgttatcc actgagaagc gaacgaaaca gtcgggaaaa tctcccatta tcgtagagat    5100
ccgcattatt aatctcagga gcctgtgtag cgtttatagg aagtagtgtt ctgtcatgat    5160
gcctgcaagc ggtaacgaaa acgatttgaa tatgccttca ggaacaatag aaatcttcgt    5220
gcggtgttac gttgaagtgg agcggattat gtcagcaatg gacagaacaa cctaatgaac    5280
acagaaccat gatgtggtct gtccttttac agccagtagt gctcgccgca gtcgagcgac    5340
agggcgaagc cctcgagtga gcgaggaagc accagggaac agcacttata tattctgctt    5400
acacacgatg cctgaaaaaa cttcccttgg ggttatccac ttatccacgg ggatatttt     5460
ataattattt ttttttatagt ttttagatct tctttttag agcgccttgt aggccttat    5520
ccatgctggt tctagagaag gtgttgtgac aaattgccct ttcagtgtga caaatcaccc    5580
tcaaatgaca gtcctgtctg tgacaaattg cccttaaccc tgtgacaaat tgccctcaga    5640
agaagctgtt ttttcacaaa gttatccctg cttattgact ctttttttatt tagtgtgaca    5700
atctaaaaac ttgtcacact tcacatggat ctgtcatggc ggaaacagcg gttatcaatc    5760
acaagaaacg taaaaatagc ccgcgaatcg tccagtcaaa cgacctcact gaggcggcat    5820
atagtctctc ccgggatcaa aaacgtatgc tgtatctgtt cgttgaccag atcagaaaat    5880
ctgatggcac cctacaggaa catgacggta tctgcgagat ccatgttgct aaatatgctg    5940
aaatattcgg attgacctct gcggaagcca gtaaggatat acggcaggca ttgaagagtt    6000
tcgcggggaa ggaagtggtt ttttatcgcc ctgaagagga tgccggcgat gaaaaggct     6060
atgaatcttt tccttggttt atcaaacgtg cgcacagtcc atccagaggg ctttacagtg    6120
tacatatcaa cccatatctc attcccttct ttatcgggtt acagaaccgg tttacgcagt    6180
ttcggcttag tgaaacaaaa gaaatcacca atccgtatgc catgcgttta tacgaatccc    6240
tgtgtcagta tcgtaagccg gatggctcag gcatcgtctc tctgaaaatc gactggatca    6300
tagagcgtta ccagctgcct caaagttacc agcgtatgcc tgacttccgc cgccgcttcc    6360
tgcaggtctg tgttaatgag atcaacagca gaactccaat gcgcctctca tacattgaga    6420
aaaagaaagg ccgccagacg actcatatcg tattttcctt ccgcgatatc acttccatga    6480
cgacaggata gtctgagggt tatctgtcac agatttgagg gtggttcgtc acatttgttc    6540
tgacctactg agggtaattt gtcacagttt tgctgtttcc ttcagcctgc atggattttc    6600
tcatacttt tgaactgtaa tttttaagga agccaaattt gagggcagtt tgtcacagtt    6660
gatttccttc tctttccctt cgtcatgtga cctgatatcg ggggtagtt cgtcatcatt    6720
gatgagggtt gattatcaca gtttattact ctgaattggc tatccgcgtg tgtacctcta    6780
cctggagttt ttcccacggt ggatatttct tcttgcgctg agcgtaagag ctatctgaca    6840
gaacagttct tctttgcttc ctcgccagtt cgctcgctat gctcggttac acggctgcgg    6900
cgagcattcg gtacgcgtcg acgcgtacgc ggcctgcatt taaatgcccg gccggccga    6960
tcgcttgcct gtaacttaca cgcgcctcgt atcttttaat gatggaataa tttgggaatt    7020
tactctgtgt ttatttattt ttatgttttg tatttggatt ttagaaagta aataaagaag    7080
gtagaagagt tacggaatga agaaaaaaaa ataaacaaag gtttaaaaaa tttcaacaaa    7140
aagcgtactt tacatatata tttattagac aagaaaagca gattaaatag atatacattc    7200
gattaacgat aagtaaaatg taaaatcaca ggattttcgt gtgtggtctt ctacacagac    7260
```

```
aagatgaaac aattcggcat taatacctga gagcaggaag agcaagataa aaggtagtat    7320
ttgttggcga tccccctaga gtcttttaca tcttcggaaa acaaaaacta ttttttcttt    7380
aatttctttt tttactttct attttttaatt tatatattta tattaaaaaa tttaaattat   7440 aattatttt atagcacgtg atgaaaaggg ccggccggcg cgcccagctt tttctttcca    7500 atttttttt tttcgtcatt ataaaaatca ttacgaccga gattcccggg taataactga    7560
tataattaaa ttgaagctct aatttgtgag tttagtatac atgcatttac ttataataca   7620 gtttttagt tttgctggcc gcatcttctc aaatatgctt cccagcctgc ttttctgtaa    7680
cgttcaccct ctaccttagc atcccttccc tttgcaaata gtcctcttcc aacaataata   7740
atgtcagatc ctgtagagac cacatcatcc acggttctat actgttgacc caatgcgtct   7800
cccttgtcat ctaaacccac accgggtgtc ataatcaacc aatcgtaacc ttcatctctt   7860
ccacccatgt ctctttgagc aataaagccg ataacaaaat ctttgtcgct cttcgcaatg   7920
tcaacagtac ccttagtata ttctccagta gatagggagc ccttgcatga caattctgct   7980
aacatcaaaa ggcctctagg ttcctttgtt acttcttctg ccgcctgctt caaaccgcta   8040
acaatacctg ggcccaccac accgtgtgca ttcgtaatgt ctgcccattc tgctattctg   8100
tatacacccg cagagtactg caatttgact gtattaccaa tgtcagcaaa ttttctgtct   8160
tcgaagagta aaaaattgta cttggcggat aatgccttta gcggcttaac tgtgccctcc   8220
atggaaaaat cagtcaagat atccacatgt gttttttagta aacaaatttt gggacctaat   8280
gcttcaacta actccagtaa ttccttggtg gtacgaacat ccaatgaagc acacaagttt   8340
gtttgctttt cgtgcatgat attaaatagc ttggcagcaa caggactagg atgagtagca   8400
gcacgttcct tatatgtagc tttcgacatg atttatcttc gtttcctgca ggttttgtt    8460 ctgtgcagtt gggttaagaa tactgggcaa tttcatgttt cttcaacact acatatgcgt   8520
atatatacca atctaagtct gtgctccttc cttcgttctt ccttctgttc ggagattacc   8580
gaatcaaaaa aatttcaagg aaaccgaaat caaaaaaaag aataaaaaaa aaatgatgaa   8640
ttgaattgaa aagctgggcg cgccttaatt aagcccgggc atttaaatat ggtgcactcg   8700
ctagtgataa taagtgactg aggtatgtgc tcttcttatc tccttttgta gtgttgctct   8760 tatttttaaac aactttgcgg ttttttgatg actttgcgat tttgttgttg ctttgcagta   8820
aattgcaaga tttaataaaa aaacgcaaag caatgattaa aggatgttca gaatgaaact   8880
catggaaaca cttaaccagt gcataaacgc tggtcatgaa atgacgaagg ctatcgccat   8940
tgcacagttt aatgatgaca gcccggaagc gaggaaaata acccggcgct ggagaatagg   9000
tgaagcagcg gatttagttg gggtttcttc tcaggctatc agagatgccg agaaagcagg   9060
gcgactaccg cacccggata tggaaattcg aggacgggtt gagcaacgtg ttggttatac   9120
aattgaacaa attaatcata tgcgtgatgt gtttggtacg cgattgcgac gtgctgaaga   9180
cgtatttcca ccggtgatcg gggttgctgc ccataaaggt ggcgtttaca aaacctcagt   9240
ttctgttcat cttgctcagg atctggctct gaaggggcta cgtgttttgc tcgtggaagg   9300
taacgacccc cagggaacag tctcaatgta tcacggatgg gtaccagatc ttcatattca   9360
tgcagaagac actctcctgc cttctatct tggggaaaag gacgatgtca cttatgcaat   9420
aaagcccact tgctggccgg ggcttgacat tattccttcc tgtctggctc tgcaccgtat   9480
tgaaactgag ttaatgggca aatttgatga aggtaaactg cccaccgatc cacacctgat   9540
gctccgactg gccattgaaa ctgttgctca tgactatgat gtcatagtta ttgacagcgc   9600
gcctaacctg ggtatcggca cgattaatgt cgtatgtgct gctgatgtgc tgattgttcc   9660
```

```
cacgcctgct gagttgtttg actacacctc cgcactgcag ttttcgata tgcttcgtga    9720 tctgctcaag aacgttgatc ttaaagggtt cgagcctgat gtacgtattt tgcttaccaa    9780
atacagcaat agtaatggct ctcagtcccc gtggatggga gagcaaattc gggatgcctg    9840
gggaagcatg gttctaaaaa atgttgtacg tgaaacggat gaagttggta aaggtcagat    9900
ccggatgaga actgttttg aacaggccat tgatcaacgc tcttcaactg gtgcctggag     9960
aaatgctctt tctatttggg aacctgtctg caatgaaatt ttcgatcgtc tgattaaacc   10020
acgctgggag attagataat gaagcgtgcg cctgttattc caaaacatac gctcaatact   10080
caaccggttg aagatacttc gttatcgaca ccagctgccc cgatggtgga ttcgttaatt   10140
gcgcgcgtag gagtaatggc tcgcggtaat gccattactt tgcctgtatg tggtcgggat   10200
gtgaagttta ctcttgaagt gctccggggt gatagtgttg agaagacctc tcgggtatgg   10260
tcaggtaatg aacgtgacca ggagctgctt actgaggacg cactggatga tctcatccct   10320 tctttctac tgactggtca acagacaccg gcgttcggtc gaagagtatc tggtgtcata    10380
gaaattgccg atgggagtcg ccgtcgtaaa gctgctgcac ttaccgaaag tgattatcgt   10440
gttctggttg gcgagctgga tgatgagcag atggctgcat tatccagatt gggtaacgat   10500
tatcgcccaa caagtgctta tgaacgtggt cagcgttatg caagccgatt gcagaatgaa   10560
tttgctggaa atatttctgc gctggctgat gcggaaaata tttcacgtaa gattattacc   10620
cgctgtatca acaccgccaa attgcctaaa tcagttgttg ctctttttc tcacccggt    10680 gaactatctg cccggtcagg tgatgcactt caaaaagcct ttacagataa agaggaatta   10740
cttaagcagc aggcatctaa ccttcatgag cagaaaaaag ctggggtgat atttgaagct   10800
gaagaagtta tcactctttt aacttctgtg cttaaaacgt catctgcatc aagaactagt   10860
ttaagctcac gacatcagtt tgctcctgga gcgacagtat tgtataaggg cgataaaatg   10920
gtgcttaacc tggacaggtc tcgtgttcca actgagtgta tagagaaaat tgaggccatt   10980
cttaaggaac ttgaaaagcc agcaccctga tgcgaccacg ttttagtcta cgtttatctg   11040
tctttactta atgtccttg ttacaggcca gaaagcataa ctggcctgaa tattctctct    11100
gggcccactg ttccacttgt atcgtcggtc tgataatcag actgggacca cggtcccact   11160
cgtatcgtcg gtctgattat tagtctggga ccacggtccc actcgtatcg tcggtctgat   11220
tattagtctg gaccacggt cccactcgta tcgtcggtct gataatcaga ctgggaccac    11280
ggtcccactc gtatcgtcgg tctgattatt agtctgggac catggtccca ctcgtatcgt   11340
cggtctgatt attagtctgg gaccacggtc ccactcgtat cgtcggtctg attattagtc   11400
tggaaccacg gtcccactcg tatcgtcggt ctgattatta gtctgggacc acggtccac    11460 tcgtatcgtc ggtctgatta ttagtctggg accacgatcc cactcgtgtt gtcggtctga   11520
ttatcggtct gggaccacgg tcccacttgt attgtcgatc agactatcag cgtgagacta   11580
cgattccatc aatgcctgtc aagggcaagt attgacatgt cgtcgtaacc tgtagaacgg   11640
agtaacctcg gt                                                       11652
```